US009499502B2

United States Patent
Wu et al.

(10) Patent No.: US 9,499,502 B2
(45) Date of Patent: Nov. 22, 2016

(54) 5-SUBSTITUTED IMINOTHIAZINES AND THEIR MONO- AND DIOXIDES AS BACE INHIBITORS, COMPOSITIONS, AND THEIR USE

(75) Inventors: Wen-Lian Wu, Edison, NJ (US); Duane A. Burnett, Bernardsville, NJ (US); Andrew W. Stamford, Chatham, NJ (US); Jared N. Cumming, Garwood, NJ (US); Chad E. Bennett, Metuchen, NJ (US); Eric J. Gilbert, Scotch Plains, NJ (US); Jack D. Scott, Scotch Plains, NJ (US); Younong Yu, East Brunswick, NJ (US); Xuanjia Peng, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/110,363

(22) PCT Filed: Apr. 12, 2012

(86) PCT No.: PCT/CN2012/000497
§ 371 (c)(1),
(2), (4) Date: Dec. 12, 2013

(87) PCT Pub. No.: WO2012/139425
PCT Pub. Date: Oct. 18, 2012

(65) Prior Publication Data
US 2014/0128382 A1    May 8, 2014

Related U.S. Application Data

(60) Provisional application No. 61/475,215, filed on Apr. 13, 2011, provisional application No. 61/503,254, filed on Jun. 30, 2011.

(30) Foreign Application Priority Data

Apr. 5, 2012    (WO) ................ PCT/CN2012/000435

(51) Int. Cl.
| | | |
|---|---|---|
| C07D 279/12 | (2006.01) |
| A61K 45/06 | (2006.01) |
| C07D 417/04 | (2006.01) |
| A61K 31/541 | (2006.01) |
| C07D 417/12 | (2006.01) |
| C07D 417/14 | (2006.01) |
| A61K 31/54 | (2006.01) |
| C07D 471/04 | (2006.01) |
| C07D 487/04 | (2006.01) |
| C07D 498/04 | (2006.01) |
| C07D 513/04 | (2006.01) |

(52) U.S. Cl.
CPC ............. *C07D 279/12* (2013.01); *A61K 31/54* (2013.01); *A61K 31/541* (2013.01); *A61K 45/06* (2013.01); *C07D 417/04* (2013.01); *C07D 417/12* (2013.01); *C07D 417/14* (2013.01); *C07D 471/04* (2013.01); *C07D 487/04* (2013.01); *C07D 498/04* (2013.01); *C07D 513/04* (2013.01)

(58) Field of Classification Search
None
See application file for complete search history.

(56) References Cited

U.S. PATENT DOCUMENTS

| 5,534,520 A | 7/1996 | Fisher et al. |
|---|---|---|
| 7,648,983 B2 | 1/2010 | Audia et al. |
| 8,338,413 B1 | 12/2012 | Rueeger |
| 2007/0287692 A1 | 12/2007 | Wu et al. |

(Continued)

FOREIGN PATENT DOCUMENTS

| EP | 1942105 | 7/2008 |
|---|---|---|
| WO | WO02058691 | 8/2002 |

(Continued)

OTHER PUBLICATIONS

Danziger, Automated Site-Directed Drug Design: A General Algorithm for Knowledge Acquisition about Hydrogen-Bonding Regions at Protein Surfaces, Proceedings of the Royal Society of London. Series B, Biological Sciences, 1989, 236(1283), pp. 101-113.*

(Continued)

*Primary Examiner* — San-Ming Hui
*Assistant Examiner* — Andrew Lee
(74) *Attorney, Agent, or Firm* — Keith D. MacMillan; John C. Todaro

(57) ABSTRACT

The present invention discloses certain iminothiazine compounds and mono- and dioxides thereof, including compounds Formula (I): and tautomers and stereoisomers thereof, and pharmaceutically acceptable salts of said compounds, said tautomers and said stereoisomers, wherein each of variables shown in the formula are as defined herein. The compounds of the invention may be useful as BACE inhibitors and/or for the treatment and prevention of various pathologies related thereto. Pharmaceutical compositions comprising one or more such compounds (alone and in combination with one or more other active agents), and methods for their preparation and uses, including Alzheimer's disease, are also disclosed.

18 Claims, No Drawings

(56) References Cited

U.S. PATENT DOCUMENTS

| | | |
|---|---|---|
| 2008/0200445 A1 | 8/2008 | Zhu et al. |
| 2010/0075957 A1 | 3/2010 | Tamura et al. |
| 2011/0046122 A1 | 2/2011 | Andreini et al. |
| 2012/0035195 A1 | 2/2012 | Banner et al. |
| 2012/0258961 A1 | 10/2012 | Suzuki et al. |

FOREIGN PATENT DOCUMENTS

| | | |
|---|---|---|
| WO | WO2004094382 | 4/2004 |
| WO | WO2006017836 | 2/2006 |
| WO | WO2007049532 A1 | 5/2007 |
| WO | WO2007120096 | 10/2007 |
| WO | 2008133273 | 6/2008 |
| WO | 2008133274 | 6/2008 |
| WO | 2008103351 | 8/2008 |
| WO | 2009020580 | 2/2009 |
| WO | 2009131974 | 10/2009 |
| WO | WO2009131975 A1 | 10/2009 |
| WO | WO2009134617 | 11/2009 |
| WO | 2009151098 | 12/2009 |
| WO | 2010128058 | 11/2010 |
| WO | 2011009943 | 1/2011 |
| WO | 2011020806 | 2/2011 |
| WO | WO2011020806 | 2/2011 |
| WO | WO2011029803 | 3/2011 |
| WO | 2011044181 | 4/2011 |
| WO | 2011044184 | 4/2011 |
| WO | 2011044185 | 4/2011 |
| WO | WO2011044187 | 4/2011 |
| WO | 2011058763 | 5/2011 |
| WO | WO2011069934 | 6/2011 |
| WO | WO2011070029 | 6/2011 |
| WO | WO2011070781 | 6/2011 |
| WO | WO2011077726 | 6/2011 |
| WO | WO2011080176 | 7/2011 |
| WO | WO2011138293 | 11/2011 |
| WO | WO2011142716 | 11/2011 |
| WO | WO2011154374 | 12/2011 |
| WO | WO2011154431 | 12/2011 |
| WO | WO2012006953 | 1/2012 |

OTHER PUBLICATIONS

PCT Search Report for PCT/US2012/000497 dated Jul. 12, 2012; 6 pages.
Written Opinion for PCT/US2012/000497 dated Jun. 29, 2012; 6 pages.
Cole, et al., Review: The Alzheimer's disease B-secretase enzyme, BACEI, , Molecular Neurodegeneration 2007, 2:22, Published Nov. 15, 2007.
Cumming JN, et al. Piperazine sulfonamide BACE1 inhibitors: Design, synthesis, and in vivo characterization. Bioorg Med Chem Lett. 2010;20:2837-42.
Cumming JN, et al. Rational design of novel, potent piperazinone and imidazolidinone BACE1 inhibitors. Bioorg Med Chem Lett. 2008;18:3236-41.
Cumming JN, et al. Structure based design of iminohydantoin BACE1 inhibitors: identification of an orally available, centrally active BACE1 inhibitor. Bioorg Med Chem Lett. Apr. 1, 2012;22(7):2444-9. doi: 10.1016/j.bmcl.2012.02.013.
Evin, et al., BACE Inhibitors as Potential Drugs for the Treatment of Alzheimer's Disease: Focus on Bioactivity, Recent Patents on CNS Drug Discovery, 2011, 6, 91-106.
Farah, et al., Reduced BACE1 Activity Enhances Clearance of MyelinDebris and Regeneration of Axons in the Injured PeripheralNervous System, The Journal of Neuroscience, Apr. 13, 2011 • 31(15):5744-5754.
Getchell, et al., 3-Nitrotyrosine immunoreactivity in olfactory receptor neurons of patients with Alzheimer's disease: implications for impaired odor sensitivity, Neurobiology of Aging 24 (2003) 663-673., accepted Oct. 8, 2002, pp. 663-673.
Ginman, et al., "Core refinement toward permeable B-Secretase (BACE-1) Inhibitors with low hERG Activity", Journal of Medicinal Chemistry.
Guo, et al., Targeting Amyloid-B in Glaucoma Treatment, pp. 13444-13449, PNAS, Aug. 14, 2007, vol. 104,No. 33.
Hilpert, et al., "B-Secretase (BACE1) Inhibitors with high in vivo efficacy suitable for clinical evaluation of Alzheimer's disease", Journal of Medicinal Chemistry, 2013, 56, 3980-3995.
Huang, et al., Pharmacophore Model Construction of ,8-Secretase Inhibitors, Acta Chimica Sinica, vol. 66, No. 16, 2008, pp. 1889-1897. (English Abstract).
Loane, et al., Amyloid Precursor Protein Secretases as Therapeutic Targets for Traumatic Brain Injury, Nature Medicine, Advance Online Publication, accepted Feb. 18, 2009; published online Mar. 15, 2009; doi:10.1038/nm.1940, pp. 1-3.
Luo, et al., mice deficient in BACE1, the Alzheimer's B-secretase, have normal phenotype and abolished B-amyloid, Nature Neuroscience, vol. 4, No. 3, Mar. 2001.
May, et al., Robust Central Reduction of B Amyloid in Humans with an Orally Available, Non-Peptidic B-Secretase Inhibitor, The Journal of Neuroscience, Nov. 16, 2011 • 31(46):16507-16516 • 16507.
McConlogue, et al., Partial reduction of BACE1 as dramatic effects on Alzheimer's plaque and synaptic pathology in APP transgenic mice, J. Biological Chem., vol. 282, No. 36, pp. 26326-26334, Sep. 7, 2007.
Ohno, et al., BACE1 deficiency rescues memory deficits and Cholinergic function in a mouse model of Alzheimer's disease, Neuron, vol. 41, 27-33, Jan. 8, 2004.
Ohno, et al.BACE1 gene deletion prevents neuron loss and memory deficits in 5XFAD APP/PS1 transgenic mice, Neurobiology of disease 26 (2006), pp. 134-145.
Osherovich, L. AB's Dry (AMD) Humor, SciBX 4(26); doi:10.1038/scibx.2011.727, Published online Jun. 30, 2011.
Probst, et al., Small-molecule BACE1 inhibitors:a patent literature review, Expert Opinion on Therapeutic Patents, (2006-2011), 2012, 22(5):511-540.
Roberds, et al. BACE knockout mice are healthy despite lacking the primary B-secretase activity in the brain: implications for Alzheimer's disease therapeutics, Human Mol. Genetics, vol. 10, No. 12, pp. 1317-1324. Apr. 3, 2004.
Scott, et al., "Novel Imino Pyrimidinone B-Secretase (BACE1) Inhibitors. P1 Thiophenes", Poster presentation, American Chemical Society, Sprint 2011.
Silvestri et al, Boom in the Development of Non-Peptidic Beta-Secretase (BACE1) Inhibitors for Treatment of Alzheimer's Disease, Medicinal Research Reviews, 2009, 295-338, 29(2).
Solloway, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 12, 2012.
Southan, BACE2 as a New Diabetes Target: a patent review 2010-2012, Expert Opinion on Therapeutic Patents, 2013, Informa UK, Ltd., ISSN 1354-3776, e-1744-7674.
Sperling, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 11, 2012.
Stamford, et al., Discovery of an Orally Available, Brain Penetrant BACE1 Inhibitor That Affords Robust CNS Aβ Reduction, ACS Med. Chem. Lett. Jul. 12, 2012, 3, 897-902.
Stamford, et al., Inhibitors of BACE for treating Alzheimer's disease: a fragment-based drug discovery story, Current Opinion in Chemical Biology; v:17 i:3 p. 320-328; Jun. 2013 Elsevier.
Stamford, et al., "Fragment-based discovery of BACE1 inhibitors, Potential disease-modifying agents for the treatment of Alzheimer's disease", Slide Presentation R. Bryan Miller Symposium, UC Davis, Mar. 7-8, 2013.
Weiner, Further insights into Alzheimer disease pathogenesis, Weiner, M. W. Nat. Rev. Neurol. 9, 65-66 (2013); published online Jan. 22, 2013.
Wyss DF, et al., Combining NMR and X-ray crystallography in fragment-based drug discovery: discovery of highly potent and selective BACE-1 inhibitors. Top Curr Chem. 2012;317:83-114. doi: 10.1007/128_2011_183.

* cited by examiner

5-SUBSTITUTED IMINOTHIAZINES AND THEIR MONO- AND DIOXIDES AS BACE INHIBITORS, COMPOSITIONS, AND THEIR USE

CROSS-REFERENCE TO RELATED APPLICATIONS

This Application is a U.S. National Stage Application under 35 U.S.C. 371 of PCT Application No. PCT/US2012/000497, filed Apr. 12, 2012, which claims priority to PCT/US2012/000435, filed Apr. 5, 2012, and to U.S. Provisional Application No. 61/503,254, filed Jun. 30, 2011, and U.S. Provisional Application No. 61/475,215, filed Apr. 13, 2011.

FIELD OF THE INVENTION

This invention provides certain 5-substituted iminothiazine compounds and mono- and dioxides thereof, and compositions comprising these compounds, which may be useful as inhibitors of BACE, and for treating or preventing pathologies related thereto.

BACKGROUND

Amyloid beta peptide ("Aβ") is a primary component of β amyloid fibrils and plaques, which are regarded playing a role in an increasing number of pathologies. Examples of such pathologies include, but are not limited to, Alzheimer's Disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis ($\beta_2$ microglobulins and complications arising therefrom), neurodegenerative diseases such as scrapie, bovine spongiform encephalitis, and Creutzfeld-Jakob disease and the like.

Aβ peptides are short peptides which are made from the proteolytic break-down of the transmembrane protein called amyloid precursor protein ("APP"). Aβ peptides are made from the cleavage of APP by β-secretase activity at the position corresponding to the N-terminus of Aβ, and by γ-secretase activity at the position corresponding to the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of abnormal Aβ by β-secretase activity. The inhibition of BACE-1 has been shown to inhibit the production of Aβ.

Alzheimer's disease is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forrest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and γ-secretase activity, can form tertiary structures that aggregate to form amyloid fibrils. Aβ peptides have also been shown to form Aβ oligomers (sometimes referred to as "Abeta aggretates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ and Aβ fibrils and plaque play a causal role in AD pathophysiology. (See Ohno et al., *Neurobiology of Disease*, No. 26 (2007), 134-145.) Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuron cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., *J. Bio. Chem.*, vol. 282, No. 36 (September 2007), have shown that partial reductions of BACE-1 enzyme activity and concomitant reductions of Aβ levels lead to a dramatic inhibition of Aβ-driven AD-like pathology (while minimizing side effects of full inhibition), making β-secretase a target for therapeutic intervention in AD. Ohno et al. *Neurobiology of Disease*, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and conclude that BACE-1 inhibition has been validated as an approach for the treatment of AD. Roberds et al., *Human Mol. Genetics*, 2001, Vol. 10, No. 12, 1317-1324, established that inhibition or loss of β-secretase activity produces no profound phenotypic defects while inducing a concomitant reduction in β-amyloid peptide. Luo et al., *Nature Neuroscience*, vol. 4, no. 3, March 2001, report that mice deficient in BACE-1 have normal phenotype and abolished β-amyloid generation.

BACE-1 has also been identified or implicated as a therapeutic target for a number of other diverse pathologies in which Aβ or Aβ fragments have been identified to play a role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 may be useful in reducing Alzheimer's type pathology in Down's syndrome patients.

Another example is in the treatment of glaucoma (Guo et al., *PNAS*, vol. 104, no. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., *Neurobiology of Aging*, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., *Ann NY Acad Sci* 2002; 855:723-31; Crino P B, Martin J A, Hill W D, et al., *Ann Otol Rhinol Laryngol*, 1995; 104:655-61; Davies D C, et al., *Neurobiol Aging*, 1993; 14:353-7; Devanand D P, et al., *Am J Psychiatr*, 2000; 157:1399-405; and Doty R L, et al., *Brain Res Bull*, 1987; 18:597-600. It is reasonable to suggest that addressing such changes by reduction of Aβ by inhibition of BACE-1 could help to restore olfactory sensitivity in patients with AD.

Other diverse pathologies characterized by the inappropriate formation and deposition of Aβ or fragments thereof, and/or by the presence of amyloid fibrils, include neurodegenerative diseases such as scrapie, bovine spongiform encephalitis, Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. Another example is the treatment of traumatic brain injury. As another example, Loane, et al. report the targeting of amyloid precursor protein secretases as therapeutic targets for traumatic brain injury. (Loane et al., "Amyloid precursor protein secretases as therapeutic targets for traumatic brain injury", *Nature Medicine*, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

The therapeutic potential of inhibiting the deposition of Aβ has motivated many groups to characterize BACE-1 and to identify inhibitors of BACE-1 and of other secretase enzyme inhibitors. Examples from the patent literature are growing and include US2005/0282826, WO2006009653, WO2007005404, WO2007005366, WO2007038271, WO2007016012, US2007072925, WO2007149033, WO2007145568, WO2007145569, WO2007145570, WO2007145571, WO2007114771, US20070299087, US2007/0287692, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, WO2007/146225, WO2006/138230, WO2006/138265, WO2006/138266, WO2007/053506, WO2007/146225, WO2008/073365, WO2008/073370, WO2008/103351, US2009/041201, US2009/041202, WO2009/131975, WO2009091016, and WO2010/047372.

BACE inhibitors, particularly BACE-2 inhibitors, are an art-recognized target for the treatment of diabetes. Type 2 diabetes (T2D) is caused by insulin resistance and inadequate insulin secretion from the pancreatic beta-cells, leading to poor blood-glucose control and hyperglycemia (M Prentki & C J Nolan, "Islet beta-cell failure in type 2 diabetes." *J. Clin. Investig.*, 2006, 116(7), 1802-1812). Patients with T2D have an increased risk of microvascular and macrovascular disease and a range of related complications including diabetic neuropathy, retinopathy, and cardiovascular disease.

Beta-cell failure and consequent dramatic decline in insulin secretion and hyperglycemia marks the onset of T2D M Prentki & C J Nolan, "Islet beta-cell failure in type 2 diabetes." *J. Clin. Investig.*, 2006, 116(7), 1802-1812). Most current treatments do not prevent the loss of beta-cell mass characterizing overt T2D. However, recent developments with GLP-1 analogues, gastrin and other agents show that prevention and proliferation of beta-cells is possible to achieve, leading to an improved glucose tolerance and slower progression to overt T2D. (L L. Baggio & D J. Drucker, "Therapeutic approaches to preserve islet mass in type 2 diabetes", *Annu. Rev. Med.* 2006, 57, 265-281.)

Tmem27 has been identified as a protein promoting beta-cell proliferation (P. Akpinar, S. Juqajima, J. Krutzfeldt, M. Stoffel, "Tmem27: A cleaved and shed plasma membrane protein that stimulates pancreatic beta-cell proliferation", *Cell. Metab.* 2005, 2, 385-397) and insulin secretion (K. Fukui, Q. Yang, Y. Cao, N. Takahashi et al., "The HNF-1 target Collectrin controls insulin exocytosis by SNARE complex formation", *Cell. Metab.* 2005, 2, 373-384.) Tmem27 is a 42 kDa membrane glycoprotein which is a constitutively shed from the surface of beta-cells, resulting from a degradation of the full-length cellular Tmem27. Over expression of Tmem27 in a transgenic mouse increases beta-cell mass and improves glucose tolerance in a DIO model of diabetes. (P. Akpinar, S. Juqajima, J. Krutzfeldt, M. Stoffel, "Tmem27: A cleaved and shed plasma membrane protein that stimulates pancreatic beta-cell proliferation", *Cell. Metab.* 2005, 2, 385-397; (K. Fukui, Q. Yang, Y. Cao, N. Takahashi et al., "The HNF-1 target Collectrin controls insulin exocytosis by SNARE complex formation", *Cell. Metab.* 2005, 2, 373-384.) Furthermore, siRNA knockout of Tmem27 in a rodent beta-cell proliferation assay (e.g., using INS1e cells) reduces the proliferation rate, indicating a role for Tmem27 in control of beta-cell mass.

In vitro, BACE-2 (but reportedly not BACE-1) cleaves a peptide based on the sequence of Tmem27. BACE-2 is a membrane-bound aspartyl protease and is colocalized with Tmem27 in rodent pancreatic beta-cells (G. Finzi, F. Franzi, C. Placidi, F. Acquati, et al., "BACE-2 is stored in secretory granules of mouse and rat pancreatic beta cells", *Ultrastruct. Pathol.* 2008, 32(6), 246-251). It is also known to be capable of degrading APP (I. Hussain, D. Powell, D. Howlett, G. Chapman, et al., "ASP1 (BACE2) cleaves the amyloid precursor protein at the beta-secretase site", *Mol. Cell. Neurosci.* 2000, 16, 609-619), IL-1 R2 (P. Kuhn, E. Marjaux, A. Imhof, B. De Strooper, et al., "Regulated intramembrane proteolysis of the interleukin-1 receitpro II by alpha-, beta-, and gamma-secretase", *J. Biol. Chem.*, 2007, 282(16), 11982-11995). Inhibition of BACE-2 is therefore proposed as a treatment for T2D with the potential to preserve and restore beta-cell mass and stimulate insulin secretion in pre-diabetic and diabetic patients. See, e.g., WO2010128058.

SUMMARY OF THE INVENTION

The present invention provides certain iminothiazine compounds and mono- and dioxides thereof, which are collectively or individually referred to herein as "compound(s) of the invention", as described herein. The compounds of the invention are expected to be useful as inhibitors of BACE-1. In some embodiments, the compounds of the invention are expected to be inhibitors of BACE-2.

In one embodiment, the compounds of the invention have the structural Formula (I):

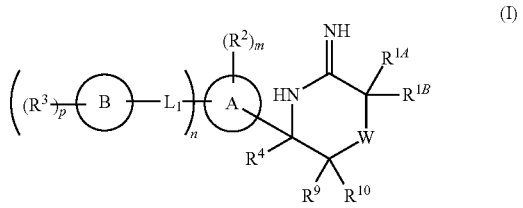

(I)

or a tautomer thereof having the structural Formula (I'):

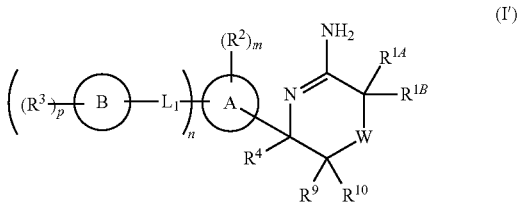

(I')

or pharmaceutically acceptable salt thereof, wherein:

W is selected from the group consisting of S, S(O), and $S(O)_2$;

$R^{1A}$ and $R^{1B}$ are each independently selected from the group consisting of: H, halogen, alkyl, alkoxy, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, -alkyl-(monocyclic heterocycloalkyl), a multicyclic group, and -alkyl-(multicyclic group);

wherein said alkyl, alkoxy, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, -alkyl-(monocyclic heterocycloalkyl), multicyclic group, -alkyl-(multicyclic group) of $R^{1A}$ and $R^{1B}$ is each optionally and independently unsubstituted or substituted with one or more groups independently selected from $R^8$;

ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

ring B (when present) is independently selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

$-L_1-$ (when present) independently represents a bond or a divalent moiety selected from the group consisting of -alkyl-, -haloalkyl-, -heteroalkyl-, -alkenyl-, -alkynyl-, $-N(R^6)-$, $-NHC(O)-$, $-C(O)NH-$, $-CH_2NHC(O)-$, $-CH_2C(O)NH-$, $-NHS(O)_2-$, $-CH_2NHS(O)_2-$, $-CH_2SO_2NH-$, $-S(O)_2NH-$, $-O-CH_2-$, $-CH_2-O-$, $-NHCH_2-$, $-CH_2NH-$, and $-CH(CF_3)NH-$, $-NHCH(CF_3)-$;

m, n, and p are each independently selected integers, wherein:
m is 0 or more;
n is 0 or 1; and
p is 0 or more,
wherein the maximum value of m is the maximum number of available substitutable hydrogen atoms on ring A, and wherein the maximum value of p is the maximum number of available substitutable hydrogen atoms on ring B;

each $R^2$ (when present) is independently selected from the group consisting of: halogen, $-OH$, $-CN$, $-SF_5$, $-OSF_5$, $-NO_2$, $-Si(R^5)_3$, $-P(O)(OR^5)_2$, $-P(O)(OR^5)(R^5)$, $-N(R^6)_2$, $-NR^7C(O)R^6$, $-NR^7S(O)_2R^6$, $-NR^7S(O)_2N(R^6)_2$, $-NR^7C(O)N(R^6)_2$, $-NR^7C(O)OR^6$, $-C(O)R^6$, $-C(O)_2R^6$, $-C(O)N(R^6)_2$, $-S(O)R^6$, $-S(O)_2R^6$, $-S(O)_2N(R^6)_2$, $-OR^6$, $-SR^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl,
wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl of $R^2$ are each optionally unsubstituted or substituted with one or more groups independently selected from $R^8$;

each $R^3$ (when present) is independently selected from the group consisting of: halogen, $-OH$, $-CN$, $-SF_5$, $-OSF_5$, $-NO_2$, $-Si(R^5)_3$, $-P(O)(OR^5)_2$, $-P(O)(OR^5)(R^5)$, $-N(R^6)_2$, $-NR^7C(O)R^6$, $-NR^7S(O)_2R^6$, $-NR^7S(O)_2N(R^6)_2$, $-NR^7C(O)N(R^6)_2$, $-NR^7C(O)OR^6$, $-C(O)R^6$, $-C(O)_2R^6$, $-C(O)N(R^6)_2$, $-S(O)R^6$, $-S(O)_2R^6$, $-S(O)_2N(R^6)_2$, $-OR^6$, $-SR^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl,
wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^3$ are each optionally unsubstituted or substituted with one or more groups independently selected from $R^8$;

$R^4$ is selected from the group consisting of alkyl, haloalkyl, heteroalkyl, alkenyl, alkynyl, aryl, -alkyl-aryl, heteroaryl, -alkyl-heteroaryl, cycloalkyl, -alkyl-cycloalkyl, cycloalkenyl, -alkyl-cycloalkenyl, heterocycloalkyl, -alkyl-heterocycloalkyl, heterocycloalkenyl, and -alkyl-heterocycloalkenyl, wherein each of said alkyl, haloalkyl, heteroalkyl, aryl, -alkyl-aryl, heteroaryl, -alkyl-heteroaryl, cycloalkyl, -alkyl-cycloalkyl, cycloalkenyl, -alkyl-cycloalkenyl, heterocycloalkyl, -alkyl-heterocycloalkyl, heterocycloalkenyl, and -alkyl-heterocycloalkenyl of $R^4$ is unsubstituted or substituted with one or more independently selected $R^{11}$ groups;

each $R^5$ (when present) is independently selected from the group consisting of alkyl, heteroalkyl, haloalkyl, cycloalkyl, -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^5$ is unsubstituted or substituted with one or more groups independently selected from halogen, alkyl, cycloalkyl, heteroalkyl, haloalkyl, alkoxy, heteroalkoxy, and haloalkoxy;

each $R^6$ (when present) is independently selected from the group consisting of H, alkyl, -alkyl-OH, alkenyl, alkynyl, heteroalkyl, -heteroalkyl-OH, haloalkyl, -haloalkyl-OH, cycloalkyl, lower alkyl-substituted cycloalkyl, lower alkyl-substituted -alkyl-cycloalkyl, heterocycloalkyl, -alkyl-heterocycloalkyl, aryl, -alkyl-aryl, heteroaryl, and -alkyl-heteroaryl, wherein each said heterocycloalkyl, -alkyl-heterocycloalkyl, aryl, -alkyl-aryl, heteroaryl, and said -alkyl-heteroaryl of $R^6$ is unsubstituted or substituted with one or more groups independently selected from halogen, alkyl, cycloalkyl, heteroalkyl, haloalkyl, alkoxy, heteroalkoxy, and haloalkoxy;

each $R^7$ (when present) is independently selected from the group consisting of H, alkyl, heteroalkyl, haloalkyl, cycloalkyl, -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^7$ is unsubstituted or substituted with one or more groups independently selected from halogen, alkyl, cycloalkyl, heteroalkyl, haloalkyl, alkoxy, heteroalkoxy, and haloalkoxy;

each $R^8$ (when present) is independently selected from the group consisting of halogen, —OH, —CN, —SF$_5$, —OSF$_5$, alkyl, alkoxy, haloalkyl, haloalkoxy, cycloalkyl, -alkyl-cycloalkyl, —O-cycloalkyl, —O-alkyl-cycloalkyl, —O-benzyl, heteroalkyl, —O-heteroalkyl, and -alkyl-OH;

$R^9$ and $R^{10}$ are each independently selected from the group consisting of H, halogen, —OH, —CN, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl and alkynyl, wherein each of said alkyl, haloalkyl, heteroalkyl, alkenyl and alkynyl of $R^9$ and $R^{10}$ is unsubstituted or substituted with one or more independently selected $R^{12}$ groups;

each $R^{11}$ (when present) is independently selected from the group consisting of halogen, —OH, —CN, —SF$_5$, —OSF$_5$, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$S(O)$_2$N(R$^6$)$_2$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, haloalkoxy, heteroalkyl, -alkyl-OH, cycloalkyl, -alkyl-cycloalkyl;

each $R^{12}$ (when present) is independently selected from the group consisting of halogen, —OH, —CN, —SF$_5$, —OSF$_5$, —P(O)(OR$^{13}$)$_2$, —P(O)(OR$^{13}$)(R$^{13}$), —N(R$^{14}$)$_2$, —NR$^{14}$C(O)R$^{14}$, —NR$^{14}$S(O)$_2$R$^{14}$, —NR$^{14}$S(O)$_2$N(R$^{14}$)$_2$, —NR$^{14}$C(O)N(R$^{14}$)$_2$, —NR$^{14}$C(O)OR$^{14}$, —C(O)R$^{14}$, —C(O)$_2$R$^{14}$, —C(O)N(R$^{14}$)$_2$, —S(O)R$^{14}$, —S(O)$_2$R$^{14}$, —S(O)$_2$N(R$^{14}$)$_2$, —OR$^{14}$, —SR$^{14}$, alkyl, haloalkyl, haloalkoxy, heteroalkyl, -alkyl-OH;

each $R^{13}$ (when present) is independently selected from the group consisting of alkyl, -alkyl-OH, alkenyl, alkynyl, heteroalkyl, -heteroalkyl-OH, haloalkyl, -haloalkyl-OH; and each $R^{14}$ (when present) is independently selected from the group consisting of H, alkyl, -alkyl-OH, alkenyl, alkynyl, heteroalkyl, -heteroalkyl-OH, haloalkyl, -haloalkyl-OH.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I) or (IA).

In one embodiment, in each of Formulas (I) and (IA):

-L$_1$- (when present) independently represents a bond or a divalent moiety selected from the group consisting of -alkyl-, -haloalkyl-, -heteroalkyl-, -alkenyl-, -alkynyl-, —N(R$^6$)—, —NHC(O)—, —C(O)NH—, —NHS(O)$_2$—, —S(O)$_2$NH—, —O—CH$_2$—, —CH$_2$—O—, —NHCH$_2$—, —CH$_2$NH—, and —CH(CF$_3$)NH—, —NHCH(CF$_3$)—;

each $R^8$ (when present) is independently selected from the group consisting of halogen, —OH, —CN, —SF$_5$, —OSF$_5$, alkyl, alkoxy, haloalkyl, haloalkoxy, cycloalkyl, -alkyl-cycloalkyl, —O-cycloalkyl, —O-alkyl-cycloalkyl, heteroalkyl, —O-heteroalkyl, and -alkyl-OH; and $R^9$ and $R^{10}$ are each independently selected from the group consisting of halogen, —OH, —CN, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl and alkynyl, wherein each of said alkyl, haloalkyl, heteroalkyl, alkenyl and alkynyl of $R^9$ and $R^{10}$ is unsubstituted or substituted with one or more independently selected $R^{12}$ groups.

In one embodiment, the compounds of the invention have the structural Formula (I) as described above.

In one embodiment, the compounds of the invention have the structural Formula (IA):

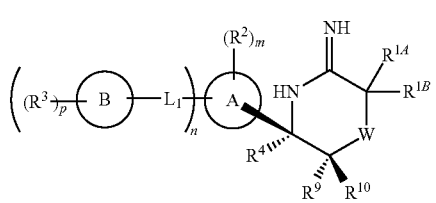

(IA)

or a tautomer thereof having the structural Formula (IA'):

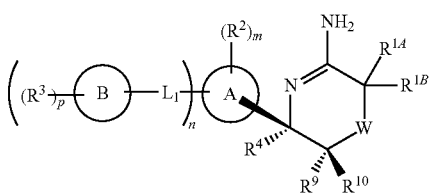

(IA')

or pharmaceutically acceptable salt thereof, wherein each variable is as described in Formula (I).

In one embodiment, the compounds of the invention have the structural Formula (IB):

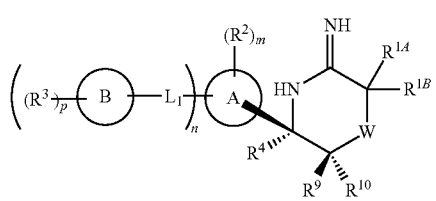

(IB)

or a tautomer thereof having the structural Formula (IB'):

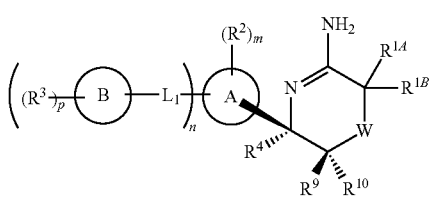

(IB')

or pharmaceutically acceptable salt thereof, wherein each variable is as described in Formula (I).

In one embodiment, in each of Formulas (I), (IA), (IA'), (IB), and (IB'), $R^9$ is H.

In one embodiment, in each of Formulas (I), (IA), (IA'), (IB), and (IB'), $R^{10}$ is H.

In one embodiment, in each of Formulas (I), (IA), (IA'), (IB), and (IB'), $R^{10}$ is H and $R^9$ is H.

In one embodiment, in each of Formulas (I), (IA), (IA'), (IB), and (IB'), $R^9$ is selected from the group consisting of H, halo, alkyl, haloalkyl, and heteroalkyl.

In one embodiment, in each of Formulas (I), (IA), (IA'), (IB), and (IB'), $R^9$ is selected from the group consisting of H, halo, lower alkyl, halo lower alkyl, and lower alkyl ether.

In one embodiment, in each of Formulas (I), (IA), (IA'), (IB), and (IB'), $R^{10}$ is selected from the group consisting of H, halo, alkyl, haloalkyl, and heteroalkyl.

In one embodiment, in each of Formulas (I), (IA), (IA'), (IB), and (IB'), $R^{10}$ is selected from the group consisting of H, halo, lower alkyl, halo lower alkyl, and lower alkyl ether.

In one embodiment, in each of Formulas (I), (IA), (IA'), (IB), and (IB'), $R^9$ is selected from the group consisting of H, halo, alkyl, haloalkyl, and heteroalkyl; and $R^{10}$ is H.

In one embodiment, in each of Formulas (I), (IA), (IA'), (IB), and (IB'), $R^9$ is selected from the group consisting of H, halo, lower alkyl, halo lower alkyl, and lower alkyl ether; and $R^{10}$ is H.

In one embodiment, in each of Formulas (I), (IA), (IA'), (IB), and (IB'), $R^9$ is H and $R^{10}$ is selected from the group consisting of H, halo, alkyl, haloalkyl, and heteroalkyl.

In one embodiment, in each of Formulas (I), (IA), (IA'), (IB), and (IB'), $R^9$ is H and $R^{10}$ is selected from the group consisting of H, halo, lower alkyl, halo lower alkyl, and lower alkyl ether.

In one embodiment, in each of Formulas (I), (IA), (IA'), (IB), and (IB'), $R^4$ is selected from the group consisting of lower alkyl and lower haloalkyl.

In one embodiment, in each of Formulas (I), (IA), (IA'), (IB), and (IB'), $R^4$ is selected from the group consisting of —$CH_3$, —$CH_2F$, —$CHF_2$, and —$CF_3$.

In one embodiment, in each of Formulas (I), (IA), (IA'), (IB), and (IB'), $R^4$ is selected from the group consisting of —$CH_3$, and —$CHF_2$.

In one embodiment, in each of Formulas (I), (IA), (IA'), (IB), and (IB'):
$R^4$ is —$CH_3$ and —$CHF_2$,
$R^9$ is H; and
$R^{10}$ is H.

In one embodiment, in each of Formulas (I), (IA), (IA'), (IB), and (IB'):
$R^4$ is —$CH_3$ and —$CHF_2$,
one of $R^9$ and $R^{10}$ is H and the other is selected from the group consisting of H, halogen, alkyl, haloalkyl, and heteroalkyl.

In one embodiment, in each of Formulas (I), (IA), (IA'), (IB), and (IB'):
$R^4$ is —$CH_3$ and —$CHF_2$, and
one of $R^9$ and $R^{10}$ is H and the other is selected from the group consisting of H, lower alkyl, lower haloalkyl, and lower alkyl ether.

In one embodiment, the compounds of the invention have the structural Formula (II):

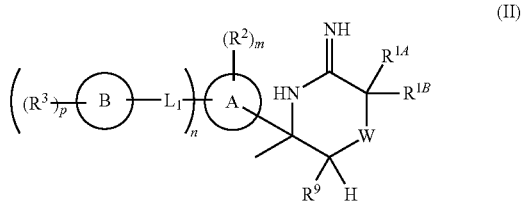

(II)

or a tautomer thereof having the structural Formula (II'):

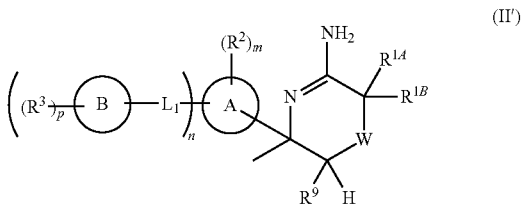

(II')

or pharmaceutically acceptable salt thereof, wherein each variable is as described in Formula (I).

In one embodiment, the compounds of the invention have the structural Formula (IIA):

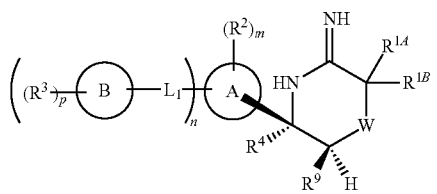

(IIA)

or a tautomer thereof having the structural Formula (IIA'):

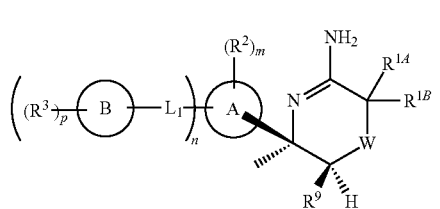

(IIA')

or pharmaceutically acceptable salt thereof, wherein each variable is as described in Formula (I).

In one embodiment, the compounds of the invention have the structural Formula (IIB):

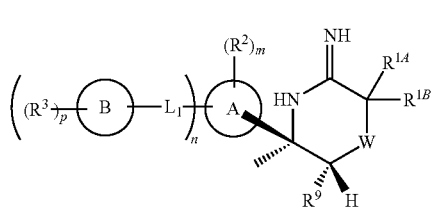

(IIB)

or a tautomer thereof having the structural Formula (IIB'):

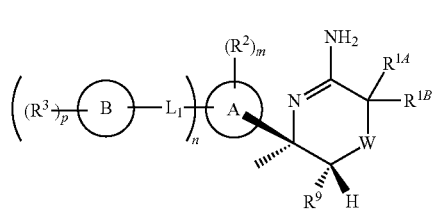

(IIB')

or pharmaceutically acceptable salt thereof, wherein each variable is as described in Formula (I).

In one embodiment, in each of Formulas (I), (IA), (IA'), (IB), (IB'), (II), (II'), (IIA), (IIA'), (IIB), and (IIB'): W is S.

In one embodiment, in each of Formulas (I), (IA), (IA'), (IB), (IB'), (II), (II'), (IIA), (IIA'), (IIB), and (IIB'): W is S(O).

In one embodiment, in each of Formulas (I), (IA), (IA'), (IB), (IB'), (II), (II'), (IIA), (IIA'), (IIB), and (IIB'): W is $S(O)_2$.

In one embodiment, in each of Formulas (I), (IA), (IA'), (IB), (IB'), (II), (II'), (IIA), (IIA'), (IIB), and (IIB'):
$R^{1A}$ and $R^{1B}$ are each independently selected from the group consisting of H, fluoro, methyl, ethyl, ethenyl, propyl, propenyl, lower haloalkyl, cyclopropyl, —$CH_2$-cyclopropyl, cyclobutyl, —$CH_2$-cyclobutyl, —$OCH_3$, —$CH_2OH$, —$CH_2OCH_3$, —$CH_2OCH_2CH_3$, trifluoromethyl, —$CH_2F$, —$CHF_2$, —$CH_2CF_3$, phenyl, pyridyl, pyrimidinyl, pyrazinyl, benzyl, benzothiazolyl, —$CH_2$-benzothiazolyl, benzoxazolyl, —$CH_2$-benzoxazolyl, tetrahydropyranyl, —$CH_2$-tetrahydropyranyl, —$CH_2$-pyridyl, —$CH_2$-pyrimidinyl, and —$CH_2$-pyrazinyl;
wherein each said phenyl, pyridyl, pyrimidinyl, pyrazinyl, benzyl, —$CH_2$-pyridyl, —$CH_2$-pyrimidinyl, —$CH_2$-pyrazinyl of $R^{1A}$ and $R^{1B}$ is unsubstituted or substituted with one or more groups independently selected from the group consisting of halogen, alkyl, cycloalkyl, heteroalkyl, alkoxy, —O-benzyl, —O-cycloalkyl, —O—$CH_2$-cycloalkyl, and haloalkyl.

In one embodiment, in each of Formulas (I), (IA), (IA'), (IB), (IB'), (II), (II'), (IIA), (IIA'), (IIB), and (IIB'):
$R^{1A}$ and $R^{1B}$ are each independently selected from the group consisting of H, fluoro, methyl, ethyl, propyl, cyclopropyl, —$CH_2$-cyclopropyl, —$OCH_3$, —$CH_2OH$, —$CH_2OCH_3$, —$CH_2OCH_2CH_3$, trifluoromethyl, —$CH_2F$, —$CHF_2$, phenyl, pyridyl, pyrimidinyl, pyrazinyl, benzyl, —$CH_2$-pyridyl, —$CH_2$-pyrimidinyl, and —$CH_2$-pyrazinyl;
wherein each said phenyl, pyridyl, pyrimidinyl, pyrazinyl, benzyl, —$CH_2$-pyridyl, —$CH_2$-pyrimidinyl, —$CH_2$-pyrazinyl of $R^{1A}$ and $R^{1B}$ is unsubstituted or substituted with one or more groups independently selected from the group consisting of halogen, alkyl, cycloalkyl, heteroalkyl, alkoxy, —O-cycloalkyl, and haloalkyl.

In one embodiment, in each of Formulas (I), (IA), (IA'), (IB), (IB'), (II), (II'), (IIA), (IIA'), (IIB), and (IIB'):
$R^{1A}$ is selected from the group consisting of methyl, ethyl, and —$CH_2OCH_3$; and
$R^{1B}$ is selected from the group consisting of H, fluoro, methyl, ethyl, ethenyl, propyl, propenyl, lower haloalkyl, cyclopropyl, —$CH_2$-cyclopropyl, cyclobutyl, —$CH_2$-cyclobutyl, —$OCH_3$, —$CH_2OH$, —$CH_2OCH_3$, —$CH_2OCH_2CH_3$, trifluoromethyl, —$CH_2F$, —$CHF_2$, —$CH_2CF_3$, phenyl, pyridyl, pyrimidinyl, pyrazinyl, benzyl, benzothiazolyl, —$CH_2$-benzothiazolyl, benzoxazolyl, —$CH_2$-benzoxazolyl, tetrahydropyranyl, —$CH_2$-tetrahydropyranyl, —$CH_2$-pyridyl, —$CH_2$-pyrimidinyl, and —$CH_2$-pyrazinyl;
wherein each said phenyl, pyridyl, pyrimidinyl, pyrazinyl, benzyl, —$CH_2$-pyridyl, —$CH_2$-pyrimidinyl, —$CH_2$-pyrazinyl of $R^{1A}$ and $R^{1B}$ is unsubstituted or substituted with one or more groups independently selected from the group consisting of halogen, alkyl, cycloalkyl, heteroalkyl, alkoxy, —O-benzyl, —O-cycloalkyl, —O—$CH_2$-cycloalkyl, and haloalkyl.

In one embodiment, in each of Formulas (I), (IA), (IA'), (IB), (IB'), (II), (II'), (IIA), (IIA'), (IIB), and (IIB'):
$R^{1A}$ and $R^{1B}$ are each independently selected from the group consisting of H, methyl, ethyl, propyl, cyclopropyl, —$CH_2$-cyclopropyl, —$CH_2OH$, —$CH_2OCH_3$, —$CH_2OCH_2CH_3$, trifluoromethyl, —$CH_2CF_3$, —$CH_2F$, and —$CHF_2$.

In one embodiment, in each of Formulas (I), (IA), (IA'), (IB), (IB'), (II), (II'), (IIA), (IIA'), (IIB), and (IIB'):
$R^{1A}$ and $R^{1B}$ are each independently selected from the group consisting of H, methyl, ethyl, propyl, cyclopropyl, —$CH_2$-cyclopropyl, —$CH_2OH$, —$CH_2OCH_3$, —$CH_2OCH_2CH_3$, trifluoromethyl, —$CH_2F$, and —$CHF_2$.

In one embodiment, in each of Formulas (I), (IA), (IA'), (IB), (IB'), (II), (II'), (IIA), (IIA'), (IIB), and (IIB'):
$R^{1A}$ is selected from the group consisting of H and methyl; and $R^{1B}$ is selected from the group consisting of H, methyl, ethyl, ethenyl, propyl, isopropyl, propenyl, butyl, butenyl, cyclopropyl, —CH$_2$-cyclopropyl, cyclobutyl, —CH$_2$-cyclobutyl, —CH$_2$OH, —CH$_2$OCH$_3$, —CH$_2$OCH$_2$CH$_3$, trifluoromethyl, —CH$_2$F, —CHF$_2$, —CH$_2$CF$_3$, phenyl, phenyl substituted with from 1 to 3 R$^8$ groups, benzyl, benzyl substituted with from 1 to 3 R$^8$ groups, pyridyl, pyridyl substituted with from 1 to 3 R$^8$ groups, tetrahydropyranyl, and —CH$_2$-tetrahydropyranyl.

In one embodiment, in each of Formulas (I), (IA), (IA'), (IB), (IB'), (II), (II'), (IIA), (IIA'), (IIB), and (IIB'):
$R^{1A}$ is selected from the group consisting of H and methyl; and
$R^{1B}$ is selected from the group consisting of H, methyl, ethyl, ethenyl, propyl, isopropyl, propenyl, butyl, butenyl, cyclopropyl, —CH$_2$-cyclopropyl, cyclobutyl, —CH$_2$-cyclobutyl, —CH$_2$OH, —CH$_2$OCH$_3$, —CH$_2$OCH$_2$CH$_3$, trifluoromethyl, —CH$_2$F, —CHF$_2$, —CH$_2$CF$_3$, phenyl, benzyl, pyridyl, tetrahydropyranyl, and —CH$_2$-tetrahydropyranyl, wherein each of said phenyl, benzyl, and pyridyl are optionally substituted with from 1 to 3 groups selected from the group consisting of F, Cl, Br, —OCH$_3$, —CH$_2$F, —CHF$_2$, and —CF$_3$.

In one embodiment, in each of Formulas (I), (IA), (IA'), (IB), (IB'), (II), (II'), (IIA), (IIA'), (IIB), and (IIB'):
$R^{1A}$ and $R^{1B}$ are each independently selected from the group consisting of H and methyl.

In one embodiment, in each of Formulas (I), (IA), (IA'), (IB), (IB'), (II), (II'), (IIA), (IIA'), (IIB), and (IIB'):
$R^{1A}$ and $R^{1B}$ are each methyl.

In some embodiments, in each of Formulas (I), (IA), (IA'), (IB), (IB'), (II), (II'), (IIA), (IIA'), (IIB), and (IIB'):
n is 1. In these embodiments, the moiety:

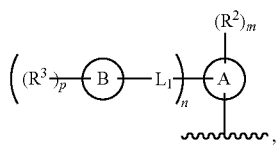

has the form:

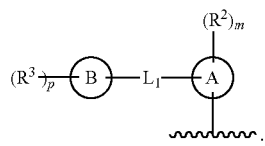

In another embodiment, in each of Formulas (I), (IA), (IA'), (IB), (IB'), (II), (II'), (IIA), (IIA'), (IIB), and (IIB'):
n is 1;
m is 0 or more; and
ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, and thienopyrazolyl.

In another embodiment, in each of Formulas (I), (IA), (IA'), (IB), (IB'), (II), (II'), (IIA), (IIA'), (IIB), and (IIB'):
n is 1;
m is 0 or more; and
ring A is selected from the group consisting of phenyl, pyridyl, thienyl, thiazolyl, naphthyl, isoquinolinyl, benzothienyl, benzimidazolyl, indazolyl, indolyl, and thienopyrazolyl.

In another embodiment, in each of Formulas (I), (IA), (IA'), (IB), (IB'), (II), (II'), (IIA), (IIA'), (IIB), and (IIB'):
n is 1;
m is 0 or more; and
ring A is selected from the group consisting of phenyl, thienyl, and pyridyl.

In another embodiment, in each of Formulas (I), (IA), (IA'), (IB), (IB'), (II), (II'), (IIA), (IIA'), (IIB), and (IIB'):
n is 1;
m is 0 or more; and
each R$^2$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_2$-(monocyclic heteroaryl),
wherein said phenyl, benzyl, lower cycloalkyl, —CH$_2$-(lower cycloalkyl), monocyclic heteroaryl, and —CH$_2$-(monocyclic heteroaryl) of R$^2$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and —OSF$_5$.

In an alternative of the immediately preceeding embodiment, m is 0, 1, 2, or 3, and each R$^6$ (when present) is independently selected from the group consisting of H, lower alkyl, lower cycloalkyl, lower haloalkyl, and lower heteroalkyl.

In another embodiment, in each of Formulas (I), (IA), (IA'), (IB), (IB'), (II), (II'), (IIA), (IIA'), (IIB), and (IIB'):
each R$^3$ group (when present) is independently selected from the group consisting of halogen, —CN, —SF$_5$, —NH$_2$, —NH(alkyl), —N(alkyl)$_2$, —OH, —O-alkyl, —SH, —S(alkyl), methyl, ethyl, propyl, haloalkyl, —C≡C—CH$_3$, cyclopropyl, —CH$_2$-cyclopropyl, —C(O)OH, —C(O)O-alkyl, —O-haloalkyl, optionally substituted phenyl, and optionally substituted monocyclic heteroaryl, wherein each said optional substituent is, independently, as defined in Formula (I).

In another embodiment, in each of Formulas (I), (IA), (IA'), (IB), (IB'), (II), (II'), (IIA), (IIA'), (IIB), and (IIB'):
n is 1;
m is 0 or more; and
each R$^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

In an alternative of the immediately preceeding embodiment, m is 0, 1, 2, or 3.

In another embodiment, in each of Formulas (I), (IA), (IA'), (IB), (IB'), (II), (II'), (IIA), (IIA'), (IIB), and (IIB'):
n is 1;
m is 0 or more; and
each R$^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCHF$_2$, and —NHC(O)R$^6$, wherein R$^6$ is selected from the group consisting of —CH$_2$CF$_3$, —CF$_2$CH$_3$, —CH$_3$, —CH$_2$CH$_3$, —CH$_2$OCH$_3$, CHF$_2$, and —CH$_2$N(CH$_3$)$_2$.

In an alternative of the immediately preceeding embodiment, m is 0, 1, 2, or 3.

In another embodiment, in each of Formulas (I), (IA), (IA'), (IB), (IB'), (II), (II'), (IIA), (IIA'), (IIB), and (IIB'):
n is 1;
m is 0, 1, or 2; and
each R$^2$ group (when present) is independently selected from F, Cl, Br, —CN, —CF$_3$, —CHF$_2$, cyclopropyl, —OCF$_3$, and —OCHF$_2$.

In another embodiment, in each of Formulas (I), (IA), (IA'), (IB), (IB'), (II), (II'), (IIA), (IIA'), (IIB), and (IIB'):
n is 1;
ring A is selected from the group consisting of phenyl, thienyl, and pyridyl;
m is 0, 1, or 2; and
each R$^2$ group (when present) is independently selected from the group consisting F, Cl, Br, —CN, —CF$_3$, —CHF$_2$, cyclopropyl, —OCF$_3$, and —OCHF$_2$.

In another embodiment, in each of Formulas (I), (IA), (IA'), (IB), (IB'), (II), (II'), (IIA), (IIA'), (IIB), and (IIB'):
n is 1; and
-L$_1$- represents a bond or a divalent moiety selected from the group consisting of —NHC(O), —C(O)NH—, —CH$_2$NHC(O)—, —CH$_2$C(O)NH—, —CH$_2$NHSO$_2$—, —CH$_2$SO$_2$NH—, —C≡C—, —NHS(O)$_2$—, —S(O)$_2$NH—, —O—CH$_2$—, —CH$_2$—O—, —NHCH$_2$—, —CH$_2$NH—, and —CH(CF$_3$)NH—.

In another embodiment, in each of Formulas (I), (IA), (IA'), (IB), (IB'), (II), (II'), (IIA), (IIA'), (IIB), and (IIB'):
n is 1; and
-L$_1$- represents a bond or a divalent moiety selected from the group consisting of —NHC(O), —C(O)NH—, —NHS(O)$_2$—, —S(O)$_2$NH—, —O—CH$_2$—, —CH$_2$—O—, —NHCH$_2$—, —CH$_2$NH—, and —CH(CF$_3$)NH—.

In another embodiment, in each of Formulas (I), (IA), (IA'), (IB), (IB'), (II), (II'), (IIA), (IIA'), (IIB), and (IIB'):
n is 1; and
-L$_1$- represents a bond or a divalent moiety selected from the group consisting of —NHC(O), —CH$_2$NHC(O)—, —CH$_2$C(O)NH—, —C(O)NH—, —NHS(O)$_2$—, —S(O)$_2$NH—, —O—CH$_2$—, —CH$_2$—O—, —NHCH$_2$—, —CH$_2$NH—, and —CH(CF$_3$)NH—.

In another embodiment, in each of Formulas (I), (IA), (IA'), (IB), (IB'), (II), (II'), (IIA), (IIA'), (IIB), and (IIB'):
n is 1; and
-L$_1$- represents a bond or a divalent moiety selected from the group consisting of —NHC(O), —CH$_2$NHC(O)—, —CH$_2$C(O)NH—, —C≡C—, and —C(O)NH—.

In another embodiment, in each of Formulas (I), (IA), (IA'), (IB), (IB'), (II), (II'), (IIA), (IIA'), (IIB), and (IIB'):
n is 1; and
-L$_1$- represents a bond or a divalent moiety selected from the group consisting of —NHC(O), —CH$_2$NHC(O)—, —CH$_2$C(O)NH—, and —C(O)NH—.

In another embodiment, in each of Formulas (I), (IA), (IA'), (IB), (IB'), (II), (II'), (IIA), (IIA'), (IIB), and (IIB'):
n is 1; and
-L$_1$- represents a bond or a divalent moiety selected from the group consisting of —NHC(O)— and —C(O)NH—.

In another embodiment, in each of Formulas (I), (IA), (IA'), (IB), (IB'), (II), (II'), (IIA), (IIA'), (IIB), and (IIB'):
n is 1; and
-L$_1$- represents a bond.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of phenyl, monocyclic heterocycloalkyl, monocyclic heteroaryl, and a multicyclic group.

In an alternative of the immediately preceeding embodiment, m and p are each independently 0, 1, 2, or 3.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of phenyl, monocyclic heterocycloalkyl, and monocyclic heteroaryl.

In an alternative of the immediately preceeding embodiment, m and p are each independently 0, 1, 2, or 3.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, pyrrolopyrimidinyl, and oxadiazolyl.

In an alternative of the immediately preceeding embodiment, m and p are each independently 0, 1, 2, or 3.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, dihydroisoxazoyl, isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, and pyrrolopyrimidinyl.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of phenyl, pyridinyl, pyrazinyl, pyrimidinyl, oxazolyl, pyrrolyl, indolyl, and oxadiazoyl.

In an alternative of the immediately preceeding embodiment, m and p are each independently 0, 1, 2, or 3.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of phenyl, pyridinyl, pyrazinyl, pyrimidinyl, oxazolyl, pyrrolyl, and indolyl.

In another embodiment, in each of Formulas (I), (IA), (IA'), (IB), (IB'), (II), (II'), (IIA), (IIA'), (IIB), and (IIB'):
  n is 1;
  p is 0 or more; and
  each $R^3$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_2$-(monocyclic heteroaryl),
    wherein said phenyl, benzyl, lower cycloalkyl, —CH$_1$-(lower cycloalkyl), monocyclic heteroaryl, and —CH$_2$-(monocyclic heteroaryl) of $R^3$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and —OSF$_5$.

In an alternative of the immediately preceeding embodiment, In an alternative of the immediately preceeding embodiment, m and p are each independently 0, 1, 2, or 3 and each $R^6$ (when present) is independently selected from the group consisting of H, lower alkyl, lower cycloalkyl, lower haloalkyl, and lower heteroalkyl.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydropyranyl, dihydroisoxazoyl, isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl.

In another embodiment, in each of Formulas (I), (IA), (IA'), (IB), OM, (II), (II'), (IIA), (IIA'), (IIB), and (IIB'):
  n is 1;
  p is 0 or more; and
  each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In an alternative of the immediately preceeding embodiment, m and p are each independently 0, 1, 2, or 3.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, dihydroisoxazoyl, Isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl.

In another embodiment, in each of Formulas (I), (IA), (IA'), (IB), (IB'), (II), (II'), (IIA), (IIA'), (IIB), and (IIB'):
  n is 1;
  p is 0 or more; and
  each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, —OCHF$_2$, optionally substituted oxadiazoyl, optionally substituted isoxazoyl, optionally substituted oxazoyl, optionally substituted triazoyl, and optionally substituted phenyl, wherein each said optional substituent is 1 to 3 substituents independently selected from the group consisting of F, Cl, CN, —CH$_3$, —OCH$_3$, and —CF$_3$.

In an alternative of the immediately preceeding embodiment, m and p are each independently 0, 1, 2, or 3.

In another embodiment, in each of Formulas (I), (IA), (IA'), (IB), (IB'), (II), (II'), (IIA), (IIA'), (IIB), and (IIB'):
  n is 1;
  ring A is selected from the group consisting of phenyl, thienyl, and pyridyl;
  m is 0 or 1;
  each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$;
  -L$_1$- is a bond or a divalent moiety selected from the group consisting of —NHC(O)—, —CH$_2$NHC(O)—, —CH$_2$C(O)NH—, and —C(O)NH—;
  ring B is selected from the group consisting of phenyl, monocyclic heterocycloalkyl, monocyclic heteroaryl, and a multicyclic group;
  p is 0 or more; and
  each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, dihydroisoxazoyl, Isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl.

In an alternative of the immediately preceeding embodiment, each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, —OCHF$_2$, optionally substituted oxadiazoyl, optionally substituted triazoyl, optionally substituted isoxazoyl, optionally substituted oxazoyl, and optionally substituted phenyl, wherein each said optional substituent is 1 to 3 substituents independently selected from the group consisting of F, Cl, CN, —CH$_3$, —OCH$_3$, and —CF$_3$.

In another embodiment, in each of Formulas (I), (IA), (IA'), (IB), (IB'), (II), (II'), (IIA), (IIA'), (IIB), and (IIB'):
  n is 1;
  ring A is selected from the group consisting of phenyl, thienyl, and pyridyl;
  m is 0 or 1;
  each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

-L$_1$- is a bond or a divalent moiety selected from the group consisting of —NHC(O)—, —CH$_2$NHC(O)—, —CH$_2$C(O)NH—, and —C(O)NH—;

ring B is selected from the group consisting of phenyl, monocyclic heterocycloalkyl, and monocyclic heteroaryl;

p is 0 or more; and each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In an alternative of the immediately preceeding embodiment, p is 0, 1, 2, or 3.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, dihydroisoxazoyl, Isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl.

In an alternative of the immediately preceeding embodiment, each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, —OCHF$_2$, optionally substituted oxadiazoyl, optionally substituted triazoyl, optionally substituted isoxazoyl, optionally substituted oxazoyl, and optionally substituted phenyl, wherein each said optional substituent is 1 to 3 substituents independently selected from the group consisting of F, Cl, CN, —CH$_3$, —OCH$_3$, and —CF$_3$.

In another embodiment, in each of Formulas (I), (IA), (IA'), (IB), (IB'), (II), (II'), (IIA), (IIA'), (IIB), and (IIB'):

n is 1;

ring A is selected from the group consisting of phenyl, thienyl, and pyridyl;

m is 0 or 1;

each R$^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

-L$_1$- is a bond or a divalent moiety selected from the group consisting of —NHC(O)—, —CH$_2$NHC(O)—, —CH$_2$C(O)NH—, and —C(O)NH—;

ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, pyrrolopyrimidinyl, and oxadiazolyl;

p is 0 or more; and each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, dihydroisoxazoyl, Isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl.

In another alternative of the immediately preceeding embodiment, each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, —OCHF$_2$, optionally substituted oxadiazoyl, optionally substituted triazoyl, optionally substituted isoxazoyl, optionally substituted oxazoyl, and optionally substituted phenyl, wherein each said optional substituent is 1 to 3 substituents independently selected from the group consisting of F, Cl, CN, —CH$_3$, —OCH$_3$, and —CF$_3$.

In another alternative of the immediately preceeding embodiment, ring B is selected from the group consisting of phenyl, pyridinyl, pyrazinyl, pyrimidinyl, oxazolyl, pyrrolyl, indolyl, and oxadiazolyl.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydropyranyl, and dihydroisoxazoyl.

In an alternative of the immediately preceeding embodiment, m and p are each independently 0, 1, 2, or 3.

In another embodiment, in each of Formulas (I), (IA), (IA'), (IB), (IB'), (II), (II'), (IIA), (IIA'), (IIB), and (IIB'):

n is 1;

ring A is selected from the group consisting of phenyl, thienyl, and pyridyl;

m is 0 or 1;

each R$^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

-L$_1$- is a bond or a divalent moiety selected from the group consisting of —NHC(O)—, —CH$_2$NHC(O)—, —CH$_2$C(O)NH—, and —C(O)NH—;

ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, and pyrrolopyrimidinyl;

p is 0 or more; and each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In an alternative of the immediately preceeding embodiment, ring B is selected from the group consisting of phenyl, pyridinyl, pyrazinyl, pyrimidinyl, oxazolyl, pyrrolyl, and indolyl.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, dihydroisoxazoyl, Isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl.

In an alternative of the immediately preceeding embodiment, m and p are each independently 0, 1, 2, or 3.

In another embodiment, in each of Formulas (I), (IA), (IA'), (IB), (IB'), (II), (II'), (IIA), (IIA'), (IIB), and (IIB'):

n is 1; ring A is phenyl or pyridyl; and the moiety

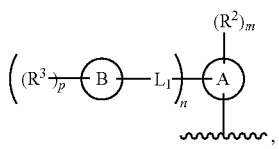

has the form:

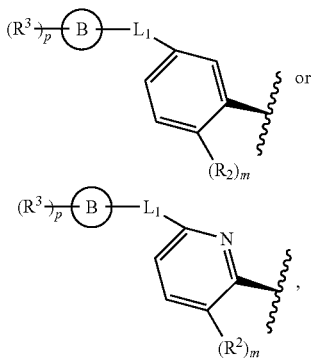

wherein:

m is 0 or 1;

each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$;

-L$_1$- is a bond or a divalent moiety selected from the group consisting of —NHC(O)—, —CH$_2$NHC(O)—, —CH$_2$C(O)NH—, and —C(O)NH—;

ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, and isothiazolyl;

p is 0 or more; and each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In an alternative of the immediately preceeding embodiment, each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, —OCHF$_2$, optionally substituted oxadiazoyl, optionally substituted triazoyl, optionally substituted isoxazoyl, optionally substituted oxazoyl, and optionally substituted phenyl, wherein each said optional substituent is 1 to 3 substituents independently selected from the group consisting of F, Cl, CN, —CH$_3$, —OCH$_3$, and —CF$_3$.

In an alternative of the immediately preceeding embodiment, ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, pyrrolopyrimidinyl, and oxadiazolyl;

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, dihydroisoxazoyl, Isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, and dihydroisoxazoyl.

In an alternative of the immediately preceeding embodiment, m and p are each independently 0, 1, 2, or 3.

In another embodiment, in each of Formulas (I), (IA), (IA'), (IB), (IB'), (II), (II'), (IIA), (IIA'), (IIB), and (IIB'):

n is 1; ring A is thienyl; and the moiety

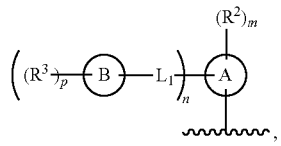

has the form:

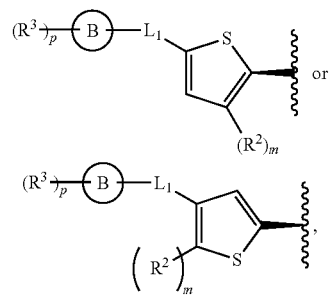

wherein:

m is 0 or 1;

each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

-L$_1$- is a bond or a divalent moiety selected from the group consisting of —NHC(O)—, —CH$_2$NHC(O)—, and —C(O)NH—;

ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, and isothiazolyl;

p is 0 or more; and each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In an alternative of the immediately preceeding embodiment, m and p are each independently 0, 1, 2, or 3.

In an alternative of the immediately preceeding embodiment, ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, pyrrolopyrimidinyl, and oxadiazolyl.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, dihydroisoxazoyl, Isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl.

In another alternative of the immediately preceeding embodiment, ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, and dihydroisoxazolyl.

In another alternative of the immediately preceeding embodiment, each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —C(O)OH, —C(O)OCH$_3$, —C(O)OCH$_2$CH$_3$, —OCF$_3$, —OCH$_2$CF$_3$, —OCHF$_2$, optionally substituted oxadiazoyl, optionally substituted triazoyl, optionally substituted isoxazoyl, optionally substituted oxazoyl, and optionally substituted phenyl, wherein each said optional substituent is 1 to 3 substituents independently selected from the group consisting of F, Cl, CN, —CH$_3$, —OCH$_3$, and —CF$_3$.

Non-limiting examples of the moiety

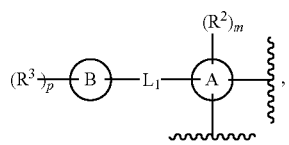

in each of Formulas (I), (IA), (IA'), (IB), (IB'), (II), (II'), (IIA), (IIA'), (IIB), and (IIB') are shown in the examples pictured in the tables below.

Non-limiting examples of the moiety

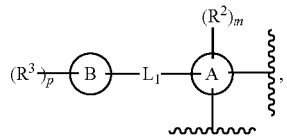

in each of Formulas (I), (IA), (IA'), (IB), (IB'), (II), (II'), (IIA), (IIA'), (IIB), and (IIB'), when -L$_1$- represents a bond are shown in the examples pictured in Table 3-1 and in the table of example compounds immediately following Method WW8.

In some embodiments, in each of Formulas (I), (IA), (IA'), (IB), (IB'), (II), (II'), (IIA), (IIA'), (IIB), and (IIB'), n is 0. In these embodiments, the moiety:

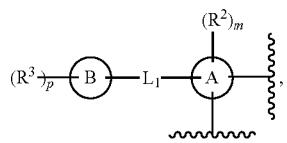

has the form

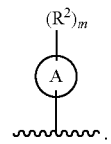

In another embodiment, in each of Formulas (I), (IA), (IA'), (IB), (IB'), (II), (II'), (IIA), (IIA'), (IIB), and (IIB'):

n is 0;

ring A is selected from the group consisting of phenyl, pyridyl, pyrazinyl, furanyl, thienyl, pyrimidinyl, pyridazinyl, thiazolyl, and oxazolyl; and R$^2$ and m are each as defined in Formula (I).

In another embodiment, in each of Formulas (I), (IA), (IA'), (IB), (IB'), (II), (II'), (IIA), (IIA'), (IIB), and (IIB'):

n is 0;

ring A is selected from the group consisting of phenyl, pyridyl, pyrazinyl, furanyl, thienyl, pyrimidinyl, pyridazinyl, thiazolyl, and oxazolyl;

m is 0 to 5; and each R$^2$ (when present) is independently selected from the group consisting of halogen, —OH, —CN, —SF$_5$, —OSF$_5$, —NO$_2$, —N(R$^6$)$_2$, —NR$^7$C(O)R$^6$, —NR$^7$S(O)$_2$R$^6$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, -(lower alkyl)-OH, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_1$-(monocyclic heteroaryl), wherein said phenyl, benzyl, lower cycloalkyl, —CH$_2$-(lower cycloalkyl), monocyclic heteroaryl, and —CH$_1$-(monocyclic heteroaryl) of R$^2$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and —OSF$_5$.

In one such embodiment, each $R^6$ (when present) is independently selected from the group consisting of H, lower alkyl, lower haloalkyl, and lower heteroalkyl, and $R^7$ (when present) is selected from the group consisting of H, lower alkyl.

In another embodiment, in each of Formulas (I), (IA), (IA'), (IB), (IB'), (II), (II'), (IIA), (IIA'), (IIB), and (IIB'):
n is 0;
ring A is selected from the group consisting of phenyl, pyridyl, and thienyl; and
$R^2$ and m are each as defined in Formula (I).

In another embodiment, in each of Formulas (I), (IA), (IA'), (IB), (IB'), (II), (II'), (IIA), (IIA'), (JIB), and (IIB'):
n is 0;
ring A is phenyl; and
$R^2$ and m are each as defined in Formula (I).

In another embodiment, in each of Formulas (I), (IA), (IA'), (IB), (IB'), (II), (II'), (IIA), (IIA'), (IIB), and (IIB'):
n is 0;
ring A is phenyl;
m is 0 to 5; and
each $R^2$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_2$-(monocyclic heteroaryl),
  wherein said phenyl, benzyl, lower cycloalkyl, —CH$_2$-(lower cycloalkyl), monocyclic heteroaryl, and —CH$_2$-(monocyclic heteroaryl) of $R^2$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and —OSF$_5$.

In an alternative of the immediately preceeding embodiment, each $R^6$ (when present) is independently selected from the group consisting of H, lower alkyl, lower haloalkyl, lower cycloalkyl, and lower heteroalkyl.

In another embodiment, in each of Formulas (I), (IA), (IA'), (IB), (IB'), (II), (II'), (IIA), (IIA'), (IIB), and (IIB'):
n is 0;
ring A is phenyl;
m is 0 to 4; and
each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCHF$_2$, and —NHC(O)R$^6$, wherein R$^6$ is selected from the group consisting of —CH$_2$CF$_3$, —CF$_2$CH$_3$, —CH$_3$, —CH$_2$CH$_3$, —CH$_2$OCH$_3$, CHF$_2$, and —CH$_2$N(CH$_3$)$_2$.

In another embodiment, in each of Formulas (I), (IA), (IA'), (IB), (IB'), (II), (II'), (IIA), (IIA'), (IIB), and (IIB'):
n is 0;
ring A is phenyl;
m is 0 to 4; and
each $R^2$ group (when present) is independently selected from the group consisting of halogen, —CN, —SF$_S$, —NH$_2$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —C(O)OH, —C(O)OCH$_3$, —C(O)OCH$_2$CH$_3$, —OCF$_3$, and —OCHF$_2$.

In another embodiment, in each of Formulas (I), (IA), (IA'), (IB), (IB'), (II), (II'), (IIA), (IIA'), (IIB), and (IIB'):
n is 0;
ring A is phenyl;
m is 0 to 4; and
each $R^2$ group (when present) is independently selected from the group consisting of halogen, haloalkyl, cyclopropyl, and —CN.

In an alternative of the immediately preceeding embodiment, each $R^2$ group (when present) is independently selected from the group consisting of halogen, —NH$_2$, —NO$_2$, haloalkyl, cyclopropyl, and —CN.

In another embodiment, in each of Formulas (I), (IA), (IA'), (IB), (IB'), (II), (II'), (IIA), (IIA'), (IIB), and (IIB'):
n is 0;
ring A is phenyl;
m is 0 to 4; and
each $R^2$ group (when present) is independently selected from the group consisting of fluorine, chlorine, bromine, cyclopropyl, —CF$_3$, and —CN.

In an alternative of the immediately preceeding embodiment, each $R^2$ group (when present) is independently selected from the group consisting of fluorine, chlorine, bromine, —NH$_2$, —NO$_2$, cyclopropyl, —CF$_3$, and —CN.

In an alternative of the immediately preceeding embodiment, m is 0, 1, 2, or 3.

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents for use in combination with the compounds of the invention include those selected from the group consisting of: (a) drugs useful for the treatment of Alzheimer's disease and/or drugs useful for treating one or more symptoms of Alzheimer's disease, (b) drugs useful for inhibiting the synthesis Aβ, (c) drugs useful for treating neurodegenerative diseases, and (d) drugs useful for the treatment of type II diabetes and/or one or more symptoms or associated pathologies thereof.

Additional non-limiting examples of additional therapeutic agents for use in combination with the compounds of the invention include drugs useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Additional non-limiting examples of additional therapeutic agents for use in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g., PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention, or a tautomer or stereoisomer thereof, or pharmaceutically acceptable salt or solvate of said compound, said stereoisomer, or said tautomer, and a pharmaceutically acceptable carrier or diluent.

Another embodiment provides a method of inhibiting β-secretase (BACE-1 and/or BACE-2) comprising exposing a population of cells expressing β-secretase to at least one compound of the invention, or a tautomer or stereoisomer thereof, or pharmaceutically acceptable salt or solvate of said compound, said stereoisomer, or said tautomer, in an amount effective to inhibit β-secretase. In one such embodiment, said population of cells is in vivo. In another such embodiment, said population of cells is ex vivo. In another such embodiment, said population of cells is in vitro. Such methods are contemplated as being useful for research and/or the therapeutic uses discussed herein.

Thus, another embodiment provides a method of inhibiting β-secretase in a patient in need thereof. Another embodiment provides a method of inhibiting the formation of Aβ from APP in a patient in need thereof. Another embodiment, the invention provides a method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer or stereoisomer thereof, or pharmaceutically acceptable salt or solvate of said compound, said stereoisomer, or said tautomer, in a therapeutically effective amount to inhibit said pathology or condition in said patient.

In another embodiment, the invention provides a method of treating, preventing, and/or delaying the onset of one or more pathologies associated with Aβ and/or one or more symptoms of one or more pathologies associated with Aβ. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or stereoisomer thereof, or pharmaceutically acceptable salt or solvate of said compound, said stereoisomer, or said tautomer, in an amount effective to inhibit said pathology or pathologies.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), optionally in further combination with one or more additional therapeutic agents effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

In one embodiment, the invention provides a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1.

In various embodiments, the compositions and methods disclosed above and below wherein the compound(s) of the invention is a compound or compounds selected from the group consisting of the exemplary compounds of the invention described below.

In another embodiment, the invention provides for the use of a compound of the invention, or a tautomer or stereoisomer thereof, or pharmaceutically acceptable salt or solvate of said compound, said stereoisomer, or said tautomer, in the manufacture of a medicament for use in the treatment, the delay of onset, and/or the prevention of one or more Aβ pathologies and/or in the treatment, the delay of onset, and/or the prevention of one or more symptoms of one or more Aβ pathologies.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

In the various embodiments described herein, each variable is selected independently of the others unless otherwise indicated.

As described herein, variables of the formulas presented herein, such as ring A and ring B may be unsubstituted or substituted with "one or more" groups. For example, ring A may be unsubstituted or substituted with one or more $R^2$ groups; ring B may be unsubstituted or substituted with one or more $R^3$ groups. It shall be understood that the upper limit of the number of substituents (referred to in the phrase "one or more substituents") is the number of available hydrogen atoms on the relevant moiety (e.g., ring A or ring B) that are available for replacement by a substituent which will result in a chemically stable and chemically neutral moiety. Thus, for example, in the various Formulas of the compounds of the invention, e.g., in Formula (I), m, n, and p are each independently selected integers, wherein:

m is 0 or more,
n is 0 or 1, and
p is 0 or more, wherein the maximum value of m is the maximum number of available substitutable hydrogen atoms on ring A, and wherein the maximum value of p is the maximum number of available substitutable hydrogen atoms on ring B. By way of non-limiting illustration, when ring A is a

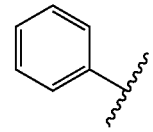 [SMILES: *c1ccccc1]

group, the maximum value of m is 5. When ring A is a

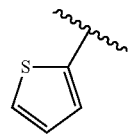

group, the maximum value of m is 3. When ring A is a

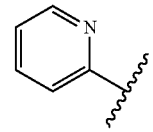 [SMILES: *c1ccccn1]

group, the maximum value of m is 4.

"Patient" includes both human and non-human animals. Non-human animals include those research animals and companion animals such as mice, rats, primates, monkeys, chimpanzees, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

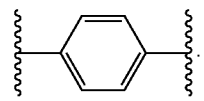

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

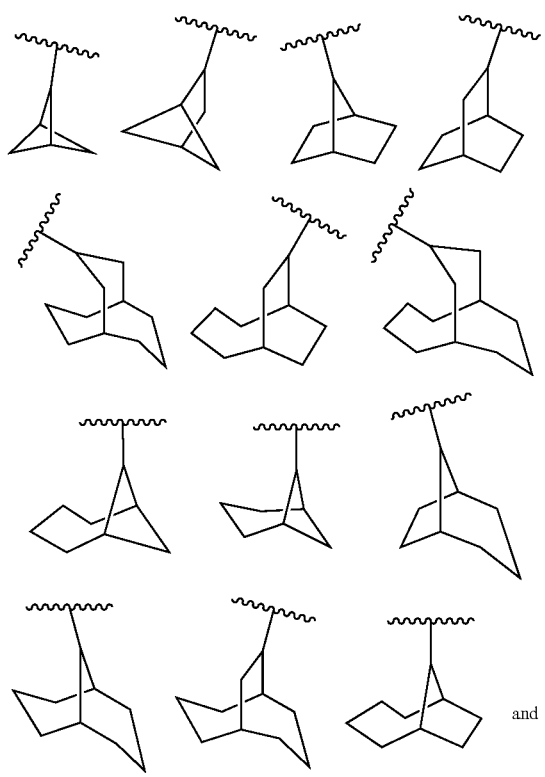

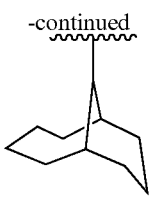

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

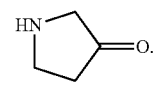

As used herein, the term "monocyclic heterocycloalkyl" refers monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N,N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

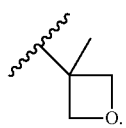 [SMILES: *C1(C)COC1]

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

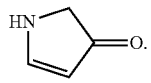

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N,N-oxide, O, S, S-oxide, S(O), and S(O)$_2$. The point of attachment to the parent moiety is to any available ring carbon or ring heteroatom. Non-limiting examples of monocyclic heterocyloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

It should be noted that in hetero-atom containing ring systems of this invention, there are no hydroxyl groups on carbon atoms adjacent to a N, O or S, as well as there are no N or S groups on carbon adjacent to another heteroatom.

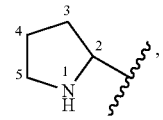

there is no —OH attached directly to carbons marked 2 and 5.

As used herein, the term "multicyclic group" refers to a fused ring system comprising two (bicyclic), three (tricyclic), or more fused rings, wherein each ring of the fused ring system is independently selected from the group consisting of phenyl, monocyclic heteroaryl, monocyclic cycloalkyl, monocyclic cycloalkenyl, monocyclic heterocycloalkyl, and monocyclic heterocycloalkenyl. The point of attachment to the parent moiety is to any available ring carbon or (if present) ring heteroatom on any of the fused rings. It shall be understood that each of the following multicyclic groups pictured may be unsubstituted or substituted, as described herein. Only the point of attachment to the parent moiety is shown by the wavy line.

The term multicyclic groups includes bicyclic aromatic groups. Non-limiting examples of multicyclic groups which are bicyclic aromatic groups include:

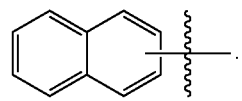

The term multicyclic groups includes bicyclic heteroaromatic groups comprising from 1 to 3 ring heteroatoms, each said ring heteroatom being independently selected from the group consisting of N, O, and S, S(O), S(O)$_2$, and oxides of N, O, and S, and oxides thereof. Non-limiting examples of multicyclic groups which are bicyclic heteroaromatic groups comprising from 1 to 3 ring heteroatoms, each said ring heteroatom being independently selected from N, O, and S are present in the example compounds of the invention shown in the tables below.

The term multicyclic group includes saturated bicyclic cycloalkyl groups. Non-limiting examples of multicyclic groups which are saturated bicyclic cycloalkyl groups include the following:

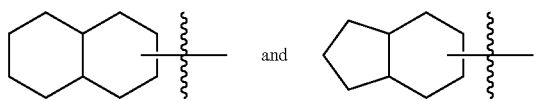

The term multicyclic group includes partially unsaturated bicyclic cycloalkyl groups. Non-limiting examples of multicyclic groups which comprise partially unsaturated bicyclic cycloalkyl groups include the following:

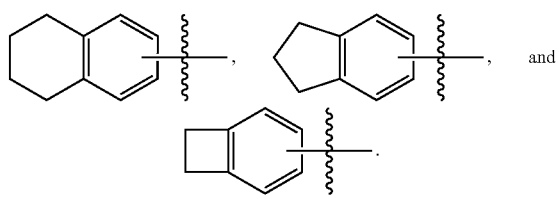

The term multicyclic groups includes partially or fully saturated bicyclic groups comprising from 1 to 3 ring heteroatoms, each said ring heteroatom is independently selected from the group consisting of N, O, and S, S(O), S(O)$_2$, and oxides of N, O, and S, Non-limiting examples of such multicyclic groups are shown in the example compounds of the invention shown in the tables below, and oxides thereof.

The term multicyclic group includes aromatic tricyclic groups, cycloalkyl tricyclic groups, as well as heteroaromatic and partially and fully saturated tricyclic groups. For tricyclic groups comprising ring heteroatoms, said tricyclic groups comprise one or more (e.g., from 1 to 5) ring heteroatoms, wherein each said ring heteroatom is independently selected from N, O, and S, S(O), S(O)$_2$, and oxides of N, O, and S: Non-limiting examples of such multicyclic groups are shown in the example compounds of the invention shown in the tables below, and oxides thereof.

"Arylalkyl" (or "aralkyl") means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety. Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl- group in which alkyl is as previously defined. Preferred cyanoalkyls contain lower alkyl. Non-limiting examples of suitable cyanoalkyl groups include cyanomethyl and 2-cyanoethyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Spirocycloalkyl" means a cycloalkyl group attached to a parent moiety at a single carbon atom. Non-limiting examples of spirocycloalkyl wherein the parent moiety is a cycloalkyl include spiro [2.5] octane, spiro [2.4] heptane, etc. Non-limiting examples of spirocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

"Spiroheterocycloalkyl" means a heterocycloalkyl group, as defined herein, attached to a parent moiety at a single carbon atom.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl- moiety or the like includes substitution on any ring portion and/or on the alkyl portion of the group.

When a variable appears more than once in a group, e.g., $R^8$ in $—N(R^6)_2$, or a variable appears more than once in a structure presented herein, the variables can be the same or different.

The solid line —, as a bond generally indicates a mixture of, or either of, the possible isomers, e.g., containing (R)- and (S)-stereochemistry. For example:

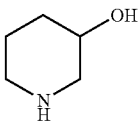

means containing either one of or both

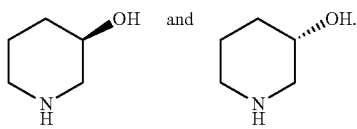

The wavy line ~~~, as used herein shown crossing a line representing a chemical bond, indicates a point of attachment to the rest of the compound. Lines drawn into the ring systems, such as, for example

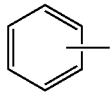

indicates that the indicated line (bond) may be attached to any of the substitutable ring atoms.

"Oxo" is defined as a oxygen atom that is double bonded to a ring carbon in a cycloalkyl, cycloalkenyl, heterocycloalkyl, heterocycloalkenyl, or other ring described herein, e.g.

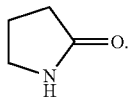

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

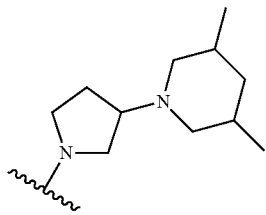 [SMILES: *N1CCC(N2CC(C)CC(C)C2)C1]

represents

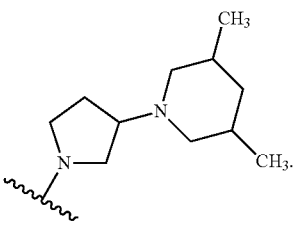 [SMILES: *N1CCC(N2CC(C)CC(C)C2)C1]

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It shall be understood that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Another embodiment provides prodrugs and/or solvates of the compounds of the invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt thereof, contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$)alkyl, and the like.

Similarly, if a compound of the invention contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$)cycloalkyl, benzyl, or R-carbonyl is a natural α-aminoacyl or natural α-aminoacyl, —$C(OH)C(O)OY^1$ wherein $Y^1$ is H, ($C_1$-$C_6$)alkyl or benzyl, —$C(OY^2)Y^3$ wherein $Y^2$ is ($C_1$-$C_4$)alkyl and $Y^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —$C(Y^4)Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Another embodiment provides pharmaceutically acceptable salts of the compounds of the invention. Thus, reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Another embodiment provides pharmaceutically acceptable esters of the compounds of the invention. Such esters include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

As mentioned herein, another embodiment provides tautomers of the compounds of the invention, and salts, solvates, esters and prodrugs thereof. It shall be understood that all tautomeric forms of such compounds are within the scope of the compounds of the invention. For example, all keto-enol and imine-enamine forms of the compounds, when present, are included in the invention. As a further non-limiting example, in the embodiments described above wherein one or both of $R^{1A}$ and $R^{1B}$ are hydrogen, an in particular when W is S(O) or S(O)$_2$, the compounds of the general formula:

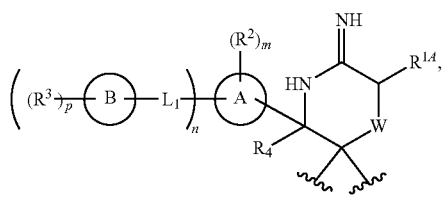

and compounds of the general formula:

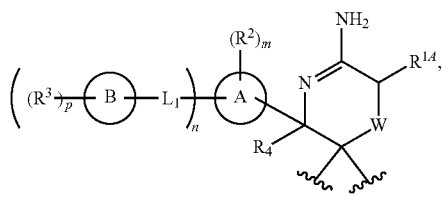

and also compounds of the general formula:

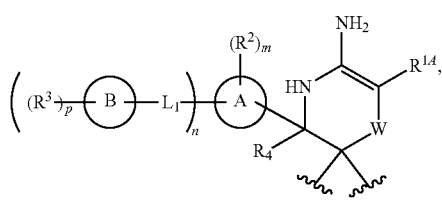

are contemplated as being within the scope of the compounds of the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. Such compounds are identical to those recited herein, but for the fact that one or more atoms are replaced by an atom having an atomic mass or mass number different from the atomic mass or mass number usually found in nature. For example, different isotopic forms of hydrogen (H) include protium ($^1$H), and deuterium ($^2$H). Protium is the predominant hydrogen isotope found in nature. Additional examples of isotopes that can be incorporated into compounds of the invention include (when present) isotopes of hydrogen, carbon, nitrogen, oxygen, phosphorus, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

In another embodiment, the compounds of the invention are isotopically labeled for use as research or diagnostic agents. For example, compounds of the invention can be labeled for use in compound and/or substrate tissue distribution assays. Tritiated (i.e., $^3$H) and carbon-14 (i.e., $^{14}$C) isotopes may be prepared for their ease of preparation and detectability. In another embodiment, the compounds of the invention can be labeled with isotopes such as deuterium (i.e., $^2$H). Deuterium enrichment of the compounds of the invention may afford certain therapeutic advantages resulting from greater metabolic stability (e.g., increased in vivo half-life or reduced dosage requirements), or may provide a compound useful as a standard for characterization of biological samples, and hence may be preferred in some circumstances. Isotopically labelled compounds of the invention can generally be prepared without undue experimentation by following procedures analogous to those disclosed in the Schemes and/or in the examples hereinbelow, by substituting an appropriate isotopically labelled reagent for a non-isotopically labelled reagent. Labels suitable for use in such research or diagnostic agents include, but are not limited to, nuclear spin markers, e.g. a $^{19}$F magnetic resonance imaging (MRI) probe, radioactive markers, e.g., $^{18}$F, $^{11}$C, $^{15}$N, $^{125}$I, and $^3$H (also referred to as "tritium") isotope marker, and complexes of metal atoms or metal ions and chelating agents. Such labeled compounds can be used for in vitro or in vivo imaging of BACE, especially in tissues such as brain, heart, liver, kidney, and lungs, to obtain quantitative measurements of BACE and determine the distribution and regional binding characteristics of these receptors in tissue. These assay-type probes may be used, inter alia, in connection with such diagnostic techniques as MRI and positron emission tomography (PET), and single photon emission computed tomography (SPECT).

Thus, for example, some of the compounds of the invention contain one or more methyl ether groups. Those of ordinary skill in the art will recognize that carbon-11 isotopic analogs of methyl ether groups can be readily made by methods well known in the art. Some of the compounds of the invention include fluoro groups. Those of ordinary skill in the art will also recognize that $^{18}$F can be used as an isotopic replacement for fluoro groups present in a compound of the invention, and $^{18}$F analogs of the compounds of the invention that contain a fluoro group can be made by a variety of methods known in the art. Non-limiting examples of compounds of the invention that include a methyl ether group for which an isotopic analog can be made and are contemplated as additional embodiments of the compounds of the invention include Examples 9a, 9d, 9p, 9m, 9o, 9u, 9y, 9ac, 9ce, 9cm-a, 9cm-b, 9cx-a, 9cx-b, 9dc-a, 9dc-b, 9dj-a, 9dj-b, 9do-a, 9do-b, 9dq-a, 9dq-b, 9dt-a, 9dx-a, 9dx-b, 9eb-a, 9eb-b, 3, 9n, 9w, 9z, 9ae, 9by, 9cg, 9cn-a, 9cn-b, 9cq-a, 9cq-b, 9ct-a, 9cy-a, 9cy-b, 9dd-a, 9dd-b, 9dg-a, 9dg-b, 9dk-a, 9dk-b, 9dm-a, 9dm-b, 9dr-a, 9dr-b, 9du-a, 9dy-a, 9dy-b, 9ec-a, 9ec-b, 9ee-a, and 9ee-b. Non-limiting examples of compounds of the invention that include a fluoro group for which an $^{18}$F isotopic analog can be made and are contemplated as additional embodiments of the compounds of the invention include those of Examples 1, 2, 7, 9c, 9d, 9f, 9k, 9o, 9s, 9x, 9aa, 9ba, 9ca, 9cd, 9cl-a, 9cl-b, 9co-a, 9cr-a, 9cv-a, 9cv-b, 9da-a, 9da-b, 9 db-a, 9 db-b, 9dc-a, 9dc-b, 9dd-a, 9dd-b, 9de-a, 9de-b, 9df-a, 9df-b, 9dg-a, 9dg-b, 9dh-a, 9dh-b, 9dn-a, 9dp-a, 9dp-b, 9ds-a, 9dv-a, 9dv-b, 9ea-a, 9ea-b, 9ed-a, 9ed-b, and 9ef.

The replacement of carbon-11 for carbon-12, or $^{18}$F for $^{19}$F, is known to have little or no adverse effect on the affinity of the compounds of the present invention for BACE, as isotopic compositions are well known in the art to have no effect on receptor affinities. Thus, another embodiment provides a preparation and use of a carbon-11 enriched analog of a compound of the invention in which a carbon-12 of a methyl ether group present on such a compound is replaced with a carbon-11, or a pharmaceutically acceptable salt thereof, pharmaceutical compositions comprising such a compound, and its use in a variety of well known imaging techniques, including positron emission tomography (PET tracers). Yet another embodiment provides a preparation and use of a $^{18}$F enriched analog a compound of the invention, or a pharmaceutically acceptable salt thereof, pharmaceutical compositions comprising such a compound, and its use in a variety of well known imaging techniques, including positron emission tomography (PET tracers). The preparation of a non-limiting example of such a carbon-11 analog is described in the preparation of Example 9dc-a-11C from Example 9dc-a below.

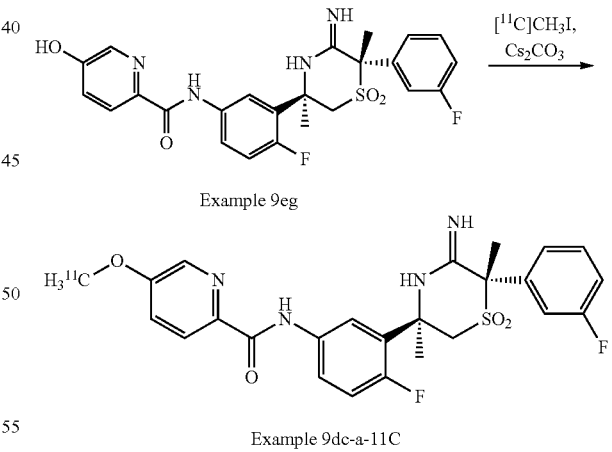

Example 9eg

Example 9dc-a-11C

[$^{11}$C]Methyliodide was trapped in a 0.9 mL vial containing Example 9eg (0.45 mg, 0.899 μmol) and cesium carbonate (2.2 mg, 6.75 μmol) in dimethylformamide (300 μL) at rt. The resulting reaction mixture was heated for 5 minutes at 70° C. The solution was transferred in a 0.9 mL vial containing water (700 μL) at rt, mixed and injected into the semi-preparative HPLC column. The product was purified using Zorbax Eclipse XDB C-18, 5 μm, 9.4×250 mm (Agilent), at a flow rate of 5 mL/min. The mobile phase was acetonitrile/aq. NaH$_2$P$_4$ (10 mM) from 50 to 80% in 10 min.

The radioactivity fraction eluting between 6.7 and 7.0 minutes was collected, evaporated under negative pressure diluted with 0.9% saline solution (3 mL) and transferred into a sterile container.

The final product was tested for chemical and radiochemical purity by means of an analytical HPLC system (Waters) using a Xbridge C18, 5 μm, 4.6×150 mm column (Waters) at a flow rate of 1.5 mL/min. The mobile phase was a mixture consisting of 45% of acetonitrile and 55% of 0.1 trifluoroacetic acid in water. Example 9dc-a-11C concentration was determined by means of an ultraviolet detector (260 nm). Confirmation of the identity of the product was determined by coinjection of a sample of Example 9dc-a, and radiochemical purity was determined using a sodium iodide detector (Bioscan). The retention time for Example 9dc-a-11C was 3.03 min, the chemical and radiochemical purities were 100%.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

The pharmacological properties of the compounds of this invention may be confirmed by a number of pharmacological assays. Certain assays are exemplified elsewhere in this document.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment provides for compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Another embodiment provides for compositions comprising a compound of the invention formulated for subcutaneous delivery. Another embodiment provides for compositions suitable for oral delivery. In some embodiments, it may be advantageous for the pharmaceutical preparation comprising one or more compounds of the invention be prepared in a unit dosage form. In such forms, the preparation is subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for said monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows:
Acetic acid: AcOH Diisopropylethylamine: DIEA or
Acetonitrile: MeCN iPr$_2$NEt
Allyl carbamate: Alloc 1,2-Dimethoxyethane: DME
Aqueous: aq. Dimethylacetamide: DMA
Benzyl: Bn 1-(3-Dimethylaminopropyl)-3
Benzyltreimethylammonium hydroxide: -ethylcarbodiimide: EDC or EDCI
Triton B Dimethylformamide: DMF
[1,1'-Bis(diphenylphosphino)ferrocene] Dimethylsulfoxide: DMSO
-dichloropalladium(II): PdCl$_2$dppf Diphenyiphosphoryl azide: DPPA
Bis(2-oxo-3-oxazolidinyl)phosphonic Equivalents: equiv.
chloride: BOPCl Ether or diethyl ether: Et$_2$O
tert-Butyl: t-Bu or tBu Ethyl: Et
Calculated: Calc'd Ethyl acetate: AcOEt, EtOAc, or EA
Centimeters: cm Example: Ex.
3-Chloroperoxybenzoic acid: mCPBA Expected: Exp.
Dibenzylideneacetone: dba Grams: g
Dichloromethane: DCM Hexanes: hex
2-Dicyclohexylphosphino-2',4',6' High performance liquid
-triisopropylbiphenyl: XPhos chromatography: HPLC
Diisopropylamine: iPr$_2$NH or DIPA High resolution mass spectrometry:
HRMS
Hydroxybenzotriazole: HOBt Number: no. or No.
Inhibition: Inh. Observed: Obs.
Iron(III) acetylacetonate: Fe(acac)$_3$ Palladium(II) acetate: Pd(OAc)$_2$
Isopropyl alcohol: IPA Para-methoxy benzyl: PMB
Liquid chromatography mass Petroleum ether: PE
Spectrometry: LCMS Retention time: t$_R$
Lithium diisopropylamide: LDA Room temperature (ambient, about
Methanesulfonyl chloride: MeSO$_2$Cl 25° C.): rt or RT
Methanol: MeOH tert-Butoxycarbonyl: t-Boc or Boc
Methoxymethyl: MOM SFC: Supercritical Fluid
Methyl t-butyl ether: MTBE Chromatography
Methyl chloromethyl ether: MOMCl Temperature: temp.
Methyl iodide: MeI Tetrahydrofuran: THF
N-Methyl morpholine: NMM Thin layer chromatography: TLC
Methyl magnesium bromide: MeMgBr Triethylamine: Et$_3$N or TEA
Microliters: μl or μL Trifluoroacetic acid: TFA
Milligrams: mg Trimethylsilyl: TMS
Milliliters: mL 2-(Trimethylsilyl)ethoxycarbonyl: Teoc
Millimoles: mmol 2,4,6-tripropyl-1,3,5,2,4,6
Minutes: min -trioxatriphosphorinane-2,4-6-trioxide:
N-bromosuccinimide: NBS T3P
n-Butyllithium: nBuLi or n-BuLi Ultra performance liquid
Nuclear magnetic resonance chromatography: UPLC
spectroscopy: NMR
Method 1

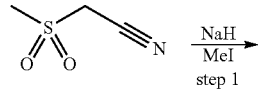

Step 1: To a stirred solution of the commercially available 2-(methylsulfonyl)-acetonitrile (11.9 g, 100 mmol) in 300 mL of THF was added NaH (8.0 g, 60% in mineral oil, 200 mmol) slowly at 0° C. After 20 min, MeI (28.4 g, 200 mmol) was added dropwise over a period of 1.5 h. The mixture was allowed to warm from 0° C. to room temperature overnight (20 h). It was quenched with H$_2$O (250 mL), and the THF was evaporated. The aqueous solution was extracted with three 250 mL portions of ethyl acetate. The combined organic extracts were washed with brine (200 mL), and concentrated. Trituration of the residue with hexanes/ether gave 2-methyl-2-(methylsulfonyl)propanenitrile (13.6 g, 93%). $^1$H NMR (CDCl$_3$ 400 MHz) δ 3.15 (s, 3 H), 1.76 (s, 6 H).

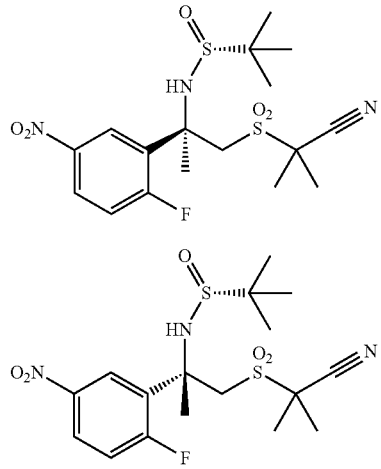

1-1a 1-1b

Step 2: To a stirred solution of 1.05 g (7.13 mmol) of 2-methyl-2-(methylsulfonyl)-propanenitrile in 20 mL of tetrahydrofuran at −78° C. was added 3.0 mL (2.5 M in hexanes, 7.5 mmol) of butyllithium. After 30 minutes, a solution of the sulfinimine 5-1 (1.30 g, 4.54 mmol) in 5 mL of THF was added. The mixture was stirred at −78° C. for additional 2 h, quenched with 60 mL of saturated aq. NH$_4$Cl solution, and extracted with two 100 mL portions of ethyl acetate. The combined organic extracts were concentrated. The residue was purified by flash chromatography (40 g of SiO$_2$, 0 to 70% EtOAc in hexanes) twice to give pure compound 1-1a (876 mg) and a mixture of two diastereoisomeric compounds (398 mg, 1-1a/1-1b 7:3). LCMS for 1-1a (conditions A): t$_R$=2.27 min, m/e=456 (M+Na). LCMS for 1-1b (conditions A): t$_R$=2.23 min, m/e=456 (M+Na).

Step 3: A solution of 0.700 g (1.62 mmol) of compound 1-1a in 10 mL of MeOH and 4 mL of 4 M HCl solution in dioxane was stirred at room temperature for 1.5 h. It was concentrated; the residue was triturated with ether and a small volume of dichloromethane to give compound 1-2 (0.585 g, 99%) as a HCl salt. LCMS for 1-2 (conditions A): t$_R$=1.36 min, m/e=330 (M+H).

Step 4: A flask containing a stirred suspension of 0.58 g (1.59 mmol) of compound 1-2 (HCl salt) and 60 mg of 10% Pd/C in 15 mL of MeOH was fitted with an H$_2$ balloon. The mixture was stirred under an atmosphere of H$_2$ at room temperature for 4 h and then filtered. The filtrate was concentrated; the residue was purified by flash chromatography (12 g of SiO$_2$: 0 to 6% MeOH in CH$_2$Cl$_2$ plus 1% NH$_4$OH) to give compound 1-3 (0.37 g, 78%). LCMS for 1-3 (conditions A): t$_R$=0.73 min, m/e=300 (M+H).

Step 5: To a suspension of the aniline compound 1-3 (0.17 g, 0.57 mmol) and 0.104 g (0.74 mmol) of 5-fluoropyridine-2-carboxylic acid in 5 mL of dichloromethane were added 0.289 g (1.14 mmol) of BOPCl and 0.22 g (1.7 mmol) of diiosopropylethylamine. The solution was stirred at room temperature for 40 min, and quenched with water (10 mL). The mixture was extracted with two 30 mL portions of dichloromethane. The combined organic extracts were concentrated; the residue was purified by flash chromatography (12 g of SiO$_2$: 0 to 4% MeOH in CH$_2$Cl$_2$ plus 1% NH$_4$OH) to give a free base, which was treated with HCl in ether to form the salt 1-4a (0.192 g, 74%). LCMS for 1-4a (conditions A): t$_R$=1.94 min, m/e=423 (M+H).

The following compounds were prepared analogously:

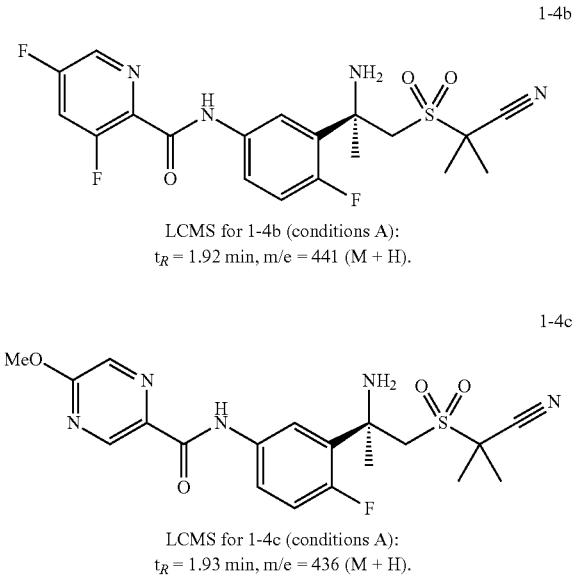

1-4b

LCMS for 1-4b (conditions A):
t$_R$ = 1.92 min, m/e = 441 (M + H).

1-4c

LCMS for 1-4c (conditions A):
t$_R$ = 1.93 min, m/e = 436 (M + H).

Step 6: A suspension of 0.15 g (0.33 mmol) of compound 1-4a (HCl salt) and 0.05 g (0.51 mmol) of CuCl in 5 mL of EtOH was heated at reflux for 4 h. It was diluted with 40 mL of saturated aq. NaHCO$_3$, and extracted with two 50 mL portions of dichloromethane. The combined organic extracts were concentrated; the residue was purified by flash chromatography (12 g of SiO$_2$: 0 to 4% MeOH in CH$_2$Cl$_2$ plus 1% NH$_4$OH) to give a free base, which was treated with HCl in ether to form Ex. 1 as an HCl salt (0.122 g, 81%). LCMS for Ex. 1 (conditions A): t$_R$=1.95 min, m/e=423 (M+H).

The following examples were prepared analogously (Ex. 2 from 1-4b and Ex. 3 from 1-4c):

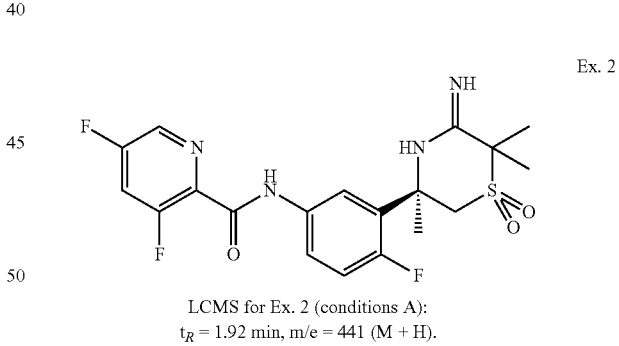

Ex. 2

LCMS for Ex. 2 (conditions A):
t$_R$ = 1.92 min, m/e = 441 (M + H).

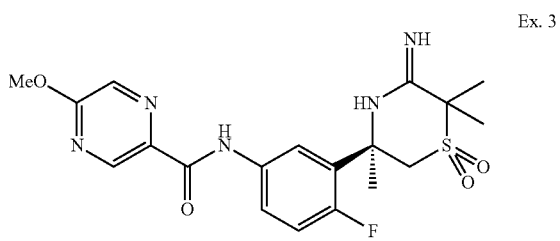

Ex. 3

LCMS for Ex. 3 (conditions A):
t$_R$ = 1.95 min, m/e = 436 (M + H).

Method 2

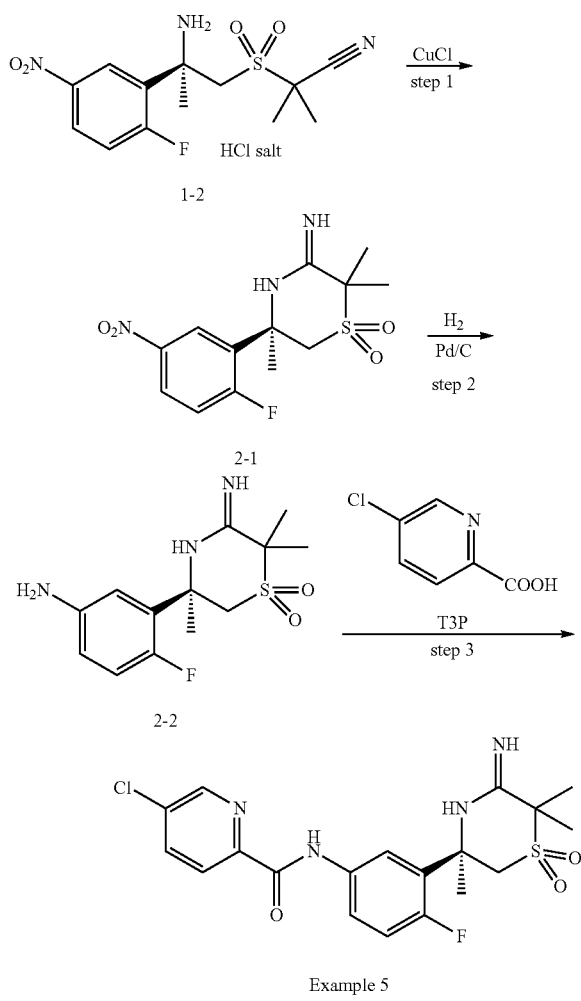

Step 1: A suspension of 1.41 g (3.85 mmol) of compound 1-2 and 0.40 g (4.04 mmol) of Cu(I)Cl in 50 mL of ethanol was stirred at reflux for 5 h. The mixture was concentrated, and the residue was diluted with 30 mL of 1N NaOH solution and extracted with three 80 mL portions of dichloromethane. The combined organic extracts were concentrated. The residue was purified by flash chromatography (40 g of $SiO_2$: gradient from 0 to 5% MeOH in $CH_2Cl_2$ plus 1% $NH_4OH$) to give compound 2-1 (1.75 g, 95%). LCMS for 2-1 (conditions A): $t_R$=1.75 min, m/e=330 (M+H).

Step 2: A flask containing a stirred suspension of 1.20 g (3.64 mmol) of compound 2-1 and 0.11 g of 10% Pd/C in 70 mL of MeOH was charged with a $H_2$ balloon. The mixture was stirred at room temperature for 6 h and filtered. The filtrate was concentrated. The residue was dissolved in 100 mL of dichloromethane and filtered through a pad of Celite. The filtrate was concentrated and the residue was triturated with ether and filtered to give 0.72 g of compound 2-2. The filtrate was concentrated and the residue was purified by flash chromatography (24 g of $SiO_2$: gradient from 0 to 4% MeOH in $CH_2Cl_2$ plus 1% $NH_4OH$) to give an additional 0.27 g of compound 2-2. LCMS for 2-2 (conditions A): $t_R$=0.69 min, m/e=300 (M+H).

Step 3: To a suspension of the compound 2-2 (0.300 g, 1.00 mmol) and 0.205 g (1.30 mmol) of 5-chloropyridine-2-carboxylic acid in 10 mL of dichloromethane was added T3P (0.957 g, 50% solution in ethyl acetate, 1.50 mmol) at 0° C. The solution was stirred at 0° C. for 1 h and at room temperature for 2 h, and then quenched with 30 mL of saturated aq. sodium bicarbonate solution. The mixture was extracted with two 50 mL portions of dichloromethane. The combined organic extracts were concentrated. The residue was purified by flash chromatography (24 g of $SiO_2$: gradient from 0 to 4% MeOH in $CH_2Cl_2$ plus 1% $NH_4OH$) to give Example 5 (0.417 g, 95%). LCMS for Example 5 (conditions A): $t_R$=2.00 min, m/e=439 (M+H).

Using the procedures outlined in Method 2, Step 3, the examples in Table 2-1 were made from compound 2-2 by employing the requisite carboxylic acid. Example 4 and Example 8 can be prepared in an analogous way. Alternatively, Example 4 and Example 8 were prepared according to Method 2B.

TABLE 2-1

| Ex. no. | Example | Expected M + H | Observed M + H | $t_R$ (min) | LCMS method | BACE1 $K_i$ (nM) |
|---|---|---|---|---|---|---|
| 1 | | 423 | 423 | 1.95 | A | 1.2 |
| 2 | | 441 | 441 | 1.92 | A | 0.9 |

TABLE 2-1-continued

| Ex. no. | Example | Expected M + H | Observed M + H | $t_R$ (min) | LCMS method | BACE1 $K_i$ (nM) |
|---|---|---|---|---|---|---|
| 3 | MeO-pyrazine-C(O)NH-phenyl(F)-thiomorpholine dioxide imine | 436 | 436 | 1.95 | A | 0.7 |
| 4 | 5-Me-pyridine-C(O)NH-phenyl(F)-thiomorpholine dioxide imine | 419 | 419.15 | 0.85 | D | 8 |
| 5 | 5-Cl-pyridine-C(O)NH-phenyl(F)-thiomorpholine dioxide imine | 439 | 439 | 2.00 | A | 1.0 |
| 6 | 5-CF3-pyridine-C(O)NH-phenyl(F)-thiomorpholine dioxide imine | 473 | 473 | 2.04 | A | 0.7 |
| 7 | 5-Cl-3-F-pyridine-C(O)NH-phenyl(F)-thiomorpholine dioxide imine | 457 | 457 | 1.95 | A | 0.6 |
| 8 | 4-Cl-phenyl-C(O)NH-phenyl(F)-thiomorpholine dioxide imine | 438 | 438.1 | 0.89 | D | 19 |
| 9 | 3,5-diCl-pyridine-C(O)NH-phenyl(F)-thiomorpholine dioxide imine | 473 | 473 | 1.99 | A | <0.5 |

TABLE 2-1-continued

| Ex. no. | Example | Expected M + H | Observed M + H | $t_R$ (min) | LCMS method | BACE1 $K_i$ (nM) |
|---|---|---|---|---|---|---|
| 9a | | 435 | 435 | 1.93 | A | 4.6 |
| 9b | | 430 | 430 | 1.90 | A | <0.5 |
| 9c | | 471 | 471 | 1.99 | A | 0.6 |
| 9d | | 453 | 453 | 1.94 | A | 5.4 |
| 9e | | 474 | 474 | 2.00 | A | 0.7 |
| 9f | | 440 | 440 | 1.95 | A | 11 |
| 9g | | 410 | 410 | 1.59 | A | 1.9 |

TABLE 2-1-continued
| Ex. no. | Example | Expected M + H | Observed M + H | $t_R$ (min) | LCMS method | BACE1 $K_i$ (nM) |
|---|---|---|---|---|---|---|
| 9h | | 410 | 410 | 1.83 | A | 2.7 |
| 9i | | 410 | 410 | 1.77 | A | 185 |
| 9j | | 444 | 444 | 1.89 | A | 0.6 |
| 9p | | 476 | 476 | 2.13 | A | 2.6 |
| 9q | | 456 | 456 | 0.66 | H | 3.6 |
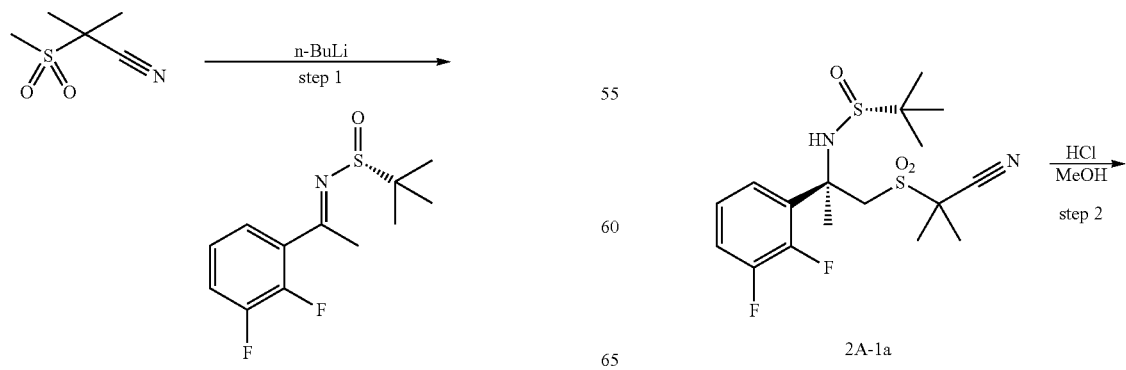
Method 2A

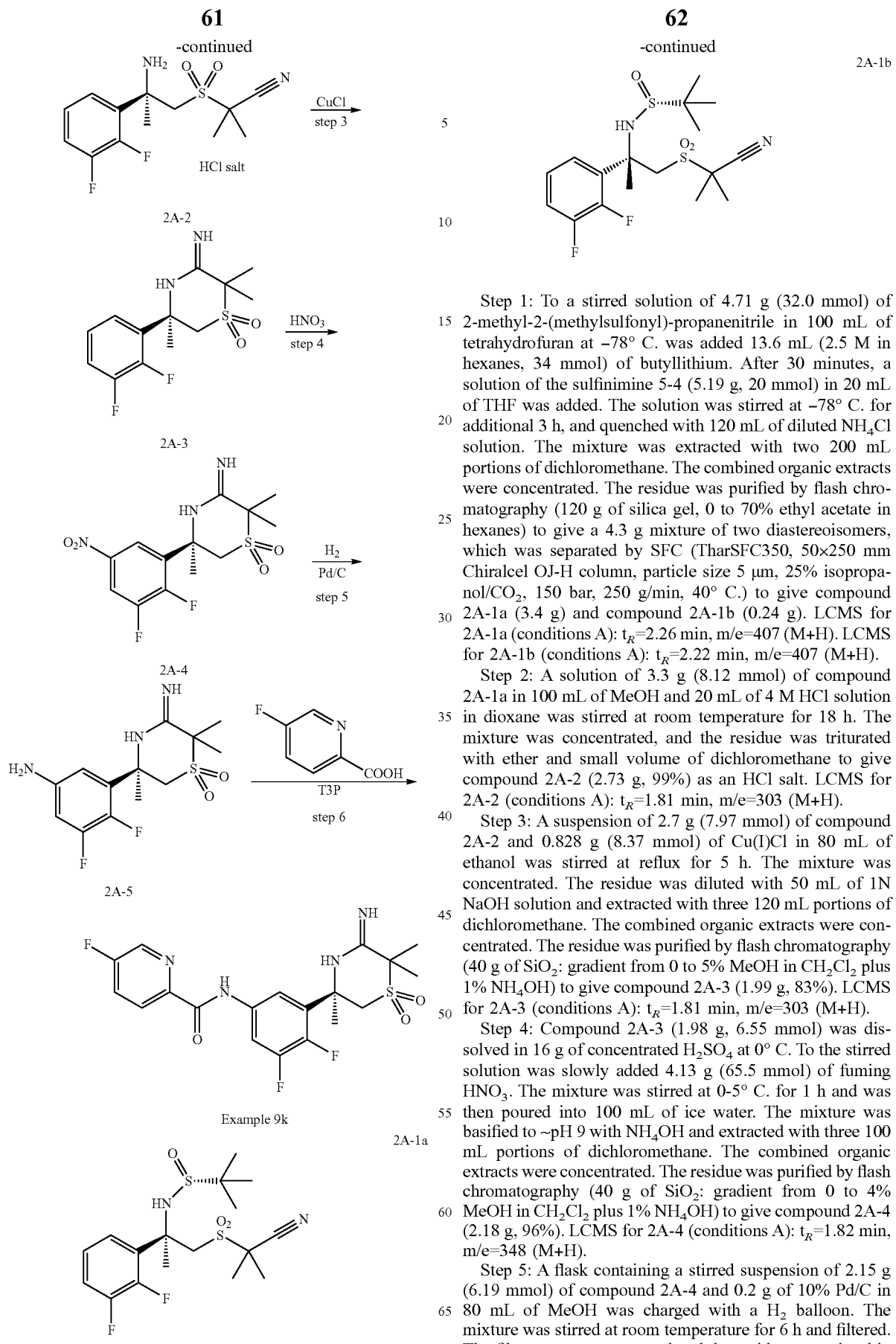

Step 1: To a stirred solution of 4.71 g (32.0 mmol) of 2-methyl-2-(methylsulfonyl)-propanenitrile in 100 mL of tetrahydrofuran at −78° C. was added 13.6 mL (2.5 M in hexanes, 34 mmol) of butyllithium. After 30 minutes, a solution of the sulfinimine 5-4 (5.19 g, 20 mmol) in 20 mL of THF was added. The solution was stirred at −78° C. for additional 3 h, and quenched with 120 mL of diluted $NH_4Cl$ solution. The mixture was extracted with two 200 mL portions of dichloromethane. The combined organic extracts were concentrated. The residue was purified by flash chromatography (120 g of silica gel, 0 to 70% ethyl acetate in hexanes) to give a 4.3 g mixture of two diastereoisomers, which was separated by SFC (TharSFC350, 50×250 mm Chiralcel OJ-H column, particle size 5 μm, 25% isopropanol/$CO_2$, 150 bar, 250 g/min, 40° C.) to give compound 2A-1a (3.4 g) and compound 2A-1b (0.24 g). LCMS for 2A-1a (conditions A): $t_R$=2.26 min, m/e=407 (M+H). LCMS for 2A-1b (conditions A): $t_R$=2.22 min, m/e=407 (M+H).

Step 2: A solution of 3.3 g (8.12 mmol) of compound 2A-1a in 100 mL of MeOH and 20 mL of 4 M HCl solution in dioxane was stirred at room temperature for 18 h. The mixture was concentrated, and the residue was triturated with ether and small volume of dichloromethane to give compound 2A-2 (2.73 g, 99%) as an HCl salt. LCMS for 2A-2 (conditions A): $t_R$=1.81 min, m/e=303 (M+H).

Step 3: A suspension of 2.7 g (7.97 mmol) of compound 2A-2 and 0.828 g (8.37 mmol) of Cu(I)Cl in 80 mL of ethanol was stirred at reflux for 5 h. The mixture was concentrated. The residue was diluted with 50 mL of 1N NaOH solution and extracted with three 120 mL portions of dichloromethane. The combined organic extracts were concentrated. The residue was purified by flash chromatography (40 g of $SiO_2$: gradient from 0 to 5% MeOH in $CH_2Cl_2$ plus 1% $NH_4OH$) to give compound 2A-3 (1.99 g, 83%). LCMS for 2A-3 (conditions A): $t_R$=1.81 min, m/e=303 (M+H).

Step 4: Compound 2A-3 (1.98 g, 6.55 mmol) was dissolved in 16 g of concentrated $H_2SO_4$ at 0° C. To the stirred solution was slowly added 4.13 g (65.5 mmol) of fuming $HNO_3$. The mixture was stirred at 0-5° C. for 1 h and was then poured into 100 mL of ice water. The mixture was basified to ~pH 9 with $NH_4OH$ and extracted with three 100 mL portions of dichloromethane. The combined organic extracts were concentrated. The residue was purified by flash chromatography (40 g of $SiO_2$: gradient from 0 to 4% MeOH in $CH_2Cl_2$ plus 1% $NH_4OH$) to give compound 2A-4 (2.18 g, 96%). LCMS for 2A-4 (conditions A): $t_R$=1.82 min, m/e=348 (M+H).

Step 5: A flask containing a stirred suspension of 2.15 g (6.19 mmol) of compound 2A-4 and 0.2 g of 10% Pd/C in 80 mL of MeOH was charged with a $H_2$ balloon. The mixture was stirred at room temperature for 6 h and filtered. The filtrate was concentrated and the residue was stirred in 100 mL of ether to give compound 2A-5 after filtration (1.84 g, 84%). LCMS for 2A-5 (conditions A): $t_R$=1.44 min, m/e=318 (M+H).

Step 6: To a suspension of compound 2A-5 (0.286 g, 0.90 mmol) and 0.165 g (1.17 mmol) of 5-fluoropyridine-2-carboxylic acid in 10 mL of dichloromethane was added T3P (0.859 g, 50% in ethyl acetate, 1.35 mmol) at 0° C. The solution was stirred at 0° C. for 1 h and at room temperature for 2 h, and then quenched with saturated aq. sodium bicarbonate solution (30 mL). The mixture was extracted with two 50 mL portions of dichloromethane. The combined organic extracts were concentrated, and the residue was purified by flash chromatography (24 g of SiO$_2$, gradient 0 to 4% MeOH in CH$_2$Cl$_2$ plus 1% NH$_4$OH) to give Example 9k (0.255 g, 65%). LCMS for Example 9k (conditions A): $t_R$=1.99 min, m/e=441 (M+H).

Using procedures similar to those outlined in Method 2A, Step 6, the examples in Table 2A-1 were made from compound 2A-5 by employing the requisite carboxylic acid.

TABLE 2A-1

| Ex. no. | Example | Expected M + H | Observed M + H | $t_R$ (min) | LCMS cond. | BACE1 $K_i$ (nM) |
|---|---|---|---|---|---|---|
| 9k | | 441 | 441 | 1.99 | A | 9.7 |
| 9l | | 457 | 457 | 2.06 | A | 4.3 |
| 9m | | 453 | 453 | 2.00 | A | 7.6 |
| 9n | | 454 | 454 | 1.99 | A | 6.6 |
| 9o | | 471 | 471 | 1.98 | A | 3.0 |

TABLE 2A-1-continued

| Ex. no. | Example | Expected M + H | Observed M + H | $t_R$ (min) | LCMS cond. | BACE1 $K_i$ (nM) |
|---|---|---|---|---|---|---|
| 9r | 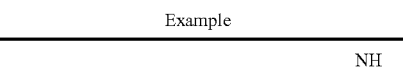 | 474 | 474 | 0.72 | H | 5.3 |

The examples in Table 2A-2 were made using procedures similar to those outlined in Method 2A with the following exceptions: (i) the specified ketimine was substituted for ketimine 5-4 in step 1, (ii) SFC chromatography was not conducted as part of step 1, (iii) the appropriate carboxylic acid was used in step 6, and (iv) by any other modification specified by the notes following the table.

TABLE 2A-2

| Ex. no. | Ketimine | Example | Exp. M + H | Obs. M + H | $t_R$ (min) | LCMS cond. | BACE1 $K_i$ (nM) |
|---|---|---|---|---|---|---|---|
| 9s | 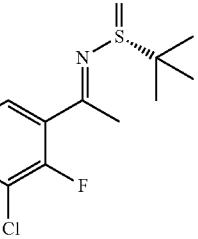 5-5 | 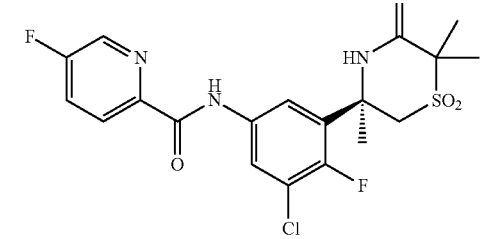 | 457 | 457 | 2.43 | F2 | 6.3 |
| 9t | 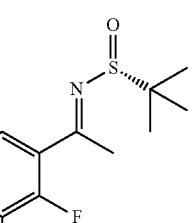 5-5 | 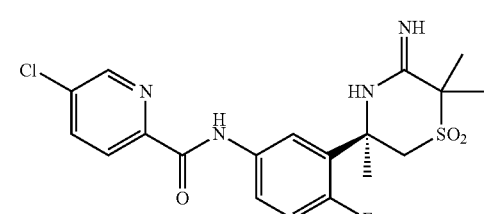 | 473 | 473 | 2.22 | F3 | 3.3 |
| 9u | 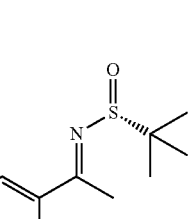 5-5 | 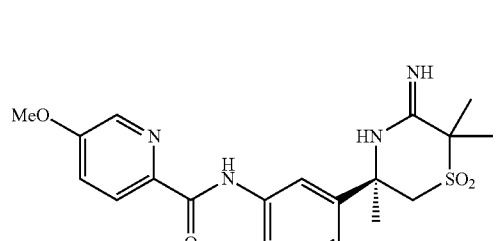 | 469 | 469 | 2.36 | F3 | 5.8 |

TABLE 2A-2-continued

| Ex. no. | Ketimine | Example | Exp. M + H | Obs. M + H | $t_R$ (min) | LCMS cond. | BACE1 $K_i$ (nM) |
|---|---|---|---|---|---|---|---|
| 9v | 5-5 | | 507 | 507 | 2.31 | F3 | 9.6 |
| 9w | 5-5 | | 470 | 470 | 2.63 | F2 | 4.4 |
| 9x | 5-5 | | 441 | 441 | 2.97 | F1 | 27.5 |
| 9y | 5-6 | | 453 | 453 | 2.74 | F1 | 44 |
| 9z | 5-6 | | 454 | 454 | 2.94 | F1 | 52.9 |

TABLE 2A-2-continued
| Ex. no. | Ketimine | Example | Exp. M + H | Obs. M + H | $t_R$ (min) | LCMS cond. | BACE1 $K_i$ (nM) |
|---|---|---|---|---|---|---|---|
| 9aa | 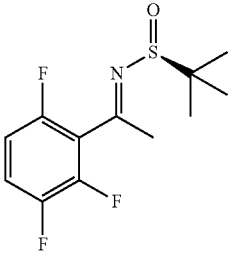 5-7 | 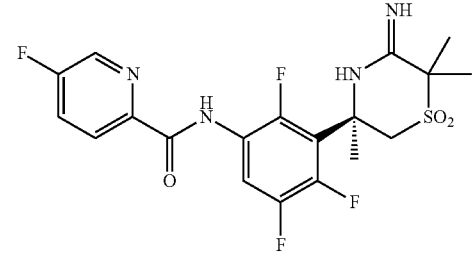 [SMILES: CC1(C)C(=N)N[C@](C)(c2c(F)c(F)cc(NC(=O)c3ccc(F)cn3)c2F)CS1(=O)=O] | 459 | 459 | 3.51 | F1 | 35.4 |
| 9ab | 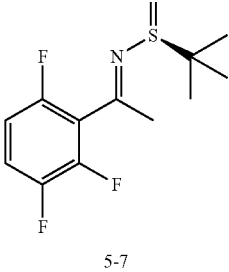 5-7 | 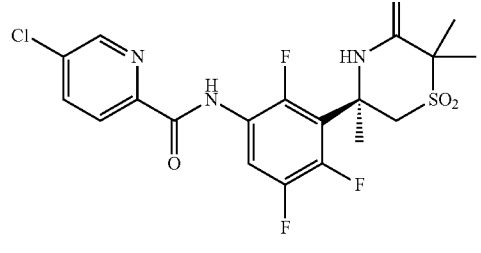 | 475 | 475 | 3.57 | F1 | 9.6 |
| 9ac | 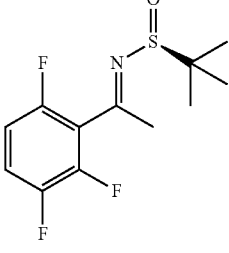 5-7 | 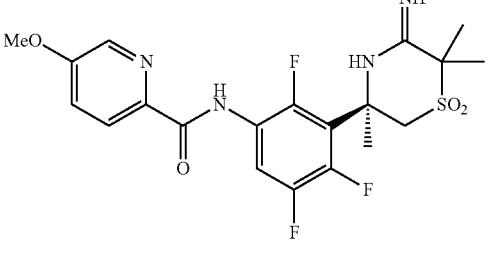 | 471 | 471 | 2.41 | F2 | 18.9 |
| 9ad | 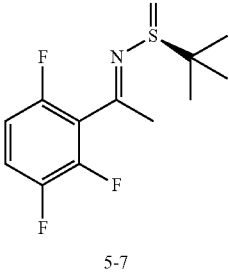 5-7 | 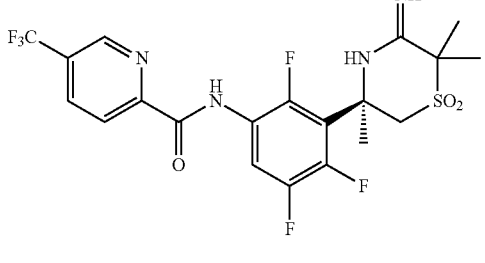 | 509 | 509 | 2.56 | F2 | 7.9 |
| 9ae | 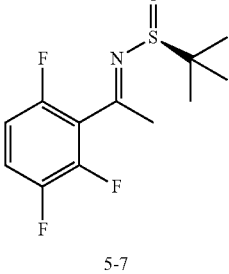 5-7 | 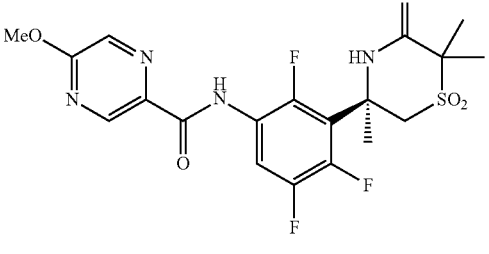 | 472 | 472 | 2.14 | F3 | 45.4 |

Notes for Table 2A-2, above:

1. For Examples 9x-9z, SFC chromatography was conducted on the product isolated from step 4 according to the following conditions: Thar 80 instrument, Chiralpak AD-H, 30×250 mm column, particle size 5 μm, 20% MeOH (with 0.05% NH$_4$OH) in CO$_2$, 100 bar, 60 mL/min, column temperature 38° C.
2. For Examples 9ab-9ad, the following coupling conditions were used in Step 6: 1.0 equivalent of carboxylic acid, 1.5 equivalent of HATU, 3.0 equivalent of DIEA, DMF as solvent, room temperature (for example, see conversion of 2A-8 to Example 9t below).
3. For Examples 9s-9w, the nitro intermediate formed in Step 4 was converted to the examples as described below for Example 9t. For Example 9s, T3P was used in place of HATU.

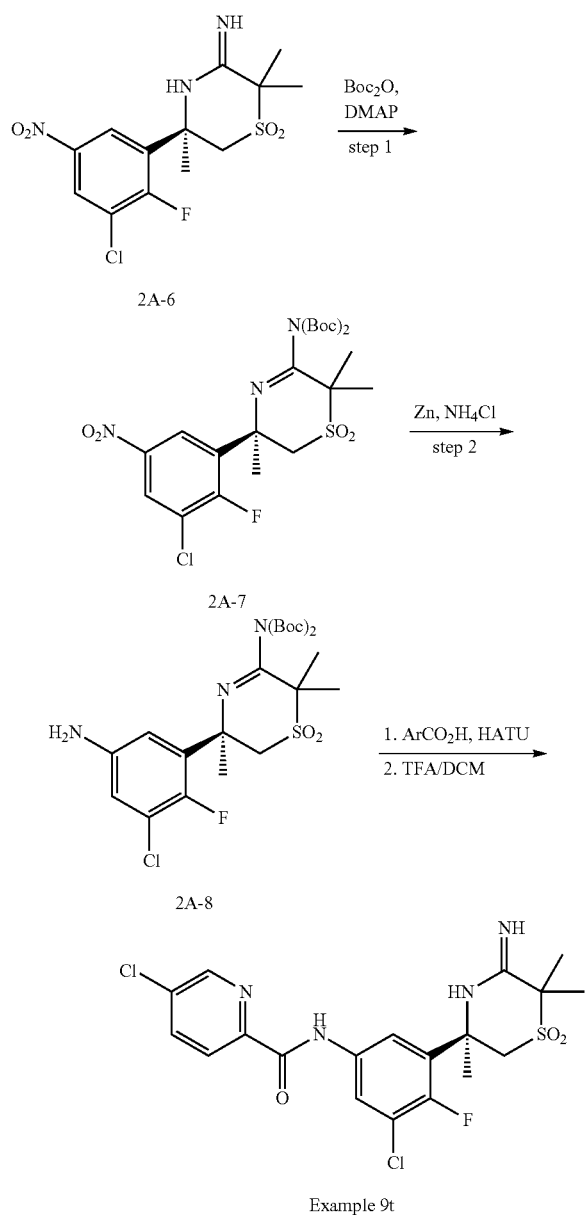

Step 1: To a solution of compound 2A-6 (7 g, 20 mmol) in DCM (70 mL) was added Boc$_2$O (13 g, 60 mmol) and DMAP (2.4 g, 20 mmol) at 25° C. Then the mixture was stirred at 25° C. for 3 h. The mixture was quenched by water, and extracted with DCM. The combined extracts were washed with brine, dried over Na$_2$SO$_4$, concentrated to afford compound 2A-7 (8 g, 71%). $^1$H NMR (CDCl$_3$): 8.40 (s, 1H), 8.29 (s, 1H), 3.53~3.71 (m, 2H), 1.88 (s, 3H), 1.67 (s, 3H), 1.59 (s, 3H), 1.56 (s, 18H).

Step 2: To a solution of compound 2A-7 (5.6 g, 10 mmol) in THF/EtOH/H$_2$O (3:1:0.3, 100 mL) was added NH$_4$Cl (2.65 g, 50 mmol) at 0° C. Then zinc power (6.5 g, 100 mmol) was added at 0° C. and stirred at 80° C. for 16 h. The mixture was filtered. The filtrate was concentrated to afford compound 2A-8 (2.5 g, 50%). It was used directly in next step without further purification.

Step 3: To a solution of compound 2A-8 (800 mg, 1.5 mmol) in DMF (26 mL) was added 5-chloropicolinic acid (236 mg, 1.5 mmol), HATU (1.14 g, 3.00 mmol) and DIEA (387 and extracted with EtOAc. The combined extracts were washed with brine, dried over Na$_2$SO$_4$, mg, 3.00 mmol) at 25° C., then stirred at 25° C. for 16 h. The mixture was quenched by water concentrated. The residue was dissolved in TFA/DCM (10%, 20 mL) and stirred for 2 hours, and then concentrated, purified by preparative HPLC to give Example 9t.

Method 2B

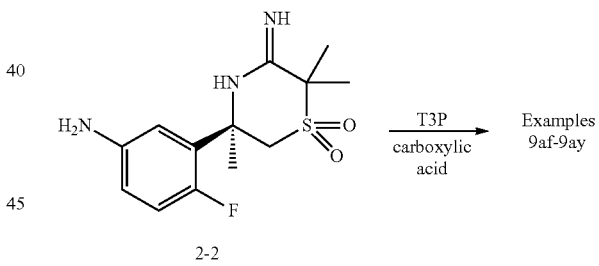

Parallel preparation of Examples 9af-9ay (Table 2B-1): To 1-dram vials containing a stir bar was added the requisite carboxylic acid (0.072 mmol). To each vial was then added a solution of compound 2-2 (18 mg, 0.060 mmol) and diisopropylethylamine (0.016 mL, 0.090 mmol) in CH$_2$Cl$_2$ (1.0 mL) followed by a solution of T3P (50% wt/wt in EtOAc, 0.050 mL, 0.084 mmol). The vials were capped and the mixtures were stirred at RT overnight. To each vial was then added water (50 μL). The mixtures were stirred at RT for 30 min. The stir bars were removed and the solvent was removed in vacuo (at maximum temperature of 40° C.). Each crude product was re-dissolved in 1 mL of DMSO and filtered. The crude products were purified by mass triggered HPLC [Waters XBridge C18 column, 5 μm, 30×100 mm, gradient ranges from 5-10% initial to 35-45% MeCN (0.1% NH$_4$OH) in water (0.1% NH$_4$OH) 25 mL/min, 8 min run time] to provide the Examples 9af-9ay.

TABLE 2B-1
Data for Examples 9af-9ay
| Example no. | Example | Expected M + H | Observed M + H | $t_R$ (min) | LCMS method | BACE1 $K_i$ (nM) |
|---|---|---|---|---|---|---|
| 9af | 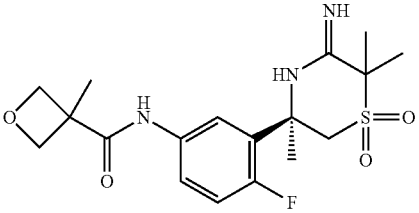 [SMILES: CC1(C(=O)Nc2ccc(F)c([C@]3(C)CS(=O)(=O)C(C)(C)C(=N)N3)c2)COC1] | 398 | 398.15 | 0.64 | D | 739 |
| 9ag | 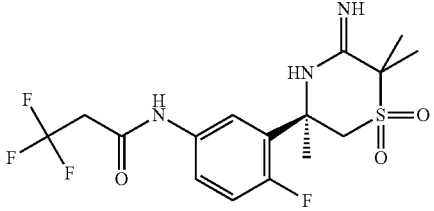 [SMILES: CC1(C)C(=N)N[C@](C)(c2cc(NC(=O)CC(F)(F)F)ccc2F)CS1(=O)=O] | 410 | 410.11 | 0.74 | D | 663 |
| 9ah | 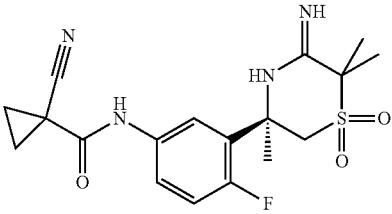 [SMILES: CC1(C)C(=N)N[C@](C)(c2cc(NC(=O)C3(C#N)CC3)ccc2F)CS1(=O)=O] | 393 | 393.13 | 0.70 | D | 210 |
| 9ai | 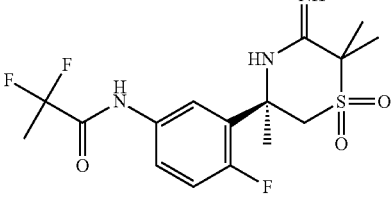 | 392 | 392.12 | 0.73 | D | 82 |
| 9aj | 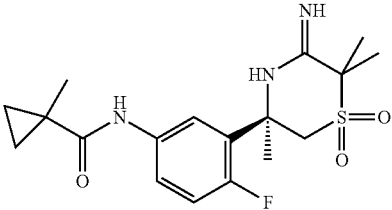 [SMILES: CC1(C(=O)Nc2ccc(F)c([C@]3(C)CS(=O)(=O)C(C)(C)C(=N)N3)c2)CC1] | 382 | 382.15 | 0.73 | D | 1494 |
| 9ak | 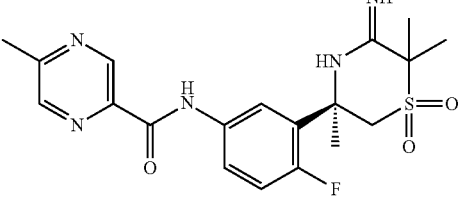 | 420 | 420.14 | 0.72 | D | 26 |

TABLE 2B-1-continued
Data for Examples 9af-9ay
| Example no. | Example | Expected M + H | Observed M + H | $t_R$ (min) | LCMS method | BACE1 $K_i$ (nM) |
|---|---|---|---|---|---|---|
| 9al | 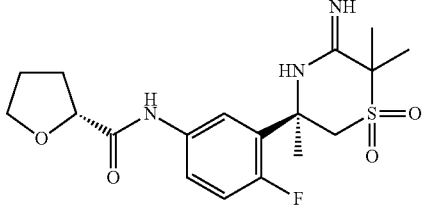 [SMILES: CC1(C)C(=N)N[C@](C)(c2cc(NC(=O)[C@H]3CCCO3)ccc2F)CS1(=O)=O] | 398 | 398.15 | 0.68 | D | 172 |
| 9am | 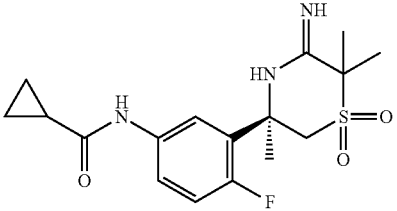 [SMILES: CC1(C)C(=N)N[C@](C)(c2cc(NC(=O)C3CC3)ccc2F)CS1(=O)=O] | 368 | 368.14 | 0.68 | D | 359 |
| 9an | 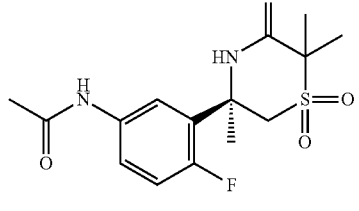 | 342 | 342.12 | 0.60 | D | 1444 |
| 9ao | 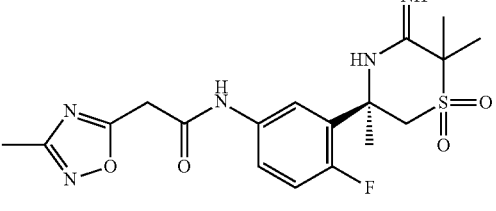 | 424 | 424.14 | 0.66 | D | 3238 |
| 9ap | 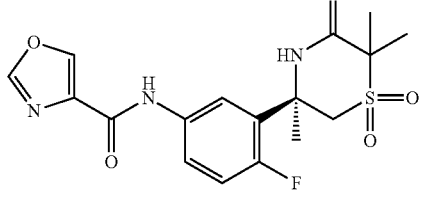 | 395 | 395.11 | 0.65 | D | 39 |
| 9aq | 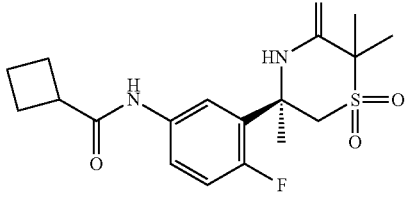 | 382 | 382.15 | 0.74 | D | 476 |

TABLE 2B-1-continued

Data for Examples 9af-9ay

| Example no. | Example | Expected M + H | Observed M + H | $t_R$ (min) | LCMS method | BACE1 $K_i$ (nM) |
|---|---|---|---|---|---|---|
| 9ar | | 382 | 382.15 | 0.72 | D | 915 |
| 9as | | 356 | 356.14 | 0.65 | D | 521 |
| 9at | | 372 | 372.13 | 0.63 | D | 60 |
| 9au | | 378 | 378.1 | 0.67 | D | 195 |
| 9av | | 412 | 412.16 | 0.65 | D | 8585 |
| 9aw | | 418 | 418.13 | 0.75 | D | 299 |

TABLE 2B-1-continued

Data for Examples 9af-9ay

| Example no. | Example | Expected M + H | Observed M + H | $t_R$ (min) | LCMS method | BACE1 $K_i$ (nM) |
|---|---|---|---|---|---|---|
| 9ax | 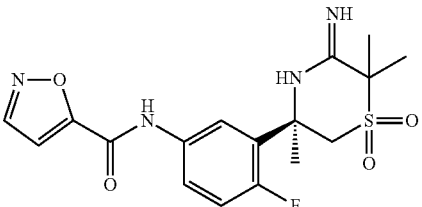 | 395 | 395.11 | 0.68 | D | 82 |
| 9ay | 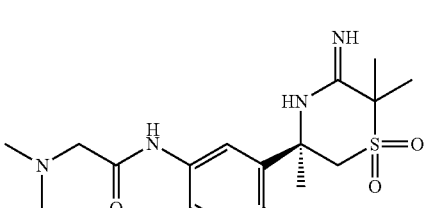 | 385 | 385.16 | 0.67 | D | 23% Inh. at 10 μM |

Using procedures analogous to those outlined in Method 2B, and substituting compound 2A-5 for 2-2 as starting material, the examples in Table 2B-2 were made by employing the requisite carboxylic acid, and with the following modifications: (i) the crude products were purified by mass triggered HPLC [Waters Sunfire C18 column, 5 μm, 19×100 mm, range of gradients of 5-15% initial to 20-45% final MeCN (0.1% formic acid) in water (0.1% formic acid) 50 mL/min, 8 min run time] to provide the Examples 9az-9bx. (ii) Example 9bx was re-purified by purified by mass triggered HPLC [Waters Sunfire C18 column, 5 μm, 19×100 mm, gradient elution 15% to 40% MeCN (0.1% TFA) in water (0.1% TFA) 50 mL/min, 8 min run time] to provide the Example 9bx.

TABLE 2B-2

Data for Examples 9az-9bx

| Example no. | Example | Expected M + H | Observed M + H | $t_R$ (min) | LCMS method | BACE1 $K_i$ (nM) |
|---|---|---|---|---|---|---|
| 9az | 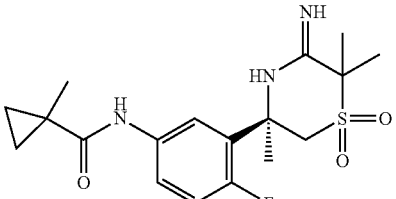 | 400 | 400 | 0.81 | D | 708 |
| 9ba | 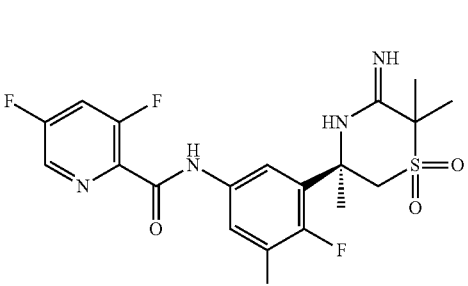 | 459 | 459 | 0.84 | D | 21 |

TABLE 2B-2-continued

Data for Examples 9az-9bx

| Example no. | Example | Expected M + H | Observed M + H | $t_R$ (min) | LCMS method | BACE1 $K_i$ (nM) |
|---|---|---|---|---|---|---|
| 9bb | | 430 | 430 | 0.72 | D | 48% Inh. at 10 μM |
| 9bc | | 428 | 428 | 0.82 | D | 703 |
| 9bd | | 396 | 396 | 0.73 | D | 233 |
| 9be | | 374 | 374 | 0.72 | D | 429 |
| 9bf | | 491 | 491 | 0.99 | D | 25 |

TABLE 2B-2-continued

Data for Examples 9az-9bx

| Example no. | Example | Expected M + H | Observed M + H | $t_R$ (min) | LCMS method | BACE1 $K_i$ (nM) |
|---|---|---|---|---|---|---|
| 9bg | | 448 | 448 | 0.85 | D | 6 |
| 9bh | | 437 | 437 | 0.91 | D | 13 |
| 9bi | | 456 | 456 | 0.96 | D | 22 |
| 9bj | | 411 | 411 | 0.78 | D | 485 |
| 9bk | | 390 | 390 | 0.69 | D | 112 |

TABLE 2B-2-continued

Data for Examples 9az-9bx

| Example no. | Example | Expected M + H | Observed M + H | $t_R$ (min) | LCMS method | BACE1 $K_i$ (nM) |
|---|---|---|---|---|---|---|
| 9bl | | 410 | 410 | 0.81 | D | 79 |
| 9bm | | 416 | 416 | 0.75 | D | 218 |
| 9bn | | 360 | 360 | 0.66 | D | 1022 |
| 9bo | | 438 | 438 | 0.80 | D | 69 |
| 9bp | | 416 | 416 | 0.71 | D | 1151 |

TABLE 2B-2-continued

Data for Examples 9az-9bx

| Example no. | Example | Expected M + H | Observed M + H | $t_R$ (min) | LCMS method | BACE1 $K_i$ (nM) |
|---|---|---|---|---|---|---|
| 9bq | | 442 | 442 | 0.73 | D | 4961 |
| 9br | | 436 | 436 | 0.84 | D | 610 |
| 9bs | | 413 | 413 | 0.74 | D | 171 |
| 9bt | | 400 | 400 | 0.83 | D | 721 |
| 9bu | | 413 | 413 | 0.72 | D | 42 |

TABLE 2B-2-continued

Data for Examples 9az-9bx

| Example no. | Example | Expected M + H | Observed M + H | $t_R$ (min) | LCMS method | BACE1 $K_i$ (nM) |
|---|---|---|---|---|---|---|
| 9bv | | 400 | 400 | 0.80 | D | 1335 |
| 9bw | | 403 | 403 | 0.74 | D | 48% Inh. at 10 µM |
| 9bx | | 438 | 438 | 0.67 | D | 7074 |

Method 2C

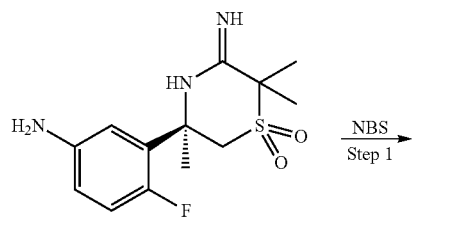

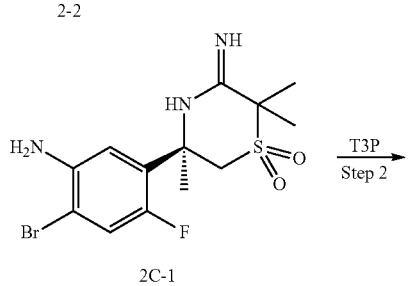

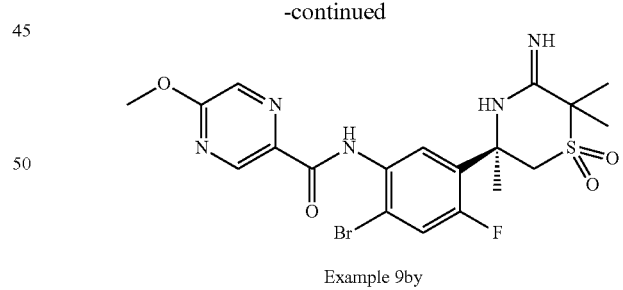

Example 9by

Step 1: To a stirred solution of 0.51 g (1.7 mmol) of the aniline 2-2 in 12 mL of DMF was added 0.364 g (2.0 mmol) of NBS at 0° C. The mixture was stirred at 0° C. for 2 h and concentrated. The residue was subjected to flash chromatography (24 g of SiO$_2$: 0 to 4% MeOH in CH$_2$Cl$_2$ plus 1% NH$_4$OH) to give 2C-1 (0.402 g, 62%). LCMS (conditions A): $t_R$=2.18 min, m/e=380 (M+H).

Step 2: Compound 2C-1 was treated according to Method 2A, step 6 to afford Example 9by. LCMS (conditions A): $t_R$=2.21 min, m/e=516 (M+H).

Method 2D

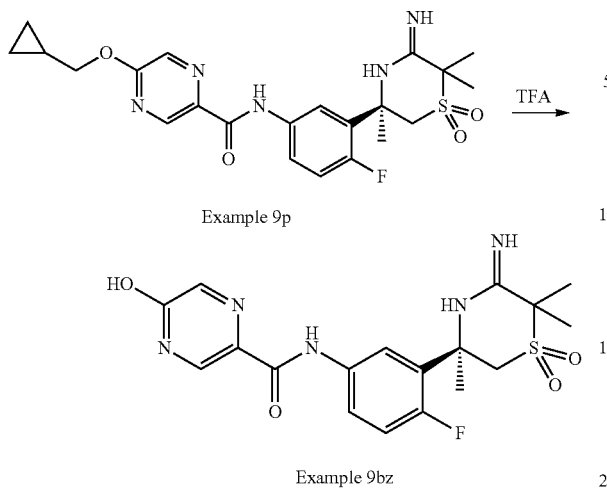

Example 9p

Example 9bz

To a stirred solution of 0.20 g (0.42 mmol) of compound Example 9p in 4 mL of methylene chloride was added 2 mL of TFA. The mixture was stirred at room temperature for 30 min, and concentrated. The residue was by flash chromatography (24 g of $SiO_2$: 0 to 5% MeOH in $CH_2Cl_2$ plus 1% $NH_4OH$) to give Example 9bz (0.135 g, 70%). LCMS (conditions A): $t_R$=1.80 min, m/e=422.0 (M+H).

Method 2E

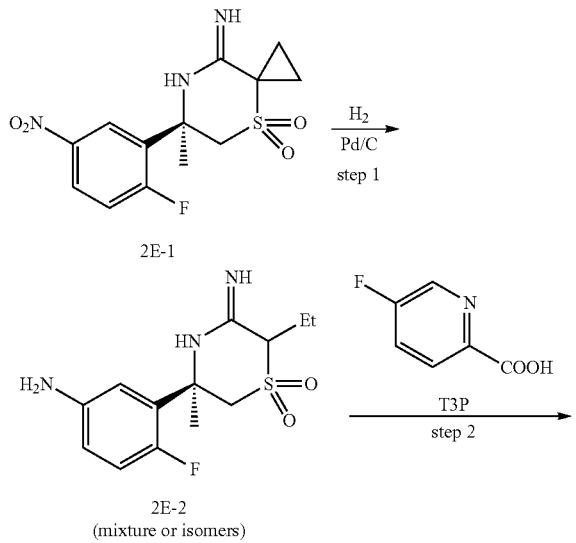

2E-1

2E-2
(mixture or isomers)

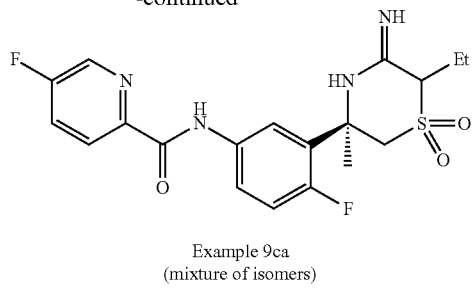

Example 9ca
(mixture of isomers)

Using the procedures described in steps 1, 2, and 3 of Method 2A, compound 2E-1 was prepared analogously, substituting sulfone 14-1 for 2-methyl-2-(methylsulfonyl)propanenitrile in step 1 and using the following SFC purification conditions after Step 2: Chiralpak 250×21 mm AD-H column at 40° C., 20% isopropanol/120 bar $CO_2$, 50 g/min on a Thar SFC Prep 80 system. LCMS (conditions A): $t_R$=1.70 min, m/e=328 (M+H).

Step 1: A stirred suspension of 0.033 g (0.10 mmol) of compound 2E-1 and 0.025 g (0.023 mmol) of 10% Pd/C in 3 mL of MeOH was charged with a $H_2$ balloon. The mixture was stirred at room temperature for 4 h and filtered through Celite. The filtrate was concentrated; the residue was purified by flash chromatography (22 g of $SiO_2$: 0 to 10% MeOH in $CH_2Cl_2$ plus 0.1% $NH_4OH$) to give 0.023 g (77%) of compounds 2E-2. LCMS (conditions A): $t_R$=0.65 min, m/e=300 (M+H).

Step 2: To a suspension of compounds 2E-2 (0.023 g, 0.077 mmol) and 0.014 g (0.1 mmol) of 5-fluoropyridine-2-carboxylic acid in 1.5 mL of dichloromethane was added T3P (50% solution in EtOAc, 0.069 mL, 0.115 mmol) at room temperature. The solution was stirred at room temperature for 1 h, and then quenched with saturated aq. sodium bicarbonate solution. It was extracted with dichloromethane (3×). The combined organic extracts were dried over $Na_2SO_4$, filtered, and concentrated. The residue was purified by flash chromatography (23 g of $SiO_2$: 0 to 7.5% MeOH in $CH_2Cl_2$ with 0.1% $NH_4OH$) to give Example 9ca (0.0016 g). LCMS (conditions A): $t_R$=1.94 min, m/e=423 (M+H).

TABLE 2E-1

Data for examples from Methods 2C, 2D, and 2E

| Ex. no. | Example | Expected M + H | Observed M + H | $t_R$ (min) | LCMS method | BACE1 $K_i$ (nM) |
|---|---|---|---|---|---|---|
| 9by | (structure) | 516 | 516 | 2.21 | A | 718 |

TABLE 2E-1-continued

Data for examples from Methods 2C, 2D, and 2E

| Ex. no. | Example | Expected M + H | Observed M + H | $t_R$ (min) | LCMS method | BACE1 $K_i$ (nM) |
|---|---|---|---|---|---|---|
| 9bz | | 422 | 422 | 1.80 | A | 13 |
| 9ca | | 423 | 423 | 1.94 | A | 33 |

Method 2F

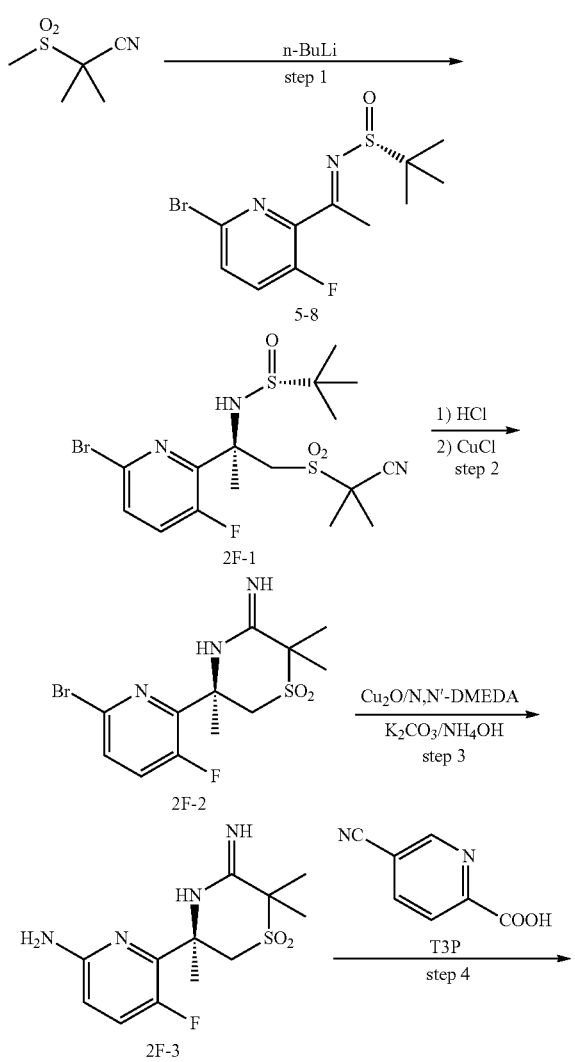

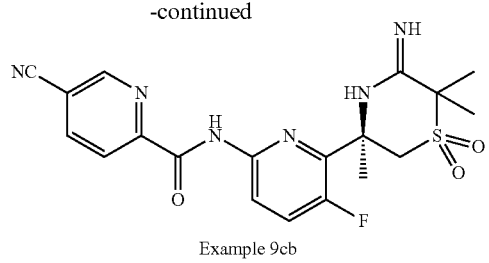

Example 9cb

Step 1: To a stirred solution of 2-methyl-2-(methylsulfonyl)propanenitrile (3.67 g, 25 mmol) in THF (120 mL) under argon at −78° C. was added 10.0 mL (2.5M in hexane, 25 mmol) of n-BuLi solution dropwise over a period of 35 minutes. After the addition was complete, the stirring was continued at −78° C. for additional 40 min. A solution of the compound 5-8 (4.00 g, 12.45 mmol) in THF (40 mL) was introduced into the mixture dropwise over 40 min. The reaction was stirred at −78° C. for 4 hrs. Then it was quenched at −78° C. with addition of 80 mL of saturated aq. NH$_4$Cl, extracted with three 200 mL portions of EtOAc. The combined organic extracts were concentrated; the residue was purified by flash chromatography (silica gel, 0 to 50% EtOAc in hexane) to give a mixture of two isomers. Separation by SFC (Thar SFC system, IC column, 25% isopropanol/supercritical CO$_2$) gave compound 2F-1 (4.60 g, 78.9%). LCMS (conditions A): $t_R$=2.40 min, m/e=468 (M+H).

Step 2: To a stirred solution of the compound 2F-1 (7.49 g, 16 mmol) in 100 mL MeOH was added 50 mL of 4N HCl in dioxane. The stirring was continued at room temperature for 4 hrs. The mixture was concentrated, and the residue was stirred with ether (150 mL), filtered, and washed with ether to give crude material (5.75 g). A suspension of 4.33 g (3.85 mmol) of this crude material and 1.24 g (12.48 mmol) of Cu(I)Cl in 100 mL EtOH was stirred at reflux for 5 h. Then it was concentrated; the residue was diluted with 30 mL of 1N NaOH solution, and extracted with three 80 mL portions of dichloromethane. The combined organic extracts were concentrated; the residue was purified by flash chromatography (120 g of SiO₂: 0 to 5% MeOH in CH₂Cl₂ plus 1% NH₄OH) to give compound 2F-2 (3.07 g, 70.9%). LCMS (conditions A): $t_R$=2.11 min, m/e=364 (M+H).

Step 3: A mixture of the compound 2F-2 (1.50 g, 4.12 mmol), Cu(I)₂O (59 mg, 0.412 mmol), K₂CO₃ (114 mg, 0.824 mmol), N,N'-dimethylethylene diamine (36 mg, 0.412 mmol) and NH₄OH (22.1 mL, 165 mmol) in ethylene glycol (8 mL) in a sealed tube was stirred at 60-65° C. for 12 hrs. The mixture was then cooled to room temperature, diluted with 150 mL H₂O, and extracted with three 200 mL portions of EtOAc. The combined EtOAc extracts were concentrated; the residue was purified by flash chromatography (120 g of SiO₂: 0 to 5% MeOH in CH₂Cl₂ plus 1% NH₄OH) to give compound 2F-3 (689 mg, 55.7%). LCMS (conditions A): $t_R$=1.57 min, m/e=301 (M+H).

Step 4: To a suspension of compound 2F-3 (422 mg, 1.40 mmol) and 5-cyano-pyridine-2-carboxylic acid (257 mg, 1.69 mmol) in 25 mL of CH₂Cl₂ was added T3P (50% in EtOAc, 1.34 g, 2.11 mmol) at 0° C. The reaction was stirred at 0° C. for 1 h and then at room temperature for 20 h, and then quenched with 10 mL of saturated aq. NaHCO₃. It was extracted with three 20 mL portions of dichloromethane. The combined organic extracts were concentrated. The residue was purified by flash chromatography (24 g of SiO₂: 0 to 4% MeOH in CH₂Cl₂ plus 1% NH₄OH) to give Example 9cb (507 mg, 77%). LCMS (conditions A): $t_R$=1.93 min, m/e=431 (M+H).

Using the procedures outlined in Method 2F, Step 6, the examples in Table 2F-1 were made from compound 2F-3 by employing the requisite carboxylic acid.

TABLE 2F-1

| Ex. no. | Example | Observed M + H | Expected M + H | $t_R$ (min) | LCMS method | BACE1 $K_i$ (nM) |
|---|---|---|---|---|---|---|
| 9cb | (structure) | 431 | 431 | 1.93 | A | 7.0 |
| 9cc | (structure) | 440 | 440 | 2.07 | A | 13.7 |
| 9cd | (structure) | 424 | 424 | 1.95 | A | 48.0 |
| 9ce | (structure) | 436 | 436 | 1.96 | A | 55.1 |
| 9cf | (structure) | 474 | 474 | 2.10 | A | 25.7 |

TABLE 2F-1-continued
| Ex. no. | Example | Observed M + H | Expected M + H | $t_R$ (min) | LCMS method | BACE1 $K_i$ (nM) |
|---|---|---|---|---|---|---|
| 9cg | | 437 | 437 | 1.95 | A | 94.2 |
| 9ch | | 407 | 407 | 1.71 | A | 100.6 |
| 9ci | | 437 | 437 | 1.72 | A | 219.2 |
| 9cj | | 457 | 457 | 0.67 | H | 26.6 |
| 9ck | | 487 | 487 | 1.79 | A | 21.7 |
Method 2G
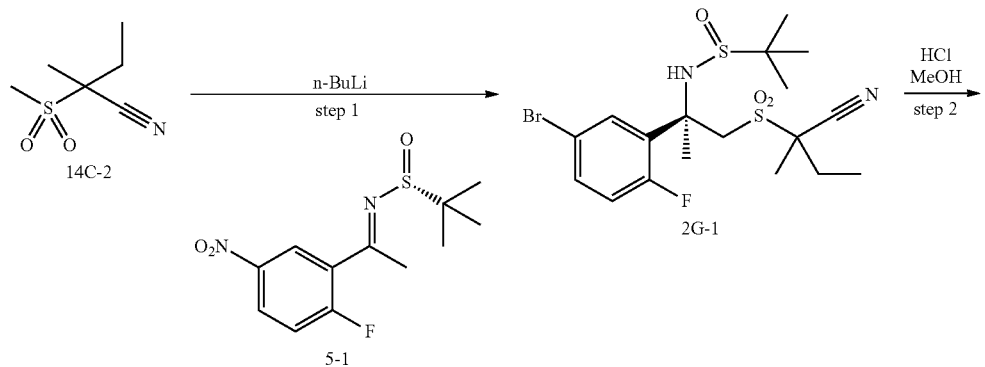

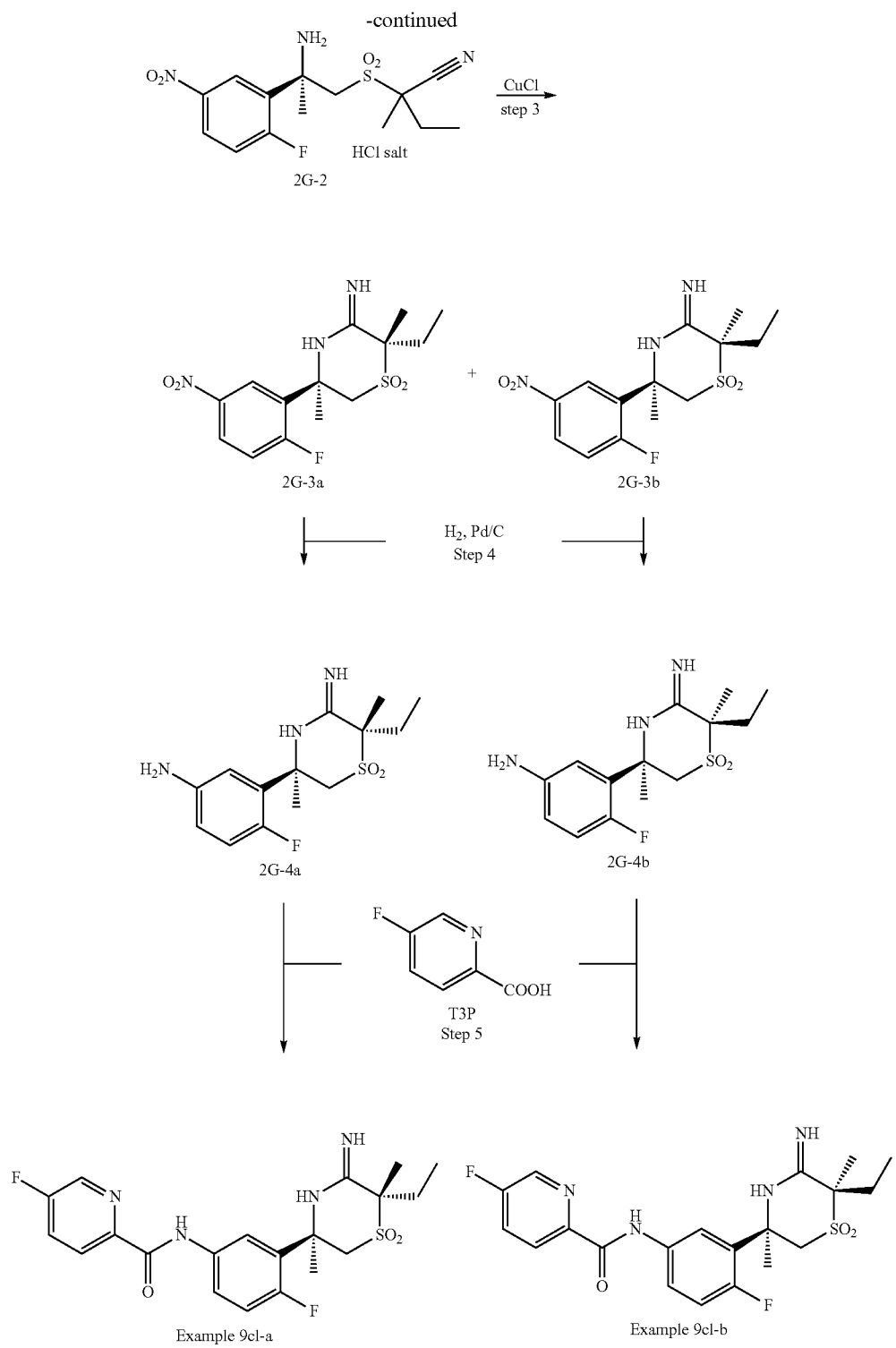

Sulfone 14C-2 was treated according to Method 2A, Steps 1-3 followed by separation of diastereomers via SFC chromatography (Berger MultiGram™ SFC, Mettler Toledo Co, Ltd, Chiralpak AD column, 250 mm×30 mm, 5 μm, 70% supercritical $CO_2$, 30% MeOH (0.05% $NH_4OH$), 50 mL/min, column temp: 38° C., nozzle pressure: 100 bar, 220 nm) to give compounds 2G-3a and 2G-3b. These compounds were treated individually according to Method 2A Steps 5 and 6 to afford Examples 9cl-a and 9cl-b.

The examples in Table 2G-1 were made using the procedures similar to those outlined in Method 2G with the following exceptions: (i) by substituting sulfone 14C-2 with the specified sulfone in step 1, (ii) by using the appropriate carboxylic acid in step 5, and (iii) by any other modification specified by the notes.

TABLE 2G-1

| Ex. no. | Sulfone | Example | M + H: Obs. (Exp.) | LCMS cond. ($t_R$ min) | BACE1 $K_i$ (nM) |
|---|---|---|---|---|---|
| 9cl-a | 14C-2 | | 437 (437) | F2 (2.47) | 5.9 |
| 9cl-b | | | 437 (437) | F2 (2.49) | 22.5 |
| 9cm-a | | | 449 (449) | F2 (2.26) | 5.6 |
| 9cm-b | | | 449 (449) | F2 (2.30) | 31.6 |
| 9cn-a | | | 450 (450) | F2 (2.45) | 6.8 |
| 9cn-b | | | 450 (450) | F2 (2.27) | 28.3 |

TABLE 2G-1-continued

| Ex. no. | Sulfone | Example | M + H: Obs. (Exp.) | LCMS cond. ($t_R$ min) | BACE1 $K_i$ (nM) |
|---|---|---|---|---|---|
| 9co-a | 14A-3 | | 553 (553) | C (3.4) | 5.8 |
| 9cp-a | | | 502 (502) | C (2.9) | 18.0 |
| 9cq-a | 14A-10 | | 462 (462) | G (1.5) | 13.3 |
| 9cq-b | | | 462 (462) | G (1.5) | 96.7 |
| 9cr-a | 14E-4 | | 507 (507) | B (1.66) | 2.1 |
| 9cs-a | | | 523 (523) | A (2.13) | 1.6 |

TABLE 2G-1-continued
| Ex. no. | Sulfone | Example | M + H: Obs. (Exp.) | LCMS cond. ($t_R$ min) | BACE1 $K_i$ (nM) |
|---|---|---|---|---|---|
| 9ct-a | | 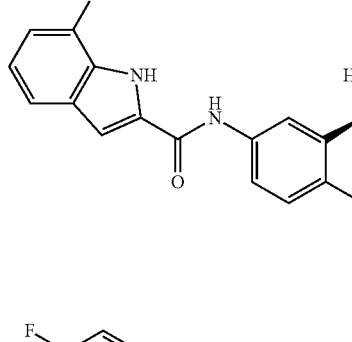 | 520 (520) | A (2.06) | 3.9 |
| 9cu-a | | 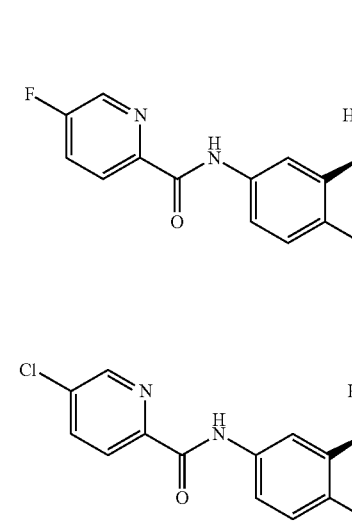 | 557 (557) | A (1.51) | 46.7 |
| 9cv-a | 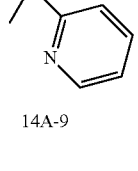<br>14A-9 | 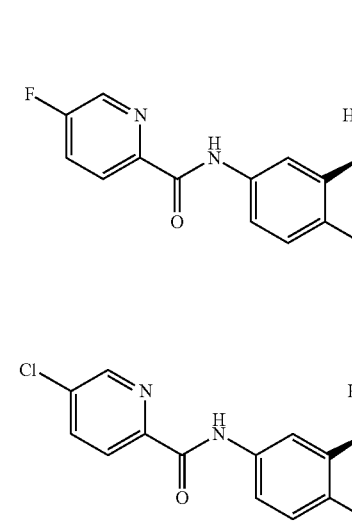 | 486 (486) | F1 (2.86) | 7.8 |
| 9cv-b | | 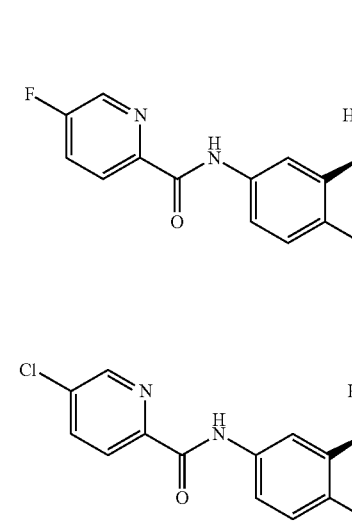 | 486 (486) | F1 (2.89) | 186.6 |
| 9cw-a | | 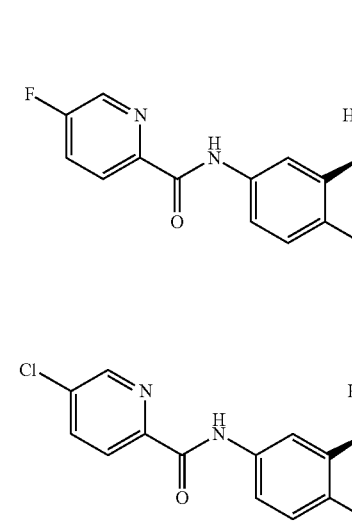 | 502 (502) | F2 (2.69) | 4.4 |
| 9cw-b | | 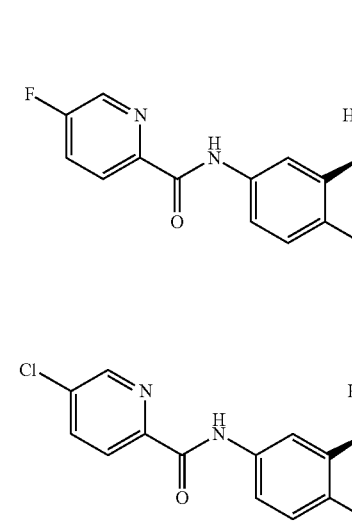 | 502 (502) | F2 (2.68) | 72.7 |

TABLE 2G-1-continued

| Ex. no. | Sulfone | Example | M + H: Obs. (Exp.) | LCMS cond. ($t_R$ min) | BACE1 $K_i$ (nM) |
|---|---|---|---|---|---|
| 9cx-a | | | 498 (498) | F1 (2.90) | 7.1 |
| 9cx-b | | | 498 (498) | F1 (3.18) | 282.2 |
| 9cy-a | | | 499 (499) | F1 (2.83) | 6.9 |
| 9cy-b | | | 499 (499) | F2 (2.58) | 208.7 |
| 9cz-a | | | 536 (536) | F2 (2.58) | 6.0 |
| 9cz-b | | | 536 (536) | F2 (2.81) | 180.8 |

TABLE 2G-1-continued

| Ex. no. | Sulfone | Example | M + H: Obs. (Exp.) | LCMS cond. ($t_R$ min) | BACE1 $K_i$ (nM) |
|---|---|---|---|---|---|
| 9da-a | 14A-6 | | 503 (503) | F3 (2.35) | 3.6 |
| 9da-b | | | 503 (503) | F3 (2.36) | 198 |
| 9db-a | | | 519 (519) | F3 (2.46) | 1.9 |
| 9db-b | | | 519 (519) | F3 (2.26) | 77.2 |
| 9dc-a | | | 515 (515) | F3 (2.15) | 3.0 |
| 9dc-b | | | 515 (515) | F3 (2.39) | 216.2 |

TABLE 2G-1-continued

| Ex. no. | Sulfone | Example | M + H: Obs. (Exp.) | LCMS cond. ($t_R$ min) | BACE1 $K_i$ (nM) |
|---|---|---|---|---|---|
| 9dd-a | | | 516 (516) | F2 (2.47) | 3.9 |
| 9dd-b | | | 516 (516) | F2 (2.46) | 228.5 |
| 9de-a | | | 553 (553) | F3 (2.55) | 3.5 |
| 9de-b | | | 553 (553) | F3 (2.35) | 175.4 |
| 9df-a | 14A-5 | | 503 (503) | F3 (2.33) | 2.3 |
| 9df-b | | | 503 (503) | F3 (2.39) | 164.9 |

TABLE 2G-1-continued

| Ex. no. | Sulfone | Example | M + H: Obs. (Exp.) | LCMS cond. (t_R min) | BACE1 K_i (nM) |
|---|---|---|---|---|---|
| 9dg-a | | (structure) | 516 (516) | F2 (2.66) | 4.5 |
| 9dg-b | | (structure) | 516 (516) | F2 (2.69) | 186.4 |
| 9dh-a | 14-C-3 | (structure) | 463 (463) | F3 (2.27) | 7.5 |
| 9dh-b | | (structure) | 463 (463) | F3 (2.33) | 47.4 |
| 9di-a | | (structure) | 479 (479) | F3 (2.37) | 4.3 |
| 9di-b | | (structure) | 479 (479) | F3 (2.43) | 15.6 |
| 9dj-a | | (structure) | 475 (475) | F3 (2.31) | 4.3 |

TABLE 2G-1-continued
| Ex. no. | Sulfone | Example | M + H: Obs. (Exp.) | LCMS cond. (t_R min) | BACE1 K_i (nM) |
|---|---|---|---|---|---|
| 9dj-b | | 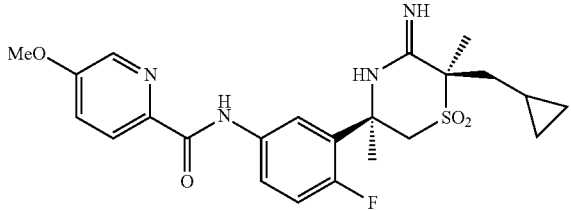 | 475 (475) | F3 (2.36) | 26.9 |
| 9dk-a | | 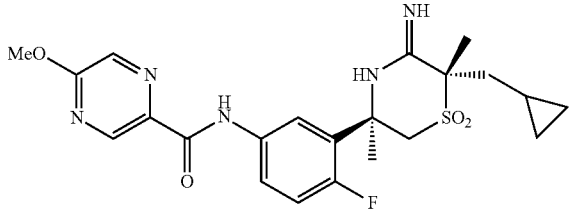 [SMILES: COc1ccc(C(=O)Nc2ccc(F)c([C@]3(C)CS(=O)(=O)[C@@](C)(CC4CC4)C(=N)N3)c2)nc1] | 476 (476) | F2 (2.58) | 7.0 |
| 9dk-b | | 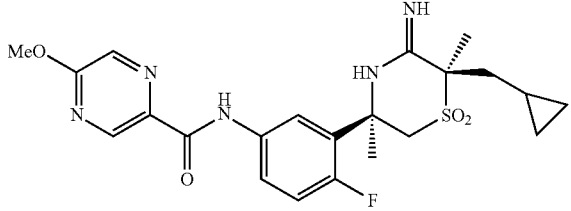 [SMILES: COc1cnc(C(=O)Nc2ccc(F)c([C@]3(C)CS(=O)(=O)[C@](C)(CC4CC4)C(=N)N3)c2)cn1] | 476 (476) | F2 (2.64) | 42.6 |
| 9dl-a | | 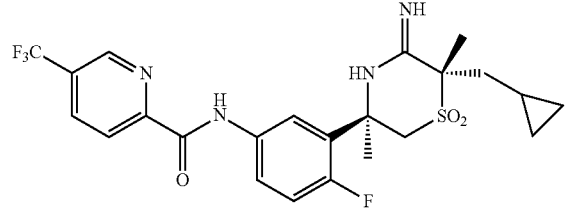 [SMILES: C[C@]1(CC2CC2)C(=N)N[C@](C)(c2cc(NC(=O)c3ccc(C(F)(F)F)cn3)ccc2F)CS1(=O)=O] | 513 (513) | F3 (2.48) | 4.4 |
| 9dl-b | | 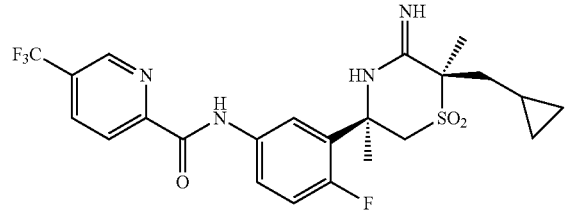 [SMILES: C[C@@]1(c2cc(NC(=O)c3ccc(C(F)(F)F)cn3)ccc2F)CS(=O)(=O)[C@](C)(CC2CC2)C(=N)N1] | 513 (513) | F3 (2.54) | 33.2 |
| 9dm-a | 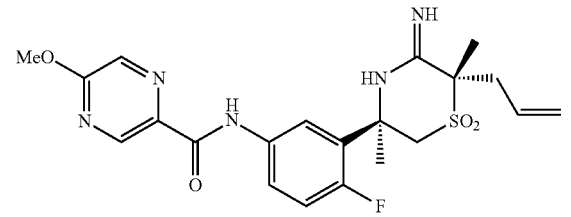 [SMILES: C=CC[C@@]1(C)C(=N)N[C@](C)(c2cc(NC(=O)c3cnc(OC)cn3)ccc2F)CS1(=O)=O] 14C-1 | 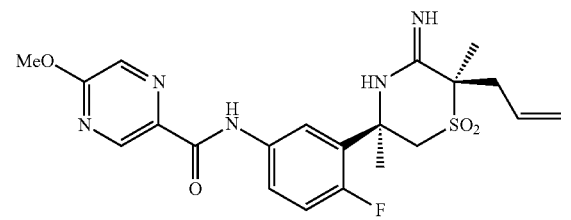 [SMILES: C=CC[C@]1(C)C(=N)N[C@](C)(c2cc(NC(=O)c3cnc(OC)cn3)ccc2F)CS1(=O)=O] | 462 (462) | H (1.00) | 4.0 |
| 9dm-b | | | 462 (462) | A (1.84) | 33.6 |

TABLE 2G-1-continued
| Ex. no. | Sulfone | Example | M + H: Obs. (Exp.) | LCMS cond. (t$_R$ min) | BACE1 K$_i$ (nM) |
|---|---|---|---|---|---|
| 9dn-a |  14A-8 | 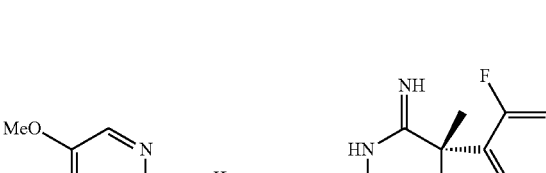 | 503 (503) | F3 (2.30) | 21.4 |
| 9do-a | | 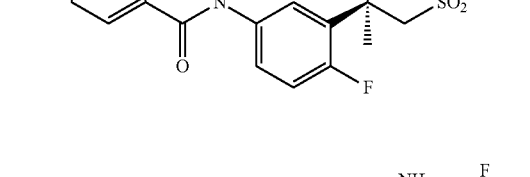 | 515 (515) | F3 (2.33) | 18.3 |
| 9do-b | | 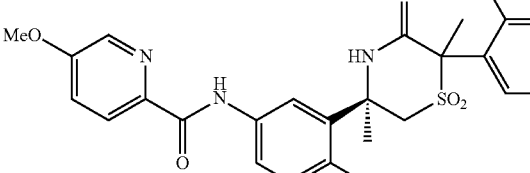 | 515 (515) | F3 (2.33) | 20.8 |
| 9dp-a | 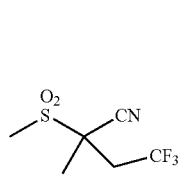 14C-5 | 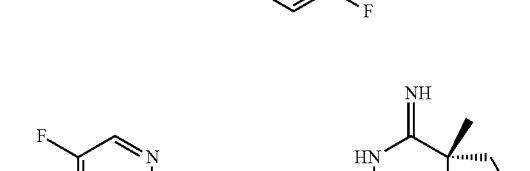 | 491 (491) | F2 (2.31) | 6.2 |
| 9dp-b | | 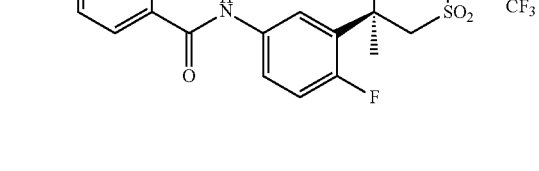 | 491 (491) | F2 (2.35) | 74.5 |
| 9dq-a | |  | 503 (503) | F2 (2.36) | 8.5 |

TABLE 2G-1-continued
| Ex. no. | Sulfone | Example | M + H: Obs. (Exp.) | LCMS cond. (t_R min) | BACE1 K_i (nM) |
|---|---|---|---|---|---|
| 9dq-b | | 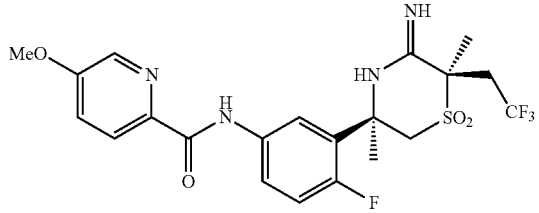 [SMILES: COc1ccc(C(=O)Nc2ccc(F)c([C@]3(C)CS(=O)(=O)[C@](C)(CC(F)(F)F)C(=N)N3)c2)nc1] | 503 (503) | F2 (2.39) | 54.3 |
| 9dr-a | | 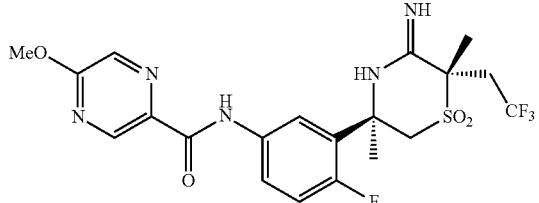 | 504 (504) | F1 (2.77) | 6.0 |
| 9dr-b | | 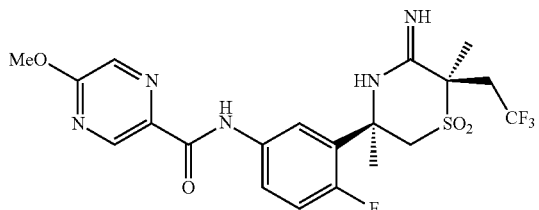 | 504 (504) | F1 (2.81) | 136.8 |
| 9ds-a | 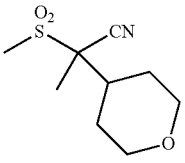<br>14B-2 | 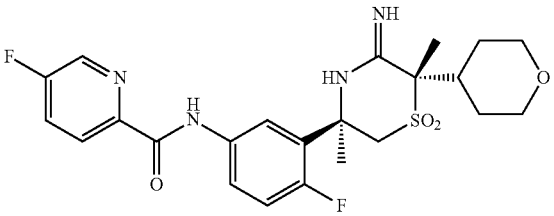 [SMILES: C[C@@]1(c2cc(NC(=O)c3ccc(F)cn3)ccc2F)CS(=O)(=O)[C@@](C)(C2CCOCC2)C(=N)N1] | 493 (493) | A (1.79) | 3.5 |
| 9dt-a | | 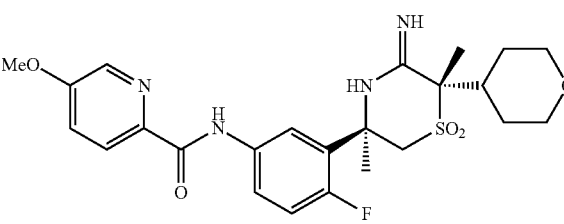 | 505 (505) | A (1.80) | 3.0 |
| 9du-a | | 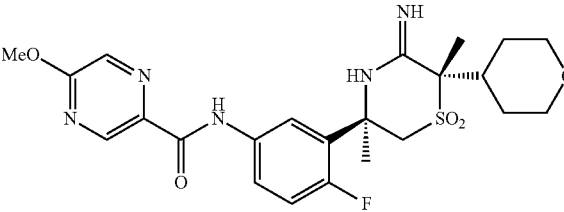 | 506 (506) | A (1.78) | 3.4 |
| 9dv-a | 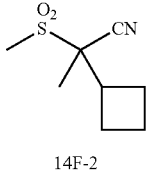<br>14F-2 | 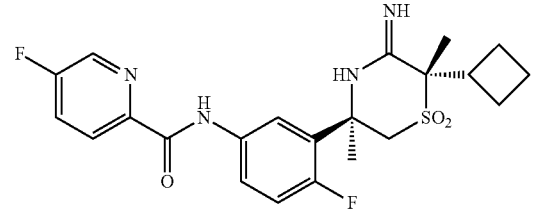 [SMILES: C[C@@]1(c2cc(NC(=O)c3ccc(F)cn3)ccc2F)CS(=O)(=O)[C@@](C)(C2CCC2)C(=N)N1] | 463 (463) | F3 (2.15) | 7.0 |

TABLE 2G-1-continued

| Ex. no. | Sulfone | Example | M + H: Obs. (Exp.) | LCMS cond. (t_R min) | BACE1 K_i (nM) |
|---|---|---|---|---|---|
| 9dv-b | | | 463 (463) | F3 (2.22) | 303.6 |
| 9dw-a | | | 479 (479) | F3 (2.22) | 2.2 |
| 9dw-b | | | 479 (479) | F3 (2.28) | 66.3 |
| 9dx-a | | | 475 (475) | F3 (2.17) | 6.1 |
| 9dx-b | | | 475 (475) | F3 (2.23) | 307.2 |
| 9dy-a | | | 476 (476) | F2 (2.41) | 7.5 |
| 9dy-b | | | 476 (476) | F2 (2.45) | 499.2 |

TABLE 2G-1-continued

| Ex. no. | Sulfone | Example | M + H: Obs. (Exp.) | LCMS cond. (t_R min) | BACE1 K_i (nM) |
|---|---|---|---|---|---|
| 9dz-a | | | 513 (513) | F3 (2.30) | 3.4 |
| 9dz-b | | | 513 (513) | F3 (2.36) | 122.8 |
| 9ea-a | 14G-2 | | 451 (451) | F3 (2.16) | 31.6 |
| 9ea-b | | | 451 (451) | F3 (2.19) | 223.6 |
| 9eb-a | | | 463 (463) | F3 (2.32) | 16.5 |
| 9eb-b | | | 463 (463) | F3 (2.06) | 257.4 |
| 9ec-a | | | 464 (464) | F2 (2.59) | 14.9 |

TABLE 2G-1-continued
| Ex. no. | Sulfone | Example | M + H: Obs. (Exp.) | LCMS cond. ($t_R$ min) | BACE1 $K_i$ (nM) |
|---|---|---|---|---|---|
| 9ec-b | | | 464 (464) | F2 (2.33) | 522.5 |
| 9ed-a | 14I-2 | | 554 (554) | F2 (2.59) | 1.6 |
| 9ed-b | | | 554 (554) | F2 (2.59) | 15.1 |
| 9ee-a | | | 567 (567) | F2 (2.57) | 1.3 |
| 9ee-b | | | 567 (567) | F2 (2.57) | 21.0 |
Notes for Table 2G-1 above:
1. For the following examples, LHMDS was used in Step 1: 9cr-a, 9cs-a, 9ct-a, 9cu-a
2. For the following examples, Zn/HOAc was used in the nitro reduction: 9ds-a, 9dt-a, 9du-a.
3. For the following examples, both of the above modifications were used: 9dm-a, 9dm-b.
Method 2H
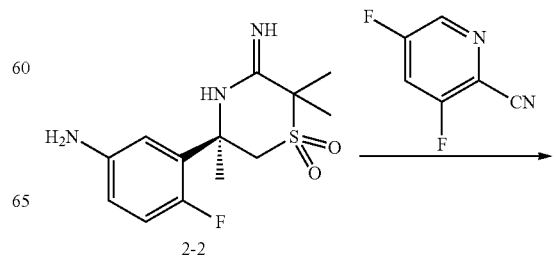
2-2

-continued

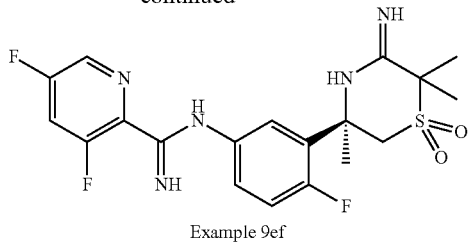

Example 9ef

A mixture of 0.053 g (0.14 mmol) of aniline 2-2 as its bis-HCl salt and 0.022 g (0.16 mmol) of 3,5-difluoropyridyl-nitrile and 0.20 g (0.20 mmol) of CuCl in 4 mL of EtOH was heated at reflux for 70 h. The mixture was concentrated, and the residue was purified by preparative TLC eluting with 5% MeOH in $CH_2Cl_2$ plus 1% $NH_4OH$ to give Example 9ef (0.009 g, 15%).

TABLE 2H-1

Data for Example 9ef

| Example no. | Example | Observed M + H | Expected M + H | $t_R$ (min) | LCMS method | BACE1 $K_i$ (nM) |
|---|---|---|---|---|---|---|
| 9ef | | 440 | 440 | 1.63 | A | 989 |

Method 2I.

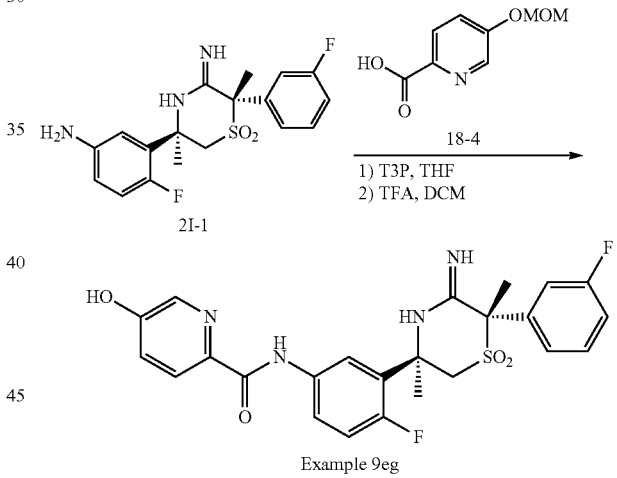

Example 9eg

Compound 2I-1 was made from sulfone 14A-6 using procedures analogous to those used to convert sulfone 14C-2 to compound 2G-4a in Method 2G.

To a solution of 2I-1 (150 mg, 0.39 mmol) and compound 18-4 (80 mg, 0.43 mmol) in THF (5 mL) at 0° C. under an atmosphere of nitrogen was added T3P (0.33 g, 0.55 mmol, 50% in EtOAc). The resulting solution was stirred at 0° C. for 30 min followed by an additional 16 h at RT. Water was added to the solution and the mixture was stirred at RT for 10 min. The aqueous layer was extracted with EtOAc. The combined extracts were washed with brine, dried over $Na_2SO_4$ and concentrated. The residue was purified by prep-HPLC to give the pure MOM-protected product that was dissolved in TFA/DCM (20%, 2 mL) and stirred for 6 h, and concentrated to afford Example 9eg (60 mg, 32%). $^1H$ NMR (400 MHz, $CD_3OD$): 8.09~8.48 (m, 3H), 7.62~7.85 (m, 1H), 7.56~7.59 (m, 1H), 7.41~7.45 (m, 2H), 7.24~7.35 (m, 3H), 4.19 (d, J=16 Hz, 1H), 3.97 (d, J=16.0 Hz, 1H), 2.29 (s, 3H), 2.15 (s, 3H). LCMS (conditions F3): $t_R$=2.12 min, m/e=501 (M+H).

Method 3

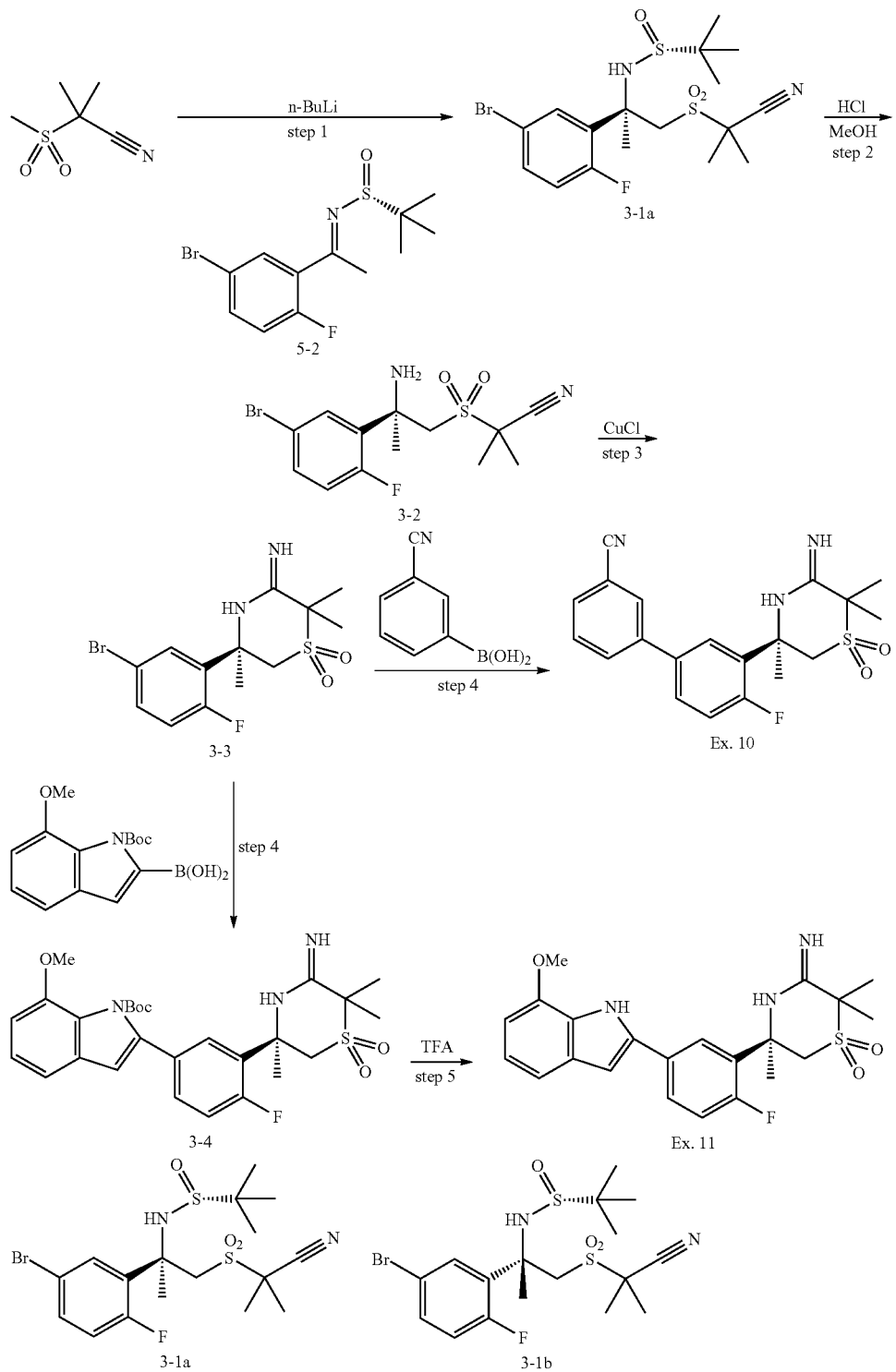

Step 1: To a stirred solution of 2.07 g (14.1 mmol) of 2-methyl-2-(methylsulfonyl)-propanenitrile in 30 mL of tetrahydrofuran was added 5.6 mL (2.5 M in hexanes, 14.0 mmol) of butyllithium at −78° C. After 30 minutes, a solution of the sulfinimine 5-2 (2.25 g, 7.03 mmol) in 10 mL of THF was added. The mixture was stirred at −78° C. for an additional 3 h, and quenched with 20 mL of saturated aq. NH$_4$Cl solution and 80 mL of water. It was extracted with two 150 mL portions of ethyl acetate. The combined organic extracts were concentrated. The residue was purified by flash chromatography (80 g of SiO$_2$, 0 to 70% EtOAc in hexanes) twice to give 1.53 g of two diastereoisomeric isomers as a mixture, which was further purified by SFC (TharSFC80, Chiralcel OJ-H Column 21×250 mm, particle size 5 μm, 150 bar of $CO_2$, 50 g/min, 10% of 2-propanol as co-solvent, 40° C.) to give compound 3-1a (1.17 g, 36%) and 3-1b (0.07 g, not pure, 2%). LCMS for 3-1a (conditions A): $t_R$=2.38 min, m/e=467 (M+H). LCMS for 3-1b (conditions A): $t_R$=2.31 min, m/e=467 (M+H).

Step 2: A solution of 1.1 g (1.62 mmol) of compound 3-1a in 5 mL of MeOH and 5 mL of 4 M HCl solution in dioxane was stirred at room temperature overnight (18 h). It was concentrated; the residue was diluted with 50 mL of saturated aq. $NaHCO_3$, and extracted with three 60 mL portions of dichloromethane. The combined organic extracts were concentrated; the residue was purified by flash chromatography (24 g of $SiO_2$: 0 to 4% MeOH in $CH_2Cl_2$ plus 1% $NH_4OH$) to give compound 3-2 (0.72 g, 84%). LCMS for 3-2 (conditions A): $t_R$=1.88 min, m/e=365 (M+H).

Step 3: A suspension of 0.55 g (1.51 mmol) of compound 3-2 and 0.20 g (2.0 mmol) of CuCl in 10 mL of EtOH was stirred at reflux for 4 h. It was diluted with 80 mL of dichloromethane, and filtered through a pad of Celite. The filtrate was concentrated; the residue was purified by flash chromatography (24 g of $SiO_2$: 0 to 4% MeOH in $CH_2Cl_2$ plus 1% $NH_4OH$) to give compound 3-3 (0.214 g, 39%). LCMS for 3-3 (conditions A): $t_R$=1.87 min, m/e=365 (M+H).

Step 4: A suspension of 0.073 g (0.20 mmol) of compound 3-3, 0.044 g (1.49 mmol) of 3-cyanophenylboronic acid, 0.023 g (0.02 mmol) of $Pd(PPh_3)_4$, and 0.15 mL (0.3 mmol) of 2M aq. $Na_2CO_3$ solution in 2 mL of EtOH and 2 mL of toluene was heated at reflux for 2 h. It was concentrated; the residue was purified by flash chromatography (12 g of $SiO_2$, 0 to 4% MeOH in $CH_2Cl_2$ plus 1% $NH_4OH$) to give Ex. 10 (0.074 g, 97%). LCMS for Ex. 10 (conditions A): $t_R$=1.99 min, m/e=386 (M+H).

Step 5: Compound 3-4 was prepared analogously to the procedures in Step 4, substituting 1-(tert-butoxycarbonyl)-7-methoxy-1H-indol-2-ylboronic acid for 3-cyanophenylboronic acid. LCMS for 3-4 (conditions A): $t_R$=1.87 min, m/e=530 (M+H). A solution of 0.08 g (0.15 mmol) of crude compound 3-4 and 1 mL (13.3 mmol) of TFA in 2 mL of $CH_2Cl_2$ was stirred at room temperature for 2 h. It was concentrated; the residue was purified by flash chromatography (12 g of $SiO_2$: 0 to 4% MeOH in $CH_2Cl_2$ plus 1% $NH_4OH$) to give a product that was further purified by preparative TLC eluting with 5% MeOH in $CH_2Cl_2$ plus 1% $NH_4OH$ to furnish compound Ex. 11 (0.03 g, 47% from compound 3-3 in two steps). LCMS for Ex. 11 (conditions A): $t_R$=2.08 min, m/e=430 (M+H).

Using the procedures described in step 4 of Method 3, Examples 12-15 in Table 3-1 can be made by coupling compound 3-3 with the requisite boronic acids. Example 16 can be made by coupling compound 3-3 with 1-(tert-butoxycarbonyl)-5-(methoxycarbonyl)-1H-pyrrol-2-ylboronic acid according to Method 3, step 4, then treating the product according to Method 3, step 5. Example 16a was prepared from intermediate 3-3 using boronate ester 16-1 in Step 4.

TABLE 3-1

| Ex. no. | Example | Expected M + H | Observed M + H | $t_R$ (min) | LCMS cond. | BACE1 $K_i$ (nM) |
|---|---|---|---|---|---|---|
| 10 | (structure) | 386 | 386 | 1.99 | A | 36% Inh. at 1 μM |
| 11 | (structure) | 430 | 430 | 2.08 | A | 305 |
| 12 | (structure) | 387 | | | | |

TABLE 3-1-continued
| Ex. no. | Example | Expected M + H | Observed M + H | $t_R$ (min) | LCMS cond. | BACE1 $K_i$ (nM) |
|---|---|---|---|---|---|---|
| 13 | | 363 | | | | |
| 14 | | 400 | | | | |
| 15 | | 392 | | | | |
| 16 | | 408 | | | | |
| 16a | | 447 | 447 | 1.97 | A | 43% Inh. at 1 μM |
Method 3A
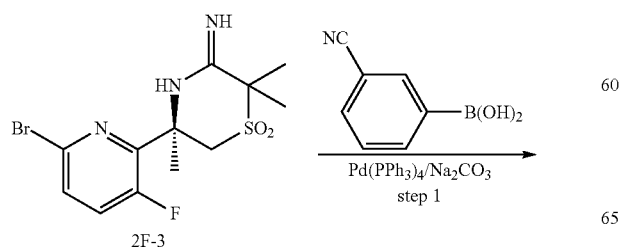
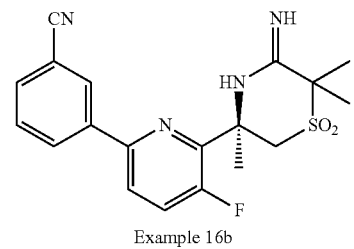
-continued
Example 16b A mixture of 0.070 g (0.192 mmol) of compound 2F-3, 0.040 g (0.269 mmol) of 3-cyanophenylboronic acid, 0.044 g (0.038 mmol) of Pd(PPh$_3$)$_4$, and 0.192 mL (0.384 mmol) of 2M aq. Na$_2$CO$_3$ solution in 2 mL EtOH and 2 mL toluene in a sealed vial was heated at 110° C. by microwave for 1 hr and then cooled and concentrated. The residue was purified by preparative TLC eluting with 5% 7M NH$_3$/MeOH in CH$_2$Cl$_2$ to give Example 16b. (72 mg, 97%). LCMS for Example 16b (conditions A): t$_R$=1.97 min, m/e=387 (M+H).

The Examples in Table 3A-1 were made according to Method 3A using the appropriate boronic acid or boronate ester as a coupling partner. Example 16e was made using (1-(tert-butoxycarbonyl)-7-methoxy-1H-indol-2-yl)boronic acid.

TABLE 3A-1

| Example no. | Example | Observed M + H | Expected M + H | t$_R$ (min) | LCMS method | BACE1 K$_i$ (nM) |
|---|---|---|---|---|---|---|
| 16b | | 387 | C$_{19}$H$_{20}$FN$_4$O$_2$S 387 | 1.97 | A | 4957 |
| 16c | | 393 | C$_{17}$H$_{18}$FN$_4$O$_2$S$_2$ 393 | 1.96 | A | 3587 |
| 16d | | 388 | C$_{18}$H$_{19}$FN$_5$O$_2$S 388 | 1.84 | A | 29% Inh. At 10 μM |
| 16e | | 431 | C$_{21}$H$_{24}$FN$_4$O$_3$S 431 | 2.16 | A | 31% Inh. At 10 μM |

Method 4

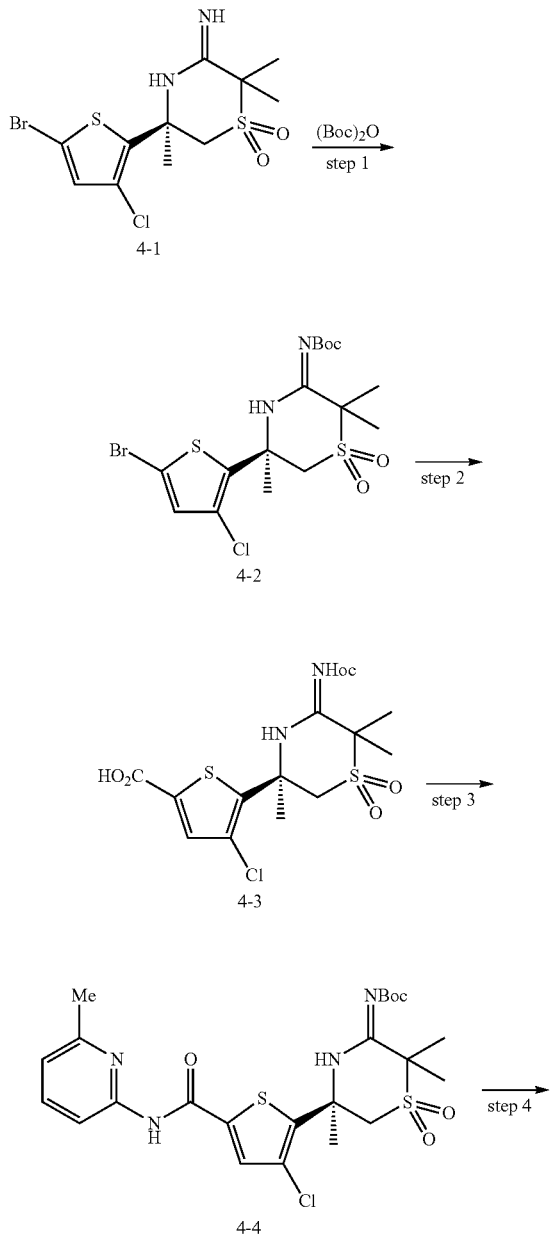

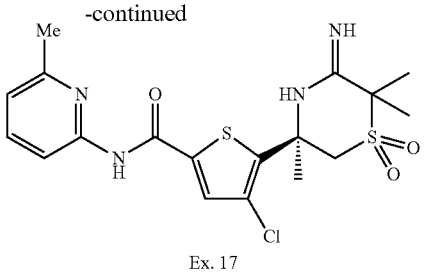

Ex. 17

Using the procedures described in steps 1, 2, and 3 of Method 3, compound 4-1 was prepared analogously, substituting ketimine 5-3 for ketimine 5-2 in step 1. LCMS for 4-1 (conditions A): $t_R$=1.95 min, m/e=387 (M+H).

Step 1: To a solution of compound 4-1 in dichloromethane is added (Boc)$_2$O. The solution is stirred at room temperature for 3 h, and concentrated. The residue is purified by flash chromatography to provide compound 4-2.

Step 2: To a solution of compound 4-2 in THF at 0° C. is added methyl magnesium bromide. The reaction is stirred at 0° C. for 30 minutes and then cooled to −78° C. A hexane solution of n-butyllithium is added over 10 minutes and the reaction is stirred for an additional hour at −78° C. CO$_2$ gas is then bubbled through the reaction for 5 minutes at which time the cold bath is removed. After warming to room temperature, 1N HCl and ethyl acetate are added to the mixture. The mixture is extracted with ethyl acetate. The combined organic layers are washed with water and brine, dried (MgSO$_4$), filtered, and concentrated in vacuo. The residue is purified by silica gel chromatography to provide 4-3.

Step 3: Using the procedures in step 5 of Method 1, compound 4-3 is coupled with 2-amino-6-methylpyridine to provide 4-4.

Step 4: A solution of compound 4-4 in TFA:dichloromethane (1:1) is stirred at RT for 3 h, and concentrated. The residue is purified by flash chromatography to give Ex. 17.

Following the procedures described in Method 4 steps 3 and 4, the examples shown in Table 4-1 can be prepared from compound 4-3 by substituting the appropriate anilines in step 3. Alternatively, Examples 18-23 were prepared from compound 4-1 according to the procedures described in Method 4A by employing the appropriate anilines in step 7. Example 17 can be prepared in a similar way.

TABLE 4-1

| Example no. | Example | Expected M + H | Observed M + H | $t_R$ (min) | LCMS method | BACE1 $K_i$ (nM) |
|---|---|---|---|---|---|---|
| 17 | 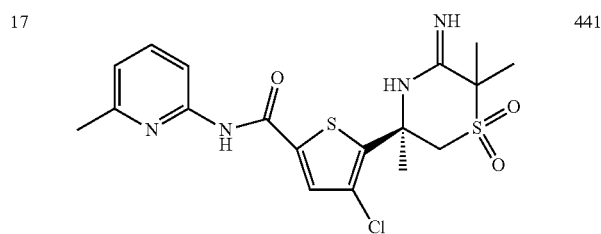 | | 441 | | | |

TABLE 4-1-continued
| Example no. | Example | Expected M + H | Observed M + H | $t_R$ (min) | LCMS method | BACE1 $K_i$ (nM) |
|---|---|---|---|---|---|---|
| 18 | 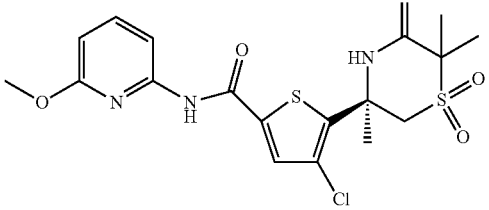 | 457 | 457 | 0.91 | D | 111.5 |
| 19 | 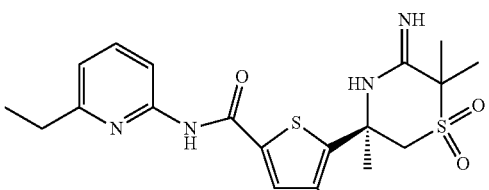 | 455 | 455 | 1.71 | E | 134.4 |
| 20 | 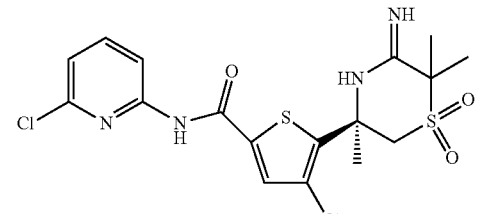 | 461 | 461 | 0.94 | D | 26.9 |
| 21 | 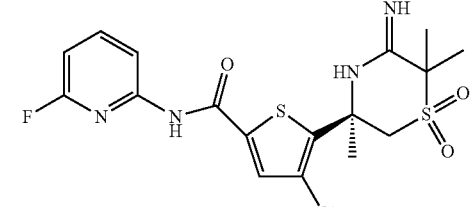 | 445 | 445 | 0.88 | D | 265.2 |
| 22 | 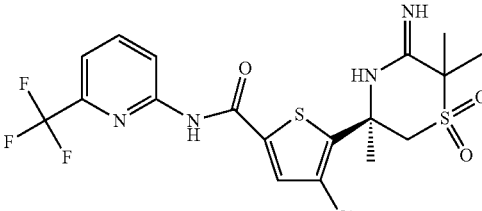 | 495 | 495 | 1.03 | D | 175 |
Method 4A
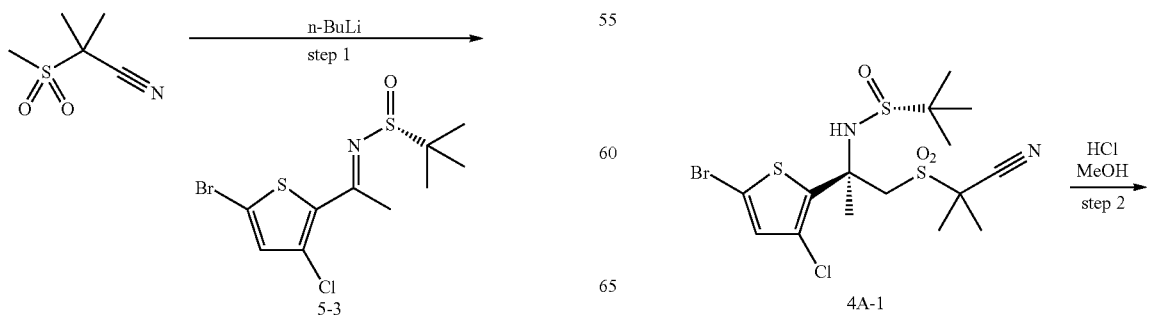

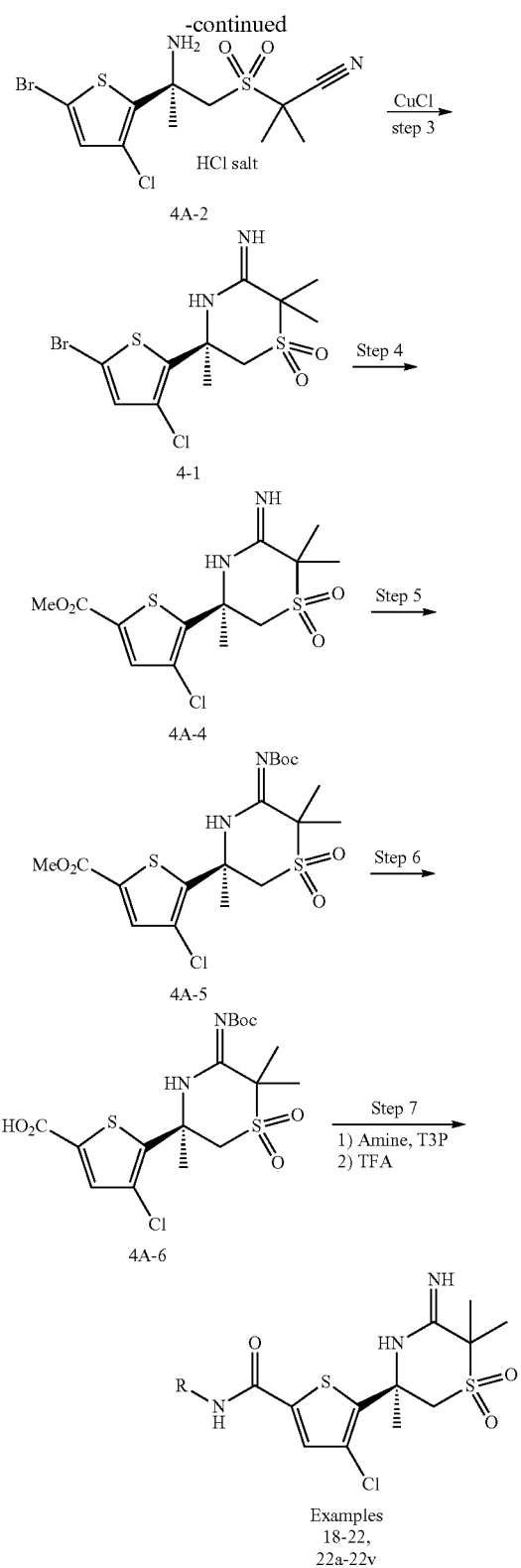

Step 1: To a stirred solution of 4.30 g (29.2 mmol) of 2-methyl-2-(methylsulfonyl)-propanenitrile in 110 mL of tetrahydrofuran at −78° C. was added 11.7 mL (2.5 M in hexanes, 29.2 mmol) of butyllithium. After 30 minutes, a solution of the sulfinimine 5-3 (5.0 g, 14.6 mmol) in 40 mL of THF was added. The solution was stirred at −78° C. for additional 3 h, and quenched with 150 mL of diluted NH₄Cl solution. It was extracted with two 200 mL portions of dichloromethane. The combined organic extracts were concentrated; the residue was purified by silica gel chromatography and then SFC (4.6×250 mm OJ-H column, 10% isopropanol/CO₂, 250 g/min) to give compound 4A-1 (3.8 g, 53%). LCMS (conditions A): $t_R$=2.45 min, m/e=491 (M+H).

Step 2: A solution of 4.0 g (8.16 mmol) of 4A-1 in 130 mL of MeOH and 20 mL of 4 M HCl solution in dioxane was stirred at room temperature for 18 h. It was concentrated; the residue was triturated with ether and small volume of dichloromethane to give compound 4A-2 (3.3 g, 96%) as a HCl salt. LCMS (condition A): $t_R$=2.0 min, m/e=387 (M+H).

Step 3: A suspension of 3.28 g (7.77 mmol) of compound 4A-2 and 0.81 g (8.16 mmol) of Cu(I)Cl in 80 mL of ethanol was heated at reflux for 5 h. It was concentrated; the residue was diluted with 70 mL of 1N NaOH solution, and extracted with three 100 mL portions of dichloromethane. The combined organic extracts were concentrated; the residue was purified by flash chromatography (80 g of SiO₂: 0 to 4% MeOH in CH₂Cl₂ plus 1% NH₄OH) to give compound 4-1 (2.82 g, 94%). LCMS (conditions A): $t_R$=1.95 min, m/e=387 (M+H).

Step 4: To the bromide 4-1 (4.1 g, 10.6 mmol) in MeOH (41 mL) was added Pd(dppf)Cl₂ (0.87 g, 1.0 mmol) and sodium acetate (1.31 g, 15.9 mmol). The vessel was purged with nitrogen (3X) and then with CO (3X). The reaction was heated to 80° C. under 200 psi CO for 18 h with agitation at 1000 RPM. The reaction was cooled and concentrated in vacuo to provide 4A-4 that was carried on directly to the next step.

Step 5: To the ester 4A-4 from step 4 in DCM (37 mL) was added di-tert-butyldicarbonate (4.8 g, 22 mmol). The reaction was stirred at room temperature for 16 h. The reaction mixture was then filtered and concentrated in vacuo to provide a residue that was purified by silica gel chromatography (0 to 25% EtOAc/hex over 30 minutes) to provide 4A-5 (4.3 g, 84% from 4A-3).

Step 6: To the ester 4A-5 (4.1 g, 8.8 mmol) in THF (29 mL) was added aqueous 2N LiOH (27 mL, 53 mmol). The reaction was stirred at room temperature for 18 h. The reaction was neutralized with 0.1 N HCl and then extracted with EtOAc. The combined organics were washed with water and brine, dried (MgSO₄), filtered, and concentrated in vacuo to provide the acid 4A-6 (3.5 g, 88%).

Step 7: Parallel preparation of Examples 18-22, 22a-22v: To 1-dram vials was added the requisite amine monomer and a stir bar. A solution of compound 4A-6 (33 mg, 0.073 mmol), T3P (61.0 μl, 0.102 mmol) and DIEA (38.3 μl, 0.220 mmol) in DCM (1.0 mL) was then added to each vial. The vials were capped and the reactions were stirred at RT overnight. After that time, water (50 μL) was added to each vial followed by TFA (500 μl, 6.49 mmol) and the vials were stirred at RT for 2 hours. The stir bars were removed from the vials. The solvent was removed in vacuo (at maximum temperature of 40° C.). Each product was re-dissolved in 1 mL of DMSO and filtered. The crude products were purified by mass triggered HPLC [Waters Sunfire C18, 5 μm, 19×100 mm using a range of gradients of 8-10% initial to 22-42% final MeCN (0.1% formic acid) in water (0.1% formic acid) 50 mL/min, 8 min run time] to provide Examples 18-22, 22a-22v.

Note: Examples 22 and 22v were re-purified by mass triggered HPLC [Waters XBridge C18 column, 5 μm, 30×100 mm, gradient ranges from 8-15% initial to 42-60% MeCN (0.1% NH₄OH) in water (0.1% NH₄OH) 25 mL/min, 8 min run] to provide Examples 22 and 22v.

TABLE 4A-1

Data for Examples 22a–22v

| Example no. | Example | Expected M + H | Observed M + H | $t_R$ (min) | LCMS method | BACE1 $K_i$ (nM) |
|---|---|---|---|---|---|---|
| 22a | | 475 | 475 | 0.81 | D | 1404 |
| 22b | | 442 | 442 | 0.63 | D | 3515 |
| 22c | | 455 | 455 | 0.76 | D | 7883 |
| 22d | | 491 | 491 | 0.76 | D | 4634 |
| 22e | | 456 | 456 | 0.64 | D | 758.7 |
| 22f | | 447 | 447 | 0.66 | D | 615.9 |

TABLE 4A-1-continued

Data for Examples 22a–22v

| Example no. | Example | Expected M + H | Observed M + H | $t_R$ (min) | LCMS method | BACE1 $K_i$ (nM) |
|---|---|---|---|---|---|---|
| 22g | | 507 | 507 | 0.86 | D | 735.9 |
| 22h | | 474 | 474 | 0.93 | D | 1620 |
| 22i | | 458 | 458 | 0.88 | D | 1161 |
| 22j | | 458 | 458 | 0.88 | D | 753 |
| 22k | | 474 | 474 | 0.94 | D | 863.1 |
| 22l | | 474 | 474 | 0.94 | D | 1271 |

TABLE 4A-1-continued

Data for Examples 22a–22v

| Example no. | Example | Expected M + H | Observed M + H | $t_R$ (min) | LCMS method | BACE1 $K_i$ (nM) |
|---|---|---|---|---|---|---|
| 22m | | 465 | 465 | 0.81 | D | 1032 |
| 22n | | 418 | 418 | 0.87 | D | 917 |
| 22o | | 493 | 493 | 0.85 | D | 1176 |
| 22p | | 509 | 509 | 0.87 | D | 1800 |
| 22q | | 431 | 431 | 0.68 | D | 358.6 |
| 22r | | 448 | 448 | 0.72 | D | 185.6 |

TABLE 4A-1-continued

Data for Examples 22a–22v

| Example no. | Example | Expected M + H | Observed M + H | $t_R$ (min) | LCMS method | BACE1 $K_i$ (nM) |
|---|---|---|---|---|---|---|
| 22s | | 480 | 480 | 0.75 | D | 127.5 |
| 22t | | 442 | 442 | 0.62 | D | 3128 |
| 22u | | 475 | 475 | 0.80 | D | 2723 |
| 22v | | 447 | 447 | 0.73 | D | 291.8 |

Method 5

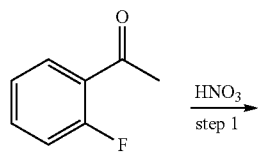

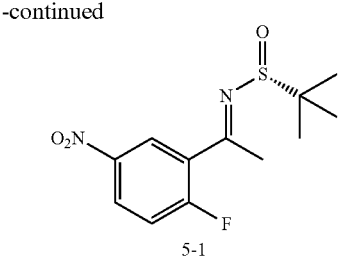

Step 1: To a mechanically stirred slurry of conc. $H_2SO_4$ (93-98%, 360 mL) at −42° C. were added dropwise 1-(2-fluorophenyl)ethanone (90.0 g, 652 mmol) and a solution of fuming nitric acid (53.1 mL) in conc. $H_2SO_4$ (129 mL). The slurry was stirred for 30 min at −42° C. The mixture was slowly poured onto 1.3 kg of ice. To the mixture was added water (1 L). The product precipitated out of solution. After all of the ice melted, the product was collected via filtration. The solid was dissolved with EtOAc. The organic layer was washed with 5% aq. $Na_2CO_3$ (2×300 mL), water (1×300 mL), and brine (1×300 mL), dried over $Na_2SO_4$, and filtered. The filtrate was concentrated to give 1-(2-fluoro-5-nitrophenyl)ethanone (115 g, 97%) as a yellow solid.

Step 2: To a solution of 1-(2-fluoro-5-nitrophenyl)ethanone (115 g, 628 mmol) in THF (900 mL) was added (R)-(+)-2-methyl-2-propanesulfinamide (87.7 g, 691 mmol) and $Ti(OEt)_4$ (315 g, 1.38 mole). The solution was heated at reflux for 20 h, cooled to RT, and poured onto ice (3 kg). The mixture was stirred for 20 min and then filtered. The organic layer of the filtrate was washed with brine, dried over $Na_2SO_4$, filtered, and concentrated. The residue was purified by flash chromatography ($SiO_2$, 15% EtOAc in hexanes) to give compound 5-1 (154 g, 86%). LCMS for 5-1 (conditions A): $t_R$=2.26 min, m/e=287 (M+H).

The ketimines in Table 5-1 were prepared from the requisite ketones according to the procedures outlined in Method 5, step 2. The ketones were commercially available unless otherwise specified. For ketimines 5-6 and 5-7, (S)-(−)-2-methyl-2-propanesulfinamide was used instead of its (R)-(+) enantiomer in Step 2.

TABLE 5-1

| Entry | Ketone | Ketimine |
|---|---|---|
| 1 | 5A-1 | 5-2 |
| 2 | 5A-1 | 5-3 |
| 3 |  | 5-4 |
| 4 |  | 5-5 |

TABLE 5-1-continued

| Entry | Ketone | Ketimine |
|---|---|---|
| 5 | | 5-6 |
| 6 | | 5-7 |
| 7 | 5B-2 | 5-8 |
| 8 | | 5-9 |
| 9 | | 5-10 |
| 10 | | 5-11 |

TABLE 5-1-continued

| Entry | Ketone | Ketimine |
|---|---|---|
| 11 | 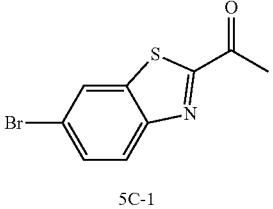<br>5C-1 | 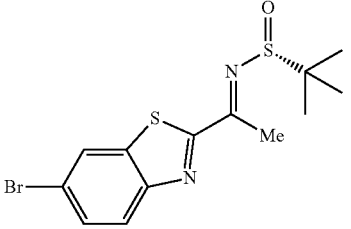 [SMILES: C/C(=N\[S@](=O)C(C)(C)C)c1nc2ccc(Br)cc2s1]<br>5-12 |
| 12 | 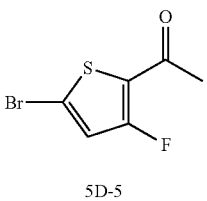<br>5D-5 | 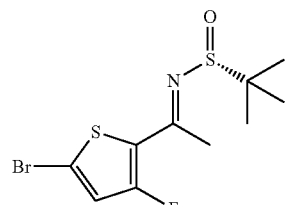<br>5-13 |
| 13 | 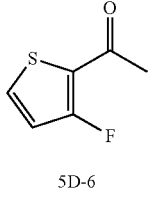<br>5D-6 | 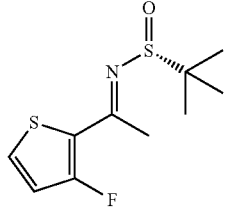<br>5-14 |

Method 5A 1-(5-Bromo-3-chlorothiophen-2-yl)ethanone 5A-1 was prepared from 5-bromo-3-chlorothiophene-2-carboxylic acid (available from e.g. S, Nomura, et al., WO2005012326, p. 163) by methods known to those skilled in the art, for example by reaction first with N-methyl-N-methoxyamine hydrochloride and EDCI followed after isolation by reaction with methylmagnesium bromide.

Additional details for the preparation of both 1-(5-bromo-3-chlorothiophen-2-yl)ethanone and 5-bromo-3-chlorothiophene-2-carboxylic acid are provided below:

To a solution of methyl 3-chlorothiophene-2-carboxylate (50 g, 0.28 mol) in MeOH (100 mL) was added a solution of aq. NaOH (2M) (400 mL) dropwise at 0° C. The resulting mixture was stirred at RT for 2 h. After removing MeOH, the aqueous was washed with ether and acidified with 2 N HCl. The solid formed was collected by filtration and dried to give 45 g of 3-chlorothiophene-2-carboxylic acid in 98% yield. MS (M+H⁺): 163.

To a solution of DIPA (26.3 g, 0.26 mol) in 400 mL of dry THF was added a solution of n-BuLi (104 mL, 0.26 mol, 2.5M in n-hexane) at −78° C. under nitrogen. After the addition was completed, the mixture was stirred for 1 h and then warmed to 0° C. and stirred for 30 mins. To above LDA solution was added a solution of 3-chlorothiophene-2-carboxylic acid (21 g, 0.13 mol) in THF (50 mL) at −78° C. After stirring for 1 h, a solution of 1,2-dibromo-ethane (48.9 g, 0.26 mmol) in THF (50 mL) was added at −78° C. The mixture was stirred at −78° C. for 1.5 h and slowly warm to RT. The mixture was poured into aq. HCl solution, and then extracted with EtOAc. The combined extracts were dried over $Na_2SO_4$, concentrated to give 25 g of 5-bromo-3-chlorothiophene-2-carboxylic acid in 80% yield. MS (M+H⁺): 241, 243. ¹H NMR (400 MHz, DMSO-d6): δ 7.50 (s, 1 H).

To a solution of compound 3 (50 g, 0.21 mol) in pyridine (500 mL) was added N,O-dimethylhydroxylamine hydrochloride (40.4 g, 0.42 mol) and EDCI (87 g, 0.42 mol) at 0° C. The mixture was stirred at RT overnight, concentrated and purified by silica gel chromatography to give 35 g of compound 4 in 60% yield. MS (M+H⁺): 284, 286. ¹H NMR (400 MHz, CDCl₃): δ 6.98 (s, 1 H), 3.70 (s, 3 H), 3.31 (s, 3 H).

To a stirred solution of 5-bromo-3-chloro-N-methoxy-N-methylthiophene-2-carboxamide (1 g, 3.5 mmol) in THF (10 mL) was added MeMgBr (1.1 mL, 3.5 mmol) under N₂ at RT. The mixture was stirred at RT for 0.5 h and quenched by aqueous NH₄Cl. The resulting solution was extracted with EtOAc. The organic layers were dried over Na₂SO₄, concentrated and purified by silica gel chromatography to give 0.6 g of 1-(5-bromo-3-chlorothiophen-2-yl)ethanone in 75% yield. MS (M+H⁺): 239, 241. ¹H NMR (400 MHz, CDCl₃): δ 6.95 (s, 1 H), 2.57 (s, 3 H).

Method 5B

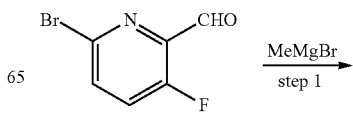

-continued

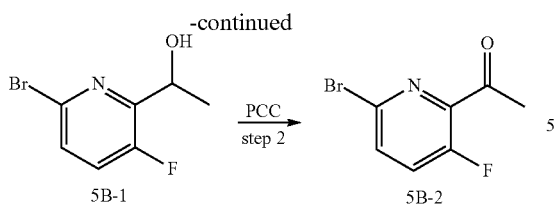

Step 1: To a stirred solution of 6-bromo-3-fluoropicolin-aldehyde (10.0 g, 49 mmol) in 200 mL of THF was added 18.0 mL of MeMgBr (3.0M in ether, 54 mmol) at −78° C. dropwise over a period of 35 min. The reaction was stirred at −78° C. for 3 hrs, then warmed up to 0° C. and stirred at 0° C. for additional 1 hr. The mixture was quenched with 150 mL of saturated aq. NH$_4$Cl at 0° C. and extracted with three 200 mL portions of EtOAc. The combined organic extracts were concentrated; the residue was purified by flash chromatography (220 g of SiO$_2$: 0 to 30% EtOAc in hexane) to give compound 5B-1 (9.41 g, 87%). LCMS (conditions A): $t_R$=1.91 min, m/e=220 (M+H).

Step 2: To a solution of 8.74 g (39.7 mmol) of compound 5B-1 in 175 mL of CH$_2$Cl$_2$ at room temperature were added 21.4 g (99.0 mmol) of pyridinium chlorochromate and 7.50 g of Celite. The reaction mixture was stirred at room temperature for 25 h and then filtered through Celite and washed with CH$_2$Cl$_2$. The CH$_2$Cl$_2$ filtrate was concentrated; the residue was purified by flash chromatography (220 g of SiO$_2$: 0 to 10% EtOAc in hexane) to give compound 5B-2 (6.82 g, 79%). LCMS (conditions A): $t_R$=2.11 min, m/e=218 (M+H).

Method 5C

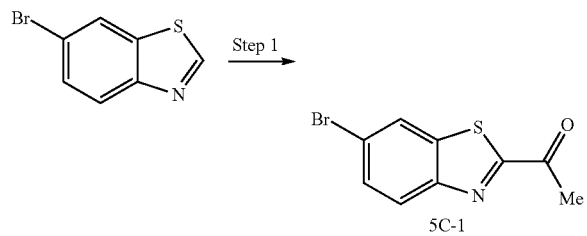

To 6-bromobenzo[d]thiazole (0.85 g, 3.9 mmol) in THF (16 mL) at −78° C. was added n-butyllithium (2.5 M, 1.7 mL, 4.2 mmol). The reaction was stirred for 1 h at −78° C. and then N-methoxy-N-methylacetamide (0.41 g, 3.9 mmol) was added. The reaction was stirred at −78° C. for 30 minutes and then quenched with saturated aqueous NH$_4$Cl. The reaction was warmed to room temperature and extracted with EtOAc. The combined organic layers were washed with water and brine, dried (MgSO$_4$), filtered, and concentrated in vacuo. The residue was purified by silica gel chromatography (0 to 4% EtOAc/hex) to provide the methyl ketone 5C-1 (0.77 g, 76%).

Method 5D

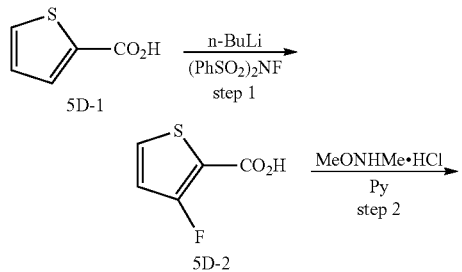

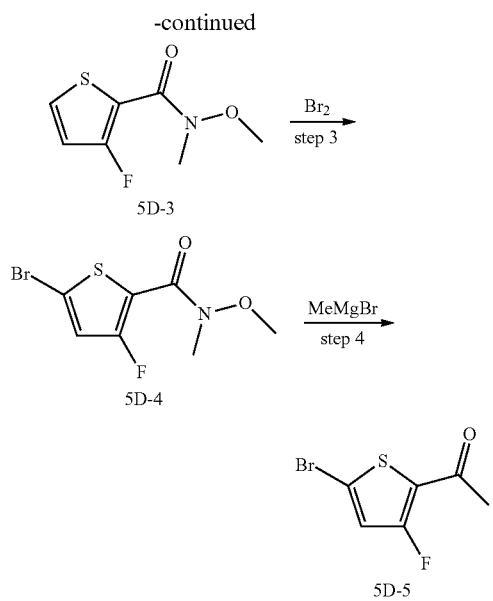

Step 1: To a solution of compound 5D-1 (17 g, 133 mmol) in THF (300 mL) cooled to −78° C. was added n-BuLi (120 mL, 293 mmol, 2.5 M in hexane), and the mixture was stirred for 30 min at −78° C. A solution of N-fluorobenze-nesulfonimide (50 g, 159 mmol) in THF (300 mL) was added and the resulting solution was stirred at −78° C. for 4 h and allowed to warm to ambient temperature overnight. The reaction was quenched with 1 N HCl (150 mL) and then extracted with EtOAc. The combined extracts were dried over Na$_2$SO$_4$, concentrated and purified by silica gel chromatography (PE:EtOAc=3:1) to afford compound 5D-2 (18 g). $^1$H NMR (CDCl$_3$): 10.7 (s, 1 H), 7.53 (dd, J=5.4, 3.6 Hz, 1 H), 6.89 (d, J=5.4 Hz, 1 H).

Step 2: To a solution of compound 5D-2 (18 g) in pyridine (150 mL) was added EDCI (53.1 g, 277 mmol) and O,N-dimethylhydroxylamine hydrochloride (27 g, 277 mmol) at 0° C., and then the mixture was stirred at RT overnight. The mixture was concentrated. The residue was dissolved in EtOAc and washed with water, dried over Na$_2$SO$_4$, concentrated and purified by silica gel chromatography (PE:E-tOAc=20:1) to afford compound 5D-3 (18 g).

Step 3: To a solution of compound 5D-3 (18 g) in AcOH/H$_2$O (1:1, 150 mL) at 0° C. was added Br$_2$ (45 g, 281 mmol). The mixture was slowly warmed to ambient temperature and stirred overnight. The reaction was quenched by water and extracted with EtOAc. The combined extracts were washed with water, concentrated and purified by silica gel chromatography (PE:EtOAc=30:1) to afford compound 5D-4 (16 g, contain 50%). $^1$H NMR (CDCl$_3$): 6.85 (s, 1 H), 3.71 (s, 3 H), 3.27 (s, 3 H).

Step 4: To a solution of compound 5D-4 (16 g) in THF (150 mL) cooled to 0° C. under N$_2$ was added a solution of MeMgBr (60 mL, 3M in ether). The mixture was stirred for 1 h and quenched by water and aqueous NH$_4$Cl. The resulting solution was extracted with EtOAc. The organic layers were dried over Na$_2$SO$_4$, concentrated and purified by silica gel chromatography (PE:EA=50:1) to afford compound 5D-5 (4 g). $^1$H NMR (CDCl$_3$): 6.90 (s, 1 H), 2.53 (s, 3 H).

By methods analogous to those described in Method 5D, but omitting Step 3, thiophene-2-carboxylic acid was converted to 1-(5-bromo-3-fluorothiophen-2-yl)ethanone 5D-6.

Method 6

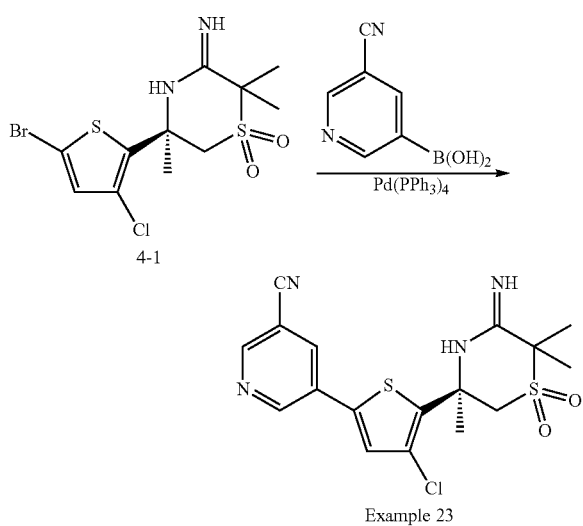

4-1

Example 23

Following the procedures described in step 4 of Method 3, compound 4-1 was converted to Examples 23 and Example 27a by using the appropriate boronic acid. Examples 24-27 can be prepared in an analogous way.

Alternatively, Examples 24-27 were prepared according to Method 6A, applying Method 3, Step 5 in addition to produce Example 27. Examples 27a-27d were formed in an analogous manner using similar procedures to Methods 6 and 6A with the appropriate boronic acids or boronate esters.

Additional details for preparation of Example 23: A mixture of 0.10 g (0.259 mmol) of compound 4-1, 0.089 g (0.389 mmol) of 3-cyanopyridylboronic acid, 0.03 g (0.026 mmol) of $Pd(PPh_3)_4$ and 0.20 mL (0.40 mmol) of 2M aq. $Na_2CO_3$ solution in 2 mL EtOH and 2 mL toluene was heated at reflux for 7 hrs and then concentrated. The residue was purified by flash chromatography (12 g of $SiO_2$: 0 to 6% MeOH in $CH_2Cl_2$ plus 1% $NH_4OH$) to give Example 23. (94 mg, 73%). LCMS (conditions A): $t_R$=1.92 min, m/e=409 (M+H).

TABLE 6-1

| | Data for Examples 23-27, 27a -27d. | | | | | |
|---|---|---|---|---|---|---|
| Ex. no. | Example | Observed M + H | Expected M + H | $t_R$ (min) | LCMS cond. | BACE1 $K_i$ (nM) |
| 23 | | 409 | 409 | 1.92 | A | 63 |
| 24 | | 385.1 | 385 | 0.69 | D | 387 |
| 25 | | 422.1 | 422 | 0.95 | D | 13.4 |

TABLE 6-1-continued

Data for Examples 23-27, 27a -27d.

| Ex. no. | Example | Observed M + H | Expected M + H | t_R (min) | LCMS cond. | BACE1 K_i (nM) |
|---|---|---|---|---|---|---|
| 26 | (structure) | 414.1 | 414 | 0.83 | D | 349.3 |
| 27 | (structure) | 430.1 | 430 | 0.87 | D | 11.2 |
| 27a | (structure) | 469 | 469 | 2.20 | A | 172 |
| 27b | (structure) | 451 | 451 | 1.97 | A | 8.2 |
| 27c | (structure) | 450 | 450 | 2.04 | A | 12.8 |
| 27d | (structure) | 450 | 450 | 1.62 | A | 64.3 |

Notes for Table 6-1: (1) For Example 27b, boronate ester 16-2 was used. (2) For Example 27c, boronate ester 16-4 was used. (3) For Example 27d, boronate ester 16-6 was used.

Method 6A.

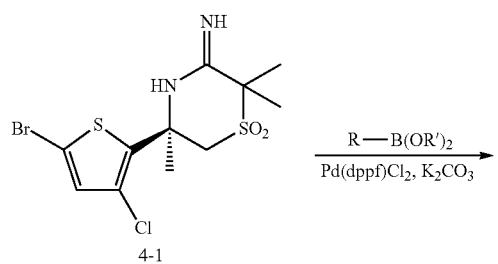

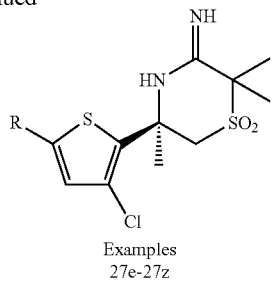

Examples 27e-27z

Parallel preparation of Examples 27e-27z: To mixtures of reactant 4-1 (20 mg, 0.052 mmol), boronic acid or pinocol ester (1.3 equiv.), and [1,1'-bis(diphenylphosphino)ferrocene]-dichloropalladium(10 (7.59 mg, 10.4 mop in 1,4-dioxane (2 mL) was added potassium carbonate (21.50 mg, 0.156 mmol) in water (0.16 mL). Reactions were carried out at 120° C. for 20 minutes under microwave reaction conditions. Water (2 mL) and EtOAc (2 mL) were added and the mixture stirred for 10 minutes. The organic layers were separated and concentrated. Each crude product was re-dissolved in 1 mL of DMSO and filtered. The crude products were purified by mass triggered HPLC (Waters XBridge C18 column, 5 μm, 30×100 mm, using gradient ranges from 10-30% initial to 30-80% final MeCN (0.1% $NH_4OH$) in water (0.1% $NH_4OH$) to provide the Examples 27e-27z in Table 6A-1.

TABLE 6A-1

| Example no. | Structure | Expected M + H | Observed M + H | $t_R$ (min) | LCMS method | BACE1 $K_i$ (nM) |
|---|---|---|---|---|---|---|
| 27e | 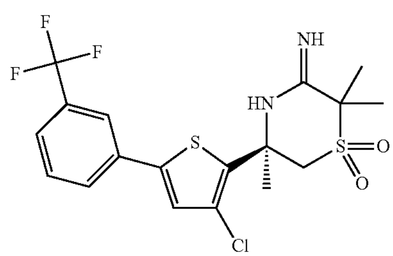 [SMILES: CC1(C)C(=N)N[C@](C)(c2sc(-c3cccc(C(F)(F)F)c3)cc2Cl)CS1(=O)=O] | 451 | 451.1 | 1.12 | D | 74.5 |
| 27f | 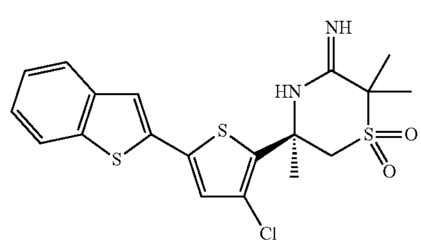 [SMILES: CC1(C)C(=N)N[C@](C)(c2sc(-c3cc4ccccc4s3)cc2Cl)CS1(=O)=O] | 439 | 439.1 | 1.16 | D | 1184.0 |
| 27g | 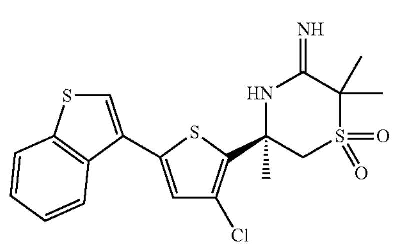 [SMILES: CC1(C)C(=N)N[C@](C)(c2sc(-c3csc4ccccc34)cc2Cl)CS1(=O)=O] | 439 | 439.1 | 1.13 | D | 2030.0 |

TABLE 6A-1-continued

| Example no. | Structure | Expected M + H | Observed M + H | $t_R$ (min) | LCMS method | BACE1 $K_i$ (nM) |
|---|---|---|---|---|---|---|
| 27h | 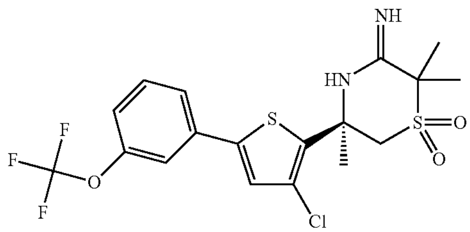 [SMILES: CC1(C)C(=N)N[C@](C)(c2sc(-c3cccc(OC(F)(F)F)c3)cc2Cl)CS1(=O)=O] | 467 | 467.1 | 1.15 | D | 70.9 |
| 27i | 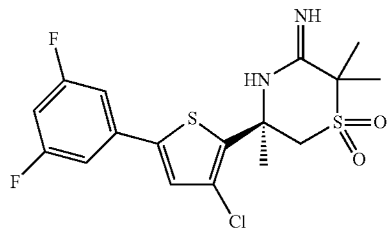 [SMILES: CC1(C)C(=N)N[C@](C)(c2sc(-c3cc(F)cc(F)c3)cc2Cl)CS1(=O)=O] | 419 | 419.1 | 1.06 | D | 170.5 |
| 27j | 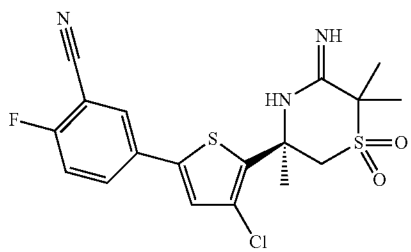 [SMILES: CC1(C)C(=N)N[C@](C)(c2sc(-c3ccc(F)c(C#N)c3)cc2Cl)CS1(=O)=O] | 426 | 426.1 | 0.97 | D | 5146.0 |
| 27k | 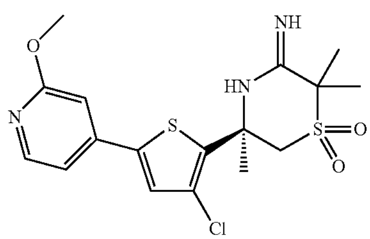 [SMILES: COc1cc(-c2cc(Cl)c([C@]3(C)CS(=O)(=O)C(C)(C)C(=N)N3)s2)ccn1] | 414 | 414.1 | 0.92 | D | 926.0 |
| 27l | 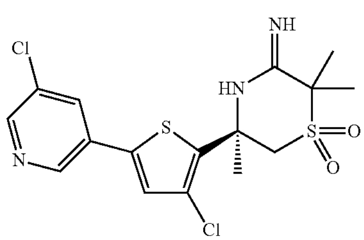 [SMILES: CC1(C)C(=N)N[C@](C)(c2sc(-c3cncc(Cl)c3)cc2Cl)CS1(=O)=O] | 418 | 418.1 | 0.93 | D | 92.2 |
| 27m | 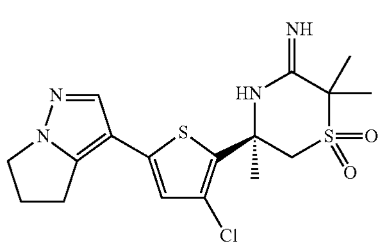 [SMILES: CC1(C)C(=N)N[C@](C)(c2sc(-c3cnn4c3CCC4)cc2Cl)CS1(=O)=O] | 413 | 413.1 | 0.80 | D | 5339.0 |

TABLE 6A-1-continued

| Example no. | Structure | Expected M + H | Observed M + H | $t_R$ (min) | LCMS method | BACE1 $K_i$ (nM) |
|---|---|---|---|---|---|---|
| 27n | 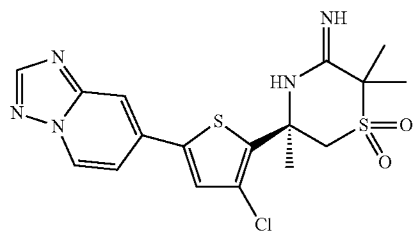 [SMILES: CC1(C)C(=N)N[C@](C)(c2sc(-c3ccn4ncnc4c3)cc2Cl)CS1(=O)=O] | 424 | 424.1 | 0.73 | D | 272.9 |
| 27o | 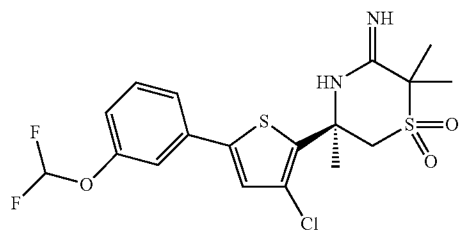 [SMILES: CC1(C)C(=N)N[C@](C)(c2sc(-c3cccc(OC(F)F)c3)cc2Cl)CS1(=O)=O] | 449 | 449.1 | 1.04 | D | 66.6 |
| 27p | 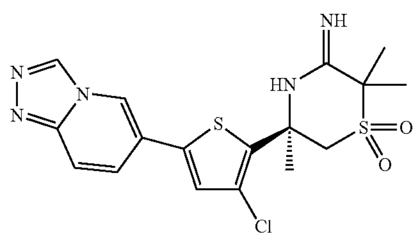 [SMILES: CC1(C)C(=N)N[C@](C)(c2sc(-c3ccc4nncn4c3)cc2Cl)CS1(=O)=O] | 424 | 424.1 | 0.67 | D | 2533.0 |
| 27q | 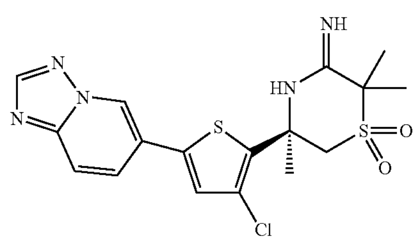 [SMILES: CC1(C)C(=N)N[C@](C)(c2sc(-c3ccc4ncnn4c3)cc2Cl)CS1(=O)=O] | 424 | 424.1 | 0.74 | D | 296.7 |
| 27r | 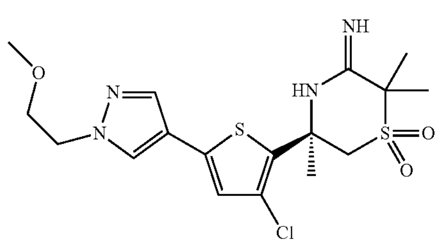 [SMILES: COCCn1cc(-c2cc(Cl)c([C@]3(C)CS(=O)(=O)C(C)(C)C(=N)N3)s2)cn1] | 431 | 431.1 | 0.79 | D | 448.1 |
| 27s | 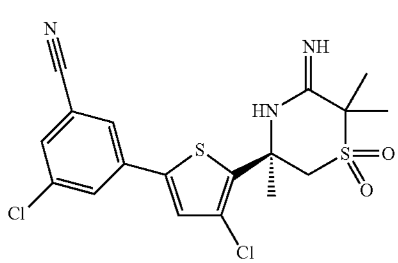 [SMILES: CC1(C)C(=N)N[C@](C)(c2sc(-c3cc(Cl)cc(C#N)c3)cc2Cl)CS1(=O)=O] | 442 | 442.1 | 1.05 | D | 64.9 |

TABLE 6A-1-continued
| Example no. | Structure | Expected M + H | Observed M + H | $t_R$ (min) | LCMS method | BACE1 $K_i$ (nM) |
|---|---|---|---|---|---|---|
| 27t | 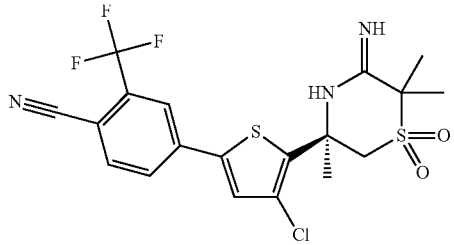 [SMILES: CC1(C)C(=N)N[C@](C)(c2sc(-c3ccc(C#N)c(C(F)(F)F)c3)cc2Cl)CS1(=O)=O] | 476 | 476.1 | 1.05 | D | 291.2 |
| 27u | 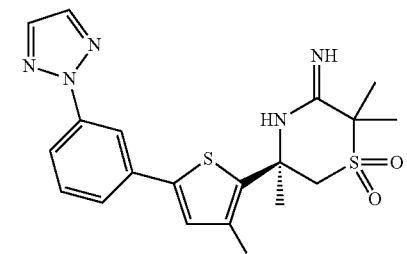 | 450 | 450.2 | 1.03 | D | 49.2 |
| 27v | 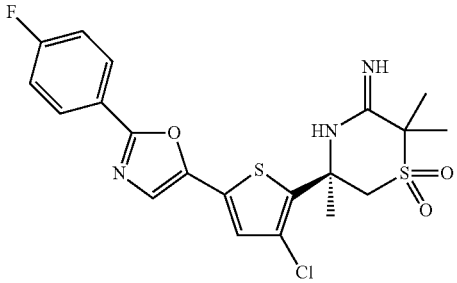 [SMILES: CC1(C)C(=N)N[C@](C)(c2sc(-c3cnc(-c4ccc(F)cc4)o3)cc2Cl)CS1(=O)=O] | 468 | 468.1 | 1.06 | D | 71.4 |
| 27w | 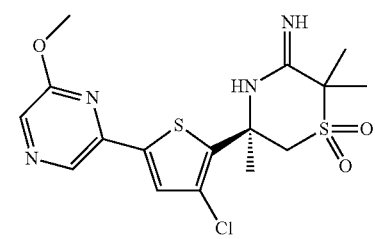 [SMILES: COc1cncc(-c2cc(Cl)c([C@]3(C)CS(=O)(=O)C(C)(C)C(=N)N3)s2)n1] | 415 | 415.1 | 0.89 | D | 1292.0 |
| 27x | 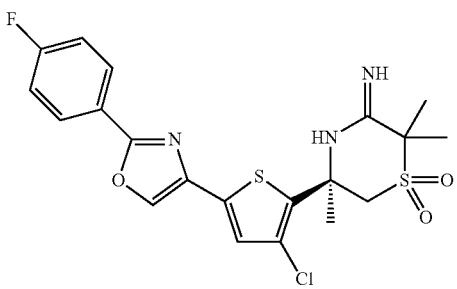 [SMILES: CC1(C)C(=N)N[C@](C)(c2sc(-c3coc(-c4ccc(F)cc4)n3)cc2Cl)CS1(=O)=O] | 468 | 468.1 | 1.09 | D | 1110.0 |
| 27y | 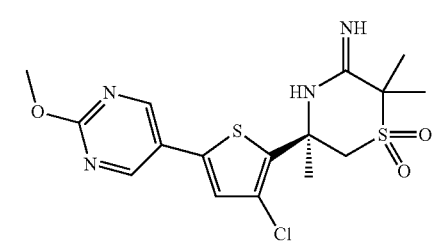 [SMILES: COc1ncc(-c2cc(Cl)c([C@]3(C)CS(=O)(=O)C(C)(C)C(=N)N3)s2)cn1] | 415 | 415.1 | 0.80 | D | 1717.0 |

TABLE 6A-1-continued

| Example no. | Structure | Expected M + H | Observed M + H | $t_R$ (min) | LCMS method | BACE1 $K_i$ (nM) |
|---|---|---|---|---|---|---|
| 27z | 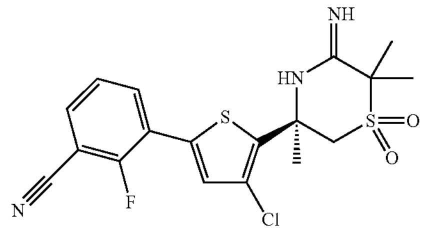 [SMILES: CC1(C)C(=N)N[C@](C)(c2sc(-c3cccc(C#N)c3F)cc2Cl)CS1(=O)=O] | 426 | 426.1 | 0.97 | D | 400.4 |

Method 6B

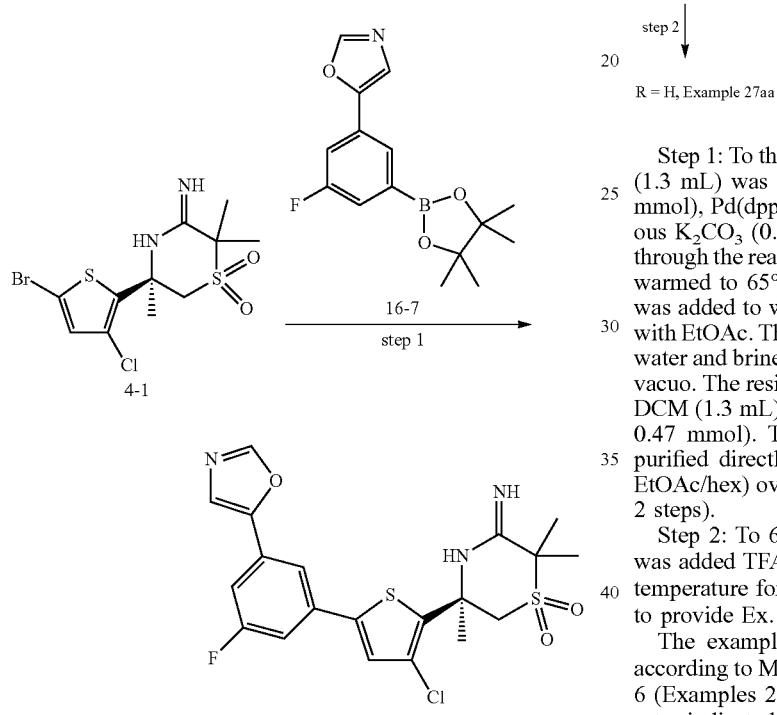

Step 1: To the bromide 4-1 (0.15 g, 0.39 mmol) in t-BuOH (1.3 mL) was added the boronate ester 16-7 (0.17 g, 0.58 mmol), Pd(dppf)Cl$_2$ (0.057 g, 0.078 mmol), and 2 M aqueous K$_2$CO$_3$ (0.029 mL, 0.58 mmol). Nitrogen was bubbled through the reaction mixture for 5 minutes. The reaction was warmed to 65° C. and stirred for 3 h. The cooled reaction was added to water and EtOAc. The mixture was extracted with EtOAc. The combined organic layers were washed with water and brine, dried (MgSO$_4$), filtered and concentrated in vacuo. The residue was carried on directly by taking up into DCM (1.3 mL) and adding di-tert-butyldicarbonate (0.10 g, 0.47 mmol). The reaction was stirred for 12 h and then purified directly by silica gel chromatography (0 to 40% EtOAc/hex) over 30 minutes to provide 6B-1 (0.19 g, 86%, 2 steps).

Step 2: To 6B-1 (0.19 g, 0.33 mmol) in DCM (1.5 mL) was added TFA (1.5 mL). The reaction was stirred at room temperature for 30 minutes and then concentrated in vacuo to provide Ex. 27aa (0.19 g, 99%) as the TFA salt.

The examples in Table 6B-1 were prepared from 4-1 according to Methods 6B (Examples 27aa-27 ad) or Method 6 (Examples 27ae-27ag) using the boronic acid or boronic ester indicated.

TABLE 6B-1

| Ex. no. | Boronic acid or boronate ester | Example | M + H Obs. (Exp.) | $t_R$ (min) | LCMS cond. | BACE1 $K_i$ (nM) |
|---|---|---|---|---|---|---|
| 27aa | 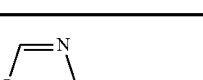 | 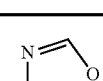 | 468.2 (468.0) | 1.86 | G | 26.1 |

TABLE 6B-1-continued
| Ex. no. | Boronic acid or boronate ester | Example | M + H Obs. (Exp.) | $t_R$ (min) | LCMS cond. | BACE1 $K_i$ (nM) |
|---|---|---|---|---|---|---|
| 27ab | 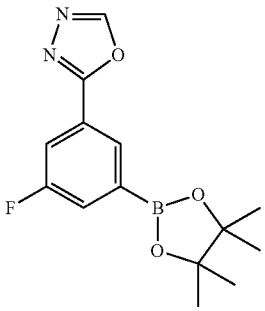 [SMILES: CC1(C)OB(c2cc(F)cc(-c3nnco3)c2)OC1(C)C] 16-1 | 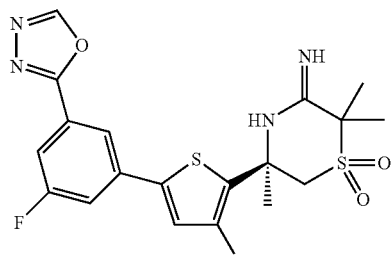 | 468.8 (469.0) | 1.52 | B | 15.4 |
| 27ac | 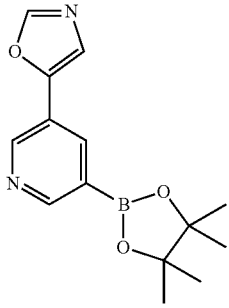 16-5 | 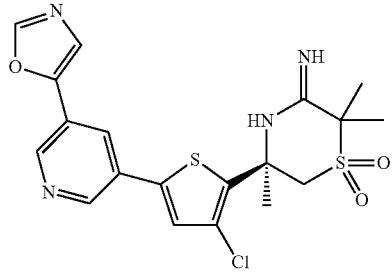 [SMILES: CC1(C)C(=N)N[C@](C)(c2sc(-c3cncc(-c4cnco4)c3)cc2Cl)CS1(=O)=O] | 451.0 (451.0) | 1.63 | G | 22.3 |
| 27ad | 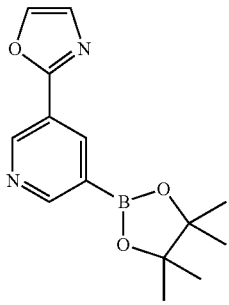 [SMILES: CC1(C)OB(c2cncc(-c3ncco3)c2)OC1(C)C] 16-3 | 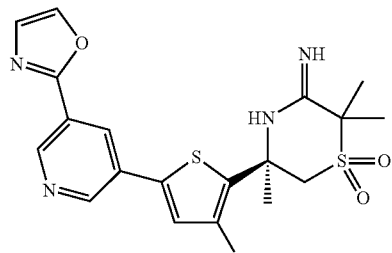 | 451.0 (451.0) | 1.68 | G | 44.4 |
| 27ae | 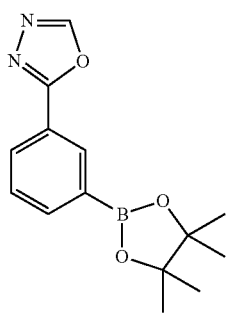 [SMILES: CC1(C)OB(c2cccc(-c3nnco3)c2)OC1(C)C] 16-2 | 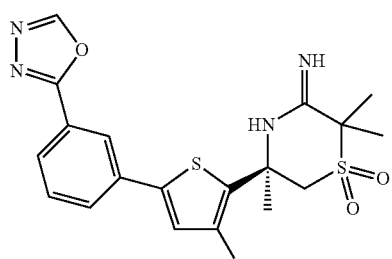 | 451 (451) | 1.97 | A | 8.2 |

TABLE 6B-1-continued

| Ex. no. | Boronic acid or boronate ester | Example | M + H Obs. (Exp.) | $t_R$ (min) | LCMS cond. | BACE1 $K_i$ (nM) |
|---|---|---|---|---|---|---|
| 27af | (structure) 16-4 | (structure) | 450 (450) | 2.04 | A | 12.8 |
| 27ag | (structure) 16-6 | (structure) | 450 (450) | 1.62 | A | 64.3 |

Method 6C

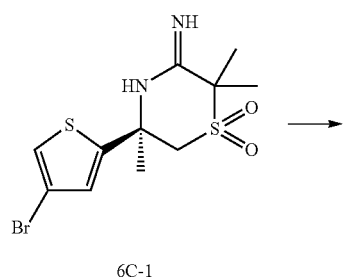

6C-1

→

Bromide 6C-1 was prepared by methods similar to those described in Method 2A, Steps 1-3, substituting ketimine 5-11 for ketimine 5-4 in Step 1 [LCMS for 6C-1 (conditions G) $t_R$=1.56 min, m/e=352.9 (M+H)]. To bromide 6C-1 (0.46 g, 1.3 mmol) in DCM (4.4 mL) was added di-tert-butyldicarbonate (0.43 g, 2.0 mmol). The reaction was stirred at room temperature for 12 h. The reaction was concentrated in vacuo and the residue was purified by silica gel chromatography (0 to 35% EtOAc/hexanes over 30 minutes) to provide bromide 6C-2 (0.48 g 81%).

The compounds in Table 6C-1 were prepared using methods similar to described in Method 6B by using the bromides and boronic acids or esters specified.

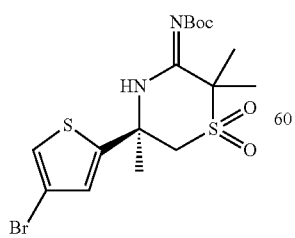

6C-2

TABLE 6C-1

| Ex. no. | Bromide | Boronic acid or boronate ester | Example | M + H Obs. (Exp.) | LCMS cond. ($t_R$ min) | BACE1 $K_i$ (nM) |
| --- | --- | --- | --- | --- | --- | --- |
| 27ah | 6C-2 | 16-2 | | 471.0 (417.0) | G (1.63) | 41.5 |
| 27ai | 6C-2 | 16-4 | | 416.0 (416.0) | G (1.72) | 74.0 |
| 27aj | 6C-2 | 16-6 | | 416.0 (416.0) | G (1.68) | 112.7 |
| 27ak | 6C-1 | 16-3 | | 417.0 (417.0) | G (1.54) | 128.4 |

TABLE 6C-1-continued
| Ex. no. | Bromide | Boronic acid or boronate ester | Example | M + H Obs. (Exp.) | LCMS cond. ($t_R$ min) | BACE1 $K_i$ (nM) |
|---|---|---|---|---|---|---|
| 27al | 6C-1 | (structure) | (structure) 16-5 | 417.0 (417.0) | G (1.47) | 93.8 |
| 27am | 6C-1 | (structure) | (structure) 16-7 | 434.0 (434.1) | G (1.79) | 80.6 |
Method 6D
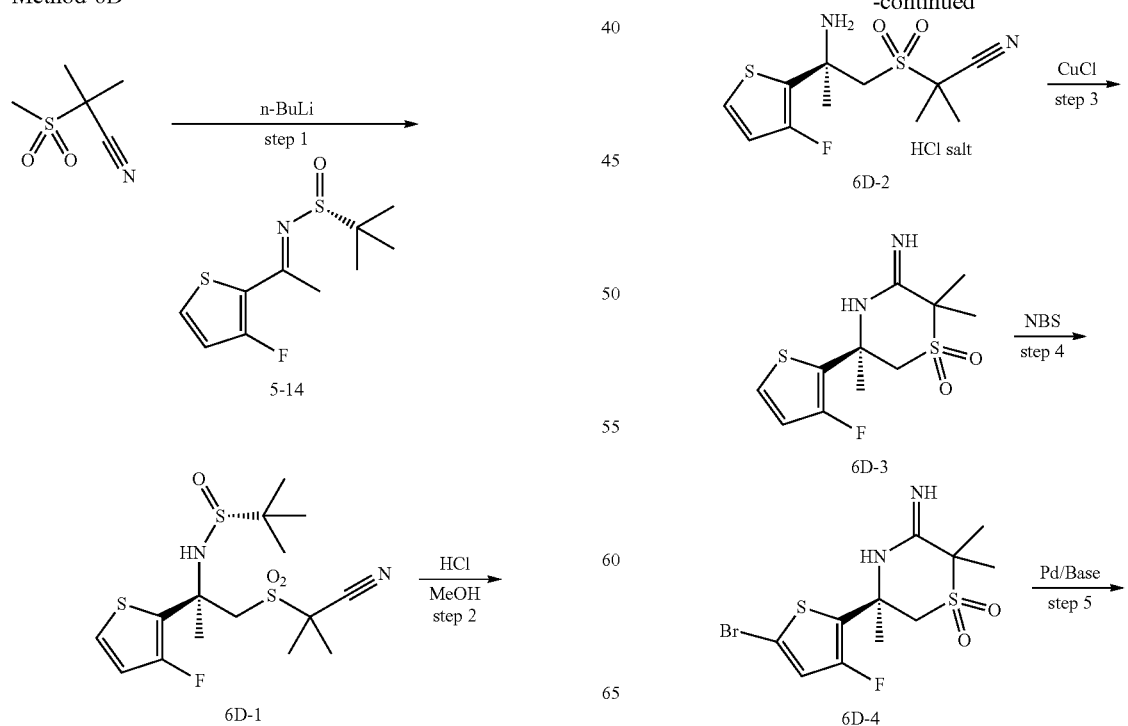

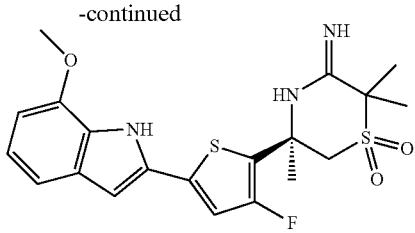

Example 27an

Step 1: To a stirred solution of 2-methyl-2-(methylsulfonyl)propanenitrile (10.71 g, 72.8 mmol) in THF (331 mL) at −78° C. was added n-butyllithium (2.5 M in hexanes, 29.1 mL, 72.8 mmol). After 30 minutes, a solution of the sulfinimine 5-14 (9.0 g, 36.4 mmol) in THF (33.1 mL) was added. The reaction mixture was stirred at −78° C. for additional 4 h, and quenched with saturated aqueous $NH_4Cl$. The organic layer was extracted with ethyl acetate (3×100 mL). The combined organic extracts were dried with magnesium sulfate, filtered, and concentrated under reduced pressure. The residue was purified by column chromatography eluting with 50% ethyl acetate in hexane to give compound 6D-1 (8.49 g, 21.5 mmol) as a single diastereomer. LCMS (conditions A): $t_R$=2.23 min, m/e=395 (M+H).

Step 2: To a stirred solution of compound 6D-1 (8.49 g, 21.5 mmol) in methanol (143 mL) was added HCl (4 M in dioxane, 25 mL, 100 mmol). The solution was stirred at room temperature for 16 h. The mixture was concentrated under reduced pressure and ether (25 mL) added. The precipitate was filtered and washed with ether (2×10 mL) to give 6D-2 (6.82 g, 20.87 mmol) as an HCl salt. LCMS (conditions A): $t_R$=1.71 min, m/e=291 (M+H).

Step 3: To a stirred solution of compound 6D-2 (6.82 g, 20.9 mmol) in EtOH (104 mL) was added Cu(I)Cl (2.17 g, 21.9 mmol). The solution was stirred at 80° C. for 5 h. The reaction was concentrated and diluted with 50 mL of 1N NaOH. The aqueous layer was extracted with dichloromethane (3×100 mL). The combined organic layers were dried with magnesium sulfate, filtered, and concentrated under reduced pressure. The residue was purified by column chromatography (0 to 5% MeOH in DCM with 0.1% $NH_4OH$) eluting at 3% MeOH in DCM. The combined fractions were concentrated under reduced pressure to afford 6D-3 (5.03, 17.3 mmol). LCMS (conditions A): $t_R$=1.62 min, m/e=291 (M+H).

Step 4: To a stirred solution of compound 6D-3 (5.56 g, 19.2 mmol) in DMF (77 mL) was added NBS (3.75 g, 21.1 mmol). The solution was stirred at 50° C. for 16 h. Another portion of NBS (3.75 g, 21.1 mmol) was added to the reaction mixture and stirred 50° C. for another 16 h. The reaction mixture was cooled to room temperature and diluted with ethyl acetate (250 mL). The organic layer was washed with water (3×100 mL). The organic layer was dried with magnesium sulfate, filtered, and concentrated under reduced pressure. The residue was purified by column chromatography eluting with 40% ethyl acetate in hexane. The combined fractions were concentrated to give compound 6D-4 (5.89 g, 16.0 mmol). LCMS (conditions A): $t_R$=1.95 min, m/e=371 (M+H).

Step 5: To a mixture of 7-methoxyindole-2-boronic acid pinacol ester (111 mg, 0.41 mmol), compound 6D-4 (100 mg, 0.27 mmol), $PdCl_2(dppf)$-$CH_2Cl_2$ adduct (22 mg, 0.03 mmol), and potassium carbonate (2 M in water, 0.34 mL, 0.68 mmol) was added dioxane (2.7 mL). The reaction mixture was sealed and purged with nitrogen by sub-surface bubbling for five minutes. The reaction mixture was heated to 100° C. for 16 h. The reaction was cooled to room temperature and diluted with saturated aq. sodium bicarbonate. The aqueous layer was extracted with ethyl acetate (3×25 mL). The combined organic layers were dried with magnesium sulfate, filtered, and concentrated under reduced pressure. The residue was purified by column chromatography eluting with 35% ethyl acetate in dichloromethane. The combined fractions were concentrated under reduced pressure to give Example 27an (31 mg, 0.070 mmol). LCMS (conditions A): $t_R$=2.15 min, m/e=436 (M+H).

The examples in Table 6D-1 were prepared from bromide 6D-4 using a procedure analogous to Method 6D, step 5 and utilizing the appropriate boronic acid or boronate ester. Where the entry in the column for boronic acid or boronate ester is blank, the reagent was commercial.

TABLE 6D-1

| Example no. | Boronic acid or boronate ester | Example | M + H Observed (Expected) | $t_R$ (min) | LCMS method | BACE1 $K_i$ (nM) |
| --- | --- | --- | --- | --- | --- | --- |
| 27an | | ![structure] | 436 (436) | 2.15 | A | 21 |
| 27ao | 16-9 | ![structure] | 435 (435) | 2.08 | A | 100 |

TABLE 6D-1-continued

| Example no. | Boronic acid or boronate ester | Example | M + H Observed (Expected) | $t_R$ (min) | LCMS method | BACE1 $K_i$ (nM) |
|---|---|---|---|---|---|---|
| 27ap | | | 393 (393) | 1.90 | A | 102 |
| 27aq | | | 392 (392) | 2.03 | A | 76 |
| 27ar | 16-2 | | 435 (435) | 1.96 | A | 11 |
| 27as | 16-1 | | 453 (453) | 2.00 | A | 9.4 |
| 27at | 16-7 | | 452 (452) | 2.08 | A | 26 |

TABLE 6D-1-continued
| Example no. | Boronic acid or boronate ester | Example | M + H Observed (Expected) | $t_R$ (min) | LCMS method | BACE1 $K_i$ (nM) |
|---|---|---|---|---|---|---|
| 27au | | 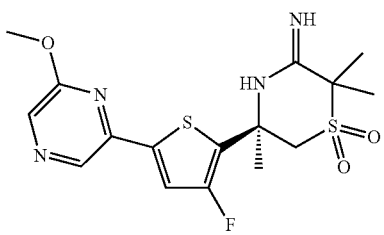 [SMILES: COc1cncc(-c2cc(F)c([C@]3(C)CS(=O)(=O)C(C)(C)C(=N)N3)s2)n1] | 399 (399) | 1.96 | A | 943 |
| 27av | | 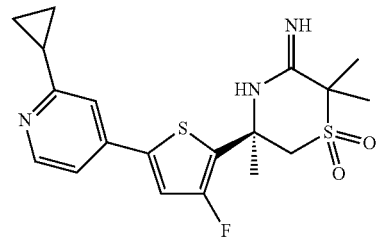 [SMILES: CC1(C)C(=N)N[C@](C)(c2sc(-c3ccnc(C4CC4)c3)cc2F)CS1(=O)=O] | 408 (408) | 1.72 | A | 663 |
| 27aw | 16-8 | 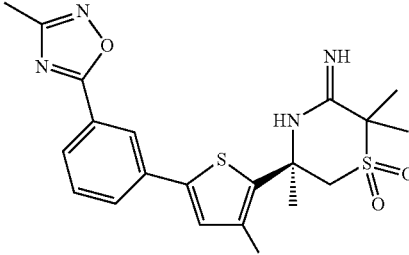 | 449 (449) | 1.86 | A | 125 |
| 27ax | 16B-1 | 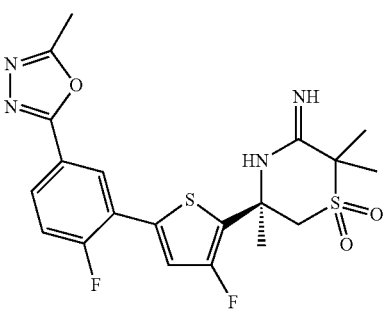 [SMILES: Cc1nnc(-c2ccc(F)c(-c3cc(F)c([C@]4(C)CS(=O)(=O)C(C)(C)C(=N)N4)s3)c2)o1] | 467 (467) | 1.79 | A | 858 |
| 27ay | | 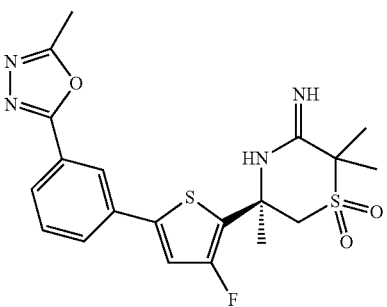 [SMILES: Cc1nnc(-c2cccc(-c3cc(F)c([C@]4(C)CS(=O)(=O)C(C)(C)C(=N)N4)s3)c2)o1] | 449 (449) | 1.79 | A | 480 |

TABLE 6D-1-continued

| Example no. | Boronic acid or boronate ester | Example | M + H Observed (Expected) | $t_R$ (min) | LCMS method | BACE1 $K_i$ (nM) |
|---|---|---|---|---|---|---|
| 27az | 16A-1 | 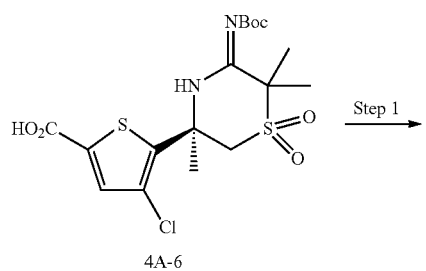 | 436 (436) | 1.29 | J | 14 |

Method 6E

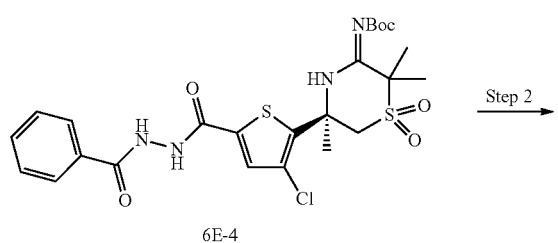

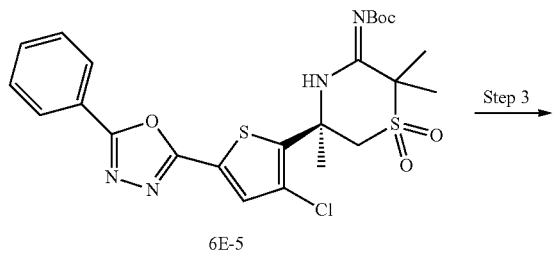

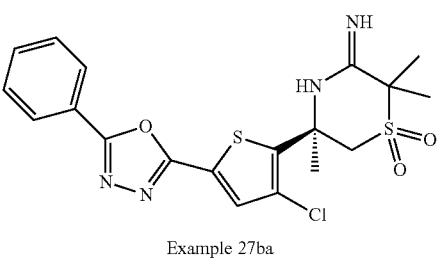

Example 27ba

Step 1: To the acid 4A-6 (0.15 g, 0.33 mmol) in EtOAc (1.1 mL) was added benzohydrazide (0.050 g, 0.37 mmol), TEA (0.14 mL, 1.0 mmol), and T3P (50% solution in EtOAc, 0.50 mL, 0.83 mmol). The mixture was stirred at room temperature for 18 h. Water was added and the mixture was stirred vigorously for 15 minutes. The mixture was then extracted with EtOAc. The combined organic layers were washed with water and brine, dried (MgSO$_4$), filtered, and concentrated in vacuo to provide 6E-4 which was used directly in the next step.

Step 2: To 6E-4 (0.19 g, 0.33 mmol) in THF (1.7 mL) was added Burgess reagent (0.20 g, 0.83 mmol). The mixture was heated to 65° C. and stirred for 1 h. The reaction was concentrated in vacuo. The residue was purified by silica gel chromatography (0 to 40% EtOAc/hex over 30 minutes) to provide 6E-5 (0.080 g, 44%).

Step 3: To 6E-5 (0.080 g, 0.15 mmol) in DCM (0.8 mL) was added TFA (0.8 mL).

The reaction was stirred at room temperature for 30 minutes and then concentrated in vacuo. The residue was purified using SFC (MeOH/CO$_2$) to provide Example 27ba (0.040 g, 59%).

The examples in Table 6E-1 were prepared from acid 6E-3 using procedures analogous to those in Method 6E, steps 4-6, and utilizing the appropriately substituted benzohydrazide in step 4. These examples were purified by reverse phase chromatography (Waters Sunfire C18, 5 μm, 19×100 mm, 50 mL/min, 12 min. run time, Mobile phase A=Water+ 0.1% formic acid, Mobile phase B=MeCN+0.1% formic acid, 10 to 50% B).

TABLE 6E-1

| Example Number | Example | M + H (Exp.) Obs. | $t_R$ min | LCMS method | BACE1 Ki (nM) |
|---|---|---|---|---|---|
| 27ba | | (451.1) 451.16 | 0.79 | H | 257.7 |
| 27bb | | (469.1) 469.13 | 0.81 | H | 102.3 |
| 27bc | | (485.1) 485.1 | 0.87 | H | 35.9 |
| 27bd | | (481.1) 481.1 | 0.8 | H | 76.1 |
| 27be | | (476.1) 476.1 | 0.75 | H | 49.2 |

The examples in Table 6E-2 were prepared from bromide 6D-4 using procedures analogous to those in Method 6E and utilizing the appropriately substituted benzohydrazide in step 4.

TABLE 6E-2

| Example no. | Example | Observed M + H | Expected M + H | $t_R$ (min) | LCMS method | BACE1 $K_i$ (nM) |
| --- | --- | --- | --- | --- | --- | --- |
| 27bf | | 469 | 469 | 1.09 | J | 30.9 |
| 27bg | | 453 | 453 | 1.05 | J | 79.3 |
| 27bh | | 465 | 465 | 1.06 | J | 74.0 |
| 27bi | | 460 | 460 | 1.03 | J | 48.9 |

Method 6F.

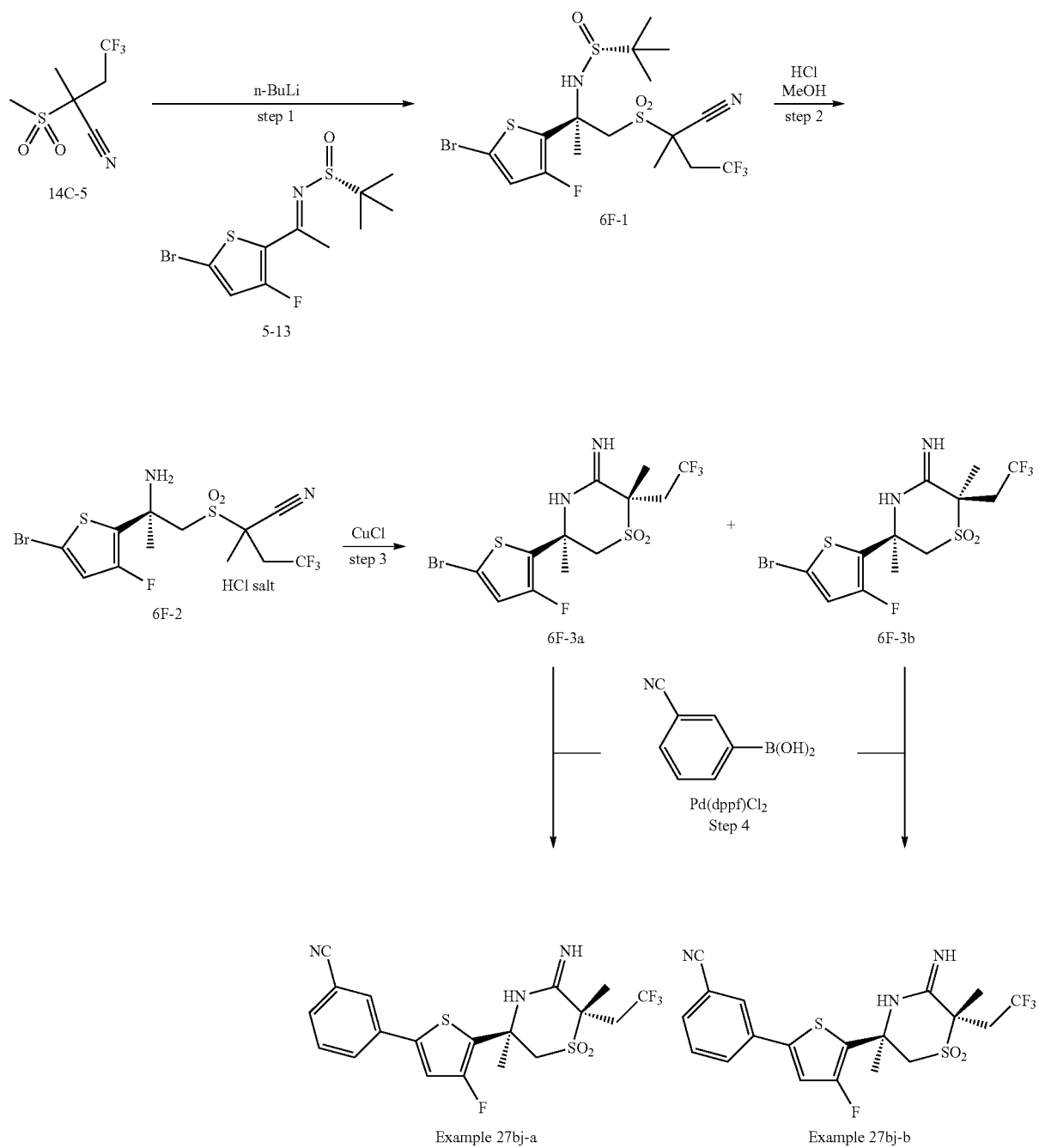

Compounds 6F-3a and 6F-3b were prepared using procedures analogous to those described in Method 4A, Steps 1-3 with the following changes: (i) Sulfone 14C-5 and ketimine 5-13 were used in step 1 instead of 2-methyl-2-(methylsulfonyl)propanenitrile and ketimine 5-3; (ii) the product of step 3 was subjected to SFC chromatography (Berger MultiGram™ SFC, Mettler Toledo Co, Ltd, Chiralpak AD column, 250 mm×30 mm, 5 μm, 70% supercritical $CO_2$, 30% MeOH (0.05% $NH_4OH$), 60 mL/min, column temp: 38° C., nozzle pressure: 100 bar, 220 nm) to give Compounds 6F-3a and 6F-3b. These two compounds then were each treated individually according to Method 6 or Method 6D, step 5 with 3-cyanophenylboronic acid as a coupling partner to give Examples 27bj-a and 27bj-b.

The examples in Table 6F-1 were made using procedures analogous to those described above for Examples 27bj-a and 27bj-b, substituting the specified sulfone reagent in step 1 and using the appropriate boronic acid or boronate ester in step 4. For Examples 27bk-a, 27bk-b, 27 bp-a, 27 bp-b, boronate ester 16-2 was used.

TABLE 6F-1

| Ex. no. | Sulfone | Example | Obs. M + H (Exp.) | LCMS cond. (tR min) | BACE1 K$_i$ (nM) |
|---|---|---|---|---|---|
| 27bj-a | 14C-5 | | 460 (460) | F3 (2.24) | 35.7 |
| 27bj-b | | | 460 (460) | F3 (2.25) | 828.7 |
| 27bk-a | | | 503 (503) | F2 (2.41) | 4.7 |
| 27bk-b | | | 503 (503) | F2 (2.42) | 105.5 |
| 27bl-a | | | 465 (465) | F3 (2.32) | 223 |
| 27bl-b | | | 465 (465) | F3 (2.32) | 7310 |

TABLE 6F-1-continued

| Ex. no. | Sulfone | Example | Obs. M + H (Exp.) | LCMS cond. (tR min) | BACE1 $K_i$ (nM) |
|---|---|---|---|---|---|
| 27bm-a | | | 478 (478) | F3 (2.29) | 35 |
| 27bn-a | | | 466 (466) | F2 (2.23) | 8018 |
| 27bo-a | 14A-9 | | 455 (455) | F2 (2.48) | 131.8 |
| 27bo-b | | | 455 (455) | F2 (2.51) | 2718 |
| 27bp-a | | | 498 (498) | F1 (3.50) | 17.8 |
| 27bp-b | | | 498 (498) | F1 (3.54) | 395.6 |

TABLE 6F-1-continued

| Ex. no. | Sulfone | Example | Obs. M + H (Exp.) | LCMS cond. (tR min) | BACE1 K$_i$ (nM) |
|---|---|---|---|---|---|
| 27bq-a | | | 456 (456) | F1 (3.44) | 268.1 |
| 27bq-b | | | 456 (456) | F1 (3.47) | 2495 |
| 27br-a | 14A-6 | | 472 (472) | F3 (2.31) | 58.5 |
| 27br-b | | | 472 (472) | F3 (2.29) | 4934 |
| 27bs-a | 14A-8 | | 472 (472) | F3 (2.28) | 68.3 |
| 27bs-b | | | 472 (472) | F3 (2.24) | 3174 |

Using methods analogous to those described in Method 6F, the examples in Table 6F-2 were made from the sulfones specified and using the appropriate boronic acid or boronate ester in step 4, with the following exception: ketimine 5-3 was used instead of ketimine 5-13 in step 1. For Example 27bu, boronate ester 16-2 was used in step 4. For Example 27by, (1-(tert-butoxycarbonyl)-7-methoxy-1H-indol-2-yl) boronic acid was used.

TABLE 6F-2

| Ex. no. | Sulfone | Example | Obs. M + H (Exp.) | LCMS cond. (tR min) | BACE1 $K_i$ (nM) |
|---|---|---|---|---|---|
| 27bt | 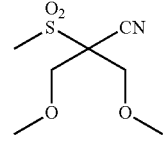<br>14D-1 | 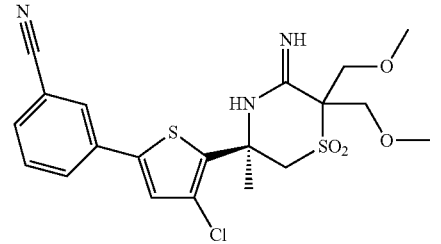 [SMILES: COCC1(COC)C(=N)N[C@](C)(c2sc(-c3cccc(C#N)c3)cc2Cl)CS1(=O)=O] | 468 (468) | A (2.13) | 135 |
| 27bu | | 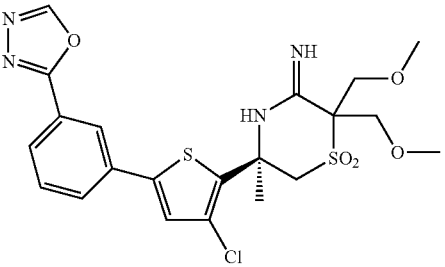 [SMILES: COCC1(COC)C(=N)N[C@](C)(c2sc(-c3cccc(-c4nnco4)c3)cc2Cl)CS1(=O)=O] | 511 (511) | A (2.06) | 1173 |
| 27bv | | 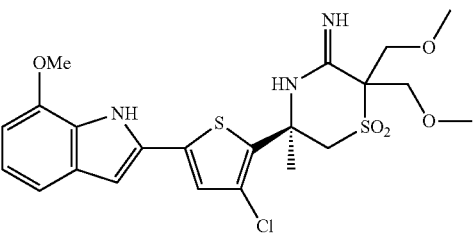 [SMILES: COCC1(COC)C(=N)N[C@](C)(c2sc(-c3cc4cccc(OC)c4[nH]3)cc2Cl)CS1(=O)=O] | 512 (512) | A (1.79) | 79 |
| 27bw | <br>14E-4 | 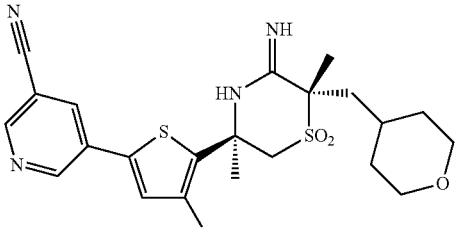 | 493 (493) | A (2.04) | 163 |
| 27bx | | 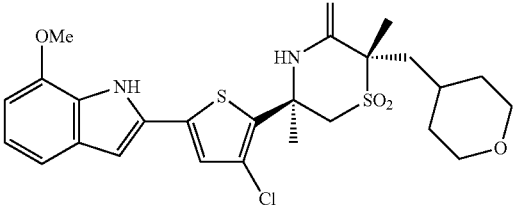 | 536 (536) | A (2.25) | 18 |

Method 6G

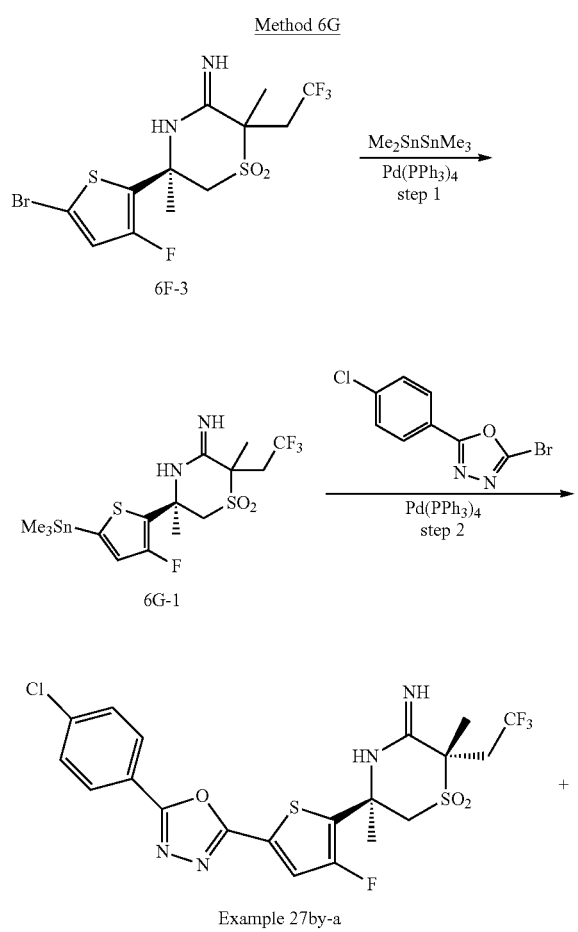

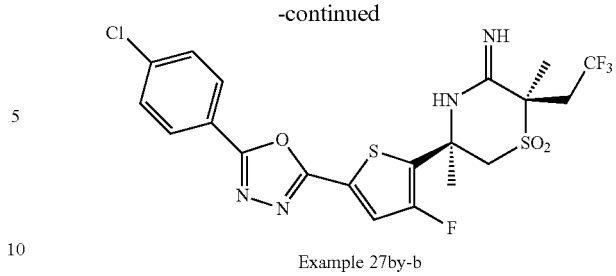

Example 27by-b

Step 1: To a mixture of 6F-3 (mixture a diastereomers, the product of Method 6F, step 3 prior to SFC chromatography, 1 g, 2.3 mmol) and hexamethylditin (835 mg, 2.5 mmol) in dioxane (10 mL) was added $Pd(PPh_3)_4$ (133 mg, 0.12 mmol) at 25° C. under $N_2$. The mixture was stirred at 110° C. for 2 h, quenched with water and extracted with EtOAc. The combined extracts were washed with water, dried over $Na_2SO_4$, concentrated and purified by silica gel column chromatography to afford compound 6G-1 (640 mg, 53%).

Step 2: To a mixture of compound 6G-1 (640 mg, 1.2 mmol) and 2-bromo-5-(4-chlorophenyl)-1,3,4-oxadiazole (321 mg, 1.2 mmol) in toluene (40 mL) was added $Pd(PPh_3)_4$ (284 mg, 0.25 mmol) at 25° C. under $N_2$. The mixture was stirred at 110° C. for 2 h, quenched with water, and extracted by EtOAc. The combined extracts were washed with water, dried over $Na_2SO_4$, concentrated and purified by column chromatography on silica gel to afford 450 mg (68%) of product as a mixture that was separated by SFC (Thar 80, Chiralpak AD 250 mm×20 mm, 10 µm, column temp 38° C., 40% MeOH (0.05% $NH_4OH$) in supercritical $CO_2$, 100 bar, 80 mL/min, 220 nm) to give Examples 27by-a and 27by-b.

The examples in Table 6G-1 were made by methods analogous to those described in Method 6G using the intermediate from Method 6F, step 3 that was made from the sulfone specified.

TABLE 6G-1

| Ex. no. | Sulfone | Example | Obs. M +H (Exp.) | LCMS cond. (tR min) | BACE1 Ki (nM) |
|---|---|---|---|---|---|
| 27by-a | 14C-5 | | 537 (537) | F3 (2.45) | 29.5 |
| 27by-b | | | 537 (537) | F3 (2.45) | 450 |

TABLE 6G-1-continued
| Ex. no. | Sulfone | Example | Obs. M+H (Exp.) | LCMS cond. (tR min) | BACE1 Ki (nM) |
|---|---|---|---|---|---|
| 27bz-a | 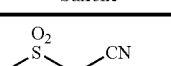 14A-9 | 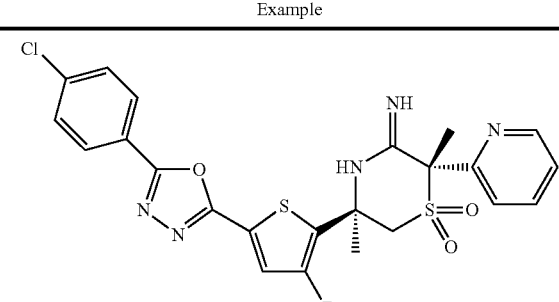 | 532 (532) | F2 (2.67) | 51 |
| 27bz-b | | 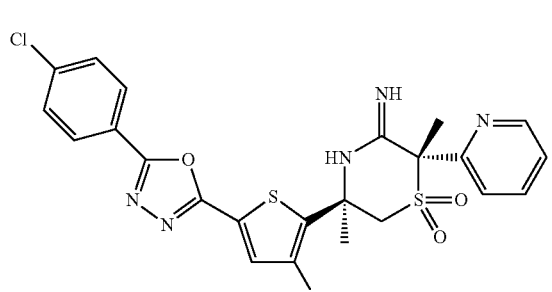 | 532 (532) | F2 (2.68) | 791 |
Method 6H
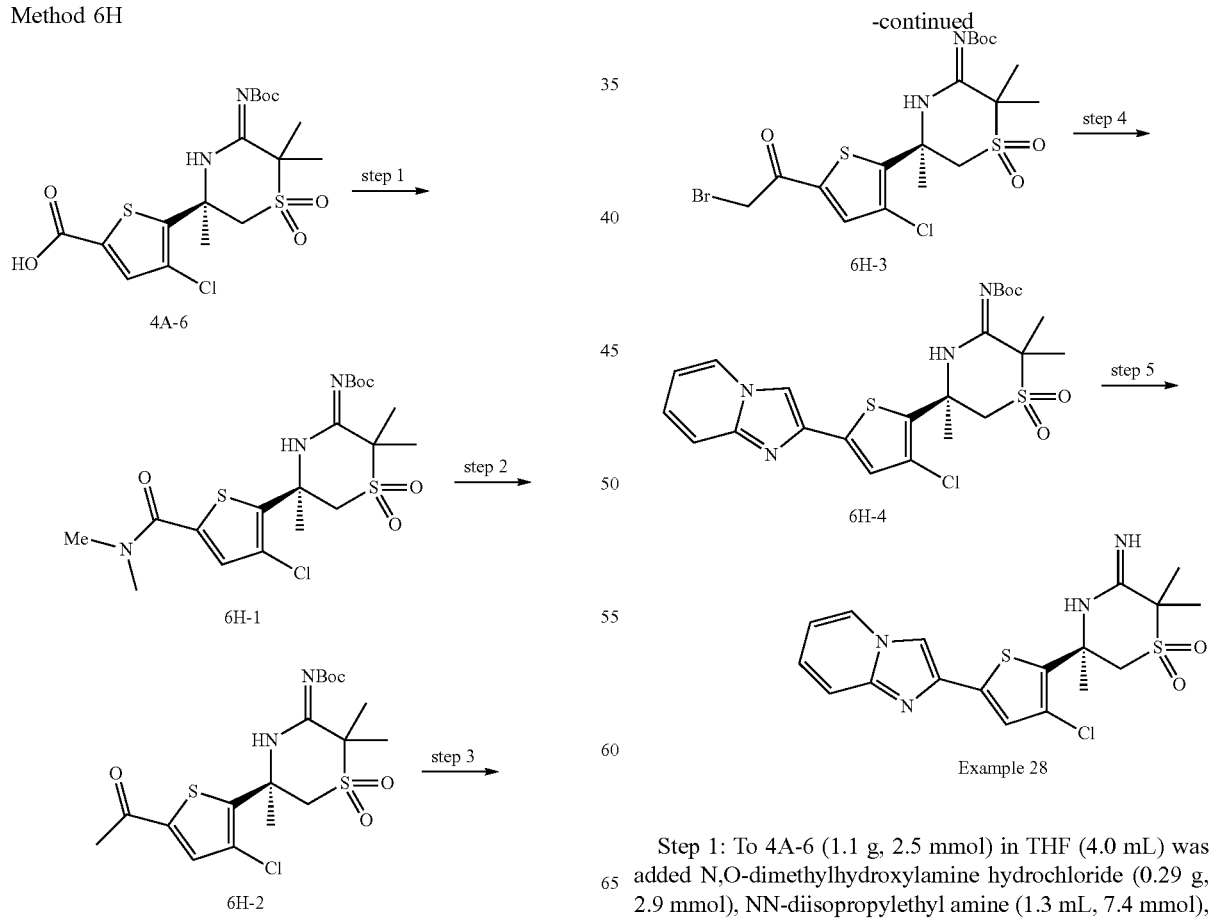
Step 1: To 4A-6 (1.1 g, 2.5 mmol) in THF (4.0 mL) was added N,O-dimethylhydroxylamine hydrochloride (0.29 g, 2.9 mmol), NN-diisopropylethyl amine (1.3 mL, 7.4 mmol), and 2,4,6-tripropyl-1,3,5,2,4,6-trioxatriphosphorinane-2,4, 6-trioxide (2.0 mL, 3.4 mmol). The reaction was stirred at room temperature for 18 h. Water was added to the reaction and the mixture was stirred vigorously for 10 minutes. The mixture was extracted with EtOAc. The combined organic layers were washed with 1N HCl, saturated aqueous NaHCO₃, water and brine, dried (MgSO₄), filtered, and concentrated in vacuo to provide 6H-1 (1.1 g, 90%).

Step 2: To 6H-1 (1.1 g, 2.2 mmol) in THF (9 mL) at 0° C. was added methylmagnesium chloride (3.0 M in THF, 1.8 mL, 5.6 mmol). The ice bath was removed and the mixture was stirred at room temperature for 5 h. To the mixture was added 0.2 N HCl$_{(aq)}$ and the mixture was stirred for 10 minutes. The mixture was then extracted with EtOAc. The combined organics were washed with water and brine, dried (MgSO₄), filtered, and concentrated in vacuo. The residue was purified by silica gel chromatography (0 to 30% EtOAc/hex over 30 minutes) to provide 6H-2 (0.80 g, 80%).

Step 3: To 6H-2 (0.30 g, 0.67 mmol) 33% HBr in acetic acid (0.8 mL, 0.67 mmol) and bromine (0.05 mL, 1.0 mmol). The reaction was stirred for 1 h at room temperature and then concentrated in vacuo. To the residue was added EtOAc (2 mL) and saturated aqueous NaHCO₃ (2 mL) followed by di-tert-butyldicarbonate (0.44 g, 2.0 mmol). The reaction was stirred at room temperature for 18 h and water was added. The reaction was extracted with EtOAc. The combined organic layers were washed with water and brine, dried (MgSO₄), filtered, and concentrated in vacuo. The residue was purified by silica gel chromatography (0 to 30% EtOAc/hex over 30 minutes) to provide 6H-3 (0.25 g, 71%)

Step 4: To 6H-3 (0.12 g, 0.23 mmol) in EtOH (1.1 mL) was added 2-aminopyridine (0.023 g, 0.25 mmol). The reaction was warmed to 85° C. and stirred for 30 minutes. The reaction was concentrated in vacuo. The residue was taken up into DCM and the mixture was washed with saturated aqueous NaHCO₃, water and brine, dried (MgSO₄), filtered, and concentrated in vacuo. The residue was purified by silica gel preparative TLC (1000 μm) eluting with 50% EtOAc/hexanes to provide 6H-4 (0.03 g, 25%).

Step 5: To 6H-4 (0.03 g, 0.05 mmol) in DCM (1 mL) was added TFA (0.3 mL). The reaction was stirred at room temperature for 30 minutes and concentrated in vacuo to provide Ex. 28 (0.027 g).

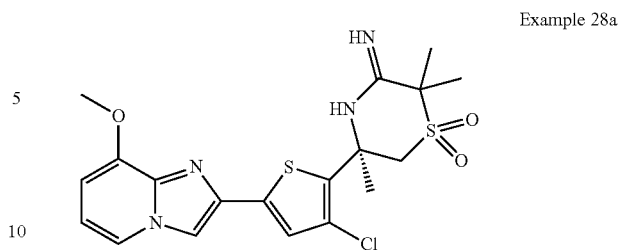

Example 28a

Ex. 28a was prepared in the same manner as Ex. 28 in Method 6H except that 2-amino-3-methoxypyridine was used instead of 2-aminopyridine and t-butanol was used in place of EtOH in step 4.

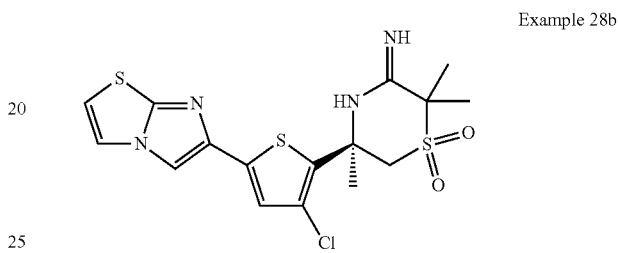

Example 28b

Ex. 28b was prepared in the same manner as Ex. 28 in Method 6H except that 2-aminothiazole was used instead of 2-aminopyridine and t-butanol was used in place of EtOH in step 4. In addition, the product mixture after step 4 was subjected to an additional Boc protection step prior to purification using the procedure described in scheme EG1. In addition, the final product was purified by reverse phase HPLC (Waters Sunfire C18 column; 5 μm, 30×250 mm; Mobile phase A=water+0.1% TFA, Mobile phase B=acetonitrile+0.1% TFA; 50 mL/min; 5-35% B over 8 minutes).

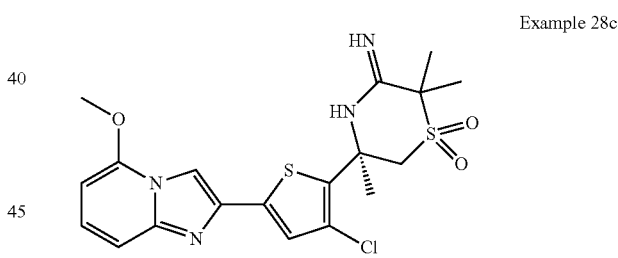

Example 28c

Ex. 28c was prepared in the same manner as Ex. 28b except that 2-amino-6-methoxypyridine was used instead of 2-aminopyridine in step 4.

TABLE 6H-1

Data for Examples 28, 28a-28c.

| Example Number | Example | Exact Mass [M + H]⁺ | $t_R$ min | LCMS method | BACE1 Ki (nM) |
|---|---|---|---|---|---|
| 28 | (structure shown) | Calc'd 423.0; found 423.1 | 0.48 | H | 2444 |

TABLE 6H-1-continued

Data for Examples 28, 28a-28c.

| Example Number | Example | Exact Mass [M + H]+ | $t_R$ min | LCMS method | BACE1 Ki (nM) |
|---|---|---|---|---|---|
| 28a | | Calc'd 453.0; found 453.1 | 0.56 | H | 804 |
| 28b | | Calc'd 429.0; found 429.1 | 0.63 | H | 2630 |
| 28c | | Calc'd 453.0; found 453.1 | 0.56 | H | 108.0 |

Method 6I

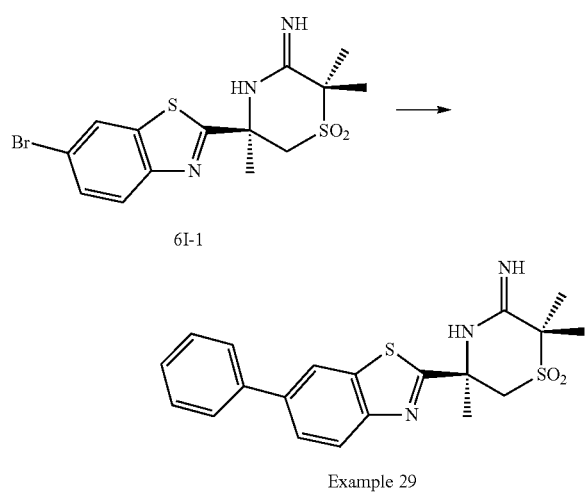

Example 29

Bromide 6I-1 was prepared by methods similar to those described in Method 2A, Steps 1-3, substituting ketimine 5-12 for ketimine 5-4 in Step 1. To bromide 6I-1 (0.10 g, 0.25 mmol) in dioxane (2 mL) was added PdCl$_2$(dppf) (0.020 mg, 0.025 mmol), 2M aqueous K$_2$CO$_3$ (0.31 mL, 0.62 mmol), and phenylboronic acid (0.045 mg, 0.37 mmol). The reaction was flushed with nitrogen and evacuated three times and then heated to 75° C. and stirred for 4 h. The cooled reaction was filtered through Celite and the filtrate was concentrated in vacuo. The residue was purified by reverse phase chromatography (conditions I) to provide Example 29 (0.012 g, 9.4%).

Using a similar procedure to that described in Method 6I and utilizing the appropriate boronic acids, the examples in Table 6I-1 were prepared.

TABLE 6I-1
| Example Number | Example | M + H (Expected) Observed | $t_R$ min | LCMS method | BACE1 Ki (nM) |
|---|---|---|---|---|---|
| 29 | | (400.0) 400.1 | 1.62 | B | 2273 |
| 29a | | (401.0) 401.1 | 1.08 | B | 3383 |
| 29b | | (418.0) 418.1 | 1.65 | B | 2329 |
| 29c | | (425.0) 425.1 | 1.56 | B | 2383 |
| 29d | | (430.0) 430.1 | 1.99 | B | 2844 |
Method 7
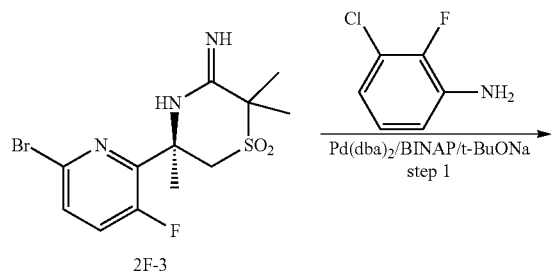
2F-3
-continued
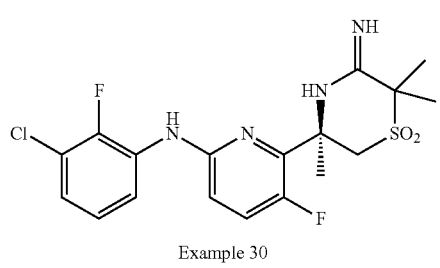
Example 30

A mixture of 0.050 g (0.137 mmol) of compound 2F-3, 0.028 g (0.192 mmol) of 3-chloro-2-fluoroaniline, 0.014 g (0.021 mmol) of BINAP, 0.006 g (0.010 mmol) of Pd(dba)$_2$ and 0.019 g (0.19 mmol) of t-BuONa in 3 mL of toluene was heated at 110° C. under nitrogen for 4 hrs and then concentrated. The residue was purified by preparative TLC plates eluting with 5% MeOH in CH$_2$Cl$_2$ to give Example 30 (5.8 mg, 9.8%). LCMS (conditions A): t$_R$=2.09 min, m/e=429 (M+H).

The compounds in Table 7-1 were made using a method analogous to that described in Method 7 using the appropriate aniline as a coupling partner.

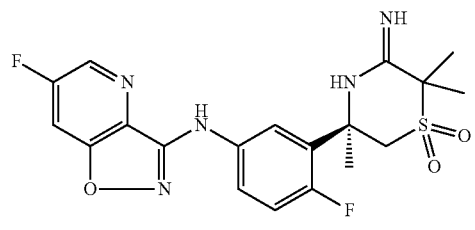

Example 30b

TABLE 7-1

| Example no. | Example | Observed M + H | Expected M + H | t$_R$ (min) | LCMS method | BACE1 K$_i$ (nM) |
|---|---|---|---|---|---|---|
| 30 | 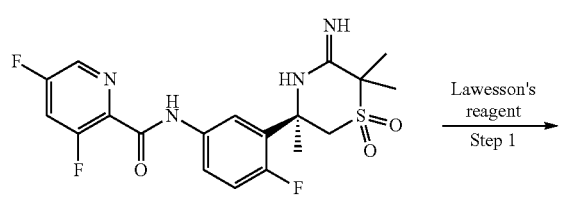 | 429 | 429 | 2.09 | A | 3198 |
| 30a | 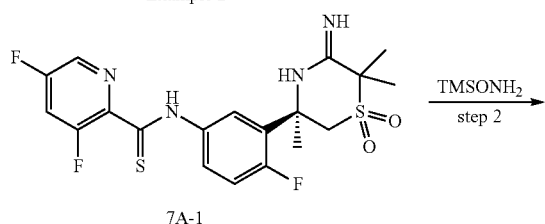 | 407 | 407 | 2.04 | A | 5277 |

Method 7A

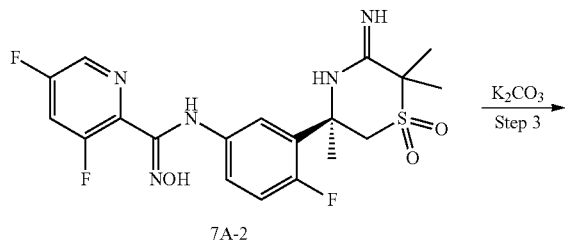

Step 1: A suspension of 0.26 g (0.59 mmol) of Example 2 and 0.48 g (1.18 mmol) of Lawesson's reagent in 5 mL of toluene plus 0.5 mL of pyridine was stirred at reflux for 4 h, and cooled to room temperature. The mixture was diluted with 20 mL of saturated aq. NaHCO$_3$ solution, and extracted with two 30 mL portions of ethyl acetate. The combined organic extracts were concentrated; the residue was purified by flash chromatography (24 g of SiO$_2$: 0 to 5% MeOH in CH$_2$Cl$_2$ plus 1% NH$_4$OH) to give 7A-1 (0.026 g, 10%). LCMS (conditions A): t$_R$=1.81 min, m/e=457.2 (M+H).

Step 2: A solution of 0.023 g (0.05 mmol) of 7A-1 and 0.016 g (0.15 mmol) of TMSONH$_2$ in 3 mL of EtOH was stirred at reflux for 3 h and concentrated to give 7A-2 that was used directly in the next step.

Step 3: To 7A-2 was added 3 mL of DMF and 0.21 g (0.15 mmol) of K$_2$CO$_3$. The mixture was stirred at 70° C. for 18 h, cooled to room temperature. It was diluted with 10 mL of brine, extracted with two 20 mL portions of ethyl acetate. The combined organic extracts were concentrated; the residue was purified by preparative TLC eluting with 8% MeOH in methylene chloride plus 1% NH$_4$OH to give 2 mg of Example 30b.

TABLE 7A-1

Data for Example 30b

| Example no. | Example | Observed M + H | Expected M + H | $t_R$ (min) | LCMS method | BACE1 $K_i$ (nM) |
|---|---|---|---|---|---|---|
| 30b | 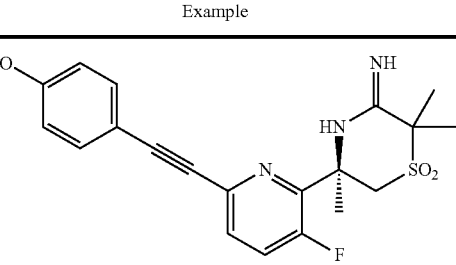 | 436 | 436 | 1.83 | A | 22 |

Method 8

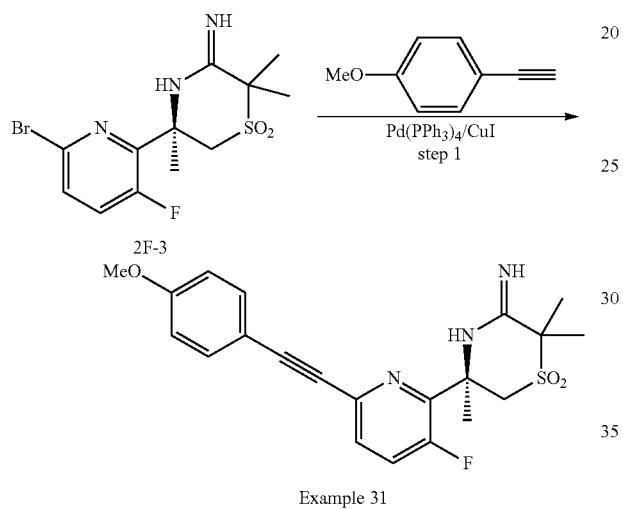

A stirred mixture of 0.068 g (0.187 mmol) of compound 2F-3 0.029 g (0.243 mmol) of 4-ethynylanisole 12, 0.006 g (0.0056 mmol) of Pd(PPh$_3$)$_4$, 0.002 g (0.011 mmol) of Cu(I)I and 0.052 g (0.373 mmol) of triethylamine in 5 mL DME was heated at 80° C. under nitrogen for 11 hrs and then concentrated. The residue was purified by preparative TLC plates eluting with 5% 7M NH$_3$/MeOH in CH$_2$Cl$_2$ to give Example 31 (19 mg, 25.2%). LCMS (conditions A): $t_R$=2.11 min, m/e=416 (M+H).

The compounds in Table 8-1 were made using a method analogous to that described in Method 8 using the appropriate acetylene as a coupling partner.

TABLE 8-1

| Example no. | Example | Observed M + H | Expected M + H | $t_R$ (min) | LCMS method | BACE1 Inhibition |
|---|---|---|---|---|---|---|
| 31 | | 416 | 416 | 2.11 | A | Ki = 7033 nM |
| 31a | | 404 | 404 | 2.12 | A | 41% Inhibition at 10 μM |

Method 9.

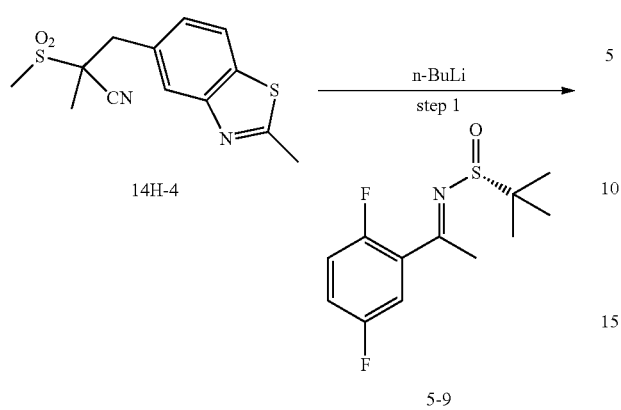

14H-4

5-9

9-1

9-2

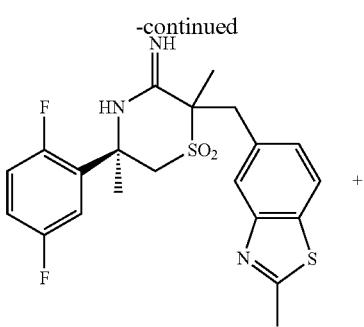

Example 32-a

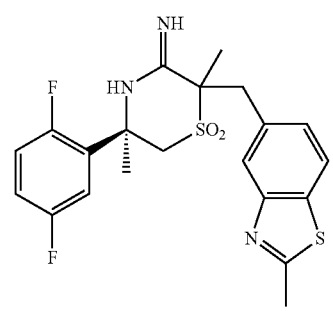

Example 32-b

Examples 32-a and 32-b were prepared using procedures analogous to those described in Method 2A, Steps 1-3 with the following changes: (i) Sulfone 14H-4 and ketimine 5-9 were used in step 1 instead of 2-methyl-2-(methylsulfonyl) propanenitrile and ketimine 5-4 in step 1; (ii) the product of step 3 was subjected to SFC chromatography (Berger MultiGram™ SFC, Mettler Toledo Co, Ltd, Chiralcel OJ column, 250 mm×30 mm, 5 μm, 75% supercritical $CO_2$, 25% MeOH (0.05% $NH_4OH$), 60 mL/min, column temp: 38° C., nozzle pressure: 100 bar, 220 nm) to give Examples 32-a and 32-b.

The examples in Table 9-1 were made using procedures analogous to those described above for Examples 32-a and 32-b, substituting the specified sulfone reagent in step 1.

TABLE 9-1

| Ex. no. | Sulfone | Example | M + H Obs. (Exp.) | LCMS cond. (tR min) | BACE1 $K_i$ (nM) |
|---|---|---|---|---|---|
| 32-a | 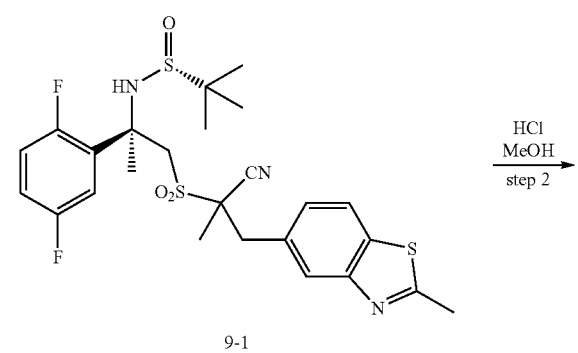<br>14H-4 | 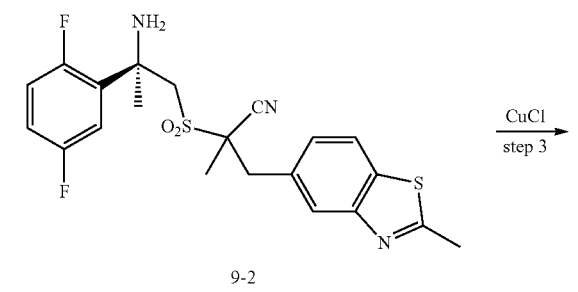 | 450 (450) | F3 (2.07) | 0% Inh at 10 μM |

TABLE 9-1-continued
| Ex. no. | Sulfone | Example | M + H Obs. (Exp.) | LCMS cond. (tR min) | BACE1 $K_i$ (nM) |
|---|---|---|---|---|---|
| 32-b | | 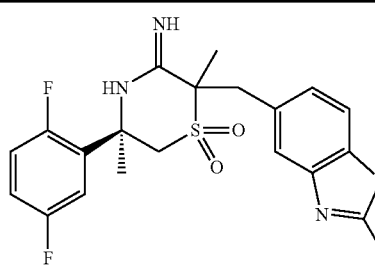 | 450 (450) | F3 (2.08) | 7% Inh at 10 μM |
| 32a-a | 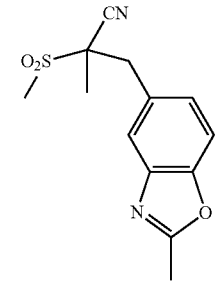<br>14H-5 | 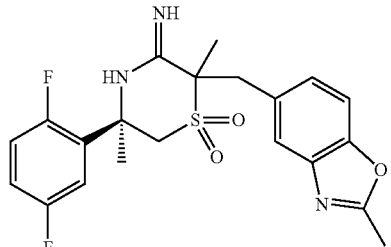 | 434 (434) | F2 (2.31) | 3856 |
| 32a-b | | 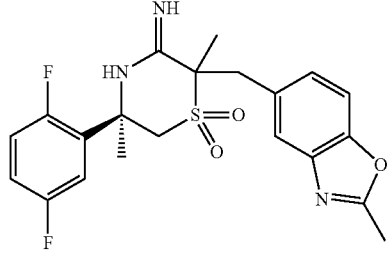 [SMILES: Cc1nc2cc(CC3(C)C(=N)N[C@](C)(c4cc(F)ccc4F)CS3(=O)=O)ccc2o1] | 434 (434) | F2 (2.33) | 4637 |
| 32b-a and 32b-b | 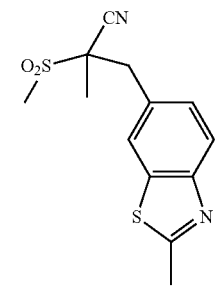<br>14H-7 | 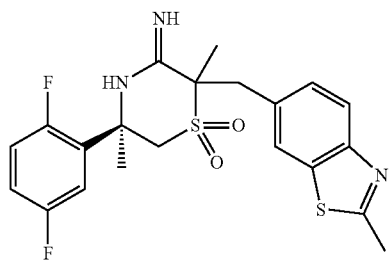<br>(mixture) | 450 (450) | F3 (2.13) | 11% Inh at 10 μM |
| 32c-a | 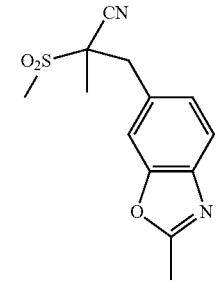<br>14H-6 | 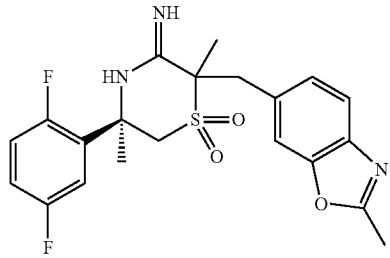 [SMILES: Cc1nc2ccc(CC3(C)C(=N)N[C@](C)(c4cc(F)ccc4F)CS3(=O)=O)cc2o1] | 434 (434) | F2 (2.33) | 3595 |

TABLE 9-1-continued

| Ex. no. | Sulfone | Example | M + H Obs. (Exp.) | LCMS cond. (tR min) | BACE1 $K_i$ (nM) |
|---|---|---|---|---|---|
| 32c-b | | | 434 (434) | F2 (2.35) | 213 |
| 32d-a | 14C-4 | | 333 (333) | F1 (3.32) | 2009 |
| 32d-b | | | 333 (333) | F1 (3.34) | 2914 |
| 32e-a | 14A-4 | | 395 (395) | F2 (2.35) | 1097 |
| 32e-b | | | 395 (395) | F2 (2.34) | 22% Inh. at 10 μM |

The examples in Table 9-2 were made using procedures analogous to those described in Method 9, with the following modifications to step 1: (i) using 5-10 as the ketimine in place of 5-9 and (ii) using the sulfone reagents specified in place of 14H-4.

TABLE 9-2

| Ex. no. | Sulfone | Example | M + H Obs. (Exp.) | LCMS cond. (tR min) | BACE1 $K_i$ (nM) |
|---|---|---|---|---|---|
| 32f-a | 14A-4 | | 395 (395) | C (2.9) | 1208 |
| 32f-b | | | 395 (395) | C (2.9) | 30% Inh. at 10 μM |
| 32g-a | 14A-7 | | 443 (443) | C (3.0) | 381.1 |
| 32g-b | | | 443 (443) | C (3.0) | 8834 |
| 32h-a | 14A-3 | | 433 (433) | C (3.1) | 361.5 |
| 32h-b | | | 433 (433) | C (3.1) | 2118.0 |
| 32i-a | 14E-6 | | 409 (409) | A (2.07) | 3119 |

TABLE 9-2-continued

| Ex. no. | Sulfone | Example | M + H Obs. (Exp.) | LCMS cond. (tR min) | BACE1 $K_i$ (nM) |
|---|---|---|---|---|---|
| 32i-b | | | 409 (409) | A (2.06) | 3815 |
| 32j-a | 14E-5 | | 459 (459) | A (2.16) | 2104 |
| 32j-b | | | 459 (459) | A (2.15) | 1269 |

Method 10

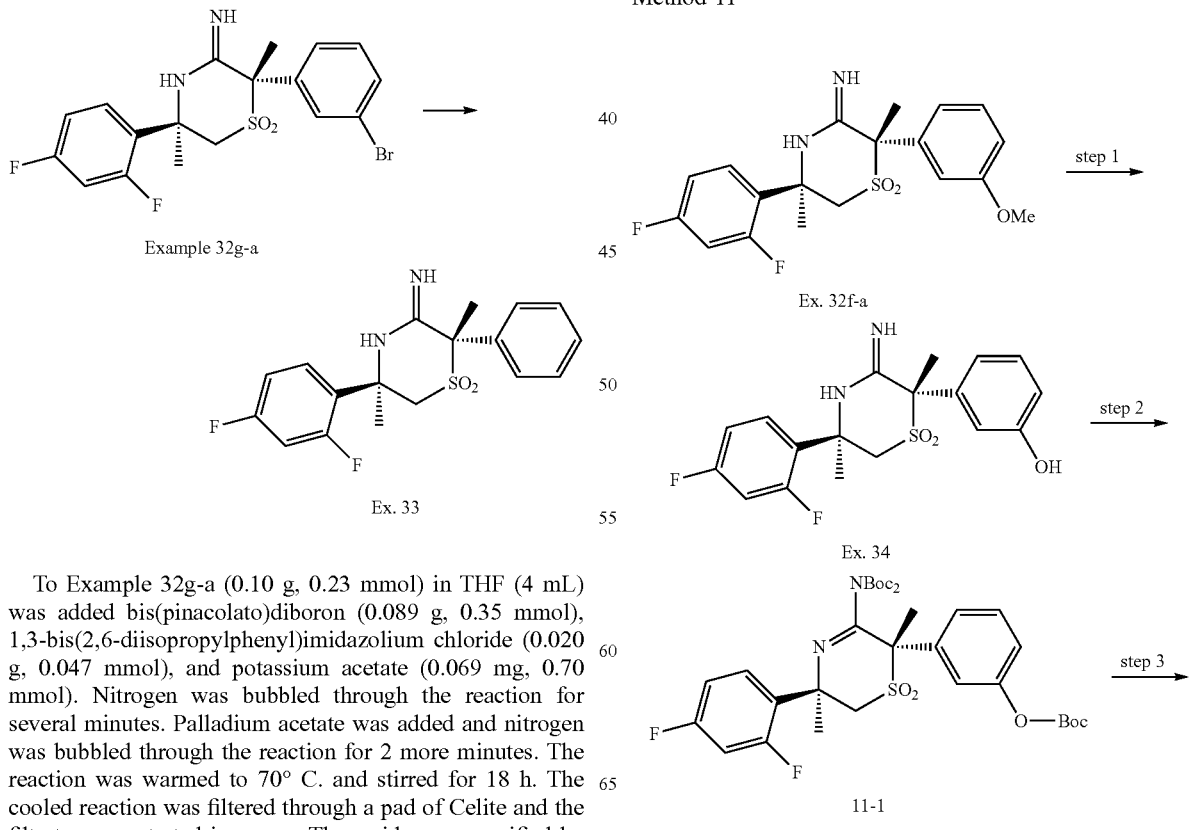

To Example 32g-a (0.10 g, 0.23 mmol) in THF (4 mL) was added bis(pinacolato)diboron (0.089 g, 0.35 mmol), 1,3-bis(2,6-diisopropylphenyl)imidazolium chloride (0.020 g, 0.047 mmol), and potassium acetate (0.069 mg, 0.70 mmol). Nitrogen was bubbled through the reaction for several minutes. Palladium acetate was added and nitrogen was bubbled through the reaction for 2 more minutes. The reaction was warmed to 70° C. and stirred for 18 h. The cooled reaction was filtered through a pad of Celite and the filtrate concentrated in vacuo. The residue was purified by silica gel chromatography (10 to 75% EtOAc/hex) to provide Example 33 as the major product.

Method 11

-continued

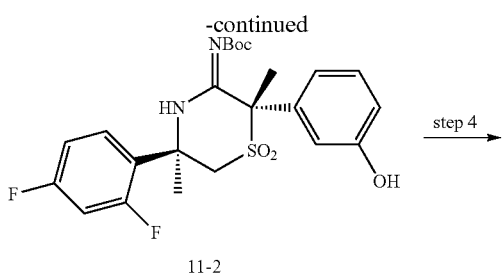

11-2

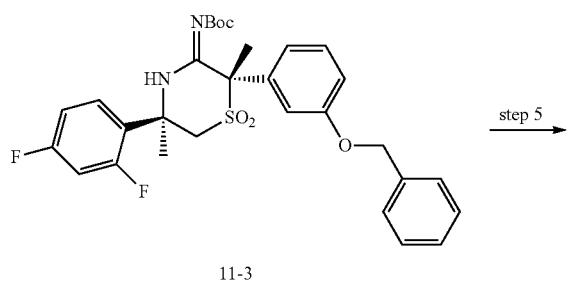

11-3

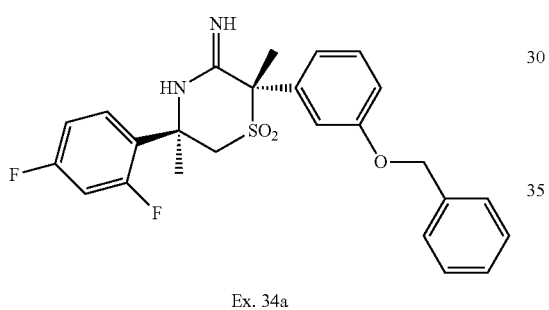

Ex. 34a

Step 1: To Ex. 32f-a (0.29 g, 0.75 mmol) in DCM (10 mL) at −78° C. was added boron tribromide (1.0 M, 3.0 mL, 3.0 mmol). It was allowed to warm to room temperature while stirring for 4 hours. Methanol (0.5 mL) was added followed by saturated aq. $K_2CO_3$ (5 mL). The reaction was extracted with DCM. The combined organic layers were washed with water and brine, dried ($MgSO_4$), filtered, and concentrated in vacuo. The residue was purified by silica gel chromatography (35 to 75% EtOAc/hex) to provide Ex. 34 (0.21 g, 74%).

Step 2: To Ex. 34 (0.20 g, 0.53 mmol) in DCM (20 mL) was added TEA (0.30 mL, 2.1 mmol), 4-dimethylaminopyridine (0.013 g, 0.11 mmol) and di-tert-butyldicarbonate (0.41 g, 1.9 mmol). The reaction was stirred at room temperature for 18 h. The reaction was diluted with DCM, washed with water and brine, dried ($MgSO_4$), filtered, and concentrated in vacuo. The residue was purified by silica gel chromatography (10 to 50% EtOAc/hex) to provide 11-1 (0.18 g, 51%).

Step 3: To 11-1 (0.18 g, 0.27 mmol) in DCM (6 mL) was added sodium methoxide (25% w/w, 0.15 mL, 0.65 mmol). The reaction was stirred at room temperature for 2 h. Aqueous 1N HCl (10 mL) was added and the mixture was extracted with DCM. The combined organic layers were washed with water and brine, dried ($MgSO_4$), filtered, and concentrated in vacuo to provide 11-2 (0.12 g, 90%).

Step 4: To 11-2 (0.065 g, 0.14 mmol) in DMF (2 mL) at 0° C. was added potassium carbonate (0.020 g, 0.15 mmol). The reaction was stirred at 0° C. for 20 minutes at which time benzyl bromide (0.018 mL, 0.15 mmol) was added. The reaction was allowed to warm to room temperature while stirring for 18 h. The reaction was then diluted with EtOAc and washed with water and brine. The organic layer was dried ($MgSO_4$), filtered, and concentrated in vacuo to provide 11-3 (0.068 g) that was used directly in the next step.

Step 5: To 11-3 (0.068 g, 0.12 mmol) in DCM (4 mL) was added TFA (2 mL). The reaction was stirred at room temperature for 2 hours and then concentrated in vacuo. The residue was purified by reverse phase HPLC (Conditions I) to provide Ex. 34a (0.033 g, 44%) as the TFA salt.

Method 11A

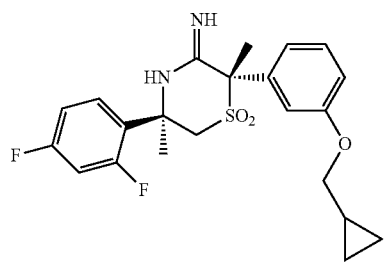

11-2

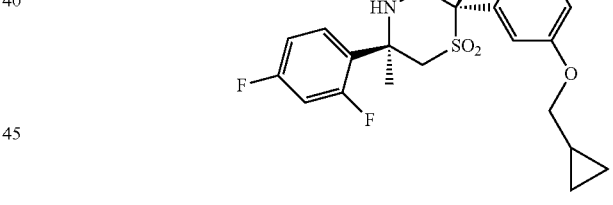

Ex. 34b

To 11-2 (0.061 g, 0.13 mmol) in DMF (2 mL) at 0° C. was added potassium tert-butoxide (0.015 g, 0.14 mmol). The reaction was stirred at 0° C. for 20 minutes and then warmed to room temperature. (Bromomethyl)cyclopropane (0.014 mL, 0.15 mmol) was added. The reaction was warmed to 45° C. and stirred for 5 h. The cooled reaction was diluted with EtOAc and washed with water and brine, dried ($MgSO_4$), filtered, and concentrated in vacuo. The crude residue was used directly by taking up in to DCM (4 mL) and adding TFA (2 mL).

The reaction was stirred for 2 h at room temperature and then concentrated in vacuo. The residue was purified by reverse phase HPLC (Conditions I) to provide Ex. 34b (0.008 g, 44%) as the TFA salt.

TABLE 11A-1

Data for examples from Methods 10, 11, and 11A.

| Example Number | Example | Exact Mass [M + H]+ | $t_R$ (min) | LCMS method | BACE1 Ki (nM) |
|---|---|---|---|---|---|
| 33 | (structure) | Calc'd 365.0; found 365.0 | 1.7 | G | 1216 |
| 34 | (structure) | Calc'd 381.0; found 381.0 | 1.7 | B | 708 |
| 34a | (structure) | Calc'd 471.0; found 471.1 | 1.8 | B | 2174 |
| 34b | (structure) | Calc'd 435.0; found 435.0 | 1.9 | G | 1133 |

Beginning with either Example 32e-a or Example 32e-b as appropriate and using procedures analogous to those described in Method 11, the examples in Table 11A-2 were made.

TABLE 11A-2

| Ex. no. | Example | Expected M + H | Observed M + H | $t_R$ (min) | LCMS cond. | BACE1 inhibition |
|---|---|---|---|---|---|---|
| 34c-a | (structure) | 381 | 381 | 2.22 | F2 | $K_i$ = 1.0 μM |

TABLE 11A-2-continued

| Ex. no. | Example | Expected M + H | Observed M + H | $t_R$ (min) | LCMS cond. | BACE1 inhibition |
|---|---|---|---|---|---|---|
| 34c-b | (structure) | 381 | 381 | 2.18 | F2 | 48% Inh. at 10 µM |
| 34d-a | (structure) | 471 | 471 | 2.40 | F3 | $K_i$ = 2.9 µM |
| 34d-b | (structure) | 471 | 471 | 2.39 | F3 | 16% Inh. at 10 µM |

Method 12

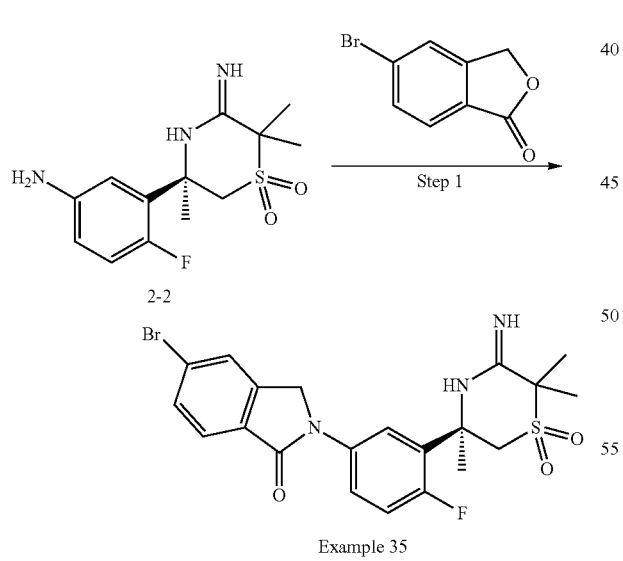

Example 35

Method 12A

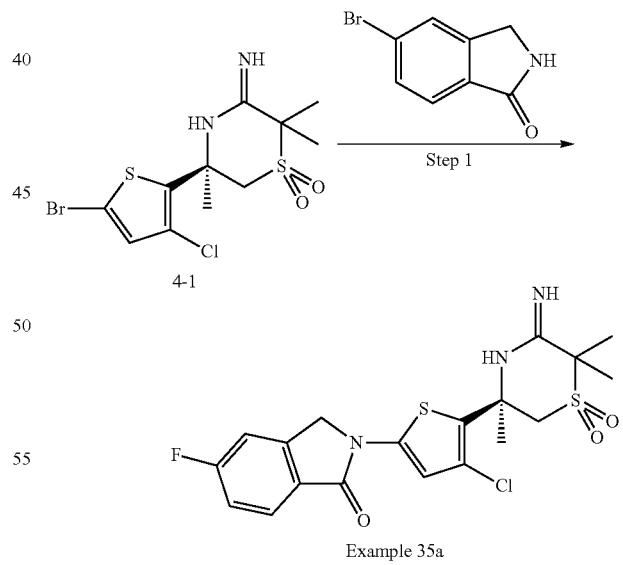

Example 35a

A solution of 0.15 g (0.50 mmol) of aniline 2-2 and 0.185 g (0.60 mmol) of 5-bromoisobenzofuran-1(3H)-one in 5 mL of 1,4-dioxane was stirred at reflux for 20 h and concentrated. The residue was purified by flash chromatography (12 g of $SiO_2$: 0 to 4% MeOH in $CH_2Cl_2$ plus 1% $NH_4OH$) to give example 35 (0.116 g, 50%). LCMS (conditions A): $t_R$=2.06 min, m/e=496 (M+H).

A mixture of 0.10 g (0.259 mmol) of bromide 4-1, 0.012 g (0.013 mmol) of $Pd_2(dba)_3$, 0.023 g (0.04 mmol) of Xphos, and 0.047 g (0.31 mmol) of fluoro, 0.118 g (0.36 mmol) of $Cs_2CO_3$ in 2 mL of 1,4-dioxane was stirred at 120° C. for 3 h, and cooled to room temperature. It was concentrated; the residue was purified by flash chromatography (24 g of $SiO_2$: 0 to 4% MeOH in $CH_2Cl_2$ plus 1% $NH_4OH$) to give a crude, which was further purified by preparative TLC eluting with 5% MeOH in CH$_2$Cl$_2$ plus 1% NH$_4$OH to give example 35a (0.005 g, 5%). LCMS (conditions A): t$_R$=1.76 min, m/e=456 (M+H).

TABLE 12A-1

Data for examples from Methods 12 and 12A.

| Example no. | Example | Observed M + H | Expected M + H | t$_R$ (min) | LCMS method | BACE1 K$_i$ (nM) |
|---|---|---|---|---|---|---|
| 35 | | 496 | 496 | 2.06 | A | 1805 |
| 35a | | 456 | 456 | 1.76 | A | 6076 |

Method 13

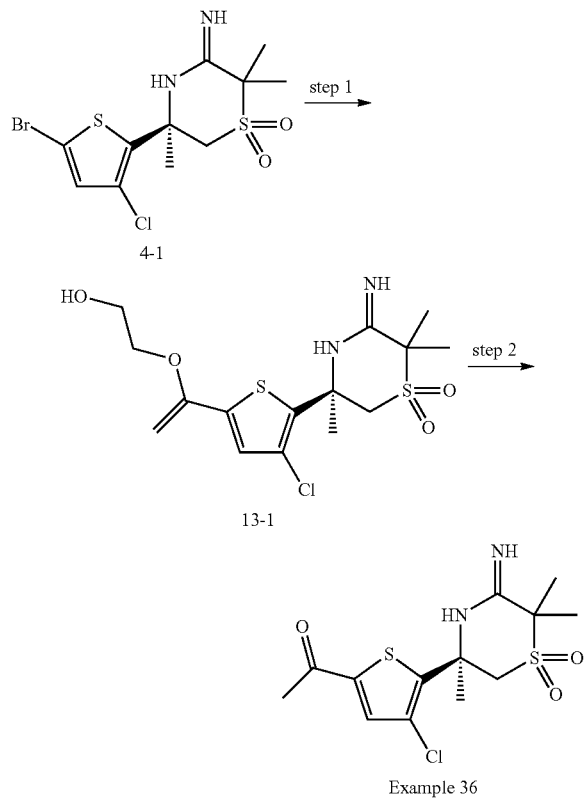

Example 36

Step 1: To 4-1 (0.50 g, 1.3 mmol) in toluene (5.2 mL) in a microwave reaction vessel was added N,N-dicyclohexylmethylamine (0.84 mL, 3.9 mmol) followed by ethylene glycol monovinyl ether (0.24 mL, 2.6 mmol). Nitrogen was then bubbled through the reaction mixture for five minutes. Compound 17-3 (0.066 g, 0.13 mmol) was added and nitrogen was bubbled through the mixture for one minute. The reaction vessel was capped and warmed to 80° C. and then stirred for 12 h. The cooled reaction mixture was filtered through a bed of Celite. The filtrate was concentrated in vacuo to provide the crude enol ether 13-1 that was used directly in the next step.

Step 2: To the enol ether prepared in step 1 in THF (5 mL) was added 1N HCl (2 mL) followed by 4N HCl in dioxane (2 mL). The reaction mixture was stirred for 30 minutes at room temperature after which it was basified to ~pH 9 with saturated aq. NaHCO$_3$. The mixture was then extracted with EtOAc. The combined organics were washed with water and brine, dried (MgSO$_4$), filtered, and concentrated in vacuo. The residue was purified by silica gel chromatography (0 to 80% EtOAc/hex over 30 minutes) to provide Ex. 36 (0.41 g, 90%). Further purification (Waters Sunfire C18, 5 μm, 19×100 mm, 50 mL/min, 20 min. run time, Mobile phase A=Water+0.1% formic acid, Mobile phase B=MeCN+0.1% formic acid, 5-40% B) provided Ex. 36 as the formic acid salt.

TABLE 13-1

Data for Example 36.

| Example Number | Example | Exact Mass [M + H]+ | $t_R$ min | LCMS method | BACE1 Ki (nM) |
|---|---|---|---|---|---|
| 36 | 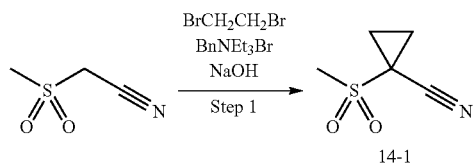 | Calc'd 349.0; found 349.0 | 0.55 | H | 2060 |

Method 14

To a room temperature mixture of methylsulfonylacetonitrile (1.00 g, 8.39 mmol) and benzyltriethylammonium bromide (0.228 g, 0.839 mmol) in 50% aq. sodium hydroxide (14 mL, 175 mmol) was added 1,2-dibromoethane (0.72 mL, 8.32 mmol). After 2 h, the reaction mixture was diluted with water (25 mL), and then extracted with EtOAc (1×75 mL, 1×25 mL). The combined organic layers were washed with brine, dried over $Na_2SO_4$, filtered, and concentrated to afford compound 14-1 (0.85 g, 5.56 mmol, 66% yield). $^1$H NMR (CDCl$_3$, 500 MHz) δ 3.18 (s, 3H), 1.88-1.86 (m, 2H), 1.76-1.73 (m, 2H).

Method 14A

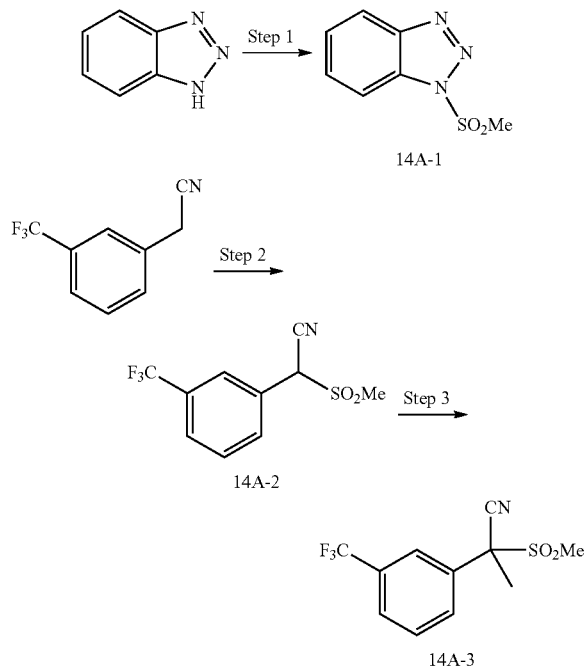

Step 1: To benzotriazole (10 g, 84 mmol) and pyridine (11 mL, 130 mmol) in toluene (100 mL) at 0° C. was added methanesulfonyl chloride (7.8 mL, 100 mmol). The reaction was allowed to warm to room temperature while stirring for 18 h. EtOAc and water were added. The organic layer was separated and dried (MgSO$_4$), filtered, and concentrated in vacuo. The residue was recrystallized from toluene to provide 14A-1 (13.4 g, 81%).

Step 2: To 2-(3-(trifluoromethyl)phenyl)acetonitrile (1.0 mL, 6.4 mmol) in DMSO (30 mL) at 8° C. was added potassium t-butoxide (1.4 g, 13 mmol). The reaction was stirred at this temp. for 10 min after which 14A-1 was added (1.2 g, 6.4 mmol). The reaction was allowed to warm to RT and stirred for 16 h. The reaction was poured into water and diluted with saturated aq. NH$_4$Cl. The mixture was extracted with EtOAc. The combined organic layers were washed with water and brine, dried (MgSO$_4$), filtered, and concentrated. The residue was purified by silica gel chromatography (20 to 50% EtOAc) to provide 14A-2 (1.0 g, 60%).

Step 3: To 14A-2 (4.0 g, 16 mmol) in THF (150 mL) at 0° C. was added potassium carbonate (3.7 g, 27 mmol). The reaction was stirred at 0° C. for 20 minutes and then iodomethane (1.8 mL, 29 mmol) was added. The reaction was allowed to warm to room temperature and stirred for 18 h. To the reaction was added saturated aqueous NH$_4$Cl. The mixture was then extracted with EtOAc. The combined organic layers were washed with water and brine, dried (MgSO$_4$), filtered, and concentrated in vacuo. The residue was purified by silica gel chromatography (10 to 50% EtOAc/hex) to provide 14A-3 (3.9 g, 88%).

The methylsulfones in Table 14A-1 were prepared using the procedure described in Method 14A and using the appropriately substituted acetonitrile in step 2.

TABLE 14A-1

| Entry | Sulfone |
|---|---|
| 1 | 14A-4 |
| 2 | 14A-5 |

TABLE 14A-1-continued

| Entry | Sulfone |
|---|---|
| 3 | 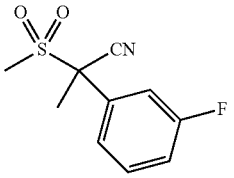<br>14A-6 |
| 4 | 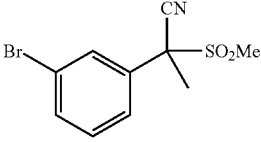<br>14A-7 |
| 5 | 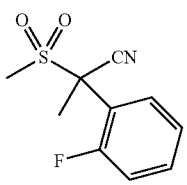<br>14A-8 |
| 6 | 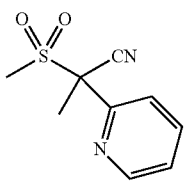<br>14A-9 |
| 7 | 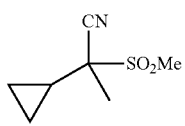<br>14A-10 |

Method 14B

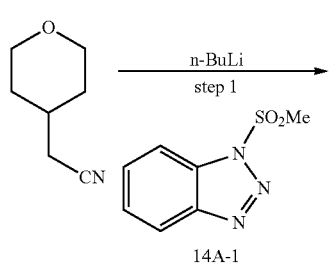
14A-1

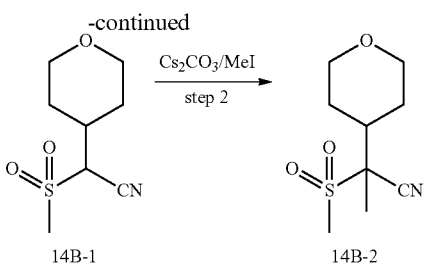
14B-1 → 14B-2

Step 1: To a solution of 7.5 g (59.9 mmol) of 2-(tetrahydro-2H-pyran-4-yl)acetonitrile in 120 mL of THF at −78° C. was added 47.9 mL (2.5 M in hexanes, 120 mmol) of n-BuLi slowly. The mixture was stirred at −78° C. for another 1 hr. A solution of 11.82 g (59.9 mmol) of 14A-1 in 70 mL of THF was added via cannula. The mixture was slowly warmed up to room temperature and stirred overnight. It was quenched by water and saturated aq. NH$_4$Cl. The mixture was extracted with EtOAc (2×). The organic extracts were combined, dried and concentrated. The residue was purified by flash chromatography (SiO$_2$: 40 to 75% EtOAc hexanes) to give 14B-1 (1.7 g, 13.96%). $^1$H NMR (CDCl$_3$): 1.75 (m, 3H), 2.05 (m, 1H), 2.65 (m, 1H), 3.2 (s, 3H), 3.5 (m, 2H), 3.9 (m, 1H), 4.05 (m, 2H).

Step 2: To a solution of 2.14 g (10.53 mmol) of 14B-1 in 100 mL of THF was added 4.12 g (12.63 mmol) of Cs$_2$CO$_3$ and 0.79 mL (12.63 mmol) of CH$_3$I. The mixture was stirred at room temperature overnight. It was quenched with water and extracted with EtOAc (2×). The combined organic extracts were dried and concentrated. The residue was purified by flash chromatography (40 g of SiO$_2$: 50 to 100% EtOAc hexanes) to give 14B-2 (2 g, 87%). $^1$H NMR (CDCl$_3$): 1.55 (m, 2H), 1.78 (S, 3H), 1.9-2.1 (m, 2H), 2.6 (m, 1H), 3.2 (s, 3H), 3.4-3.6 (m, 2H), 4.1 (m, 2H).

Method 14C

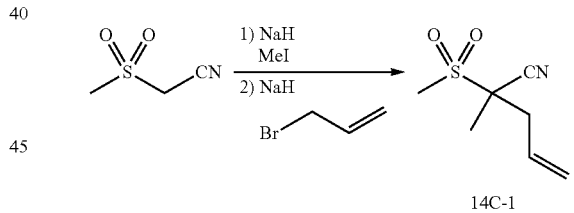
14C-1

To a suspension of 60% NaH in mineral oil (1.68 g, 42.0 mmol) in THF (100 mL) was added methylsulfonyl acetonitrile (5.0 g, 42.0 mmol) portionwise at 0° C. The reaction was stirred for 20 minutes at 0° C. A solution of methyl iodide (5.96 g, 42.0 mmol) in THF (5 mL) was added dropwise and the reaction stirred at 0° C. for 3 h. Water was added and extracted with DCM (2×200 mL). The combined organic layers were dried and the solvent removed in vacuo. The crude sample was dissolved in THF (100 mL) and cooled to 0° C. 60% NaH in mineral oil (1.2 g, 30.0 mmol) was added portionwise and stirred for 20 min at 0° C. A solution of allyl bromide (4.5 g, 37.2 mmol) in THF (5 mL) was added at 0° C. and stirred for 2 h. The reaction was slowly warmed to room temperature and stirred overnight. Water was added and extracted with DCM (2×200 mL). The combined organic layers were washed with brine and dried over sodium sulfate. The solvent was removed in vacuo. The residue was purified by silica gel chromatography (0 to 100% EtOAc in Hexane) to give 2-methyl-2-(methylsulfonyl)pent-4-enenitrile 14C-1 (4.8 g, 27.7 mmol).

The methylsulfones in Table 14C-1 were prepared using the procedure described in Method 14C and using the appropriate electrophile instead of allyl bromide in the second alkylation.

TABLE 14C-1

| Entry | Sulfone |
|---|---|
| 1 | 14C-2 |
| 2 | 14C-3 |
| 3 | 14C-4 |
| 3 | 14C-5 |

Method 14D

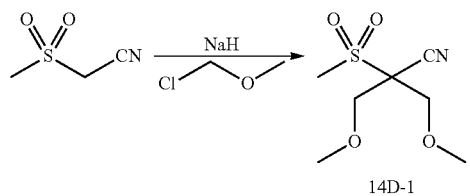

14D-1

To a solution of methylsulfonyl acetonitrile (5.0 g, 42.0 mmol) was added 60% NaH in mineral oil (3.52 g, 88.0 mmol) portionwise at 0° C. The reaction was stirred for 30 minutes at 0° C. A solution of chloromethyl methyl ether (7.86 g, 88.0 mmol) in THF (10 mL) was added dropwise and the reaction stirred at 0° C. for 1 h. Aqueous saturated aq. ammonium chloride was added and extracted with EtOAc (2×200 mL). The combined organic layers were washed with brine, dried with magnesium sulfate and the solvent removed in vacuo to give 3-methoxy-2-(methoxymethyl)-2-(methylsulfonyl) propanenitrile 14D-1 (8.0 g, 38.6 mmol).

Method 14E.

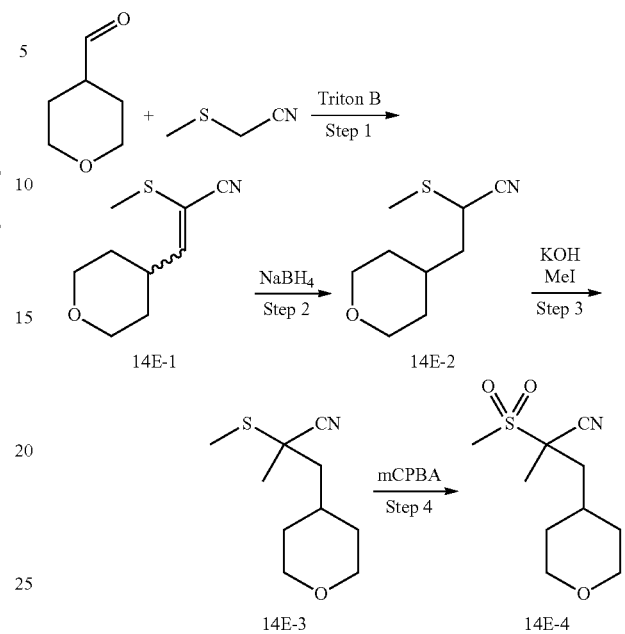

Step 1: To a stirred solution of tetrahydro-2H-pyran-4-carbaldehyde (5.0 g, 43.8 mmol) and (methylsulfanyl)acetonitrile (4.35 g, 49.9 mmol) in THF (100 mL) was added benzyltrimethylammonium hydroxide (40% solution, 22.7 mL, 49.9 mmol) dropwise at 0° C. The reaction was stirred at 0° C. for 3 h. Water was added and the aqueous layer extracted with ether (2×200 mL). The combined organic layers were washed with brine and dried with sodium sulfate. The solvent was removed in vacuo and the residue was passed through a short pad of silica gel to give 14E-1 (5.6 g, 30.6 mmol). LCMS for 14E-1 (conditions A): $t_R$=2.14 min, m/e=184 (M+H).

Step 2: To a stirred solution of compound 14E-1 (5.6 g, 30.6 mmol) in methanol (100 mL) was added sodium borohydride (3.47 g, 92.0 mmol) portionwise at 0° C. The solution was stirred at 0° C. for 30 minutes then warmed to room temperature for 1 h. Water was added and extracted with ether (3×100 mL). The solvent was dried and removed in vacuo to provide 14E-2 (5.5 g, 29.7 mmol). LCMS for 14E-2 (conditions A): $t_R$=2.06 min, m/e=186 (M+H).

Step 3: To a stirred solution of compound 14E-2 (3.0 g, 16.19 mmol) in DMSO (25 mL) was added KOH (2.73 g, 48.6 mmol) at room temperature. The reaction mixture was stirred for 1 minute. Methyl iodide (1.62 mL, 25.9 mmol) was added dropwise and stirred at room temperature for 15 h. Water was added and extracted with ether (2×200 mL). The solvent was dried and removed in vacuo to give 14E-3 (2.8 g, 14.0 mmol). LCMS for 3 (conditions A): $t_R$=2.15 min, m/e=200 (M+H).

Step 4: To as stirred solution of 14E-3 (2.8 g, 14.05 mmol) in DCM (100 mL) was added mCPBA (70%, 6.93 g, 28.1 mmol) at 0° C. The reaction mixture was stirred at 0° C. for 3 h. The reaction was washed with 5% aqueous sodium bicarbonate and water. The organic layer was dried and concentrated in vacuo to give 14E-4 (3.2 g, 13.83 mmol). LCMS for 14E-4 (conditions A): $t_R$=1.80 min, m/e=233 (M+H).

The methylsulfones in Table 14E-1 were prepared from the requisite aldehyde in step 1 by using procedures analogous to those described in Method 14E

TABLE 14E-1

| Entry | Sulfone |
|-------|---------|
| 1 | 14E-5 |
| 2 | 14E-6 |

Method 14F.

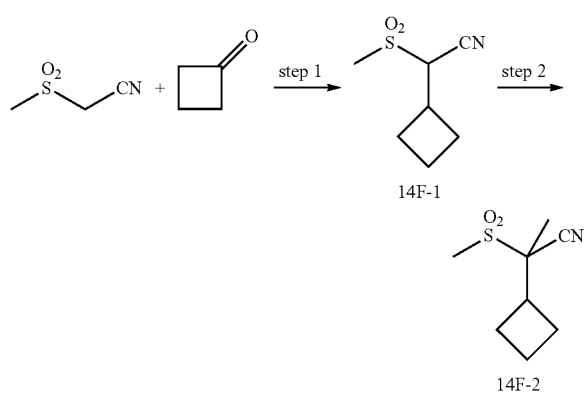

14F-1

14F-2

Step 1: To a solution of methylsulfonylacetonitrile (16.8 g, 240 mmol) in 200 mL of THF at room temperature was added cyclobutanone (12 g, 100 mmol) and DL-proline (2.4 g, 20 mmol). The reaction mixture was refluxed for 6 h, and cooled to 0° C. NaBH$_4$ (8 g, 200 mmol) was added to the above mixture in portions. The mixture was stirred at room temperature overnight and quenched with water, extracted with EtOAc (2×). The organic extracts were washed with brine, dried over sodium sulfate and concentrated. The residue was purified by silica gel chromatography to give 14F-1 (4 g, 24%). $^1$H NMR (CDCl$_3$): 1.98~2.32 (m, 6H), 3.09 (s, 3H), 3.16~3.22 (m, 1H), 3.92 (d, J=6.8 Hz, 1H).

Step 2: To a suspension of NaH (580 mg, 14.5 mmol) in 20 mL of THF at 0° C. was added a solution of 14F-1 (2.5 g, 14.5 mmol) in 20 mL of THF. After stirring at 0° C. for 30 min, CH$_3$I (4.8 g, 33.8 mmol) was added to the above mixture. The mixture was stirred at room temperature overnight, quenched with saturated aq. NH$_4$Cl and extracted with EtOAc (2×). The combined organic extracts were washed with brine, dried over sodium sulfate and concentrated. The residue was purified by silica gel chromatography to give 14F-2 (1.9 g, 70%). $^1$H NMR (CDCl$_3$): 1.61 (s, 3H), 1.90~2.29 (m, 6H), 2.87~2.93 (m, 1H), 3.05 (s, 3H).

Method 14G

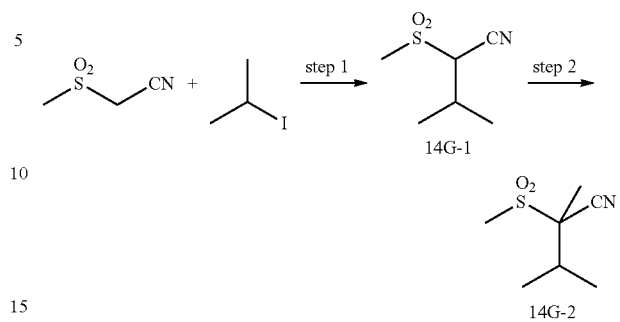

14G-1

14G-2

Step 1: A mixture of methylsulfonylacetonitrile (10.0 g, 84 mmol), 2-iodopropane (28.6 g, 168 mmol) and DBU (14 g, 92.4 mmol) in toluene (140 mL) was stirred at rt for 4 h, and then filtered. The filtrate was washed with dilute HCl (10%), brine, dried over sodium sulfate and concentrated. The residue was purified by silica gel chromatography (PE:EA=10:1) to give 14G-1 (5.5 g, 40%). $^1$H NMR (CDCl$_3$): 3.82 (d, J=4 Hz, 1H), 3.15 (s, 3H), 2.70-2.74 (m, 1H), 1.29 (d, J=8 Hz, 3H), 1.22 (d, J=8 Hz, 3H).

Step 2: To a suspension of NaH (1.2 g, 30.5 mmol) in 90 mL of THF at 0° C. was added 14G-1 (2.5 g, 14.5 mmol). After stirring at 0° C. for 30 min, CH$_3$I (4.4 g, 30.5 mmol) was added to the above mixture. The mixture was stirred at room temperature overnight, quenched with saturated aq. NH$_4$Cl and extracted with EtOAc (2×). The combined organic extracts were washed with brine, dried over sodium sulfate and concentrated. The residue was purified by silica gel chromatography (PE:EA=20:1) to give 14G-2 (2.8 g, 59%). $^1$H NMR (CDCl$_3$): 3.15 (s, 3H), 2.59-2.65 (m, 1H), 1.71 (s, 3H), 1.29 (d, J=8 Hz, 3H), 1.17 (d, J=8 Hz, 3H).

Method 14H

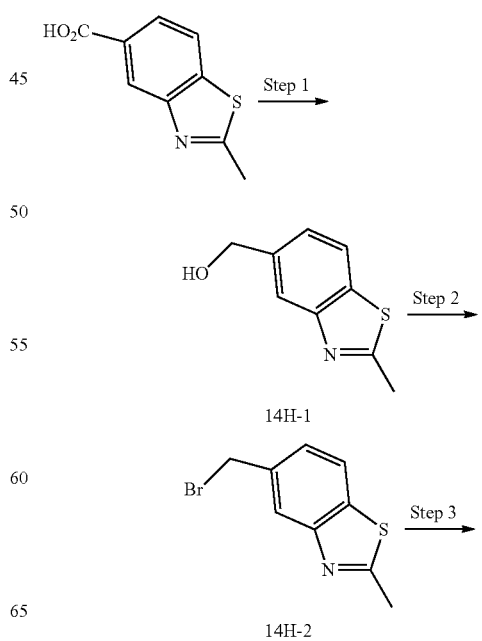

14H-1

14H-2

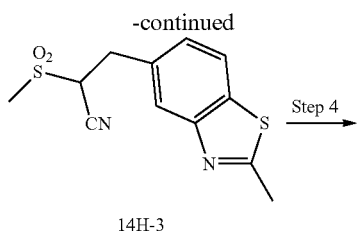

14H-3

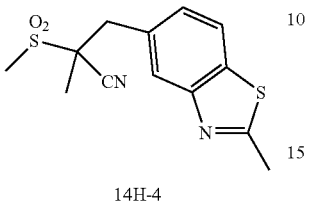

14H-4

Step 1: To a suspension of LiAlH$_4$ (8.72 g, 218 mmol) in THF (100 mL) at 0° C. was added a solution of 2-methyl-benzo[d]thiazole-5-carboxylic acid (21 g, 109 mmol) in THF dropwise. The mixture was stirred at rt for 2 h, then quenched with water and 1 M NaOH, filtered. The filtrate was extracted with EtOAc, washed with brine, dried over sodium sulfate and concentrated. The residue was purified by silica gel chromatography (PE:EA=3:1) to give 14H-1 (12 g, 57%). $^1$H NMR (MeOD): 7.83 (d, J=8.4 Hz, 2 H), 7.36 (d, J=8.4 Hz, 1H), 4.71 (s, 2 H), 2.79 (s, 3 H).

Step 2: A mixture of 14H-1 (12 g, 67 mmol), PPh$_3$ (26.3 g, 100.5 mmol) and CBr$_4$ (33.4 g, 100.5 mmol) in DCM (250 mL) was stirred at rt for 6 h. The solution was concentrated and purified by silica gel chromatography (PE:EA=5:1) to give 14H-2 (10 g, 62%). $^1$H NMR (CDCl$_3$): 7.93 (d, J=1.2 Hz, 1 H), 7.79 (t, J=8.0 Hz, 1 H), 7.37~7.39 (m, 1 H), 4.71 (s, 1 H), 4.62 (s, 1 H), 2.82 (d, J=2.0 Hz, 3 H).

Step 3: To a suspension of NaH (1.8 g, 45.6 mmol) in THF (25 mL) was added methanesulfonylacetonitrile (5.43 g, 45.6 mmol) dropwise at 0° C. and stirred at 0° C. for 1 h. To this mixture was added dropwise a solution of 14H-2 (10 g, 41.5 mmol) in THF (30 mL). The resulting mixture was stirred at 0° C. for 2 h, and quenched with H$_2$O, extracted with EtOAc. The organic layers were washed with brine, dried over sodium sulfate, concentrated and purified by silica gel chromatography (PE:EA=5:1) to give 14H-3 (7.8 g, 67%). $^1$H NMR (CDCl$_3$): 7.85 (s, 1 H), 6.78 (d, J=8.0 Hz, 1 H), 7.25~7.28 (m, 1 H), 4.05~4.09 (m, 1 H), 3.59~3.64 (m, 1 H), 3.28~3.43 (m, 1 H), 3.10 (s, 3 H), 2.79 (s, 3 H).

Step 4: To a suspension of NaH (1.3 g, 33.4 mmol) in THF (20 mL) was added dropwise 14H-3 (7.8 g, 27.8 mmol) in THF (50 mL) at 0° C. and stirred at 0° C. for 1 h. To this mixture was added MeI (7.9 g, 55.6 mmol) dropwise. The resulting mixture was stirred at 0° C. for 4 h, and quenched with H$_2$O, extracted with EtOAc. The organic layers were washed with brine, dried over sodium sulfate, concentrated and purified by silica gel chromatography (PE:EA=5:1) to give 14H-4 (7.5 g, 91%). $^1$H NMR (CDCl$_3$): 7.95 (d, J=0.8 Hz, 1 H), 7.86 (d, J=8.0 Hz, 1H), 7.40-7.42 (m, 1 H), 3.62 (d, J=13.6 Hz, 1 H), 3.23 (d, J=13.6 Hz, 1 H), 3.14 (s, 3 H), 2.89 (s, 3 H), 1.67 (s, 3 H).

The methylsulfones in Table 14H-1 were prepared using the procedure described in Method 14H and using the appropriate carboxylic acid in place of 2-methylbenzo[d]thiazole-5-carboxylic acid in step 1.

TABLE 14H-1

| Entry | Sulfone |
|---|---|
| 1 | 14H-5 |
| 2 | 14H-6 |
| 3 | 14H-7 |

Method 14I

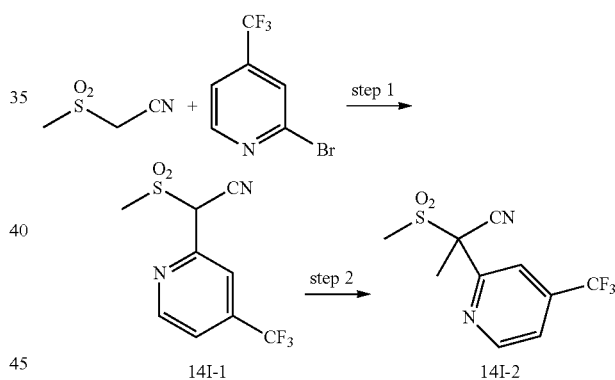

Step 1: A mixture of methylsulfonylacetonitrile (292 mg, 2.5 mmol), 2-bromo-4-(trifluoromethyl)pyridine (500 mg, 2.2 mmol) and Cs$_2$CO$_3$ (2.2 g, 6.7 mmol) in 10 mL of DMSO was heated at 120° C. overnight, and then cooled to room temperature. The mixture was diluted with water and extracted with EtOAc (2×). The organic extracts were washed with brine, dried over sodium sulfate and concentrated. The residue was purified by silica gel chromatography to give 14I-1 (500 mg, 85%). $^1$H NMR (CD$_3$OD): 3.33 (s, 3H), 4.86 (s, 1H), 6.93 (d, J=6.8 Hz, 1H), 7.93 (s, 1H), 8.97 (d, J=5.2 Hz, 1H).

Step 2: To a mixture of 14I-1 (300 mg, 1.2 mmol), K$_2$CO$_3$ (315 mg, 2.3 mmol) and CH$_3$I (324 mg, 2.3 mmol) in 10 mL of THF was stirred at room temperature overnight. It was quenched with saturated aq. NH$_4$Cl and extracted with EtOAc (2×). The combined organic extracts were washed with brine, dried over sodium sulfate and concentrated. The residue was purified by silica gel chromatography to give 14I-2 (154 mg, 49%). $^1$H NMR (CDCl$_3$): 2.28 (s, 3H), 3.11 (s, 3H), 7.68 (d, J=4.8 Hz, 1H), 7.87 (s, 1H), 8.92 (d, J=4.8 Hz, 1H).

Method 15

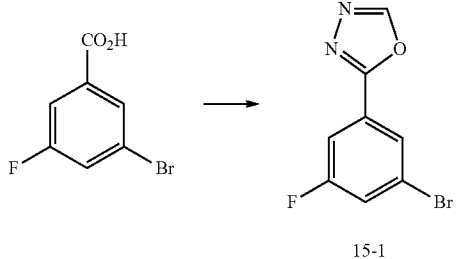 [SMILES: O=C(O)c1cc(F)cc(Br)c1 ; Fc1cc(Br)cc(-c2nnco2)c1]

15-1

To 3-bromo-5-fluorobenzoic acid (4.0 g, 18.3 mol) in EtOAc (45 mL) was added formic acid hydrazide (1.1 g, 18.3 mmol), TEA (7.6 mL, 54.8 mmol), and 1-propanephosphonic acid cyclic anhydride (50% solution in EtOAc, 27.2 mL, 45.7 mmol). The mixture was warmed to 80° C. and stirred for 12 h. The cooled mixture was added to water and then extracted with EtOAc. The combined organic layers were washed with water and brine, dried (MgSO$_4$), filtered, and concentrated in vacuo. The residue was purified by silica gel chromatography (0 to 25% EtOAc/hex) to provide 15-1 (2.8 g, 62%).

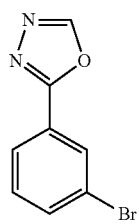

15-2

Bromide 15-2 was prepared in the same manner as 15-1 except that 3-bromobenzoic acid was used instead of 3-bromo-5-fluorobenzoic acid.

Method 15A

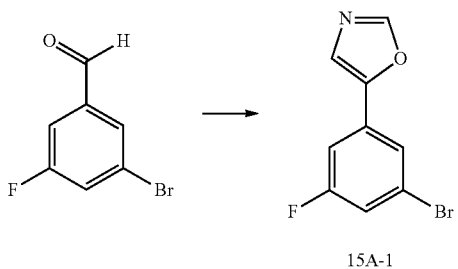 [SMILES: O=Cc1cc(F)cc(Br)c1 ; Fc1cc(Br)cc(-c2cnco2)c1]

15A-1

To 3-bromo-5-fluorobenzaldehyde (4.8 g, 24 mmol) in MeOH (79 mL) was added potassium carbonate (6.6 g, 48 mmol) and toluenesulphonylmethyl isocyanide (5.1 g, 26 mmol). The reaction was warmed to reflux and stirred for 4 h. The cooled reaction was concentrated in vacuo and water was added to the residue. The precipitate was filtered, washed with water, and air-dried. The solid was taken up into DCM and dried (MgSO$_4$), filtered, and concentrated in vacuo to provide 15A-1 (5.5 g, 95%).

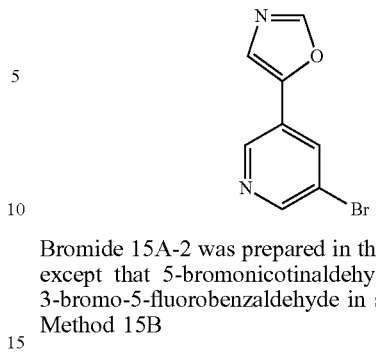

15A-2

Bromide 15A-2 was prepared in the same manner as 15A-1 except that 5-bromonicotinaldehyde was used instead of 3-bromo-5-fluorobenzaldehyde in step 1.

Method 15B

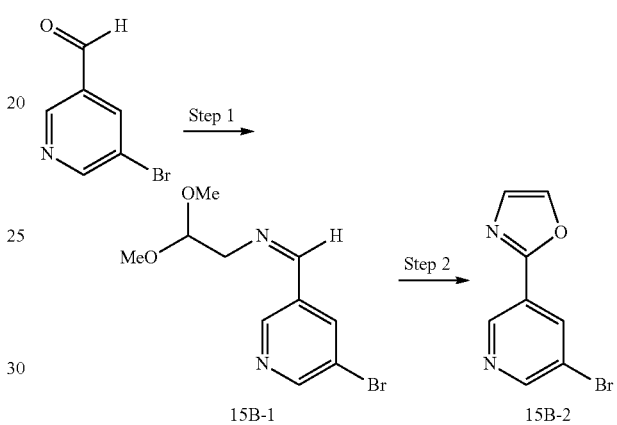

Step 1: To 5-bromonicotinaldehyde (1.5 g, 8.1 mmol) in toluene (80 mL) was added 2,2-dimethoxyethanamine (1.1 mL, 10 mmol). The mixture was warmed to reflux and water was removed using a Dean-Stark apparatus. After 2.5 h, the reaction was cooled and poured into EtOAc. The mixture was washed with water and brine, dried (MgSO$_4$), filtered, and concentrated in vacuo to provide 15B-1 (2.1 g, 95%).

Step 2: To the imine 15B-1 prepared in step 1 (5.5 g, 20 mmol) cooled to 0° C. was added concentrated sulfuric acid (40 mL, 750 mmol) followed by phosphorous pentoxide (3.7 g, 26 mmol). The mixture was then warmed to 100° C. and stirred for 30 minutes. The cooled reaction mixture was poured onto ice and the pH was adjusted to ~pH 8 using concentrated NH$_4$OH. The resultant mixture was extracted with DCM. The combined organic layers were washed with water and brine, dried (MgSO$_4$), filtered, and concentrated in vacuo. The residue was purified by silica gel chromatography (0 to 30% EtOAc/hex) over 30 minutes to provide 15B-2 (2.3 g, 51%).

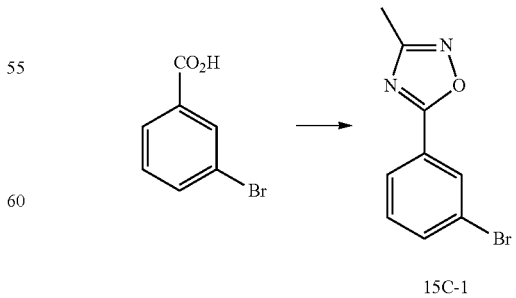

15C-1

Method 15C

To 3-bromobenzoic acid (2.0 g, 9.9 mmol) in EtOAc (34 mL) was added N-hydroxyacetamide (0.74 g, 9.9 mmol) and TEA (4.2 mL, 30 mmol). T3P (50% solution in EtOAc, 15 mL, 25 mmol) was slowly added to the reaction mixture. The reaction was warmed to 80° C. and stirred for 3 h. The cooled reaction was poured into water and the mixture was extracted with EtOAc. The combined organic layers were washed with saturated aqueous NaHCO$_3$ and brine, dried (MgSO$_4$), filtered, and concentrated in vacuo. The residue was purified by silica gel chromatography (0 to 30% EtOAc/hex) to provide 15C-1 (1.1 g, 48%).

Method 15D

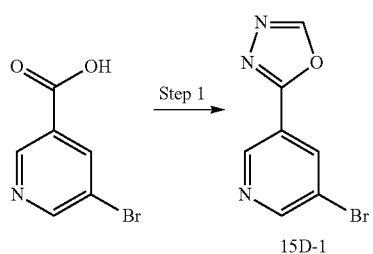 [SMILES: O=C(O)c1cncc(Br)c1 ; Brc1cncc(-c2nnco2)c1]

15D-1

To 5-bromonicotinic acid (2.1 g, 10 mmol) in EtOAc (52 mL) was added formic hydrazide (0.62 g, 10 mmol), TEA (4.3 mL, 31 mmol), and T3P (50% solution in EtOAc, 15 mL, 26 mmol). The reaction was warmed to 80° C. and stirred for 12 h. Water was added to the cooled reaction and the mixture was extracted with EtOAc. The combined organic layers were washed with water and brine, dried (MgSO$_4$), filtered, and concentrated in vacuo to provide bromide 15D-1 (1.9 g, 84%).

Method 15E

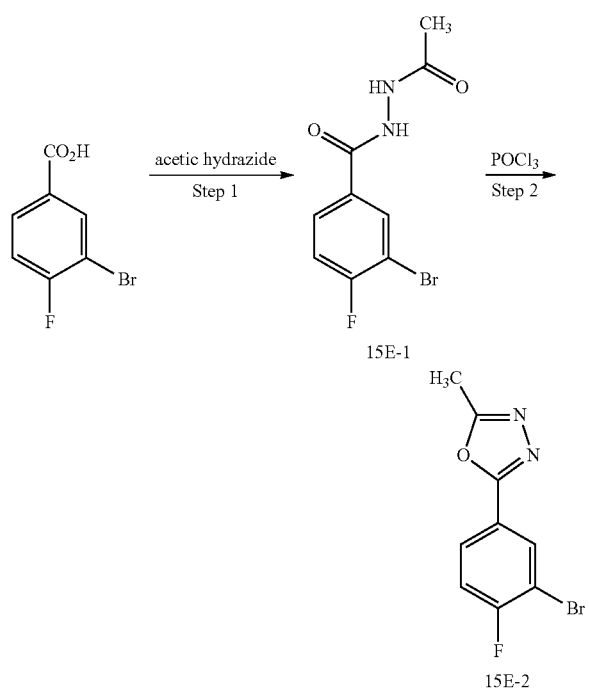

15E-1

15E-2

Step 1: A stirred solution of 3-bromo-4-fluorobenzoic acid (148 g, 0.855 mol) in CH$_2$Cl$_2$ (750 mL, 15 vol) was charged with acetic hydrazide (66.4 g, 0.898 mol), HOBt (34.6 g, 0.256 mol), NMM (281 mL, 2.56 mol), and EDC.HCl (245 g, 1.28 mol) at rt. The reaction mixture was stirred for 16 h at the same temperature. The reaction mixture was concentrated to dryness, water (2.00 L) was added, and the mixture was stirred for 30 min. The solids obtained were filtered, washed with EtOAc (400 mL), and azeotroped with toluene (2×500 mL) to afford 15E-1 (168 g, 71%). $^1$H NMR (300 MHz, DMSO-d$_6$): δ 10.43 (s, 1H), 9.95 (s, 1H), 8.21-8.18 (m, 1H), 7.96-7.91 (m, 1H), 7.52 (t, J=8.4 Hz, 1H), 1.93 (s, 3H).

Step 2: A 5 L, three-neck, round-bottom flask equipped with a reflux condenser was charged with 15E-1 (168 g, 0.610 mol) and POCl$_3$ (1.68 L) at room temperature. The reaction mixture was heated to reflux for 1 h. The reaction mixture was concentrated to dryness; cold water (3.00 L) was added and extracted with EtOAc (3×2.00 L). The combined organics were washed with brine (800 mL), dried over anhydrous Na$_2$SO$_4$, and concentrated under reduced pressure to afford 15E-2 (135 g, 86%). $^1$H NMR (300 MHz, DMSO-d$_6$): δ 8.23-8.20 (m, 1H), 8.03-7.98 (m, 1H), 7.60 (t, J=8.7 Hz, 1H), 2.59 (s, 3H).

Method 16

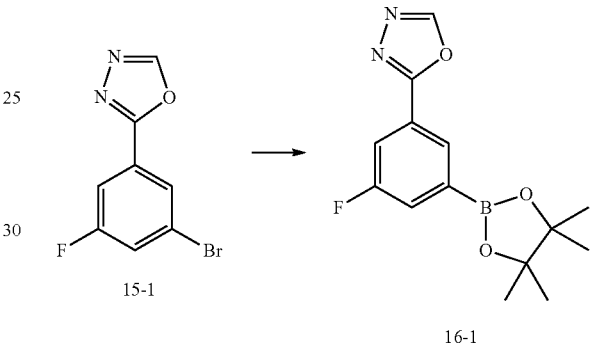

15-1

16-1

To bromide 15-1 (1.7 g, 7.1 mmol) in THF (8.9 mL) was added bis(pinacolato)diboron (2.1 g, 8.3 mmol), 1,3-bis-(diisopropylphenyl)-imidazolium chloride (0.18 g, 0.43 mmol), palladium acetate (0.05 g, 0.2 mmol) and potassium acetate (1.7 g, 17.8 mmol). Nitrogen was bubbled through the reaction mixture for 5 minutes. The reaction was then warmed to reflux and stirred for 2 h. The cooled mixture was passed through a pad of silica gel. The filtrate was concentrated in vacuo and the residue was purified by silica gel chromatography (0 to 30% EtOAc/hex) to provide boronate ester 16-1 (1.6 g, 78%).

The bromides in Table 16-1 were converted to their boronate esters using the conditions analogous to those described in Method 16

TABLE 16-1

| Entry | Bromide | Boronate Ester |
|---|---|---|
| 1 | 15-2 | 16-2 |

TABLE 16-1-continued
| Entry | Bromide | Boronate Ester |
|---|---|---|
| 2 | 15B-2 | 16-3 |
| 3 | commercial | 16-4 |
| 4 | 15A-2 | 16-5 |
| 5 | commercial | 16-6 |
| 6 | 15A-1 | 16-7 |
| 7 | 15C-1 | 16-8 |
| 8 | commercial | 16-9 |
Method 16A
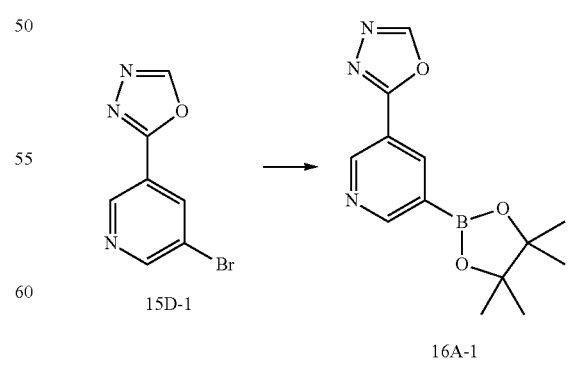
15D-1 → 16A-1
To 15D-1 (1.1 g, 4.7 mmol) in DMSO (19 mL) was added bis(pinacolato)diboron (1.3 g, 5.2 mmol) and potassium acetate (1.4 g, 14 mmol). Nitrogen was bubbled through the reaction for 5 minutes. PdCl₂(dppf) (0.17 g, 0.23 mmol) was added and nitrogen was bubbled through the reaction for 1 minute. The reaction was warmed to 80° C. and stirred for 24 h. Water was added to the cooled reaction and the mixture was extracted with EtOAc. The combined organic layers were washed with water and brine, dried (MgSO₄), filtered, and concentrated in vacuo. The residue was purified by reverse phase chromatography (C18 column; solvent A: 0.1% formic acid/water; solvent B: 0.1% formic acid/acetonitrile; 5-100% B over 10 column volumes) to provide 16A-1 (0.20 g, 15%).

Method 16B

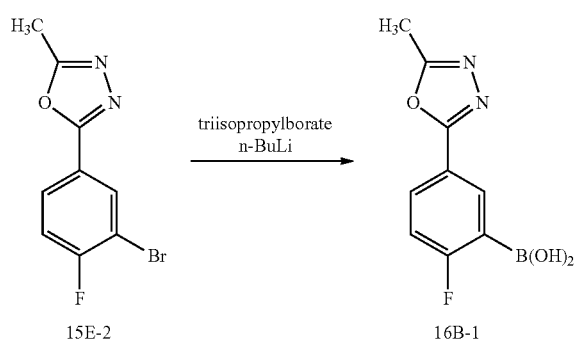 [SMILES: Cc1nnc(-c2ccc(F)c(Br)c2)o1 ; Cc1nnc(-c2ccc(F)c(B(O)O)c2)o1]

A stirred solution of 15E-2 (110 g, 0.429 mol) in THF (1.10 L) was cooled to −78° C., charged with n-BuLi in n-hexanes (268 mL, 0.429 mol, 1.60 M) dropwise over 45 min, and stirred for 30 min at −78° C. The reaction mixture was charged with triisopropyl borate (198.6 mL, 0.858 mol) dropwise over 30 min. The reaction mixture was stirred for 30 min at −78° C., warmed to room temperature, and stirred for 2 h. At that time, 2 N HCl (800 mL) was added and the reaction mixture was extracted with EtOAc/MeOH (9:1, 4×1.00 L). The combined organics were washed with brine, dried over anhydrous Na₂SO₄, and concentrated. The crude compound was washed with MTBE/THF (9:1, 200 mL) and IPA/MTBE (1:9, 200 mL) and dried under high vacuum to afford 16B-1 (41.5 g, 80%). NMR (300 MHz, DMSO-d₆): δ 8.48 (bs, 2H), 8.18-8.16 (m, 1H), 8.05-8.00 (m, 1H), 7.32 (t, J=8.7 Hz, 1H), 2.58 (s, 3H). MS (MM) m/z 223 [M+H]⁺.

Method 17

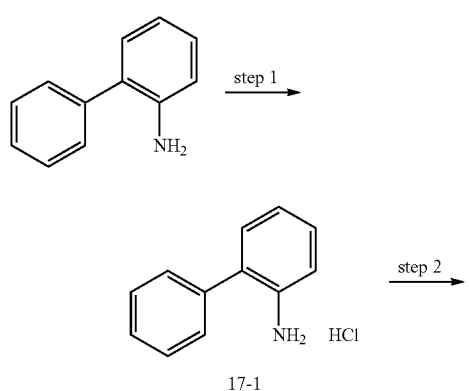

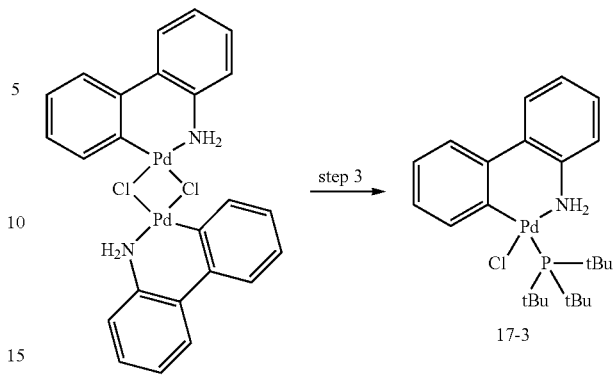

Step 1: To isopropylacetate (600 mL) and MeOH (36 mL, 886 mmol) was added trimethylsilyl chloride (85 mL, 665 mmol) at room temperature. The mixture was stirred for 30 minutes and [1,1′-biphenyl]-2-amine (75 g, 440 mmol) was added. The reaction was aged for 18 h and the solid was collected by filtration and washed with isopropylacetate to provide 17-1 (90 g, 99%).

Step 2: To 17-1 (4.0 g, 19.5 mmol) slurried in nitrogen degassed THF (120 mL) was added palladium acetate (4.4 g, 19.5 mmol). The reaction was warmed to 60 C and stirred for 75 minutes. A portion of the solvent (50-60 mL) was removed in vacuo. Heptane (50 mL) was added to the stirred solution at room temperature over 20 minutes at which point the slurry was aged for 30 minutes. The solid was filtered washing with 25% heptane/THF (2×50 mL) to provide 17-2 (5.8 g, 93%).

Step 3: To 17-2 (4.1 g, 6.5 mmol) in degassed acetone (20 mL) was added tri-t-butylphosphine (2.6 g, 13.1 mmol). The reaction was stirred at room temperature for 30 minutes and then the solids were filtered washing with hexanes to provide 17-3 (5.8 g, 87%).

Method 18

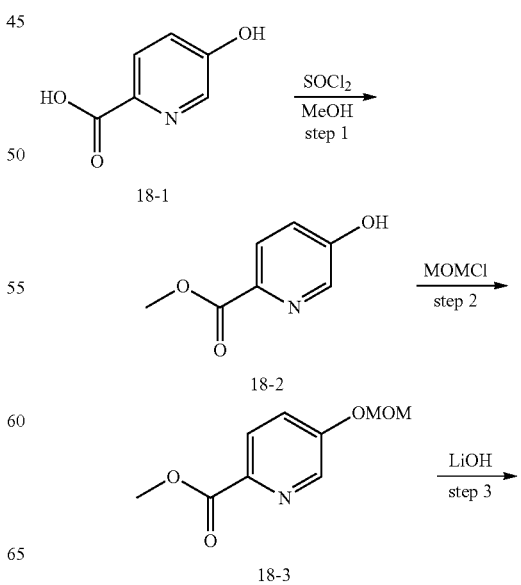

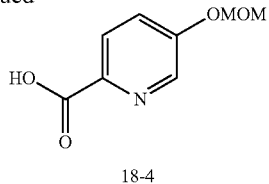

18-4

Step 1: To a solution of compound 18-1 (0.6 g, 4.3 mmol) in MeOH (10 mL) was added SOCl$_2$ (1.1 g, 8.6 mmol). The mixture was stirred at 70° C. for 8 h, and concentrated to afford compound 18-2 (0.66 g, 100%).

Step 2: To a solution of compound 18-2 (0.5 g, 3.2 mmol) and DIEA (0.64 g, 4.9 mmol) in THF (10 mL) at 0° C. was added MOMCl (0.4 g, 4.9 mmol) dropwise. The solution was stirred at RT for 4 h, and then quenched with water, extracted with EtOAc. The combined extracts were washed with brine, dried over Na$_2$SO$_4$, concentrated and purified by column (PE:EA=3:1) to afford compound 18-3 (0.4 g, 67%). $^1$H NMR (400 MHz, CDCl$_3$): 8.46 (d, J=2.4 Hz, 1H), 8.09 (d, J=4.8 Hz, 1H), 7.43~7.46 (m, 1H), 5.26 (s, 2H), 3.97 (s, 3H), 3.48 (s, 3H).

Step 3: A solution of compound 18-3 (0.4 g, 2 mmol) in LiOH solution (5 mL, 4M) and THF (5 mL) was stirred at RT for 2 h. The solution was neutralized with AcOH, extracted with EtOAc. The combined extracts were washed with brine, dried over Na$_2$SO$_4$, concentrated to give compound 18-4 (0.2 g, 57%). $^1$H NMR (400 MHz, CD$_3$OD): 8.41 (d, J=2.4 Hz, 1H), 8.14 (d, J=8.4 Hz, 1H), 7.63~7.65 (m, 1H), 5.36 (s, 2H), 3.51 (s, 3H).

In addition to the examples listed above, compounds of the invention include those in Table A below:

TABLE A

| Entry | Compound | Expected M + H | Observed M + H | tR (min) | LCMS cond. | BACE1 inhibition |
|---|---|---|---|---|---|---|
| 1 | 2-1 | 330 | 330 | 1.75 | A | 45% Inh. at 10 µM |
| 2 | 2-2 | 300 | 300 | 0.69 | A | $K_i$ = 6.1 µM |
| 3 | 2A-3 | 303 | 303 | 1.91 | A | |
| 4 | 2A-4 | 348 | 348 | 1.82 | A | |

TABLE A-continued

| Entry | Compound | Expected M + H | Observed M + H | tR (min) | LCMS cond. | BACE1 inhibition |
|---|---|---|---|---|---|---|
| 5 | 2A-5 | 318 | 318 | 1.44 | A | 51% Inh. at 10 μM |
| 6 | 3-3 | 365 | 365 | 1.87 | A | 56% Inh. at 10 μM |
| 7 | | 319 | 319 | 2.14 | F2 | $K_i = 1.4$ μM |
| 8 | 2A-6 | 364 | 364 | 1.0 | F6 | |
| 9 | 2A-7 | 334 | 334 | 2.45 | F1 | $K_i = 3.1$ μM |

TABLE A-continued

| Entry | Compound | Expected M + H | Observed M + H | tR (min) | LCMS cond. | BACE1 inhibition |
|---|---|---|---|---|---|---|
| 10 | | 399 | 399 | 1.05 | F6 | |
| 11 | | 303 | 303 | 2.62 | F1 | $K_i = 1.3\ \mu M$ |
| 12 | | 348 | 348 | 1.11 | F6 | |
| 13 | | 318 | 318 | 2.09 | F1 | $K_i = 3.6\ \mu M$ |
| 14 | | 321 | 321 | 3.23 | F1 | $K_i = 2.4\ \mu M$ |
| 15 | | 366 | 366 | 2.06 | F2 | 45% Inh. at 10 μM |

TABLE A-continued

| Entry | Compound | Expected M + H | Observed M + H | tR (min) | LCMS cond. | BACE1 inhibition |
|---|---|---|---|---|---|---|
| 16 | | 336 | 336 | 0.49 | F6 | |
| 17 | | 380 | 380 | 2.18 | A | |
| 18 | | 300 | 300 | 0.65 | A | |
| 19 | 2F-2 | 364 | 364 | 2.11 | A | |
| 20 | 2F-3 | 301 | 301 | 1.57 | A | $K_i = 6.2\ \mu M$ |
| 21 | 2G-3a | 344 | 344 | 0.70 | F6 | |

TABLE A-continued

| Entry | Compound | Expected M + H | Observed M + H | tR (min) | LCMS cond. | BACE1 inhibition |
|---|---|---|---|---|---|---|
| 22 | 2G-3b | 344 | 344 | 0.69 | F6 | |
| 23 | 2G-4a | 314 | 314 | 0.49 | F6 | |
| 24 | 2G-4b | 314 | 314 | 0.45 | F6 | |
| 25 | | 358 | 358 | 0.74 | F6 | |
| 26 | | 358 | 358 | 0.78 | F6 | |
| 27 | | 328 | 328 | 3.19 | F1 | $K_i$ = 4.8 μM |

TABLE A-continued

| Entry | Compound | Expected M + H | Observed M + H | tR (min) | LCMS cond. | BACE1 inhibition |
|---|---|---|---|---|---|---|
| 28 | | 328 | 328 | 3.16 | F1 | $K_i$ = 7.3 μM |
| 29 | | 356 | 356 | 1.78 | B | |
| 30 | | 356 | | | | 30% Inh. at 10 μM |
| 31 | | 326 | | | | |
| 32 | | 326 | 326 | 1.0 | B | |
| 33 | | 398 | 398 | 0.97 | F6 | |
| 34 | | 398 | 398 | 0.97 | F6 | |

TABLE A-continued
| Entry | Compound | Expected M + H | Observed M + H | tR (min) | LCMS cond. | BACE1 inhibition |
|---|---|---|---|---|---|---|
| 35 | 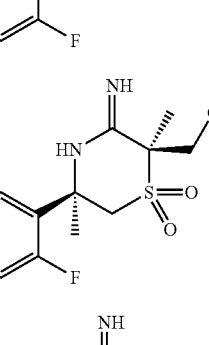 | 368 | 368 | 2.14 | F1 | $K_i$ = 3.0 μM |
| 36 | 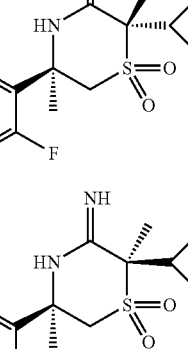 | 368 | 368 | 2.13 | F1 | 37% Inh. at 10 μM |
| 37 | 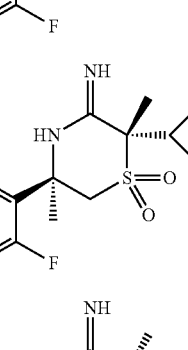 | 370 | 370 | 0.78 | F6 | |
| 38 | 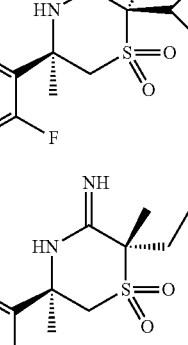 | 370 | 370 | 0.79 | F6 | |
| 39 | 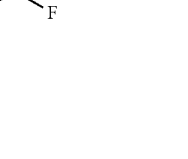 | 340 | 340 | 3.19 | F1 | $K_i$ = 1.7 μM |
| 40 | | 340 | 340 | 3.21 | F1 | 20% Inh. at 10 μM |
| 41 | | 356 | 356 | 1.92 | A | |

TABLE A-continued
| Entry | Compound | Expected M + H | Observed M + H | tR (min) | LCMS cond. | BACE1 inhibition |
|---|---|---|---|---|---|---|
| 42 | 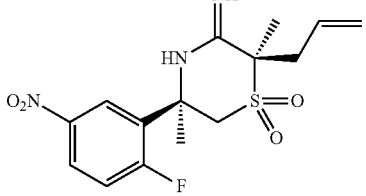 | 356 | 356 | 1.92 | A | |
| 43 | 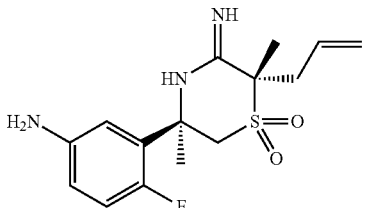 | 326 | 326 | 0.17 | J | |
| 44 | 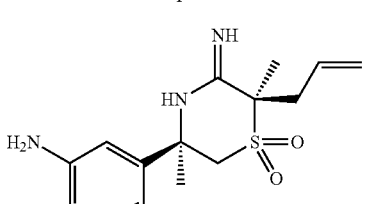 | 326 | 326 | 1.57 | B | 38% Inh. at 10 μM |
| 45 | 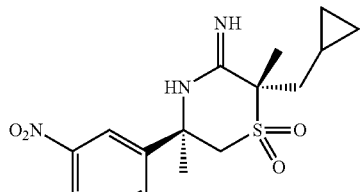 | 370 | 370 | 0.75 | F6 | |
| 46 | 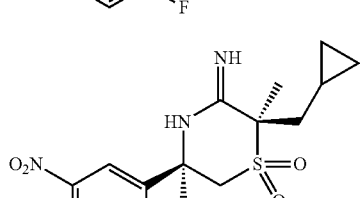 | 370 | 370 | 0.86 | F6 | |
| 47 | 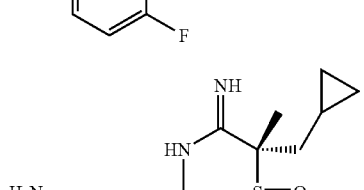 | 340 | 340 | 2.50 | F1 | $K_i$ = 1.8 μM |
| 48 | 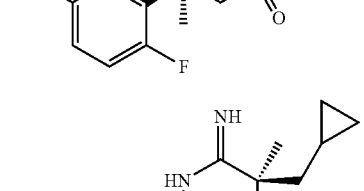 | 340 | 340 | 2.53 | F1 | 37% Inh. at 10 μM |

TABLE A-continued

| Entry | Compound | Expected M + H | Observed M + H | tR (min) | LCMS cond. | BACE1 inhibition |
|---|---|---|---|---|---|---|
| 49 | | 400 | 400 | 1.70 | B | |
| 50 | | 370 | 370 | 1.16 | B | $K_i = 0.5\ \mu M$ |
| 51 | | 414 | 414 | 1.93 | A | |
| 52 | | 414 | 414 | 1.93 | A | |
| 53 | | 384 | 384 | 1.72 | A | $K_i = 1.3\ \mu M$ |
| 54 | | 410 | 410 | 0.99 | F6 | |

TABLE A-continued

| Entry | Compound | Expected M + H | Observed M + H | tR (min) | LCMS cond. | BACE1 inhibition |
|---|---|---|---|---|---|---|
| 55 | | 410 | 410 | 0.99 | F6 | |
| 56 | | 380 | 380 | 0.95 | F6 | |
| 57 | | 380 | 380 | 0.95 | F6 | |
| 58 | | 410 | 410 | 0.97 | F6 | |
| 59 | | 410 | 410 | 0.97 | F6 | |
| 60 | | 380 | 380 | 2.15 | F2 | $K_i = 1.1\ \mu M$ |

TABLE A-continued

| Entry | Compound | Expected M + H | Observed M + H | tR (min) | LCMS cond. | BACE1 inhibition |
|---|---|---|---|---|---|---|
| 61 | | 380 | 380 | 2.10 | F2 | 27% Inh. at 10 µM |
| 62 | | 410 | 410 | 1.02 | F6 | |
| 63 | | 410 | 410 | 0.98 | F6 | |
| 64 | | 380 | 380 | 0.47 | F6 | |
| 65 | | 380 | 380 | 0.42 | F6 | |
| 66 | | 460 | 460 | 2.9 | C | $K_i$ = 0.6 µM |

TABLE A-continued

| Entry | Compound | Expected M + H | Observed M + H | tR (min) | LCMS cond. | BACE1 inhibition |
|---|---|---|---|---|---|---|
| 67 | | 460 | 460 | 2.9 | C | |
| 68 | | 430 | 430.2 | 2.7 | C | $K_i$ = 1.4 μM |
| 69 | | 430 | 430.0 | 2.3 | C | 17% Inh. at 10 μM |
| 70 | | 461 | 461 | 0.88 | F6 | |
| 71 | | 461 | 461 | 0.88 | F6 | |
| 72 | | 431 | 431 | 3.35 | F1 | $K_i$ = 1.4 μM |

TABLE A-continued

| Entry | Compound | Expected M + H | Observed M + H | tR (min) | LCMS cond. | BACE1 inhibition |
|---|---|---|---|---|---|---|
| 73 | | 431 | 431 | 3.36 | F1 | $K_i$ = 4.6 μM |
| 74 | | 393 | 393 | 0.94 | F6 | |
| 75 | | 393 | 393 | 0.94 | F6 | |
| 76 | | 363 | 363 | 1.99 | F4 | $K_i$ = 6.6 μM |
| 77 | | 363 | 363 | 1.84 | F2 | 25% Inh. at 10 μM |
| 78 | | 387 | 387 | 1.95 | A | $K_i$ = 1.5 μM |

TABLE A-continued

| Entry | Compound | Expected M + H | Observed M + H | tR (min) | LCMS cond. | BACE1 inhibition |
|---|---|---|---|---|---|---|
| 79 | 6D-3 | 291 | 291 | 1.62 | A | |
| 80 | 6D-4 | 371 | 371 | 1.95 | A | |
| 81 | 6F-3a | 439 | 439 | 2.33 | F2 | $K_i = 0.5\ \mu M$ |
| 82 | 6F-3b | 439 | 439 | 2.34 | F2 | |
| 83 | | 411 | 411 | 2.04 | F3 | |
| 84 | | 411 | 411 | 2.11 | F3 | |

TABLE A-continued

| Entry | Compound | Expected M + H | Observed M + H | tR (min) | LCMS cond. | BACE1 inhibition |
|---|---|---|---|---|---|---|
| 85 | | 434 | 434 | 3.47 | F1 | $K_i$ = 1.5 μM |
| 86 | | 434 | 434 | 3.49 | F1 | 44% Inh. at 10 μM |
| 87 | | 451 | 451 | 2.18 | F3 | $K_i$ = 0.6 μM |
| 88 | | 451 | 451 | 2.17 | F3 | 34% Inh. at 10 μM |
| 89 | | 445 | 445 | 1.85 | G | $K_i$ = 1.9 μM |
| 90 | | 471 | 471 | 1.57 | B | |

TABLE A-continued

| Entry | Compound | Expected M + H | Observed M + H | tR (min) | LCMS cond. | BACE1 inhibition |
|---|---|---|---|---|---|---|
| 91 | | 471 | 471 | 1.54 | B | |
| 92 | 6C-1 | 353 | 353 | 1.56 | G | $K_i$ = 4.7 μM |
| 93 | 6I-1 | 401 | 401 | 1.51 | B | |

LC/MS Conditions

Conditions A: Column: Agilent Zorbax SB-C18 (3.0×50 mm) 1.8 μm; Mobile phase: A: 0.05% Trifluoroacetic acid in water, B: 0.05% Trifluoroacetic acid in acetonitrile; Gradient: 90:10 (A:B) for 0.3 min, 90:10 to 5:95 (A:B) over 1.2 min, 5:95 (A:B) for 1.2 min, Flow rate: 1.0 mL/min; UV detection: 254 and 220 nm; Mass spectrometer: Agilent 6140 quadrupole.

Conditions B: Column: Agilent Zorbax SB-C18 (3.0×50 mm) 1.8 μm; Column temp 50° C.; Mobile phase: A: 0.1% Trifluoroacetic acid in water, B: 0.1% Trifluoroacetic acid in acetonitrile; Gradient: 90:10 to 5:95 (A:B) over 1.5 min, 5:95 (A:B) for 1.2 min; Flow rate: 1.0 mL/min; UV detection: 254 and 220 nm; Mass spectrometer: Agilent 6140 quadrupole.

Conditions C: Column: Agilent SB-C18 (3.0×50 mm) 1.8 μm; Column temp 50° C.; Mobile phase: A: 0.1% Trifluoroacetic acid in water, B: 0.1% Trifluoroacetic acid in acetonitrile, Gradient: 90:10 (A:B) for 0.3 min, 90:10 to 5:95 (A:B) over 5 min, 5:95 (A:B) for 1.2 min; Flow rate: 1.0 mL/min; UV detection: 254 and 220 nm; Mass spectrometer: Agilent 6140 quadrupole.

Conditions D: Acquity UPLC BEH-C18, 1.7 μm, 2.1×50 mm; 5%-100% MeCN/water with 0.1% $NH_3$ in 1.4 min, 1 mL/min flow.

Conditions E: Agilent 1100 LC/MS, Column: Waters Xterra C18 (2.1×20 mm) 3.5 μm; Mobile phase: A 0.1% Trifluoroacetic acid in water, B: 0.1% Trifluoroacetic acid in acetonitrile; Gradient: 90:10 (A:B) to 2:98 (A:B) over 3.25 min, 2:98 (A:B) for 0.75 min; Flow rate: 1.5 mL/min; UV detection: 254 and 220 nm; Mass spectrometer: Agilent ESI+.

Conditions F1: Column: Agilent TC-C18 (2.1×50 mm) 5 μm; Mobile phase: A: 0.0375% Trifluoroacetic acid in water, B: 0.01875% Trifluoroacetic acid in acetonitrile; Gradient: 100:0 (A:B) for 0.4 min, 100:0 to 20:80 (A:B) over 3 min, 20:80 to 0:100 (A:B) over 0.6 min; Flow rate: 0.6 mL/min; UV detection: 254 and 220 nm; Mass spectrometer: Agilent 6110 quadrupole.

Conditions F2: Column: Agilent TC-C18 (2.1×50 mm) 5 μm; Mobile phase: A: 0.0375% Trifluoroacetic acid in water, B: 0.01875% Trifluoroacetic acid in acetonitrile; Gradient: 99:1 (A:B) for 0.4 min, 99:1 to 10:90 (A:B) over 3 min, 10:90 to 0:100 (A:B) over 0.6 min; Flow rate: 0.8 mL/min; UV detection: 254 and 220 nm; Mass spectrometer: Agilent 6110 quadrupole Conditions F3: Column: Agilent TC-C18 (2.1×50 mm) 5 ii m; Mobile phase: A: 0.0375% Trifluoroacetic acid in water, B: 0.01875% Trifluoroacetic acid in acetonitrile; Gradient: 90:10 (A:B) for 0.4 min, 90:10 to 0:100 (A:B) over 3 min, 0:100 (A:B) for 0.6 min; Flow rate: 0.8 mL/min; UV detection: 254 and 220 nm; Mass spectrometer: Agilent 6110 quadrupole.

Conditions F4: Column: Xbridge RP 18 (2.1×50 mm) 5 ii m; Mobile phase: A: 0.05% $NH_3$ in water, B: 100% acetonitrile; Gradient: 95:5 (A:B) for 0.4 min, 95:5 to 10:90 (A:B) over 3 min, 10:90 to 0:100 (A:B) over 0.6 min; Flow rate:

0.8 mL/min; UV detection: 254 and 220 nm; Mass spectrometer: Agilent 6110 quadrupole Conditions F5: Column: Agilent TC-C18 (2.1×50 mm) 5 µm ; Mobile phase: A: 0.0375% Trifluoroacetic acid in water, B: 0.01875% Trifluoroacetic acid in acetonitrile; Gradient: 75:25 (A:B) for 0.4 min, 75:25 to 0:100 (A:B) over 3 min, 0:100 (A:B) for 0.6 min; Flow rate: 0.8 mL/min; UV detection: 254 and 220 nm; Mass spectrometer: Agilent 6110 quadrupole.

Conditions F6: Column: Shimadzu ODS 2.1×30 mm 3 µm column; Mobile phase: A: 0.0375% Trifluoroacetic acid in water, B: 0.01875% Trifluoroacetic acid in acetonitrile; Gradient: 90:10 to 20:80 (A:B) over 2 min; Flow rate: 1.2 mL/min Conditions G: Column: Agilent Zorbax SB-C18 (3.0×50 mm) 1.8 µm; Column temp 50° C.; Mobile phase: A: 0.05% Trifluoroacetic acid/0.5% Acetic acid in water; B: 0.05% Trifluoroacetic acid/0.5% Acetic acid in acetonitrile; Gradient: 90:10 to 5:95 (A:B) over 1.5 min, 5:95 (A:B) for 1.2 min; Flow rate: 1.0 mL/min; UV detection: 254 and 220 nm; Mass spectrometer: Agilent 6140 quadrupole.

Conditions H: System: Waters Acquity UPLC/MS, Electrospray positive ion mode; Column: Waters Acquity UPLC BEH C18, 2.1×50 mm, 1.7 µm; Mobile Phase: A: $H_2O$/0.05% TFA, B: ACN/0.05% TFA; Gradient: 0-1.8 min, 5-99% B; Flow Rate: 0.8 mL/min; UV: 254 nm Conditions I: HPLC: Column: Novapak HR-C18 (25×100 mm) 6 m in Waters PrepLC 25 mm module; mobile phase: A: 0.1% TFA in water, B: 0.1% TFA in acetonitrile; gradient: 90:10 (A:B) for 1 min, 90:10 to 5:95 (A:B) over 10 min, 5:95 (A:B) for 5 min; Flow rate: 30 mL/min; UV detection: 254 or 220 nm.

Conditions J: System: Agilent 1100/Waters ZQ LC/MS. Column: Waters XTerra MS C18, 3.5 µm, 3.0×50 mm; mobile phase: A: $H_2O$/0.05% TFA, B: ACN/0.05% TFA; Flow rate: 1.5 mL/min. Gradient: 0-1.28 min, 5-98% B; UV detection: 190-400 nm.

Assays

Protocols that may be used to determine the recited potency values for the compounds of the invention are described below.

BACE1 HTRF FRET Assay

Reagents $Na^+$-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine $IC_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme. Inhibition of BACE1 cleavage of the QSY7-APP$^{swe}$-Eu substrate by inhibitors is manifested as a suppression of 620 nm fluorescence.

Varying concentrations of inhibitors at 3× the final desired concentration in a volume of 10 µl are preincubated with purified human BACE1 catalytic domain (3 nM in 10 µl) for 30 minutes at 30° C. in reaction buffer containing 20 mM Na-Acetate pH 5.0, 10% glycerol, 0.1% Brij-35 and 7.5% DSMO. Reactions are initiated by addition of 10 µl of 600 nM QSY7-APP$^{swe}$-Eu substrate (200 nM final) to give a final reaction volume of 30 µl in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window. Inhibitor $IC_{50}$ values are derived from non-linear regression analysis of concentration response curves. $K_i$ values are then calculated from $IC_{50}$ values using the Cheng-Prusoff equation using a previously determined µm value of 8 µM for the QSY7-APP$^{swe}$-Eu substrate at BACE1. The compounds of Examples 1, 2, and 3 were measured in this assay and each exhibited a $K_i$ value of less than about 5 nM. Additional $K_i$ values for example compounds of the invention measured using this assay are reported in the Tables above.

BACE-2 Assay

Inhibitor $IC_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light Inhibitor compounds, prepared at 3× the desired final concentration in 1×BACE assay buffer (20 mM sodium acetate pH 5.0, 10% glycerol, 0.1% Brij-35) supplemented with 7.5% DMSO are pre-incubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, $K_m$=8 µM for 4 µM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 µs delay on a RUBYstar HTRF plate reader (BMG Labtechnologies). Raw RFU data is normalized to maximum (1.0 nM BACE/DMSO) and minimum (no enzyme/DMSO) RFU values. $IC_{50}$ values are determined by nonlinear regression analysis (sigmoidal dose response, variable slope) of percent inhibition data with minimum and maximum values set to 0 and 100 percent respectively. Similar $IC_{50s}$ are obtained when using raw RFU data. The $K_i$ values are calculated from the $IC_{50}$ using the Cheng-Prusoff equation. Examples 1 through 3, 5 through 7, 9 through 9o, 10, 11, 23, and 27a have BACE2 $K_i$ values of less than 200 nM. Compounds 2-2, 2A-5, 3-3, 4-1 in Table A have BACE2 $K_i$ values between about 0.5 µM and 10 µM.

Unless otherwise noted below, the examples and compounds in the Tables above for which BACE1 inhibition data are noted have BACE2 $K_i$ values that range from <0.2 nM to 9.0 µM.

The examples in Table 2-1 have BACE2 $K_i$ values ≤10 nM with the following exceptions: Examples 9i (49 nM), 9p (16 nM).

The examples in Table 2A-1 have BACE2 $K_i$ values ≤10 nM with the following exceptions: Example 9n (12 nM).

The examples in Table 2A-2 have BACE2 $K_i$ values ≤10 nM with the following exceptions: Examples 9v (13 nM), 9y (11 nM), 9z (59 nM), 9ac (13 nM), 9ad (41 nM), 9ae (69 nM).

The examples in Table 2B-1 have BACE2 $K_i$ values between 50 nM and 4.0 µM with the following exceptions:

Examples 9ai (18 nM), 9ak (13 nM), 9al (44 nM), 9ap (4 nM), 9 at (14 nM), 9aw (47 nM), 9ax (22 nM).

The examples in Table 2B-2 have BACE2 $K_i$ values between 50 nM and 5.0 µM with the following exceptions: Examples 9ba (1 nM), 9bd (40 nM), 9bf (11 nM), 9bg (3 nM), 9bh (4 nM), 9bi (9 nM), 9bk (12 nM), 9bl (40 nM), 9bo (22 nM), 9bu (5 nM).

The examples in Table 2E-1 have the following BACE2 $K_i$ values: Examples 9by (2.9 µM), 9bz (13 nM), 9ca (9 nM).

The examples in Table 2F-1 have BACE2 $K_i$ values ≤20 nM with the following exceptions: Examples 9cf (40 nM), 9cg (85 nM), 9ci (44), 9cj (21 nM). Furthermore Examples 9 cc and 9ck both had BACE2 $K_i$ values ≤10 nM.

The examples in Table 2G-1 have BACE2 $K_i$ values that range from 0.3 nM to 700 nM. Furthermore, the examples in Table 2G-1 have BACE2 $K_i$ values ≤10 nM with the following exceptions: (i) the following have BACE2 $K_i$ values from 11 nM to 100 nM: Examples 9 cm-b, 9cn-b, 9cq-b, 9cu-a, 9cv-b, 9cw-b, 9cy-a, 9cz-a, 9da-b, 9 db-b, 9dc-a, 9df-b, 9dk-b, 9dl-b, 9dm-b, 9dp-b, 9dq-b, 9dv-b, 9dw-b, 9ea-b, 9ec-a, 9ee-b; (ii) the following have BACE2 $K_i$ values from 101 nM to 700 nM: Examples 9cx-b, 9cy-b, 9cz-b, 9dd-b, 9de-b, 9dg-b, 9dr-b, 9dx-b, 9dy-b, 9dz-b, 9eb-b, 9ec-b.

In Table 2H-1, Example 9ef has a BACE2 $K_i$ value of 218 nM.

In Table 3-1, the examples have the following BACE2 $K_i$ values: Examples 10 (176 nM), 11 (13 nM), 16a (445 nM).

The examples in Table 3A-1 have BACE2 $K_i$ values that range from 1.0 µM to 8.0 µM.

The examples in Table 4-1 have BACE2 $K_i$ values ≤50 nM. In particular, Example 20 has a BACE2 $K_i$ value of 8 nM.

The examples in Table 4A-1 have BACE2 $K_i$ values that range from 100 nM to 1.0 µM with the following exceptions: Examples 22g (51 nM), 22u (77 nM), 22f (1.8 µM).

The examples in Table 6-1 have BACE2 $K_i$ values ≤50 nM with the following exceptions: Example 24 (314 nM). Furthermore, Examples 25 and 27 have BACE2 $K_i$ values ≤10 nM.

The examples in Table 6A-1 have BACE2 $K_i$ values that range from 3 nM to 1.2 µM. Furthermore, the following examples have BACE2 $K_i$ values ≤10 nM: Examples 27e, 27l, 27s, 27u, and 27v.

The examples in Table 6B-1 have BACE2 $K_i$ values ≤20 nM with the following exceptions: Example 27ae (21 nM).

The examples in Table 6C-1 have BACE2 $K_i$ values that range from 15 nM to 160 nM.

The examples in Table 6D-1 have BACE2 $K_i$ values ≤100 nM. Furthermore, Examples 27an, 27ao, 27aq, 27 as, and 27 at have BACE2 $K_i$ values ≤20 nM.

The examples in Table 6E-1 have BACE2 $K_i$ values ≤100 nM. Furthermore, Examples 27bb, 27bc, 27bf, 27bg, and 27bh have BACE2 $K_i$ values ≤20 nM.

The examples in Table 6F-1 have BACE2 $K_i$ values that range from 30 nM to 2.0 µM with the following exceptions: Examples 27bj-a (7 nM), 27bk-a (9 nM), 27bl-a (9 nM), 27bm-a (7 nM), 27br-a (10 nM), 27bs-a (9 nM).

The examples in Table 6F-2 have BACE2 $K_i$ values that range from 1 nM to 240 nM. Furthermore, the following examples have BACE2 $K_i$ values ≤10 nM: Examples 27by and 27bx.

The examples in Table 6G-1 have BACE2 $K_i$ values that range from 9 nM to 320 nM.

The examples in Table 6H-1 have BACE2 $K_i$ values that range from 4 nM to 120 nM.

The examples in Table 6I-1 have BACE2 $K_i$ values that range from 100 nM to 500 nM.

In Table 7-1, the examples have the following BACE2 $K_i$ values: Examples 30 (862 nM), 30a (517 nM).

In Table 7A-1, Example 30b has a BACE2 $K_i$ value of 5 nM.

The examples in Table 8-1 have BACE2 $K_i$ values of 5 µM.

The examples in Table 9-1 have BACE2 $K_i$ values that range from 400 nM to 2.5 µM with the following exceptions: Examples 32-a, 32-b, 32e-b, and the mixture of 32b-a and 32b-b show inhibitions of BACE2 at 10 µM in the range of 1% to 24%.

The examples in Table 9-2 have BACE2 $K_i$ values that range from 100 nM to 4.5 µM. In particular, Examples 32g-a and 32h-a have BACE2 $K_i$ values of 145 nM and 126 nM, respectively.

The examples in Table 11A-1 have BACE2 $K_i$ values that range from 200 nM to 750 nM.

The examples in Table 11A-2 have BACE2 $K_i$ values that range from 800 nM to 7.5 µM with the following exceptions: Example 34d-b shows 10% inhibition of BACE2 at 10 µM.

In Table 12A-1, the examples have the following BACE2 $K_i$ values: Examples 35 (779 nM), 35a (1.4 µM).

In Table 13-1, Example 36 has a BACE2 $K_i$ value of 1.2 µM.

In Table A, compounds for which BACE1 inhibition is given have BACE2 $K_i$ values that range from 100 nM to 9 µM with the following exceptions: Entries 30, 40, 61, 69, 77, and 88 show inhibitions of BACE2 at 10 µM in the range of 29% to 47%.

BACE Inhibitor Whole Cell $IC_{50}$ Determination Using HEK293-APP$^{swe/lon}$ Cells HEK293 cells are obtained from the American Type Culture Collection (ATCC) and stably transfected with the human amyloid precursor protein cDNA containing the FAD Swedish (enhances β-secretase processing) and London (enhances Aβ42 cleavage) mutations. A HEK293 stable clone with Aβ expression (HEK293-APP$^{swe/lon}$) is identified and maintained at 37° C., 5% $CO_2$ in the ATCC-recommended growth media supplemented with hygromycin. Determination of compound $IC_{50}$ values for inhibition of APP processing (reduction of Aβ1-40, Aβ1-42 and sAPPβ levels) in HEK293-APP$^{swe/lon}$ cells is accomplished by treatment of cells with various concentrations of compounds diluted in fresh complete growth media for 4 hours at 37° C., 5% $CO_2$. Aβ40 or Aβ42 are measured in 15 µl of media using a mesoscale based ELISA assay. Full length Aβ40 and Aβ42 peptides are captured with the N-terminal specific biotinylated-WO2 monoclonal antibody and detected using either the ruthenylated Aβ40 C-terminal specific monoclonal antibody, G2-10 or the ruthenylated Aβ42 C-terminal specific monoclonal antibody G2-11 respectively. Raw electrochemiluminescence values are measured using a Mesoscale Sector Imager plate reader and are plotted as a function of compound concentration. $IC_{50}$ values are interpolated from the data using nonlinear regression analysis (Sigmoidal dose response fit with variable slope) of the data using GraphPad Prism software.

The invention claimed is:
1. A compound, or a stereoisomer of said compound, or a pharmaceutically acceptable salt of said compound or said stereoisomer, said compound having the structural Formula (I):

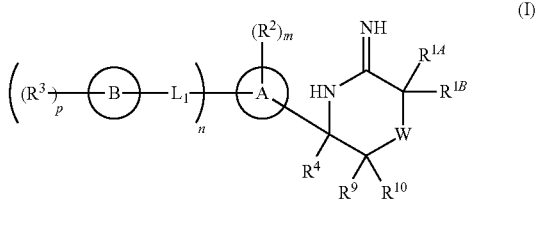

(I)

or a tautomer thereof having the structural Formula (I'):

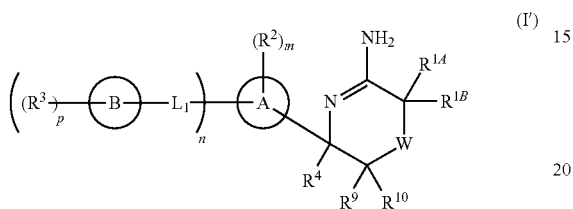

(I')

or pharmaceutically acceptable salt thereof, wherein:

W is selected from the group consisting of S, S(O), and S(O)$_2$;

$R^{1A}$ and $R^{1B}$ are each independently selected from the group consisting of: H, halogen, alkyl, alkoxy, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, -alkyl-(monocyclic heterocycloalkyl), a multicyclic group, and -alkyl-(multicyclic group);

wherein said alkyl, alkoxy, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, -alkyl-(monocyclic heterocycloalkyl), multicyclic group, -alkyl-(multicyclic group) of $R^{1A}$ and $R^{1B}$ is each optionally and independently unsubstituted or substituted with one or more groups independently selected from $R^8$;

ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

ring B (when present) is independently selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

-L$_1$- (when present) independently represents a bond or a divalent moiety selected from the group consisting of -alkyl-, -haloalkyl-, -heteroalkyl-, -alkenyl-, -alkynyl-, —N(R$^6$)—, —NHC(O)—, —C(O)NH—, —CH$_2$NHC(O)—, —CH$_2$C(O)NH—, —NHS(O)$_2$—, —CH$_2$NHS(O)$_2$—, —CH$_2$SO$_2$NH—, —S(O)$_2$NH—, —O—CH$_2$—, —CH$_2$—O—, —NHCH$_2$—, —CH$_2$NH—, and —CH(CF$_3$)NH—, —NHCH(CF$_3$)—;

m, n, and p are each independently selected integers, wherein:

m is 0 or more;
n is 0 or 1; and
p is 0 or more, wherein the maximum value of m is the maximum number of available substitutable hydrogen atoms on ring A, and wherein the maximum value of p is the maximum number of available substitutable hydrogen atoms on ring B;

each $R^2$ (when present) is independently selected from the group consisting of: halogen, —OH, —CN, —SF$_5$, —OSF$_5$, —NO$_2$, —Si(R$^5$)$_3$, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$S(O)$_2$N(R$^6$)$_2$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl of $R^2$ are each optionally unsubstituted or substituted with one or more groups independently selected from $R^8$;

each $R^3$ (when present) is independently selected from the group consisting of: halogen, —OH, —CN, —SF$_5$, —OSF$_5$, —NO$_2$, —Si(R$^5$)$_3$, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$S(O)$_2$N(R$^6$)$_2$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^3$ are each optionally unsubstituted or substituted with one or more groups independently selected from $R^8$;

$R^4$ is selected from the group consisting of alkyl, haloalkyl, heteroalkyl, alkenyl, alkynyl, aryl, -alkyl-aryl, heteroaryl, -alkyl-heteroaryl, cycloalkyl, -alkyl-cycloalkyl, cycloalkenyl, -alkyl-cycloalkenyl, heterocycloalkyl, -alkyl-heterocycloalkyl, heterocycloalkenyl, and -alkyl-heterocycloalkenyl, wherein each of said alkyl, haloalkyl, heteroalkyl, aryl, -alkyl-aryl, heteroaryl, -alkyl-heteroaryl, cycloalkyl, -alkyl-cycloalkyl, cycloalkenyl, -alkyl-cycloalkenyl, heterocycloalkyl, -alkyl-heterocycloalkyl, heterocycloalkenyl, and -alkyl-heterocycloalkenyl of $R^4$ is unsubstituted or substituted with one or more independently selected $R^{11}$ groups;

each $R^5$ (when present) is independently selected from the group consisting of alkyl, heteroalkyl, haloalkyl, cycloalkyl, -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^5$ is unsubstituted or substituted with one or more groups independently selected from halogen, alkyl, cycloalkyl, heteroalkyl, haloalkyl, alkoxy, heteroalkoxy, and haloalkoxy;

each $R^6$ (when present) is independently selected from the group consisting of H, alkyl, -alkyl-OH, alkenyl, alkynyl, heteroalkyl, -heteroalkyl-OH, haloalkyl, -haloalkyl-OH, cycloalkyl, lower alkyl-substituted cycloalkyl, lower alkyl-substituted -alkyl-cycloalkyl, heterocycloalkyl, -alkyl-heterocycloalkyl, aryl, -alkyl-aryl, heteroaryl, and -alkyl-heteroaryl, wherein each said heterocycloalkyl, -alkyl-heterocycloalkyl, aryl, -alkyl-aryl, heteroaryl, and said -alkyl-heteroaryl of $R^6$ is unsubstituted or substituted with one or more groups independently selected from halogen, alkyl, cycloalkyl, heteroalkyl, haloalkyl, alkoxy, heteroalkoxy, and haloalkoxy;

each $R^7$ (when present) is independently selected from the group consisting of H, alkyl, heteroalkyl, haloalkyl, cycloalkyl, -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^7$ is unsubstituted or substituted with one or more groups independently selected from halogen, alkyl, cycloalkyl, heteroalkyl, haloalkyl, alkoxy, heteroalkoxy, and haloalkoxy;

each $R^8$ (when present) is independently selected from the group consisting of halogen, —OH, —CN, —$SF_5$, —$OSF_5$, alkyl, alkoxy, haloalkyl, haloalkoxy, cycloalkyl, -alkyl-cycloalkyl, —O-cycloalkyl, —O-alkyl-cycloalkyl, —O-benzyl, heteroalkyl, —O-heteroalkyl, and -alkyl-OH;

$R^9$ and $R^{10}$ are each independently selected from the group consisting of H, halogen, —OH, —CN, —P(O)$(OR^5)_2$, —P(O)$(OR^5)(R^5)$, —N$(R^6)_2$, —$NR^7C(O)R^6$, —$NR^7S(O)_2R^6$, —$NR^7C(O)N(R^6)_2$, —$NR^7C(O)OR^6$, —$C(O)R^6$, —$C(O)_2R^6$, —$C(O)N(R^6)_2$, —$S(O)R^6$, —$S(O)_2R^6$, —$S(O)_2N(R^6)_2$, —$OR^6$, —$SR^6$, alkyl, haloalkyl, heteroalkyl, alkenyl and alkynyl, wherein each of said alkyl, haloalkyl, heteroalkyl, alkenyl and alkynyl of $R^9$ and $R^{10}$ is unsubstituted or substituted with one or more independently selected $R^{12}$ groups;

each $R^{11}$ (when present) is independently selected from the group consisting of halogen, —OH, —CN, —$SF_5$, —$OSF_5$, —P(O)$(OR^5)_2$, —P(O)$(OR^5)(R^5)$, —N$(R^6)_2$, —$NR^7C(O)R^6$, —$NR^7S(O)_2R^6$, —$NR^7S(O)_2N(R^6)_2$, —$NR^7C(O)N(R^6)_2$, —$NR^7C(O)OR^6$, —$C(O)R^6$, —$C(O)_2R^6$, —$C(O)N(R^6)_2$, —$S(O)R^6$, —$S(O)_2R^6$, —$S(O)_2N(R^6)_2$, —$OR^6$, —$SR^6$, alkyl, haloalkyl, haloalkoxy, heteroalkyl, -alkyl-OH, cycloalkyl, -alkyl-cycloalkyl;

each $R^{12}$ is independently selected from the group consisting of halogen, —OH, —CN, —$SF_5$, —$OSF_5$, —P(O)$(OR^{13})_2$, —P(O)$(OR^{13})(R^{13})$, —N$(R^{14})_2$, —$NR^{14}C(O)R^{14}$, —$NR^{14}S(O)_2R^{14}$, —$NR^{14}S(O)_2N(R^{14})_2$, —$NR^{14}C(O)N(R^{14})_2$, —$NR^{14}C(O)OR^{14}$, —$C(O)R^{14}$, —$C(O)_2R^{14}$, —$C(O)N(R^{14})_2$, —$S(O)R^{14}$, —$S(O)_2R^{14}$, —$S(O)_2N(R^{14})_2$, —$OR^{14}$, —$SR^{14}$, alkyl, haloalkyl, haloalkoxy, heteroalkyl, -alkyl-OH;

each $R^{13}$ (when present) is independently selected from the group consisting of alkyl, -alkyl-OH, alkenyl, alkynyl, heteroalkyl, -heteroalkyl-OH, haloalkyl, -haloalkyl-OH; and each $R^{14}$ (when present) is independently selected from the group consisting of H, alkyl, -alkyl-OH, alkenyl, alkynyl, heteroalkyl, -heteroalkyl-OH, haloalkyl, -haloalkyl-OH.

2. A compound of claim 1, or a tautomer thereof, or a stereoisomer of said compound or said tautomer, or a pharmaceutically acceptable salt of said compound, said tautomer, or said stereoisomer, wherein:

W is $S(O)_2$.

3. A compound of claim 2, or a tautomer thereof, or a stereoisomer of said compound or said tautomer, or a pharmaceutically acceptable salt of said compound, said tautomer, or said stereoisomer, wherein:

$R^4$ is selected from the group consisting of lower alkyl and lower haloalkyl.

4. A compound of claim 3, or a tautomer thereof, or a stereoisomer of said compound or said tautomer, or a pharmaceutically acceptable salt of said compound, said tautomer, or said stereoisomer, wherein:

one of $R^9$ and $R^{10}$ is H and the other is selected from the group consisting of H, lower alkyl, lower haloalkyl, and lower alkyl ether.

5. A compound of claim 3, or a tautomer thereof, or a stereoisomer of said compound or said tautomer, or a pharmaceutically acceptable salt of said compound, said tautomer, or said stereoisomer, wherein:

$R^{1A}$ is selected from the group consisting of H and methyl; and $R^{1B}$ is selected from the group consisting of H, methyl, ethyl, ethenyl, propyl, isopropyl, propenyl, butyl, butenyl, cyclopropyl, —$CH_2$-cyclopropyl, cyclobutyl, —$CH_2$-cyclobutyl, —$CH_2OH$, —$CH_2OCH_3$, —$CH_2OCH_2CH_3$, trifluoromethyl, —$CH_2F$, —$CHF_2$, —$CH_2CF_3$, phenyl, benzyl, pyridyl, tetrahydropyranyl, and —$CH_2$-tetrahydropyranyl, wherein each of said phenyl, benzyl, and pyridyl are optionally substituted with from 1 to 3 groups selected from the group consisting of F, Cl, Br, —$OCH_3$, —$CH_2F$, —$CHF_2$, and —$CF_3$.

6. A compound of claim 3, or a tautomer thereof, or a stereoisomer of said compound or said tautomer, or a pharmaceutically acceptable salt of said compound, said tautomer, or said stereoisomer, wherein:

$R^{1A}$ is methyl; and $R^{1B}$ is selected from the group consisting of H, F, Cl, methyl, —$CH_2F$, —$CHF_2$, and —$CF_3$.

7. A compound according to claim 5, or a tautomer thereof, or a stereoisomer of said compound or said tautomer, or a pharmaceutically acceptable salt of said compound, said tautomer, or said stereoisomer, wherein:

n is 1;

ring A is selected from the group consisting of phenyl, thienyl, and pyridyl;

m is 0, 1, 2, or 3;

each $R^2$ group (when present) is independently selected from the group consisting of halogen, —CN, —$SF_5$, —$NHCH_3$, —N$(CH_3)_2$, —$OCH_3$, —$OCH_2CH_3$, —O-cyclopropyl, —S$(CH_3)$, methyl, ethyl, propyl, cyclopropyl, —$CH_2$-cyclopropyl, —C≡C—$CH_3$, —$CF_3$, —$CHF_2$, —C(O)OH, —C(O)$OCH_3$, —C(O)$OCH_2CH_3$, —$OCF_3$, and —$OCHF_2$.

-$L_1$- is a bond or a divalent moiety selected from the group consisting of —NHC(O)—, —$CH_2$NHC(O)—, —$CH_2$C(O)NH—, and —C(O)NH—;

ring B is selected from the group consisting of phenyl, pyridinyl, pyrazinyl, pyrimidinyl, oxazolyl, pyrrolyl, indolyl, oxadiazolyl, cyclopropyl, cyclobutyl, oxetanyl, tetrahydropyranyl, tetrahydrofuranyl, dihydroisoxazoyl, Isoquinolinyl, thiophenyl, 5,6-dihydro-4H-pyrrolinyl, triazolopyridinyl, imidazolinyl, imidazothiazolyl, imidazopyridinyl, benzothiazolyl, and benzoxazoyl;

p is 0 or more; and each $R^3$ group (when present) is independently selected from the group consisting of halogen, —OH, —CN, —$SF_5$, —$NH_2$, —NH$(CH_3)$, —N$(CH_3)_2$, —$OCH_3$, —$OCH_2CH_3$, —O-cyclopropyl, —S$(CH_3)$, methyl, ethyl, propyl, cyclopropyl, —$CH_2$-cyclopropyl, —C≡C—CH₃, —CF₃, —CHF₂, —C(O)OH, —C(O)OCH₃, —C(O)OCH₂CH₃, —OCF₃, —OCH₂CF₃, and —OCHF₂.

8. A compound of claim 5, or a tautomer thereof, or a stereoisomer of said compound or said tautomer, or a pharmaceutically acceptable salt of said compound, said tautomer, or said stereoisomer, wherein:
n is 0;
ring A is selected from the group consisting of phenyl, pyridyl, pyrazinyl, furanyl, thienyl, pyrimidinyl, pyridazinyl, thiazolyl, and oxazolyl;
m is 0 to 5; and
each R² (when present) is independently selected from the group consisting of halogen, —OH, —CN, —SF₅, —OSF₅, —NO₂, —N(R⁶)₂, —NR⁷C(O)R⁶, —NR⁷S(O)₂R⁶, —NR⁷C(O)N(R⁶)₂, —NR⁷C(O)OR⁶, —C(O)R⁶, —C(O)₂R⁶, —C(O)N(R⁶)₂, —S(O)R⁶, —S(O)₂R⁶, —S(O)₂N(R⁶)₂, —OR⁶, —SR⁶, lower alkyl, -(lower alkyl)-OH, lower haloalkyl, lower heteroalkyl, lower alkenyl, lower alkynyl, phenyl, benzyl, lower cycloalkyl, -CH₂-(lower cycloalkyl), monocyclic heteroaryl, and —CH₂-(monocyclic heteroaryl),
wherein said phenyl, benzyl, lower cycloalkyl, —CH₂-(lower cycloalkyl), monocyclic heteroaryl, and —CH₂-(monocyclic heteroaryl) of R² is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF₅, and —OSF₅.

9. A compound of claim 5, or a tautomer thereof, or a stereoisomer of said compound or said tautomer, or a pharmaceutically acceptable salt of said compound, said tautomer, or said stereoisomer, wherein:
n is 0;
ring A is selected from the group consisting of phenyl, thienyl, and pyridyl;
m is 0 to 4; and
each R² group (when present) is independently selected from the group consisting of halogen, —CN, —SF₅, —NHCH₃, —N(CH₃)₂, —OCH₃, —OCH₂CH₃, —O-cyclopropyl, —S(CH₃), methyl, ethyl, propyl, cyclopropyl, —CH₂-cyclopropyl, —C≡C—CH₃, —CF₃, —CHF₂, —C(O)OH, —C(O)OCH₃, —C(O)OCH₂CH₃, —OCF₃, —OCHF₂, and —NHC(O)R⁶, wherein R⁶ is selected from the group consisting of —CH₂CF₃, —CF₂CH₃, —CH₃, —CH₂CH₃, —CH₂OCH₃, CHF₂, and —CH₂N(CH₃)₂.

10. A compound according to claim 1, or a tautomer thereof, or a stereoisomer of said compound or said tautomer, or a pharmaceutically acceptable salt of said compound, said tautomer, or said stereoisomer, wherein:
each R⁶ (when present) is independently selected from the group consisting of H, lower alkyl, lower haloalkyl, and lower heteroalkyl, and
and R⁷ (when present) is selected from the group consisting of H, lower alkyl.

11. A compound according to claim 5, or a tautomer thereof, or a stereoisomer of said compound or said tautomer, or a pharmaceutically acceptable salt of said compound, said tautomer, or said stereoisomer, wherein:
n is 1;
ring A is selected from the group consisting of phenyl and pyridyl;
m is 0, 1, 2, or 3;
each R² group (when present) is independently selected from the group consisting of fluoro and chloro,
-L₁- is —C(O)NH—;

ring B is selected from the group consisting of pyridinyl and pyrazinyl;
p is 0, 1, or 2; and
each R³ group (when present) is independently selected from the group consisting of fluoro, chloro, methyl, cyclopropyl, —CN, —OCH₃, —OCH₂—C≡C—H, —OCH₂—C≡C—CH₃, —CF₃, —CHF₂, —OCF₃, and —OCHF₂.

12. A compound according to claim 5, or a tautomer thereof, or a stereoisomer of said compound or said tautomer, or a pharmaceutically acceptable salt of said compound, said tautomer, or said stereoisomer, wherein:
n is 1;
ring A is selected from the group consisting of phenyl and pyridyl;
-L₁- is —NH—;
ring B is selected from the group consisting of aryl, monocyclic heteroaryl, and a multicyclic group;
p is 0 or more; and
each R³ (when present) is independently selected from the group consisting of halogen, —CN, —SF₅, —OSF₅, —NO₂, —NH₂, —N(alkyl)₂, —NH(alkyl), —NHC(O)R⁶, —NHS(O)₂R⁶, —NHC(O)N(R⁶)₂, —NHC(O)OR⁶, —C(O)R⁶, —C(O)₂R⁶, —C(O)N(R⁶)₂, —S(O)R⁶, —S(O)₂R⁶, —S(O)₂N(R⁶)₂, —OR⁶, —SR⁶, lower alkyl, lower haloalkyl, lower heteroalkyl, lower alkenyl, lower alkynyl, phenyl, benzyl, lower cycloalkyl, —CH₂-(lower cycloalkyl), monocyclic heteroaryl, and —CH₂-(monocyclic heteroaryl),
wherein said phenyl, benzyl, lower cycloalkyl, —CH₂-(lower cycloalkyl), monocyclic heteroaryl, and —CH₂-(monocyclic heteroaryl) of R³ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF₅, and —OSF₅.

13. A compound of claim 1, or a tautomer thereof, or a stereoisomer of said compound or said tautomer, or a pharmaceutically acceptable salt of said compound, said tautomer, or said stereoisomer, wherein:

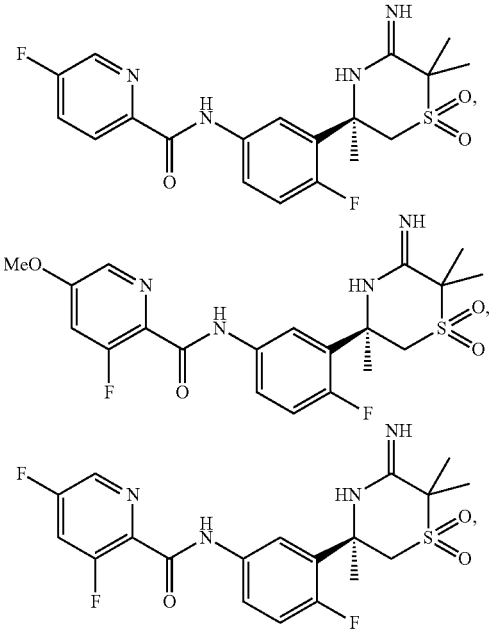

295
-continued
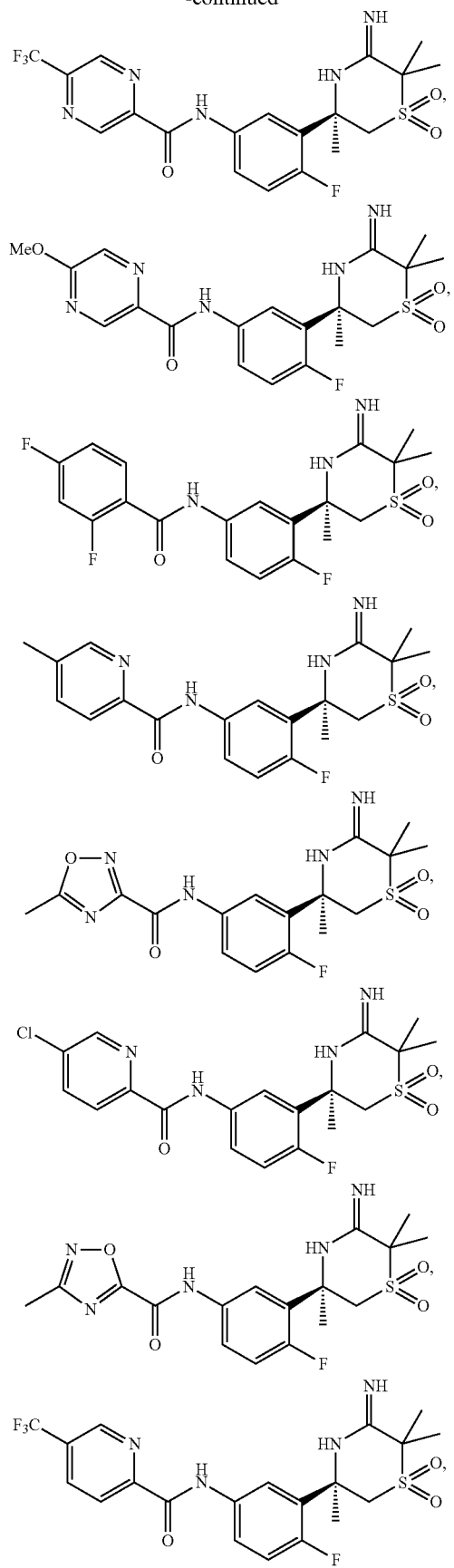
296
-continued
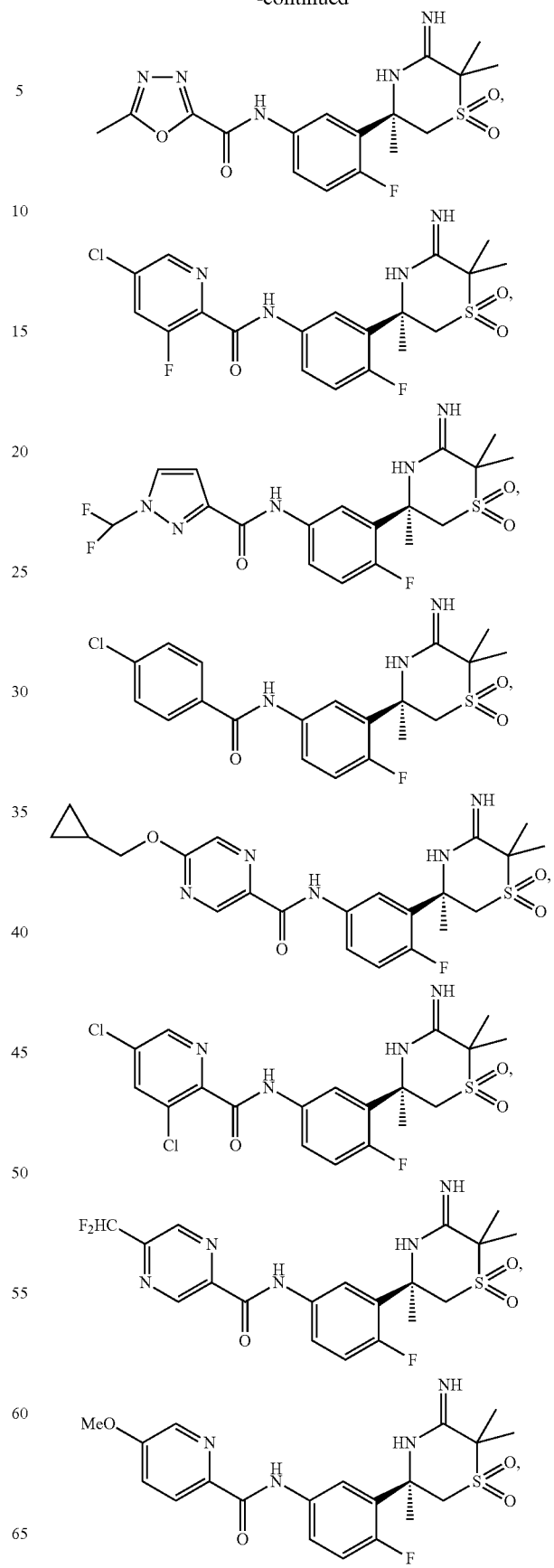

-continued
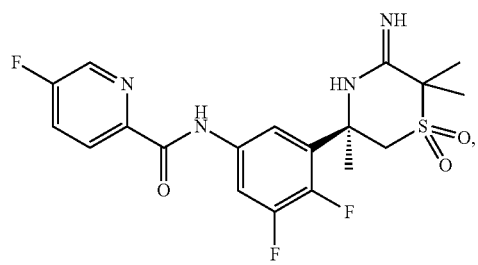
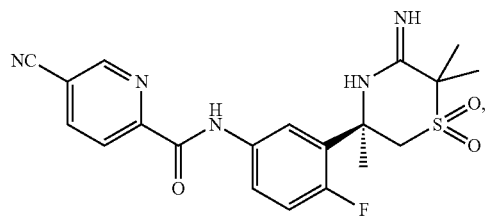
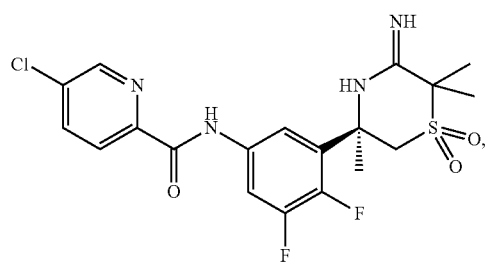
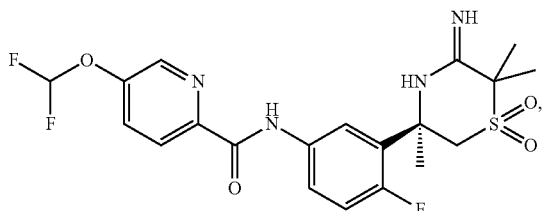
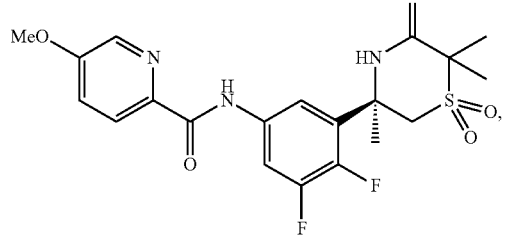
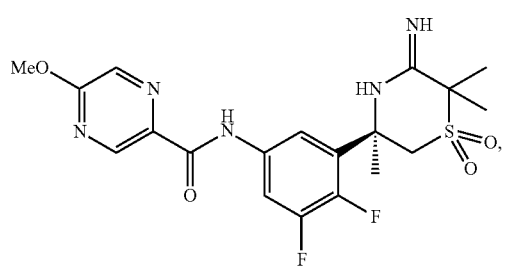
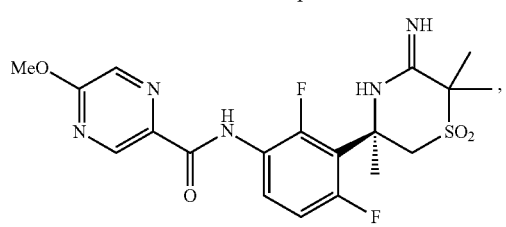
-continued
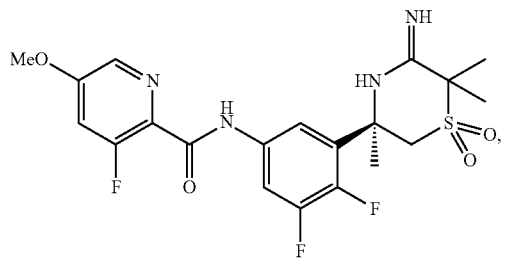
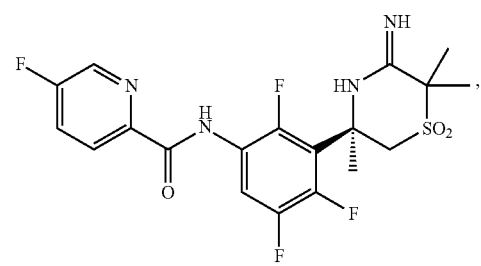
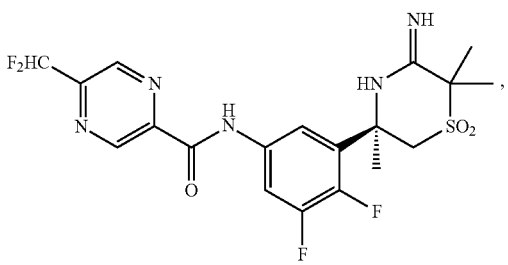
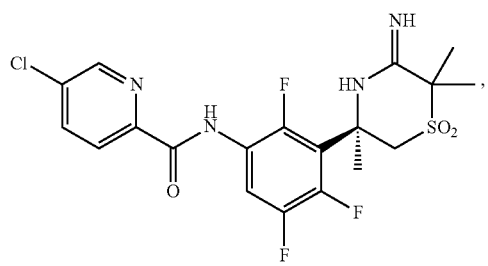
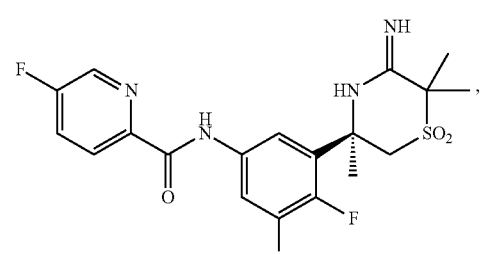
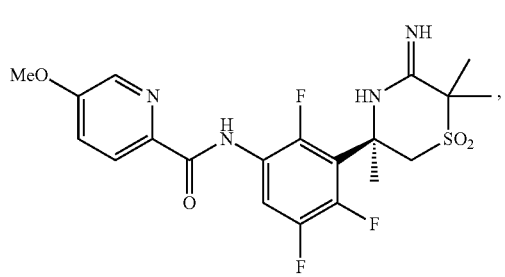

-continued
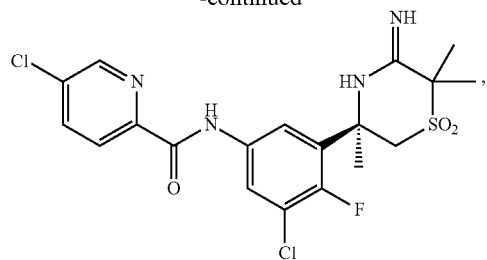
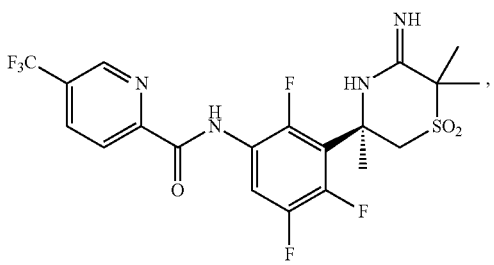
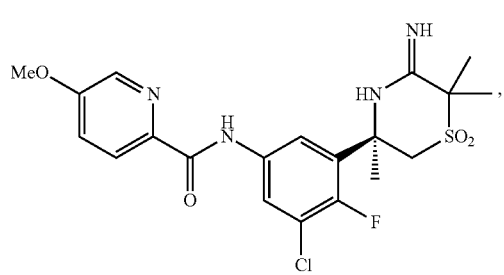
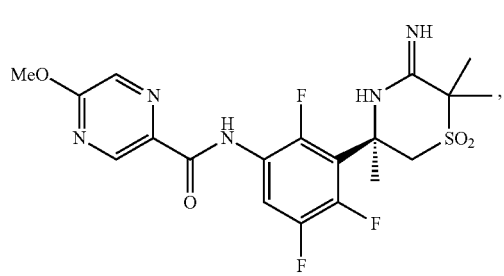
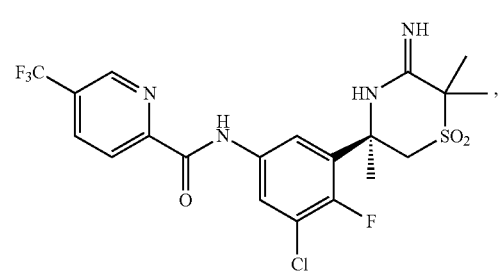
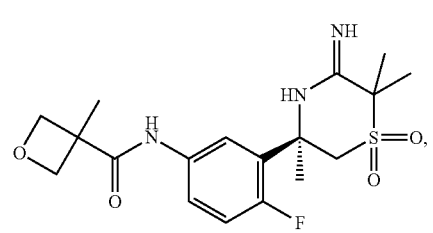
-continued
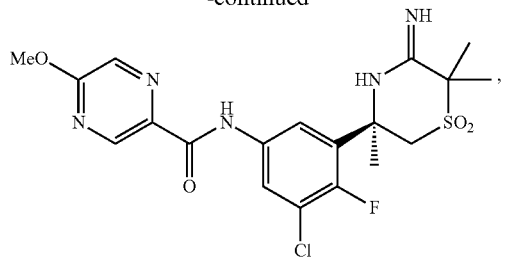
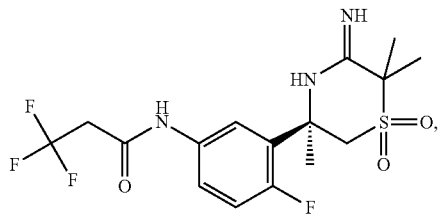
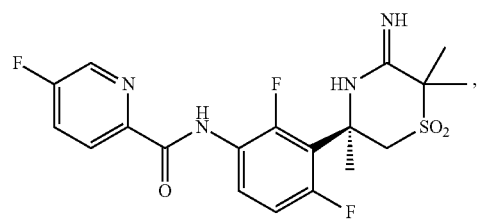
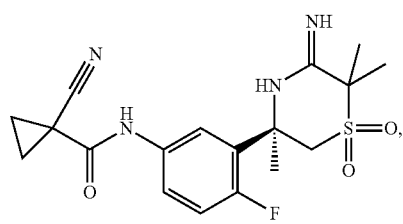
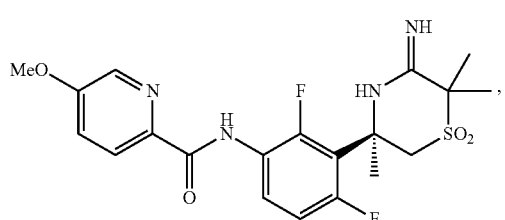
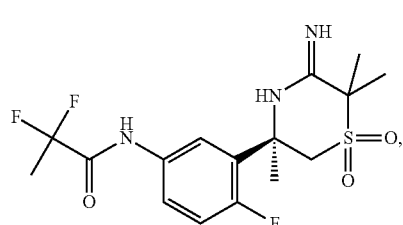
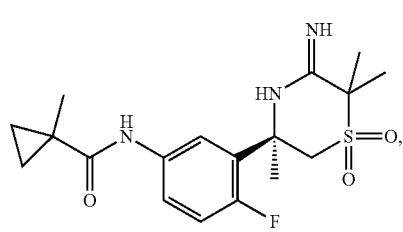

301
-continued
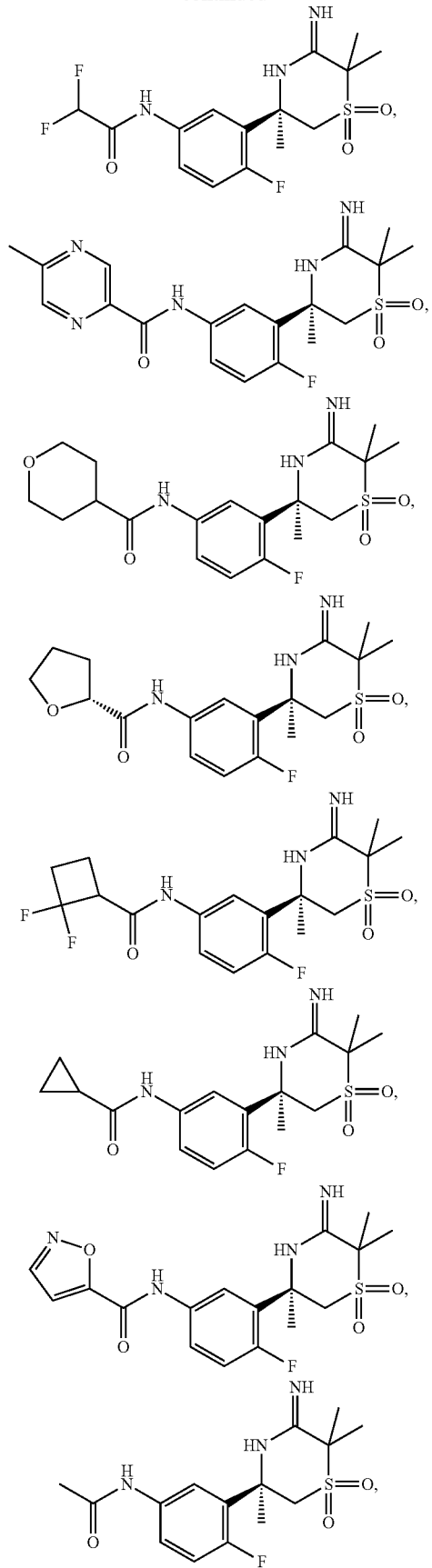
302
-continued
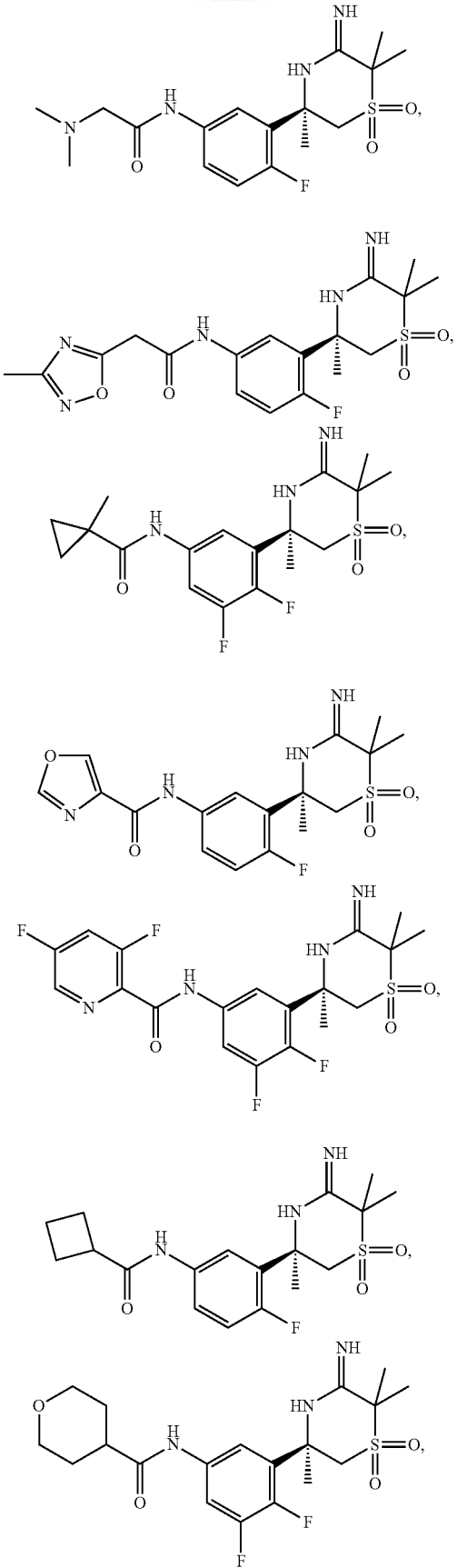

303
-continued
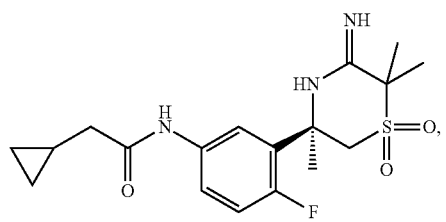
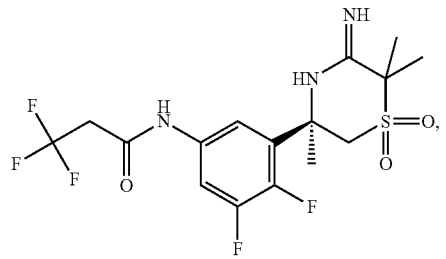
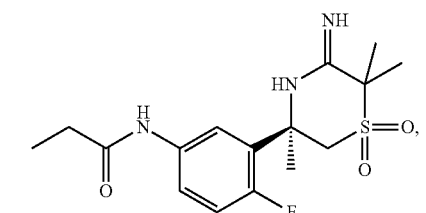
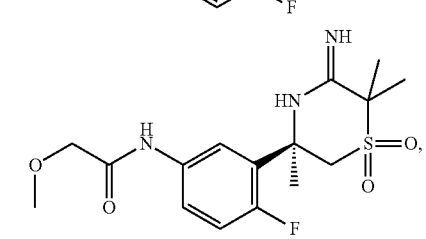
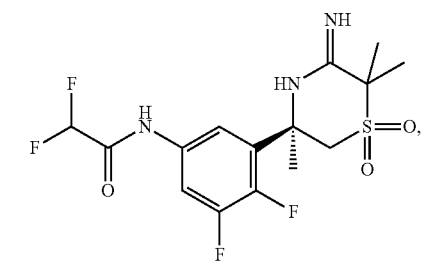
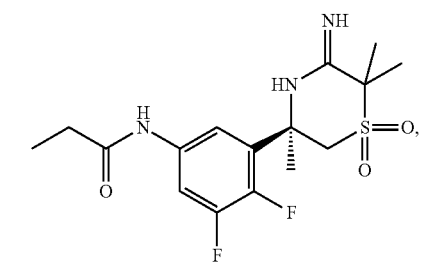
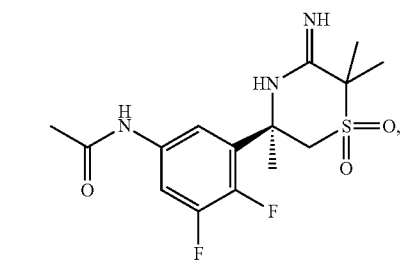
304
-continued
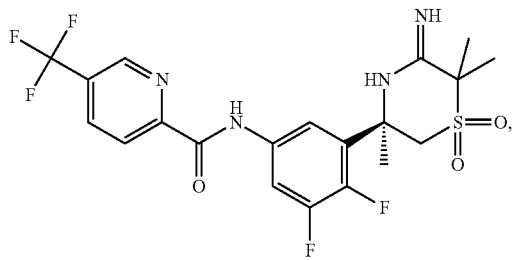
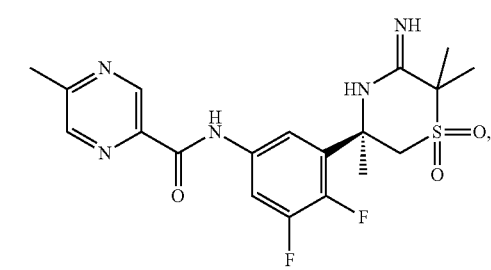
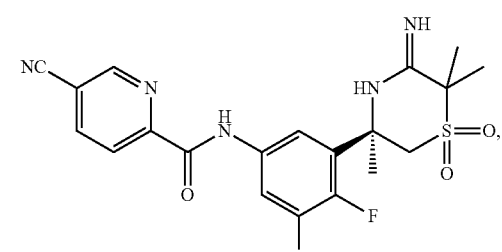
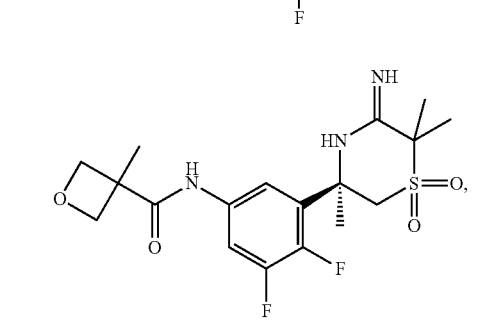
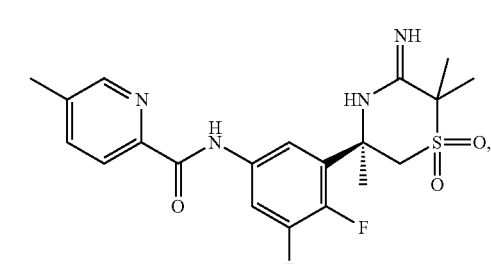
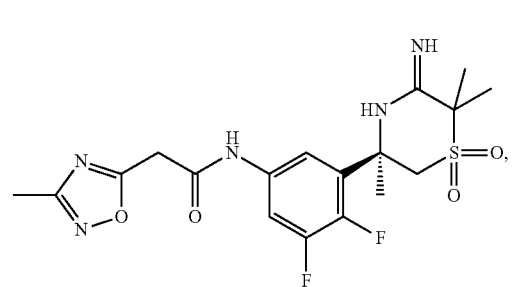

305
-continued
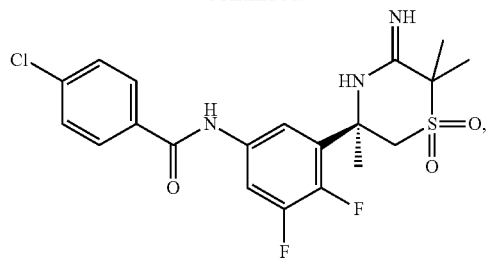
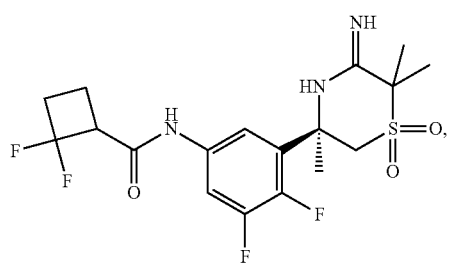
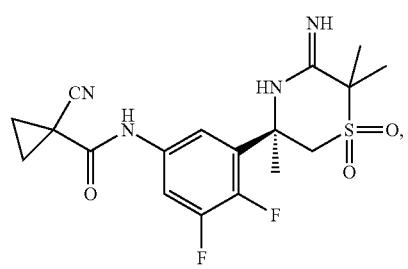
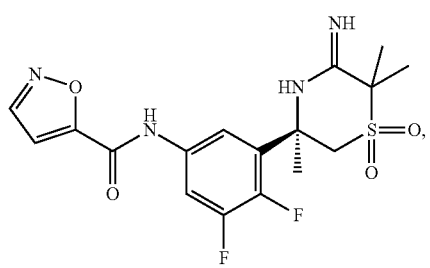
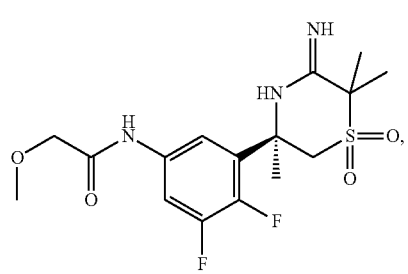
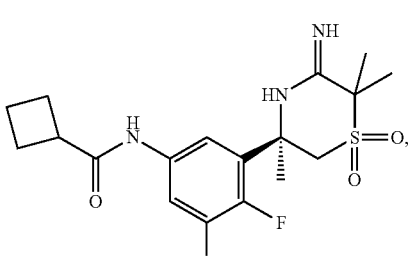
306
-continued
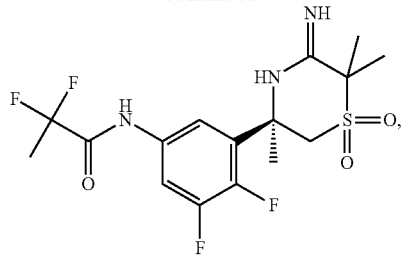
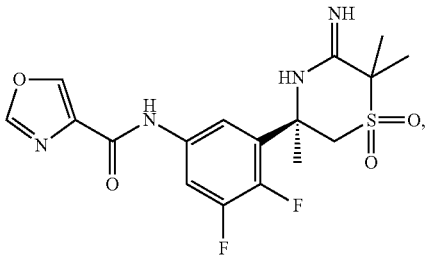
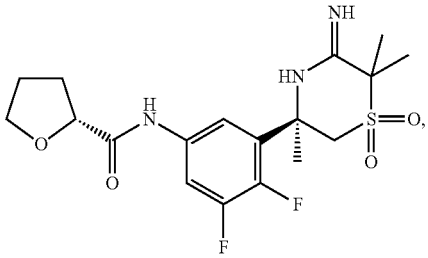
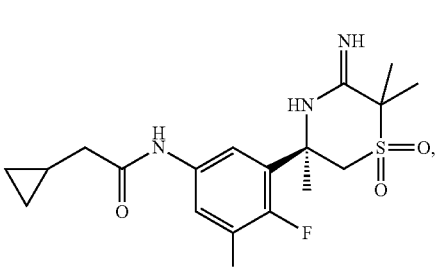
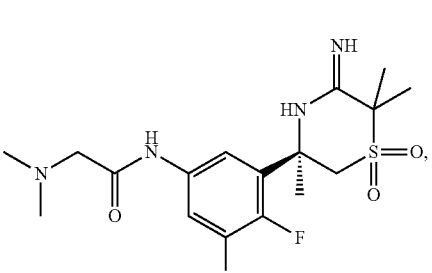
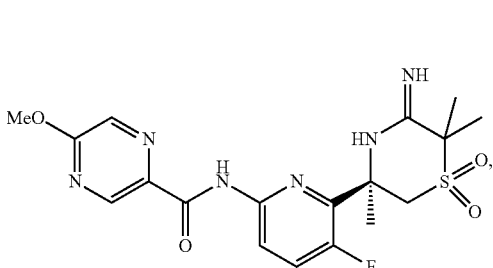

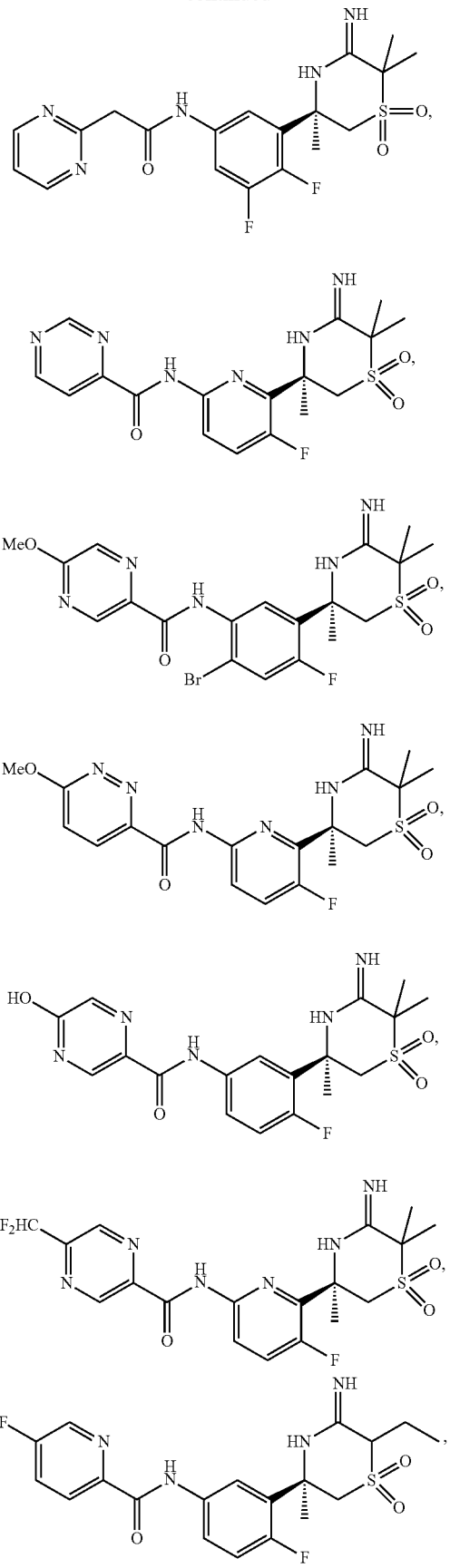
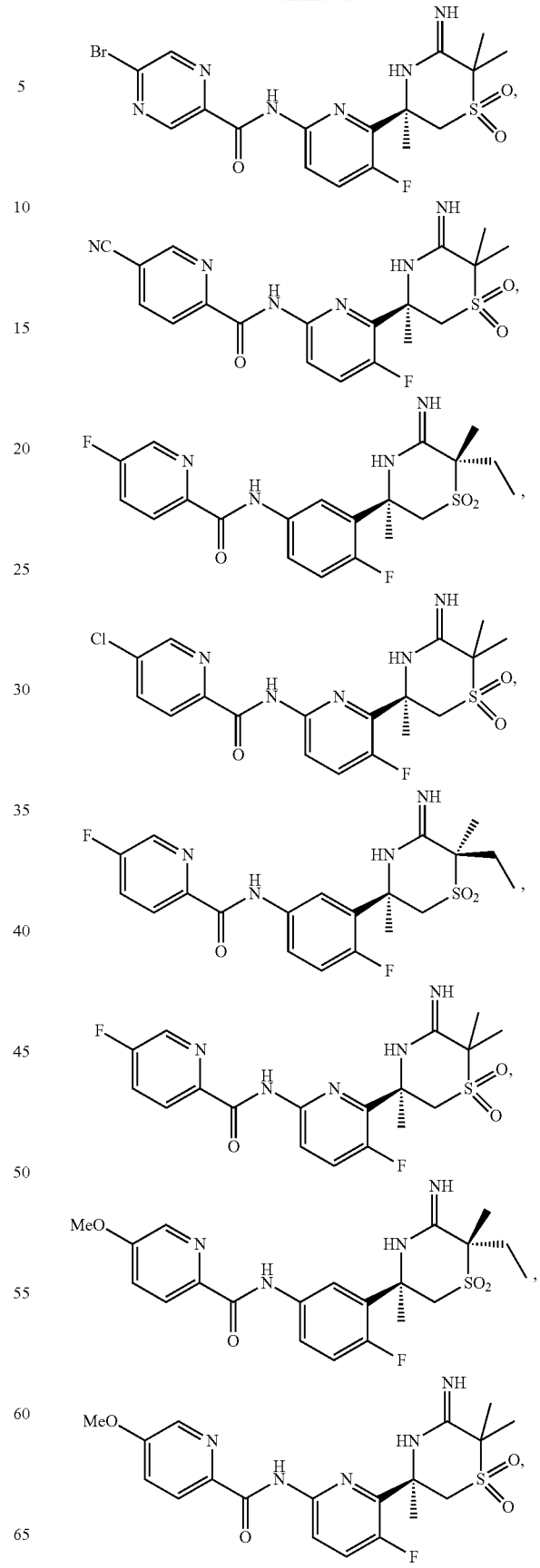

309
-continued
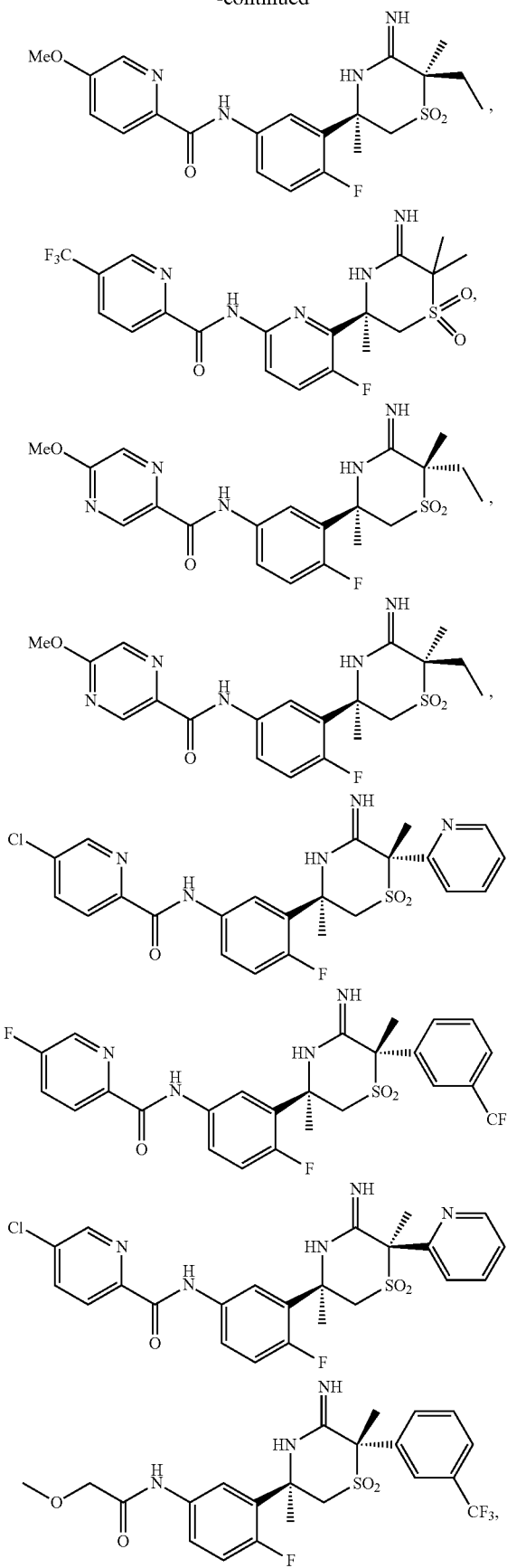
310
-continued
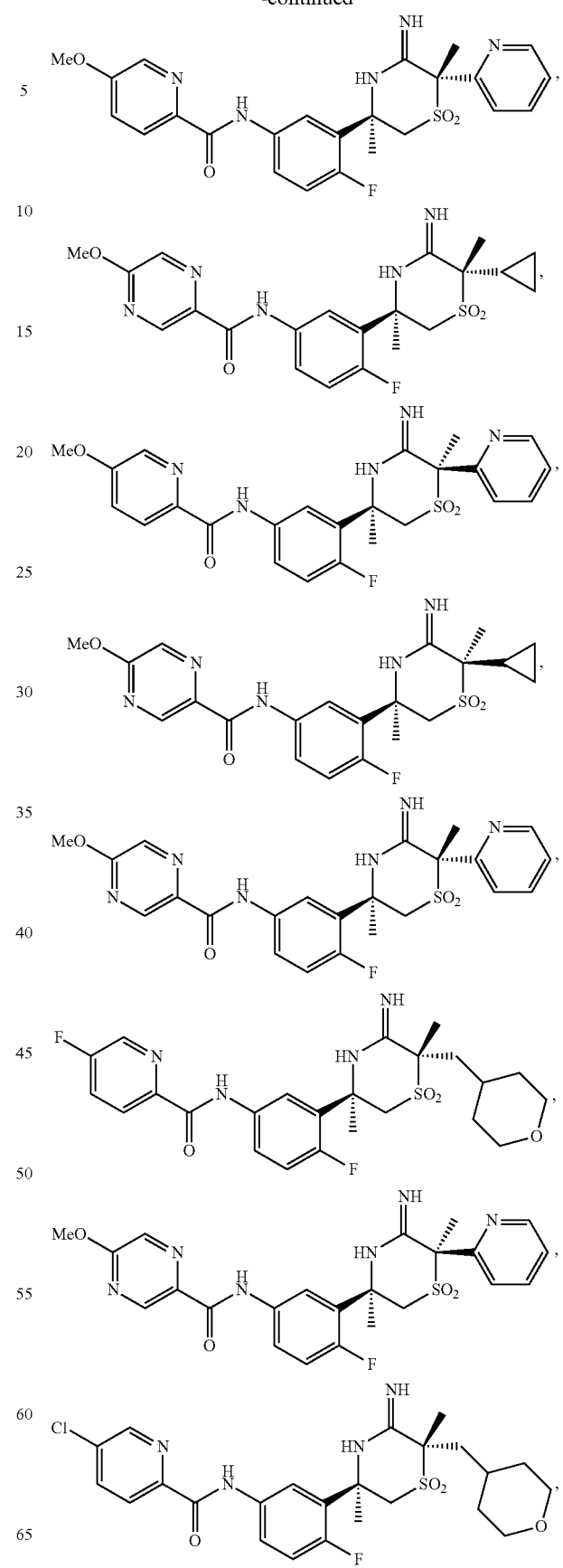

311
-continued
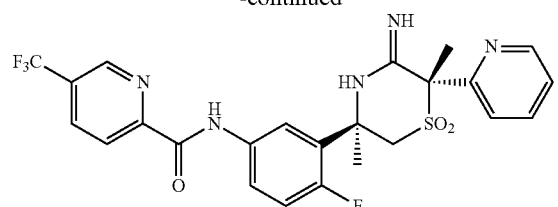
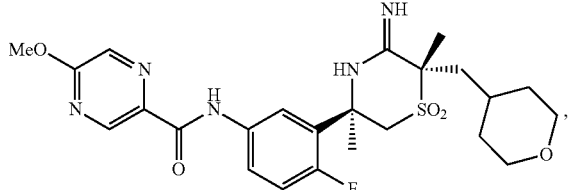
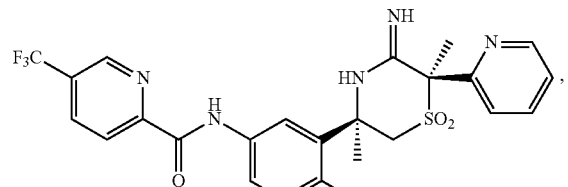
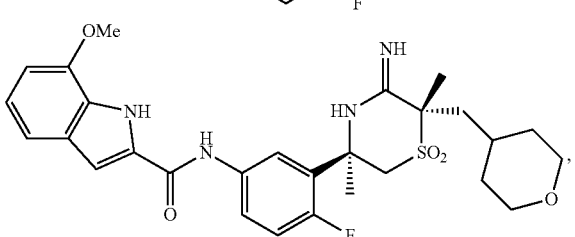
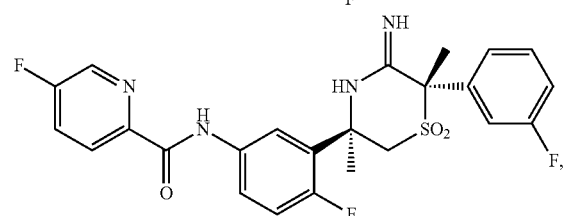
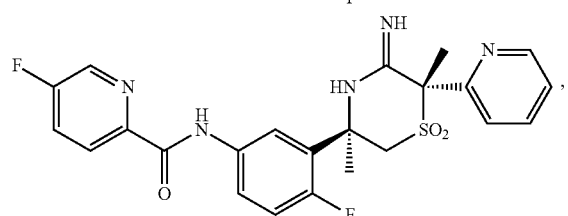
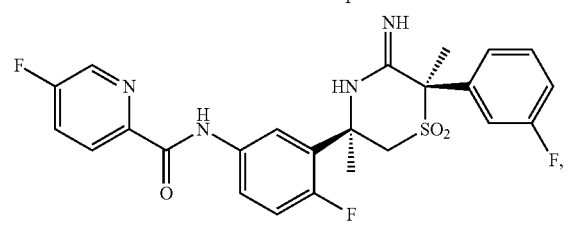
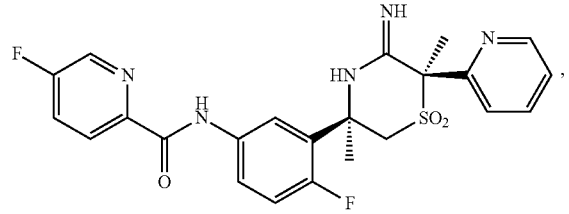
312
-continued
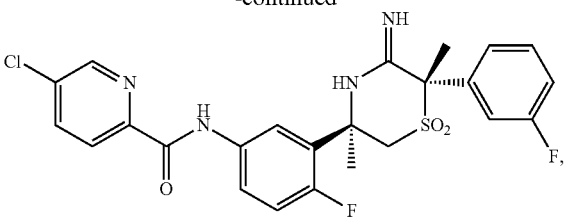
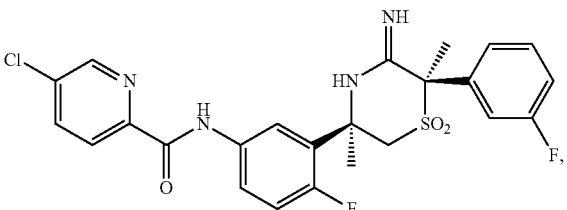
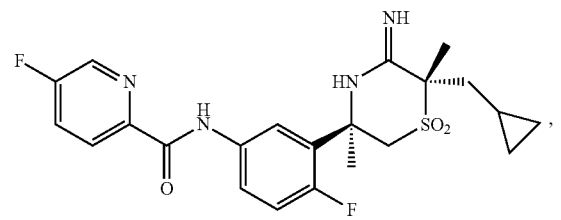
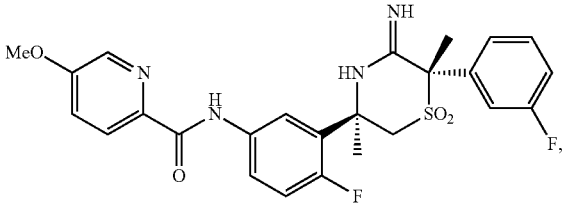
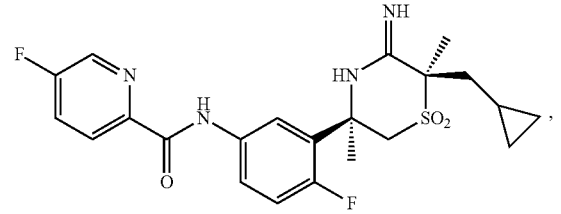
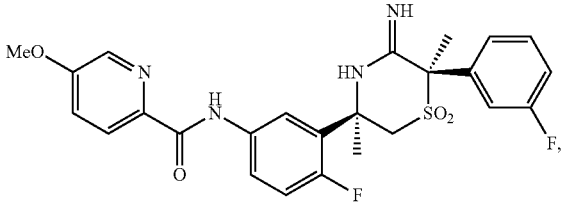
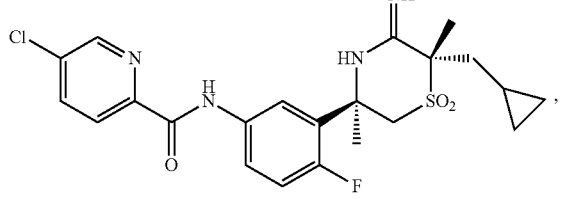
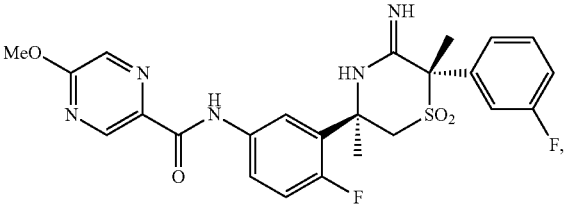

313
-continued
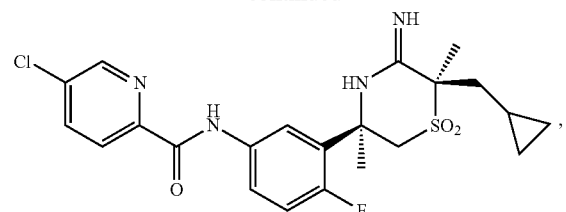
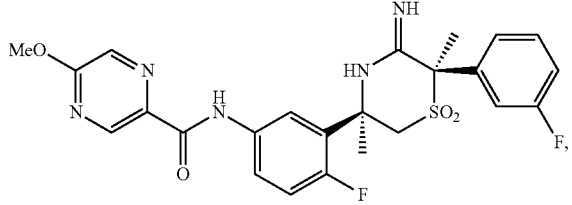
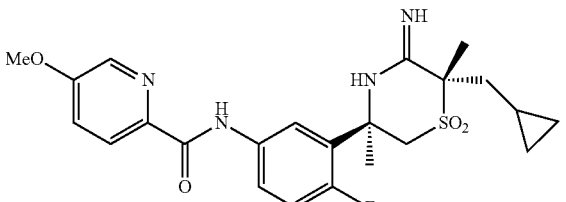
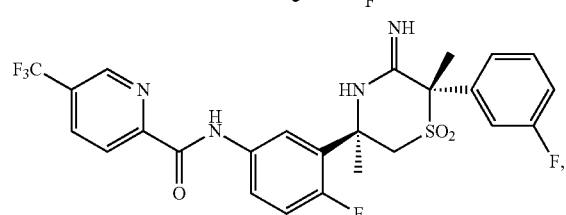
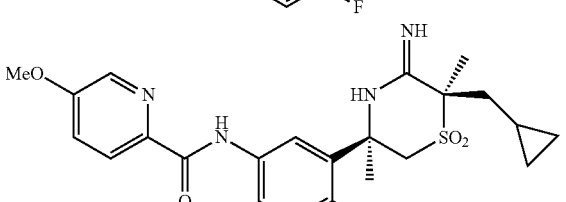
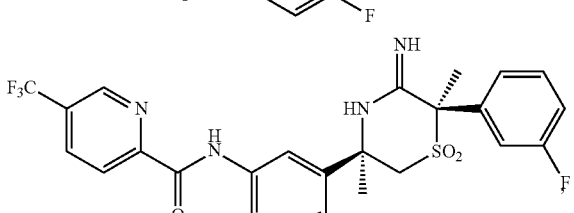
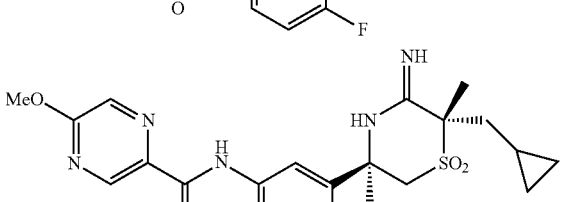
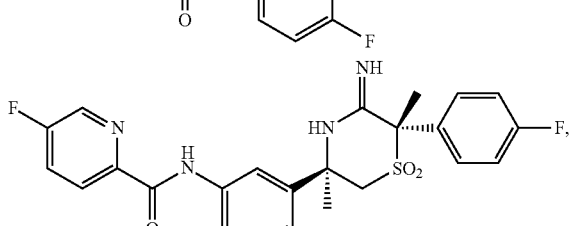
314
-continued
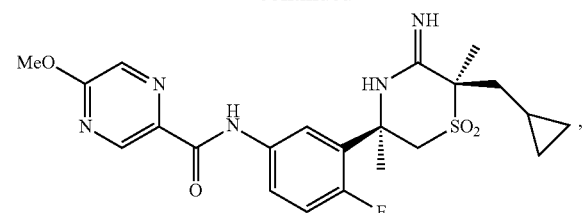
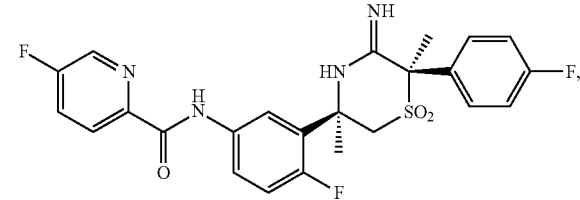
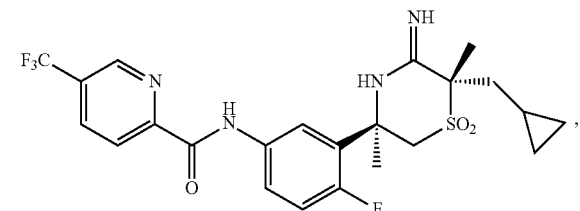
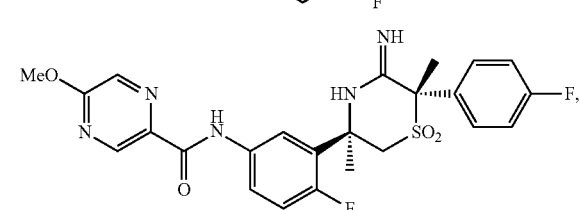
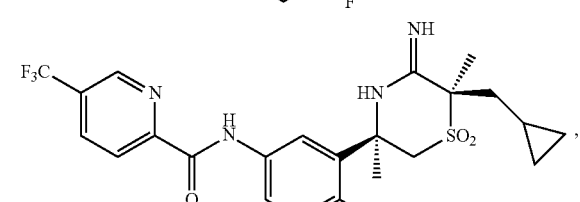
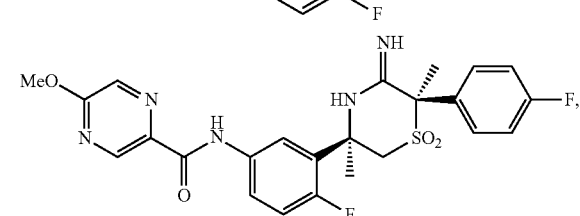
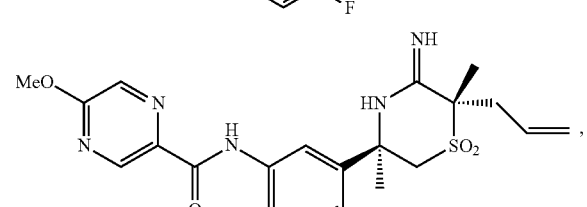
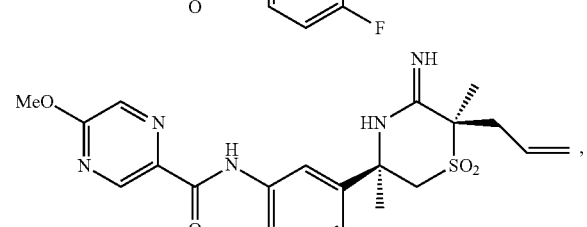

315
-continued
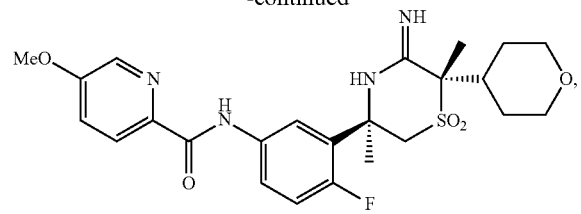
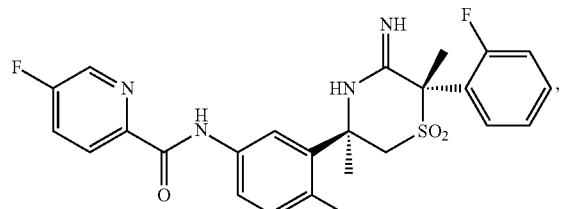
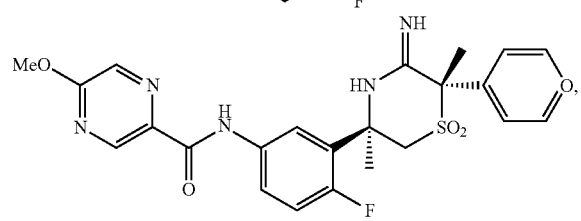
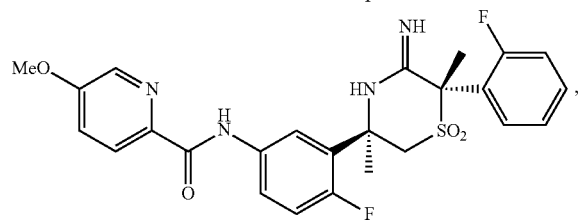
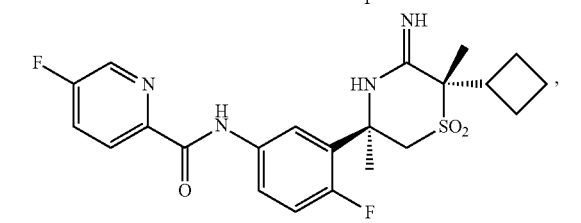
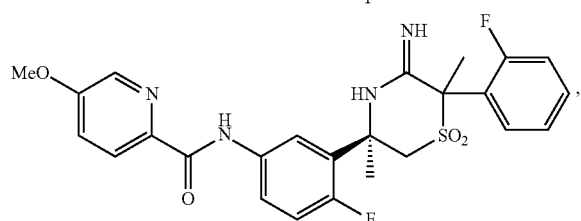
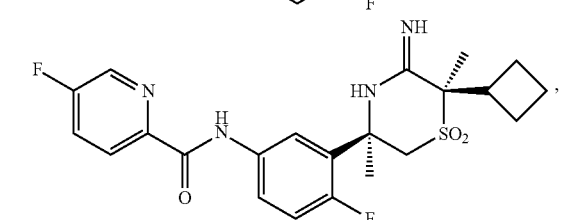
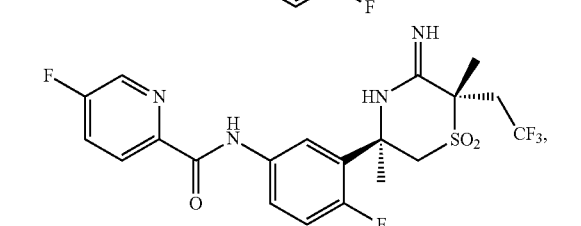
316
-continued
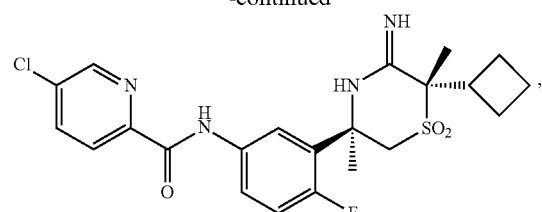
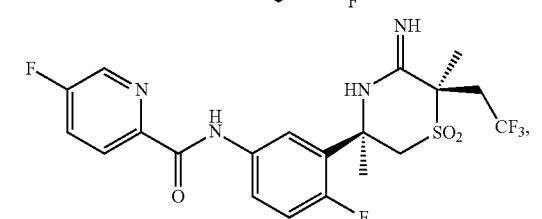
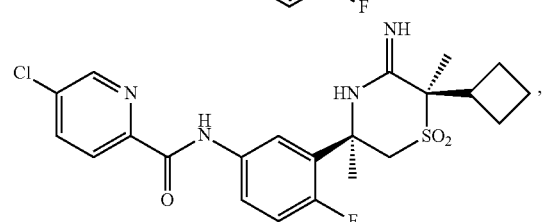
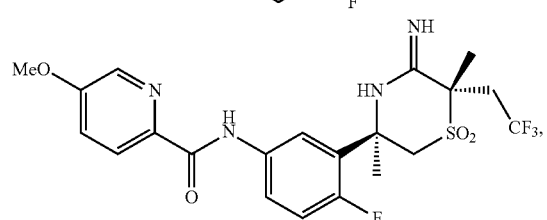
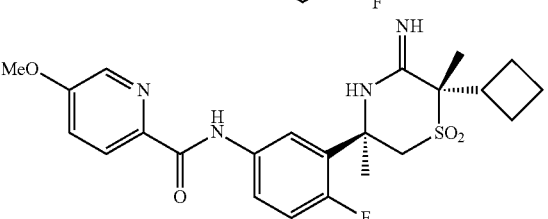
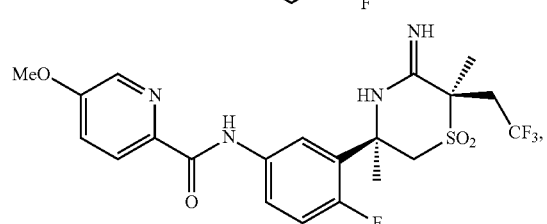
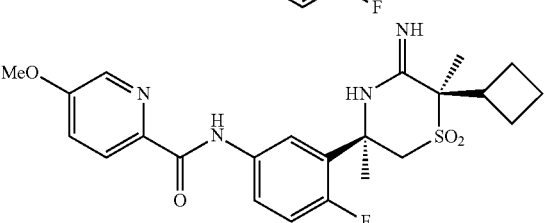
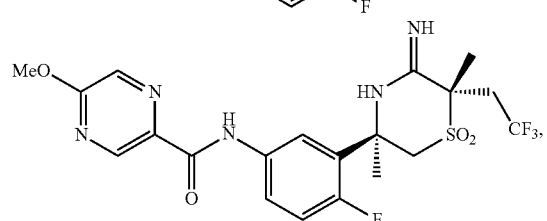

317
-continued
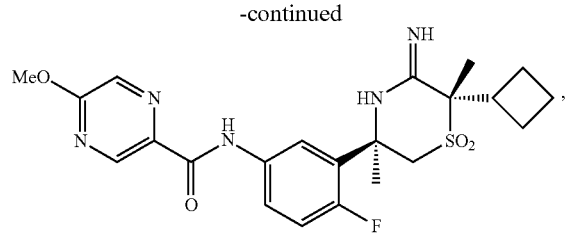
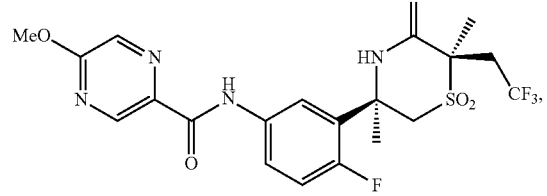
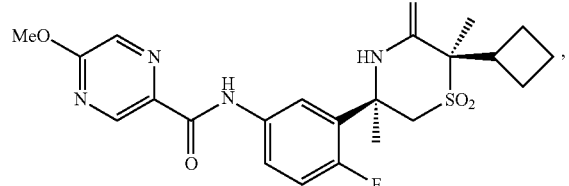
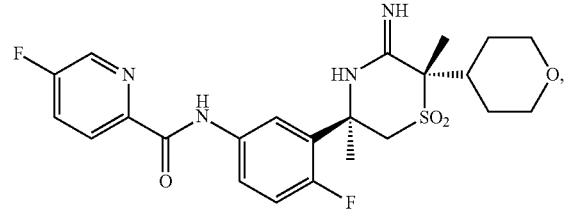
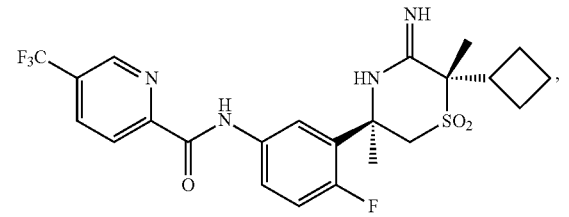
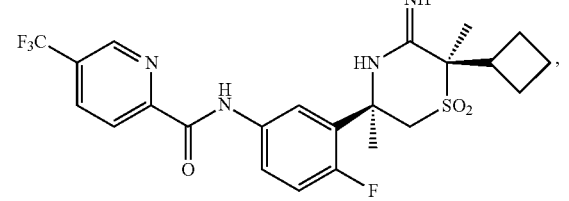
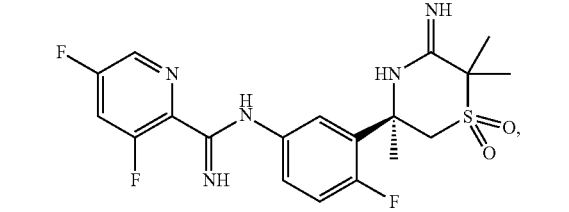
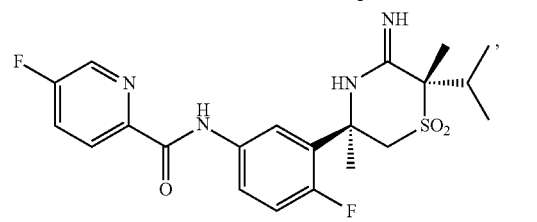
318
-continued
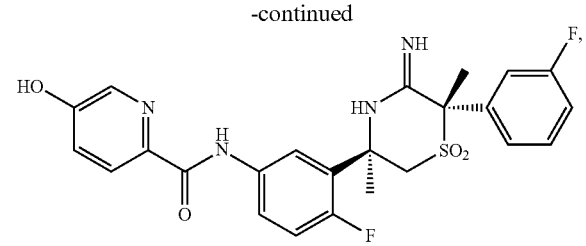
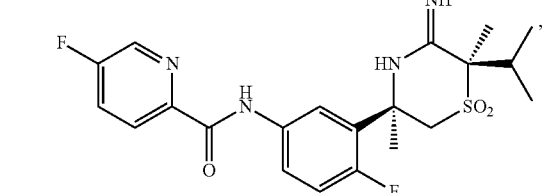
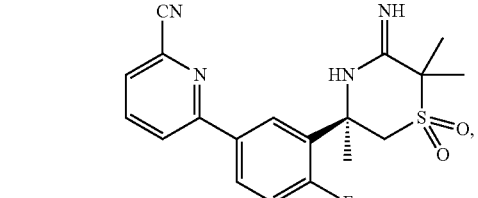
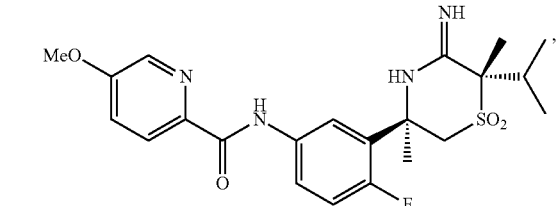
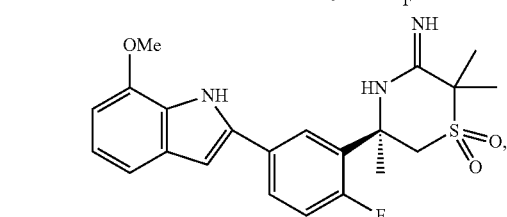
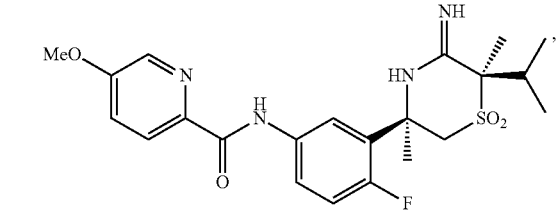
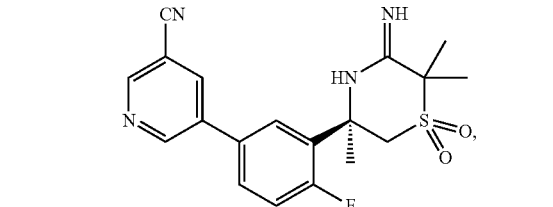
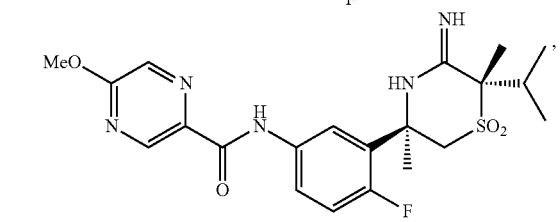

319
-continued
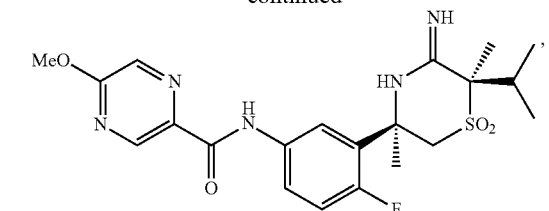
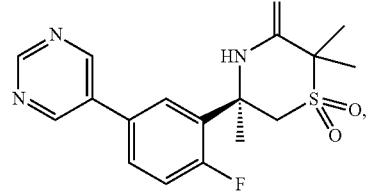
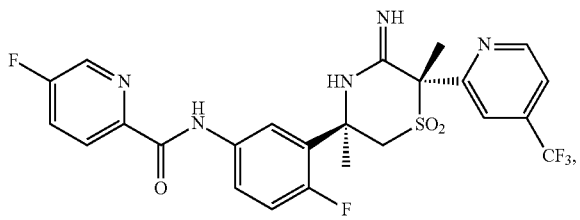
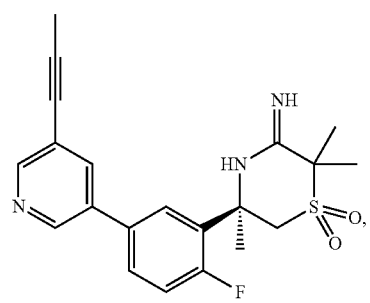
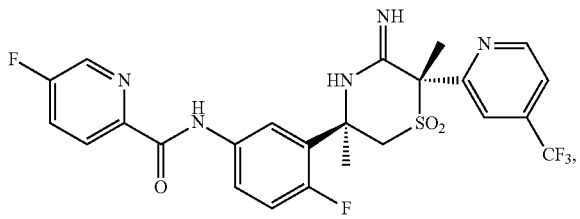
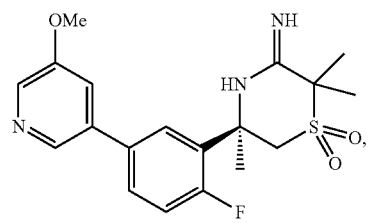
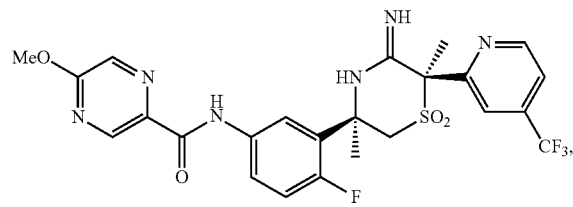
320
-continued
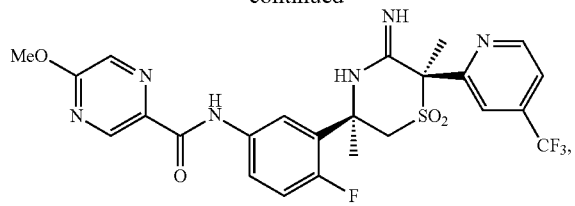
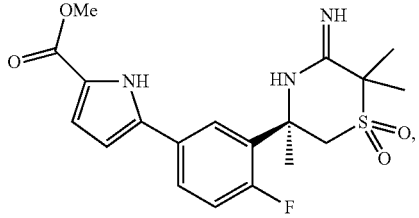
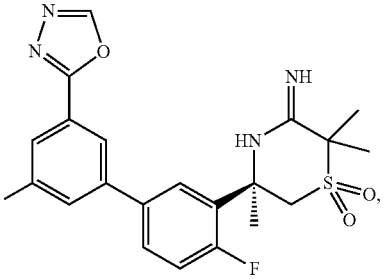
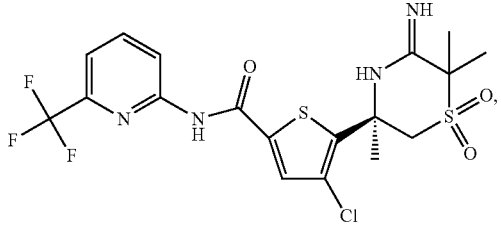
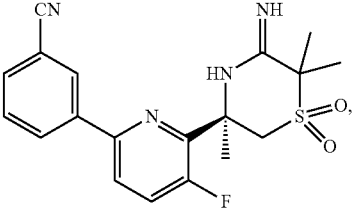
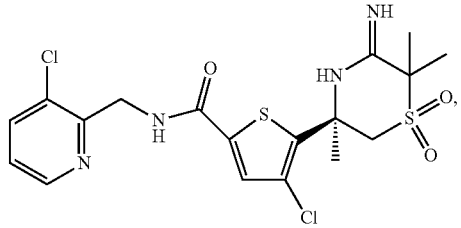
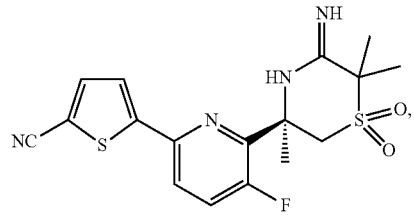

321
-continued
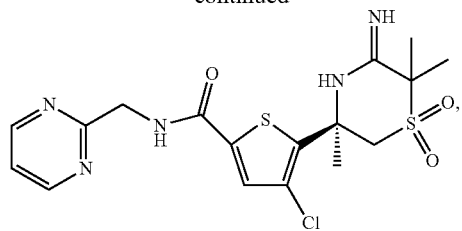
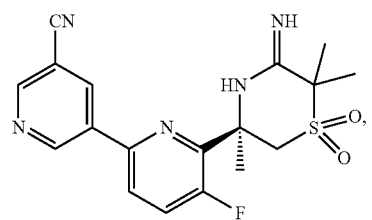
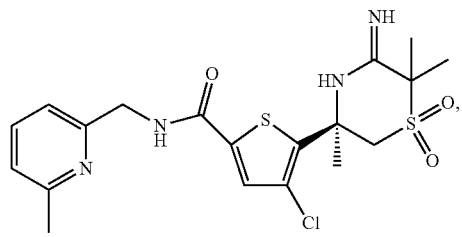
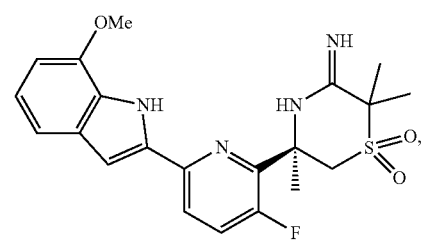
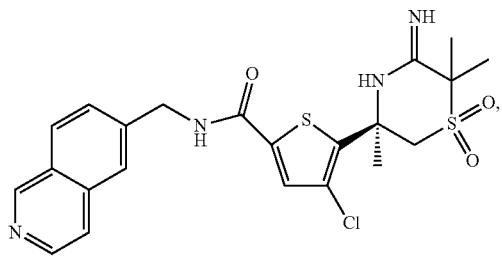
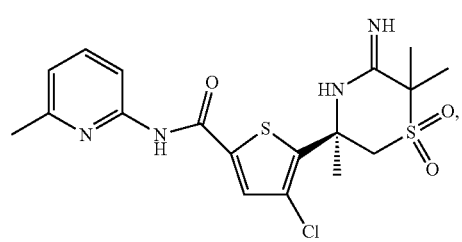
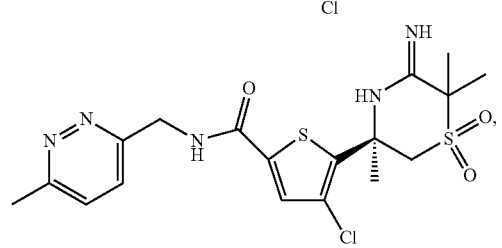
322
-continued
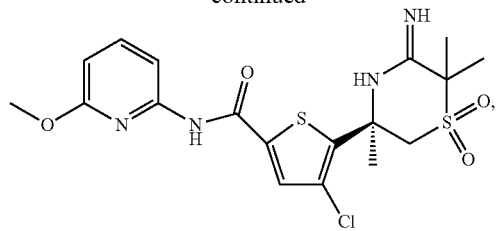
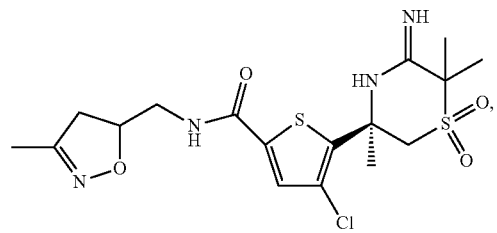
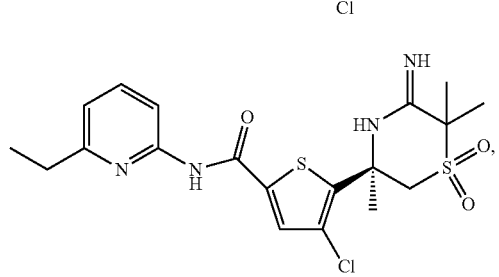
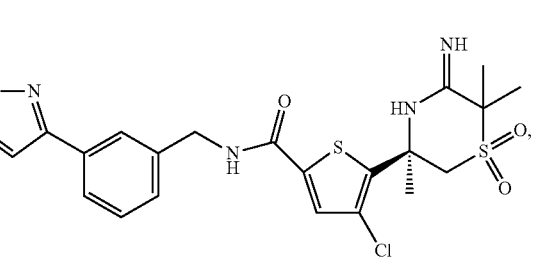
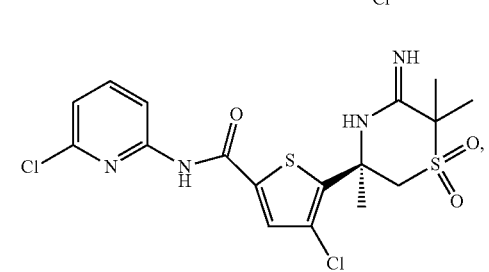
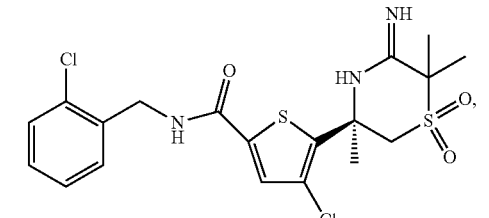
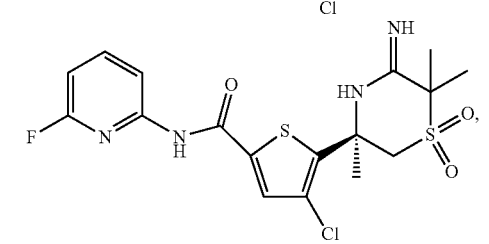

323
-continued
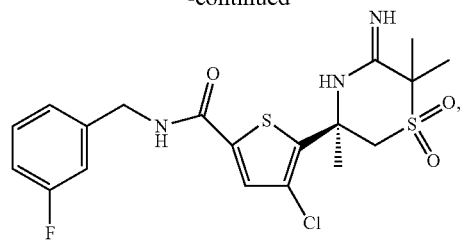
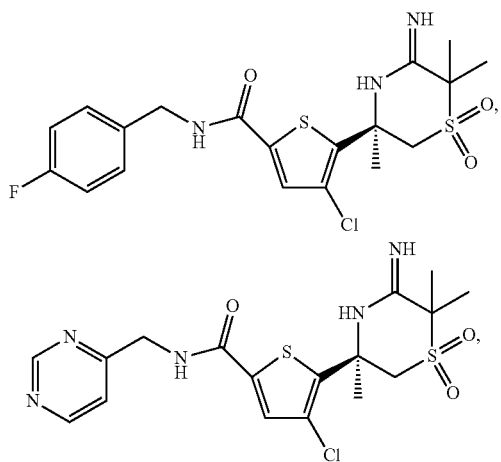
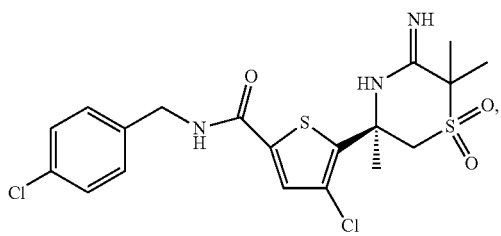
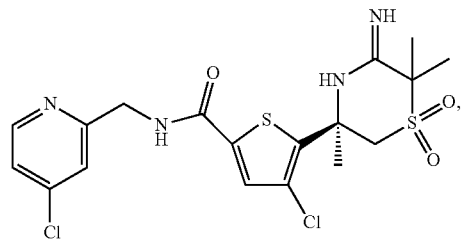
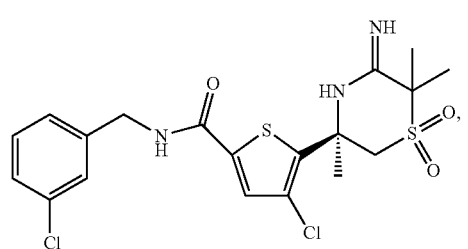
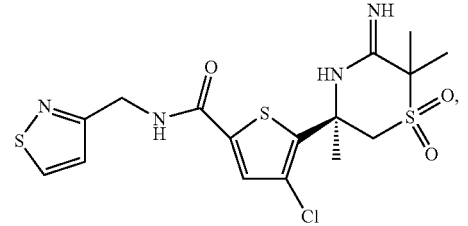
324
-continued
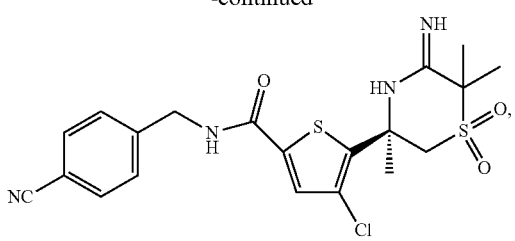
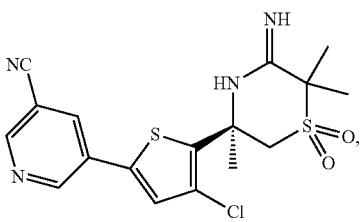
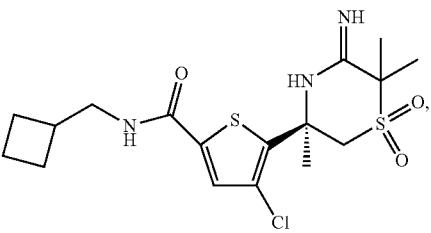
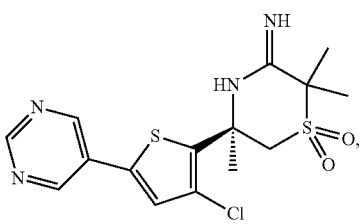
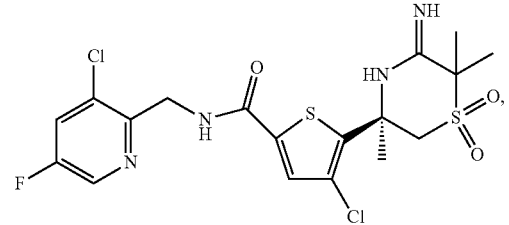
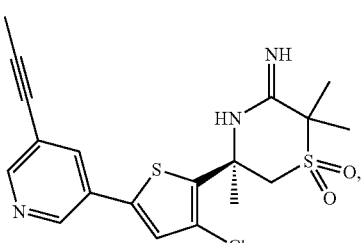
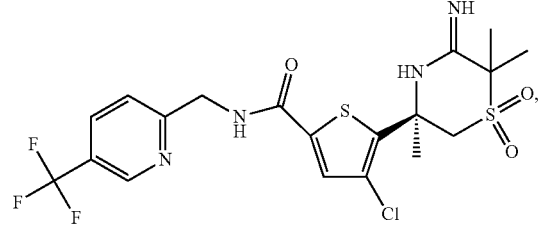

325
-continued
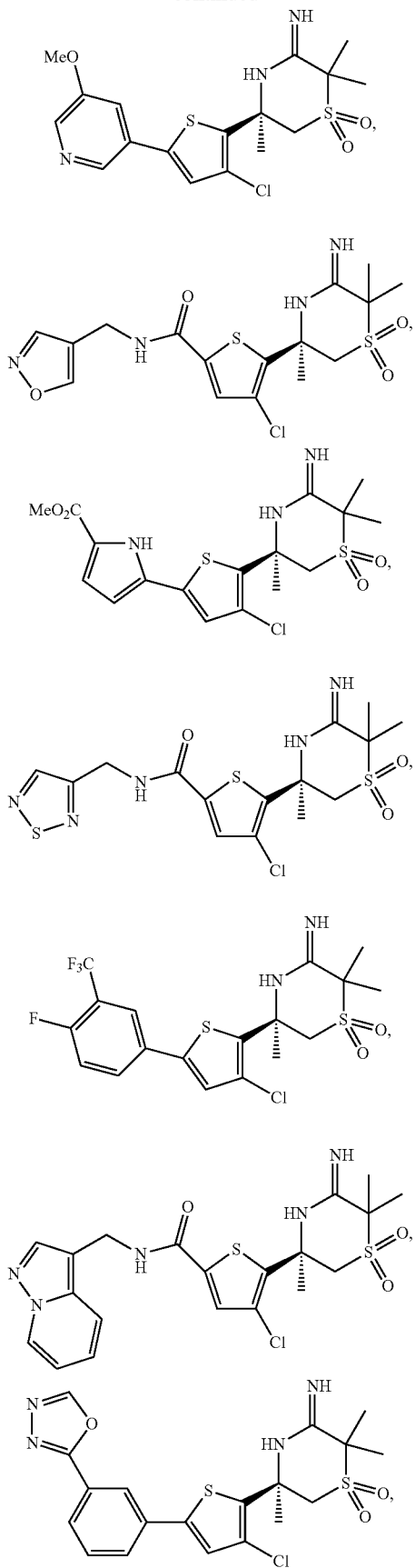
326
-continued
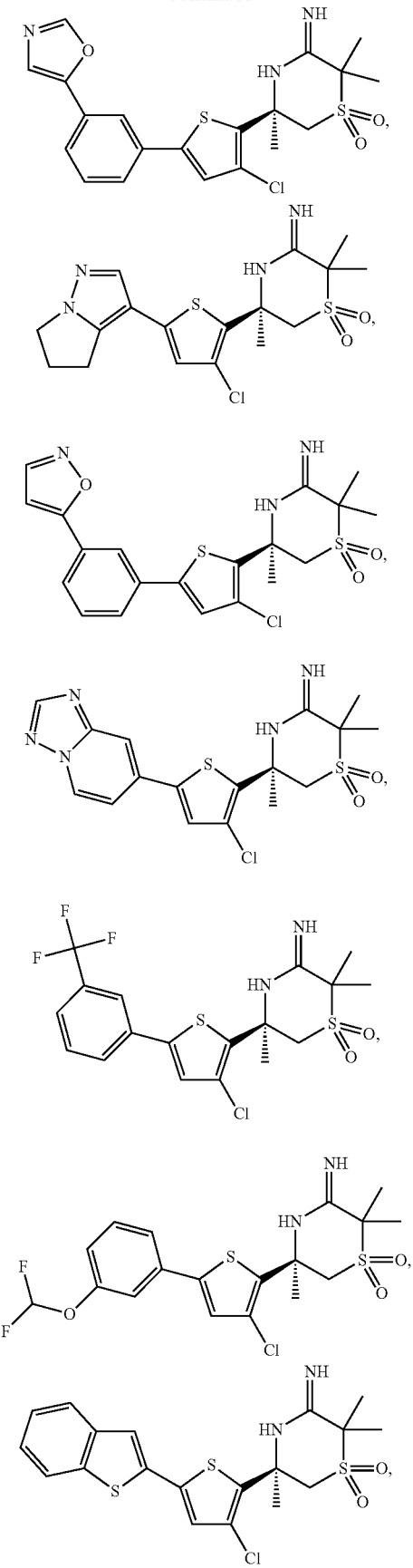

327
-continued
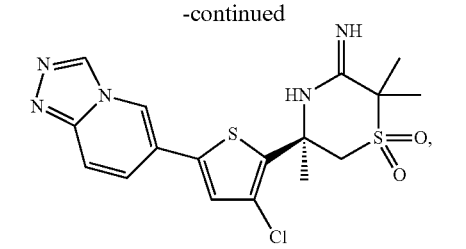
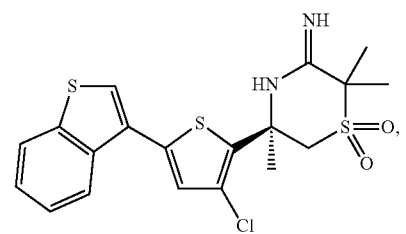
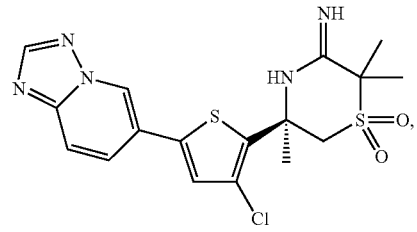
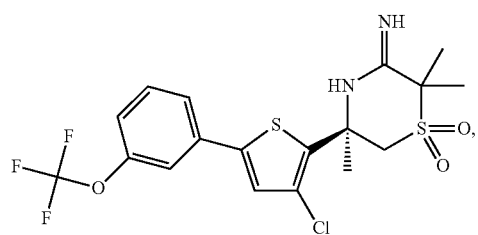
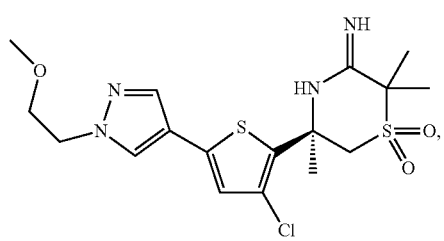
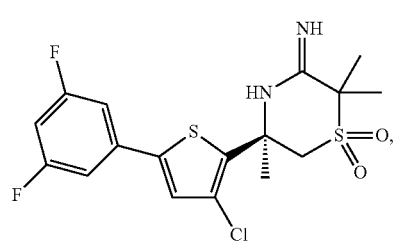
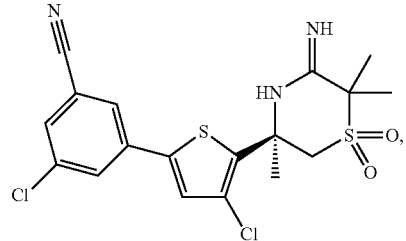
328
-continued
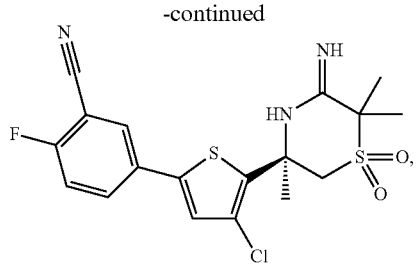
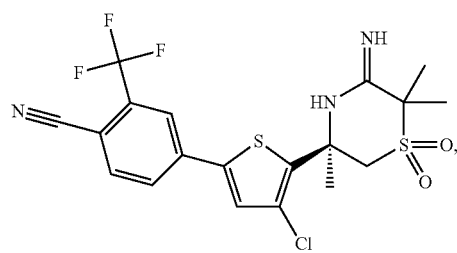
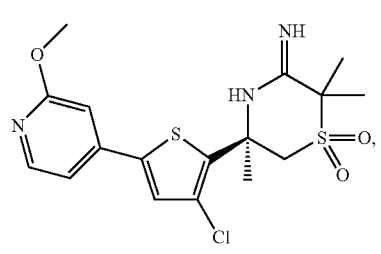
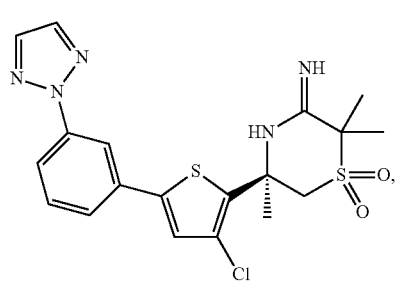
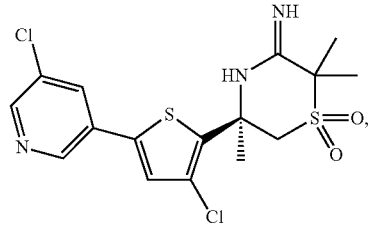
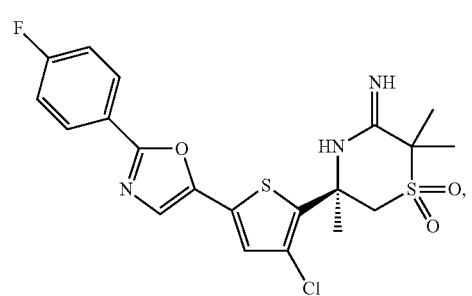

329
-continued
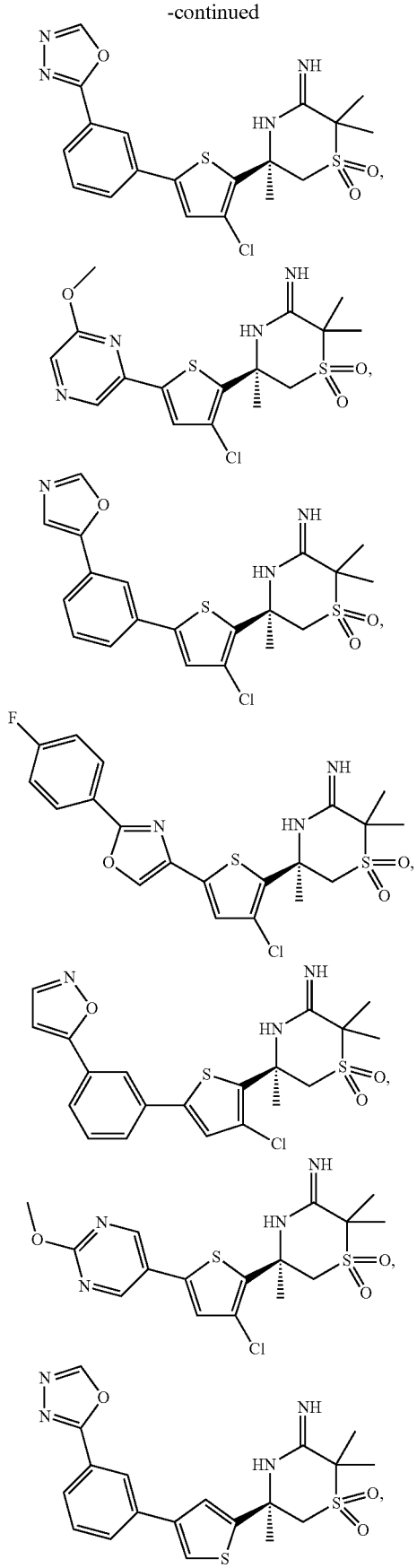
330
-continued
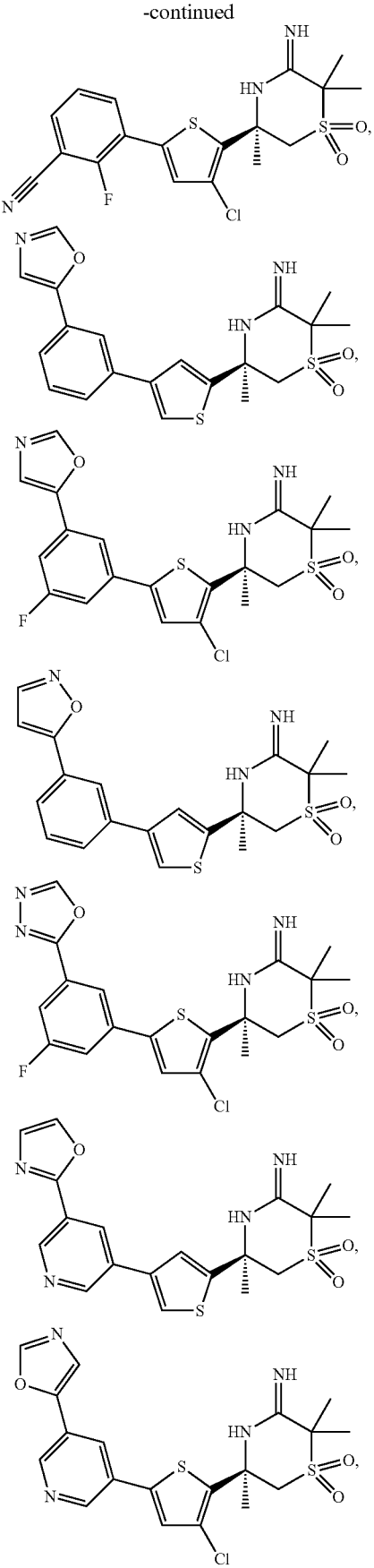

331
-continued
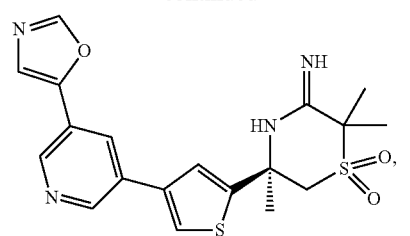
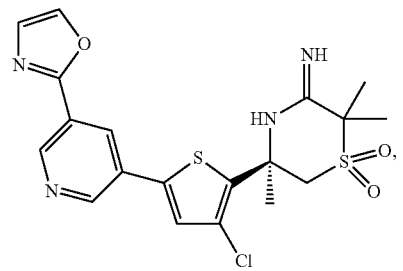
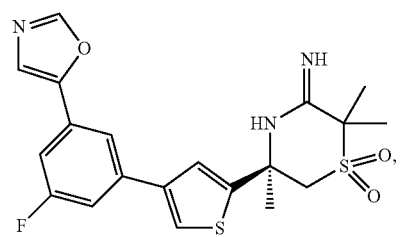
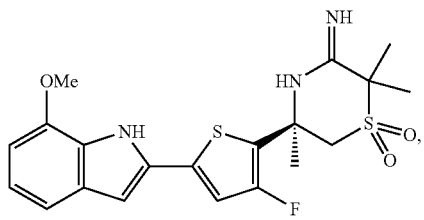
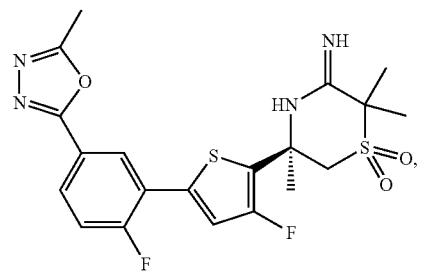
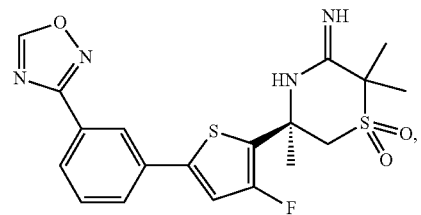
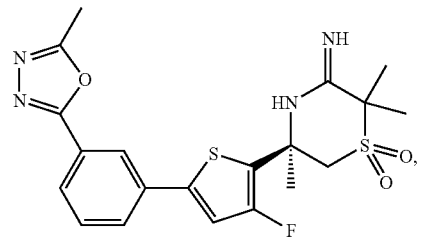
332
-continued
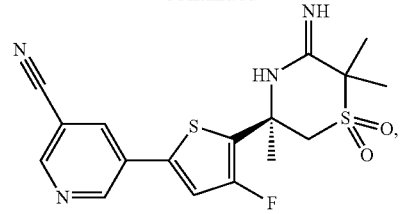
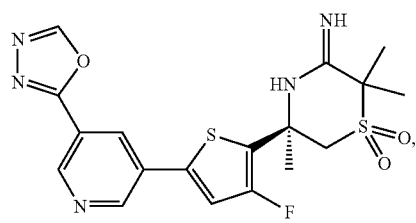
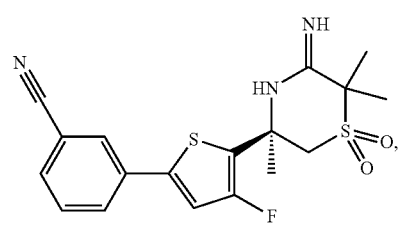
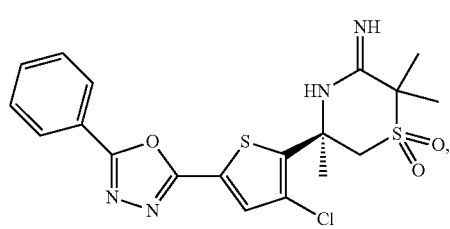
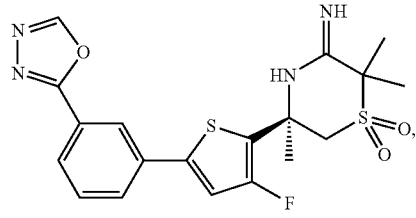
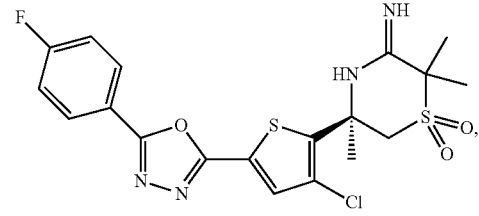
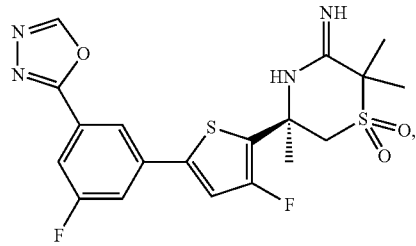

333
-continued
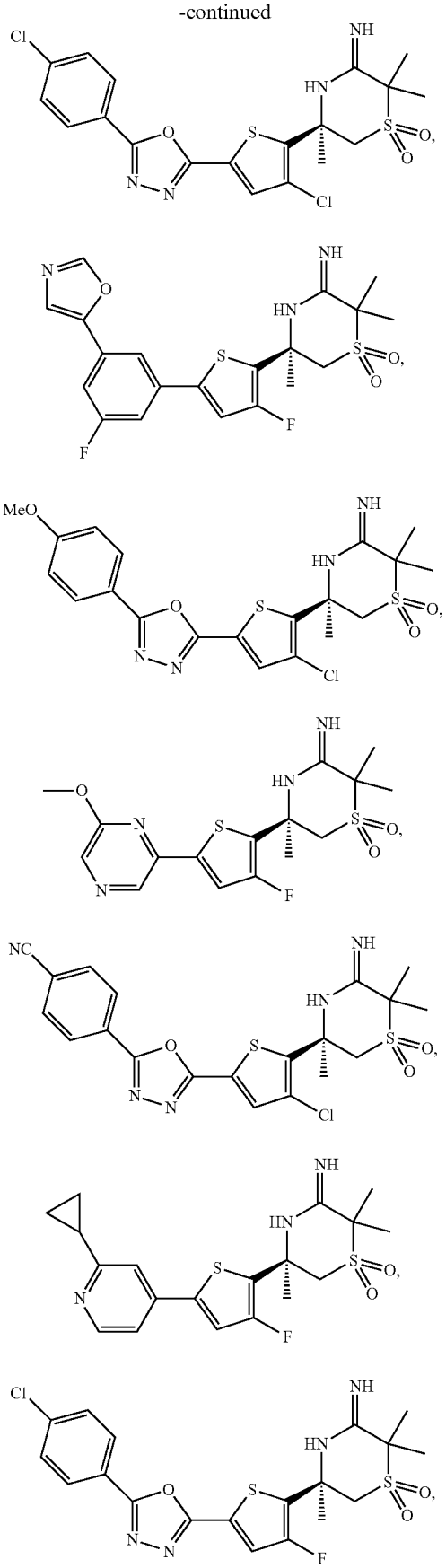
334
-continued
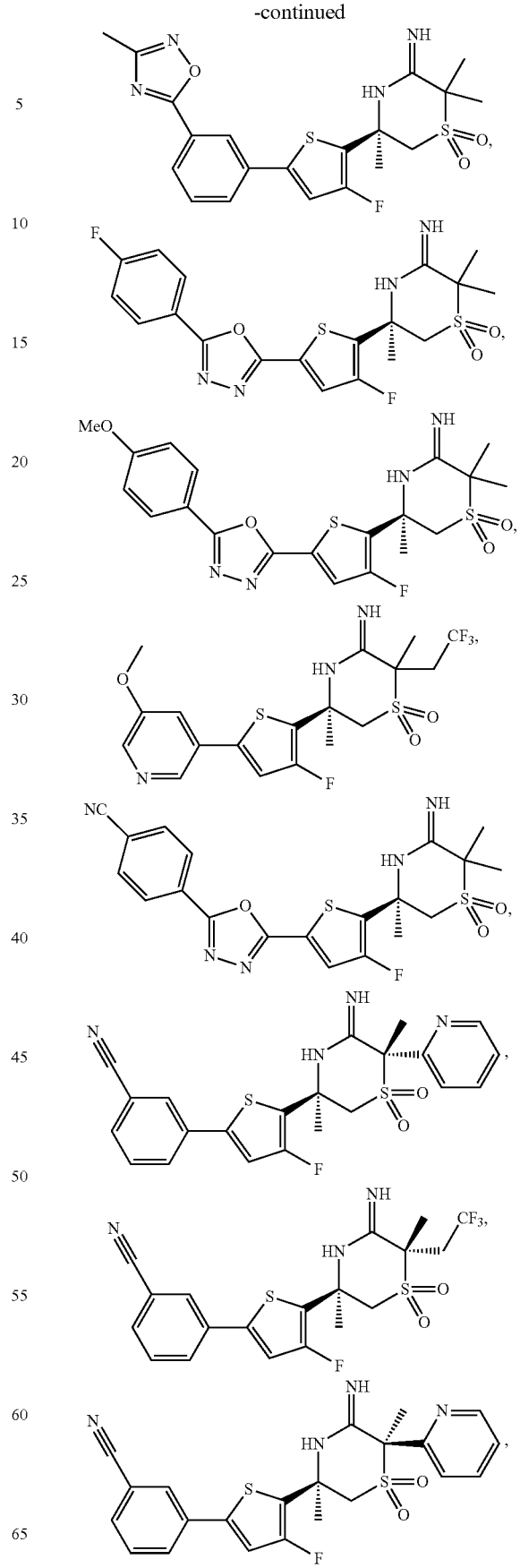

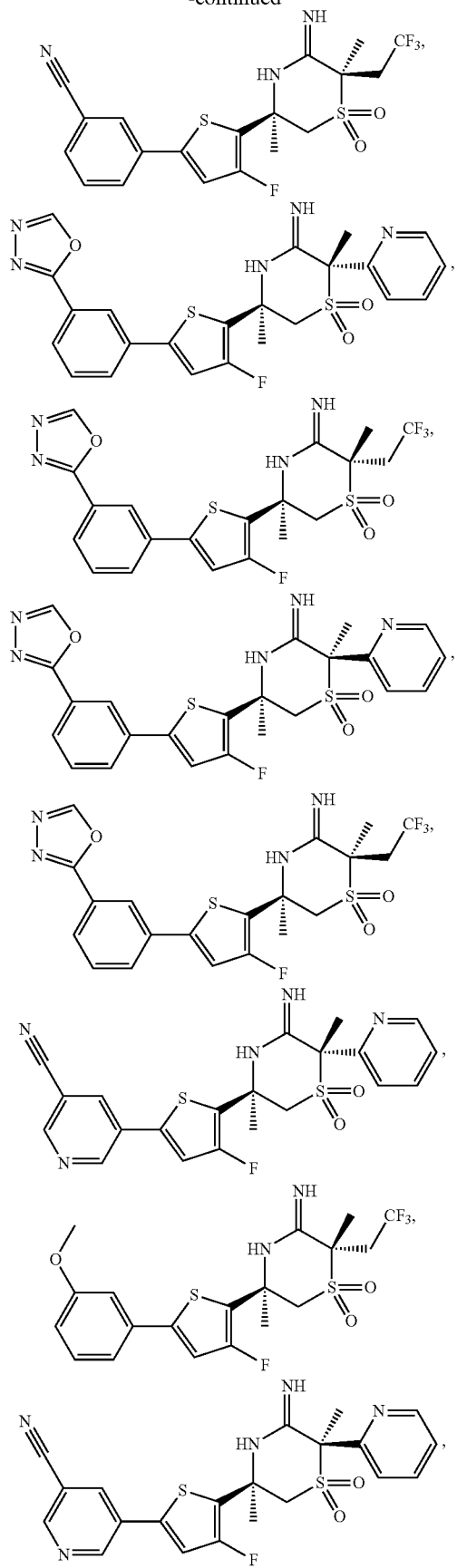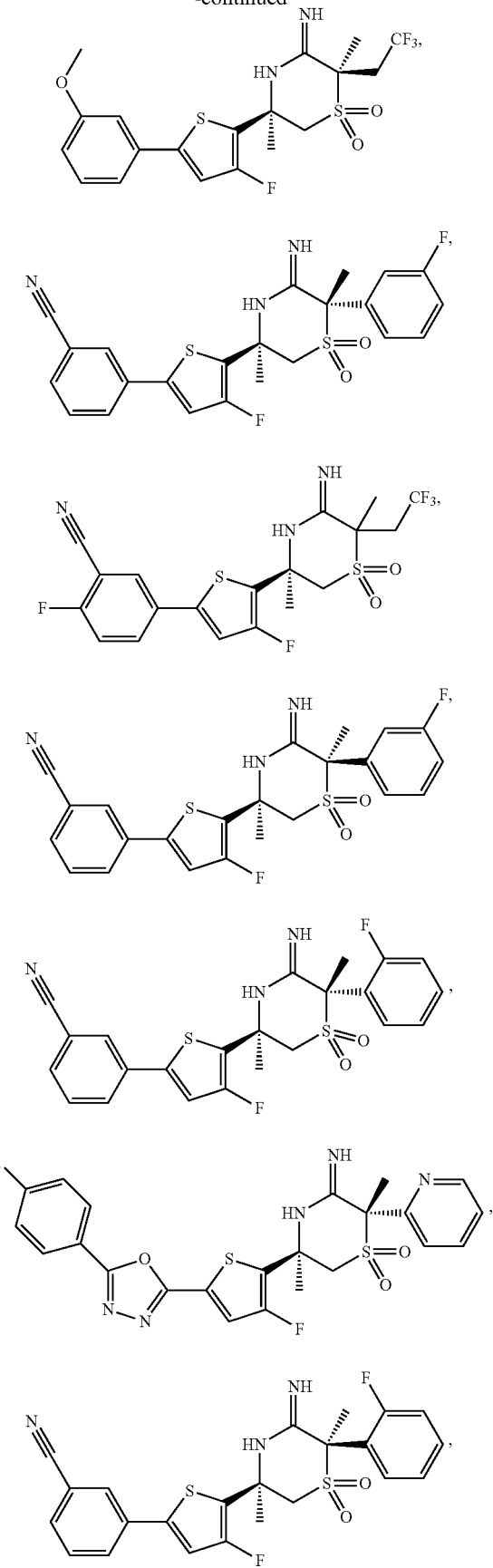

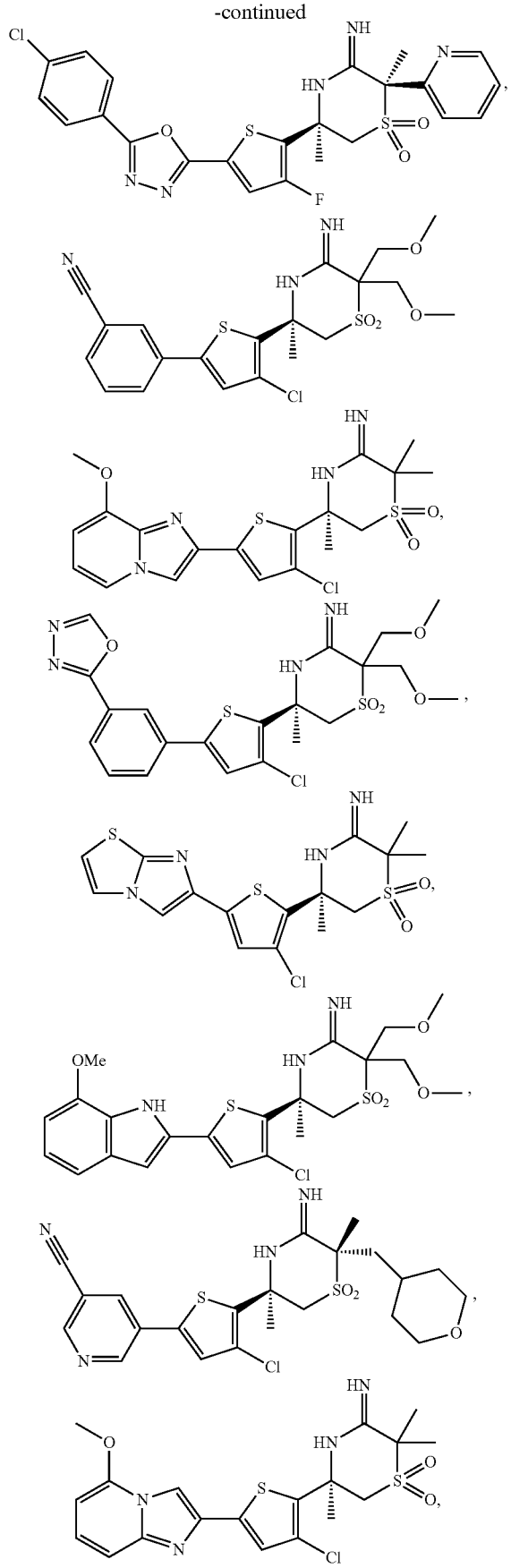
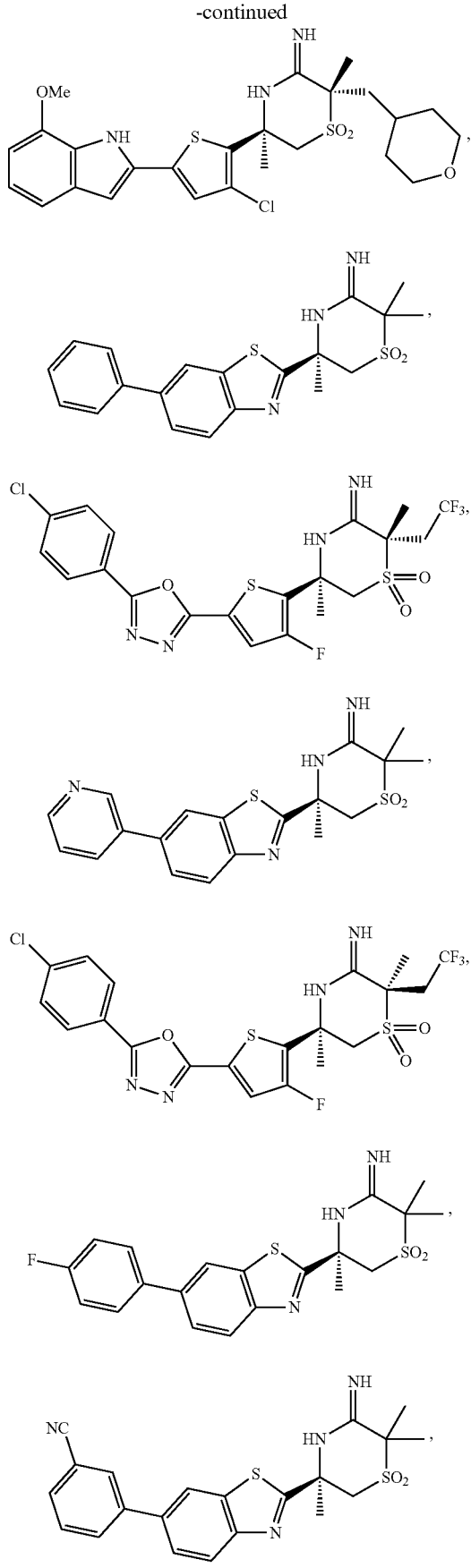

339
-continued
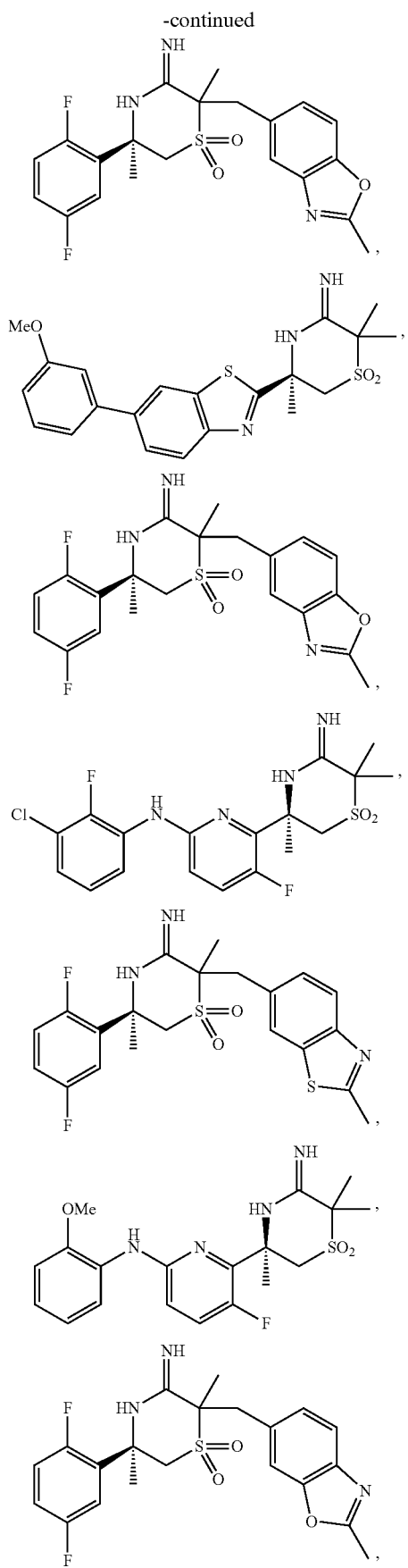
340
-continued
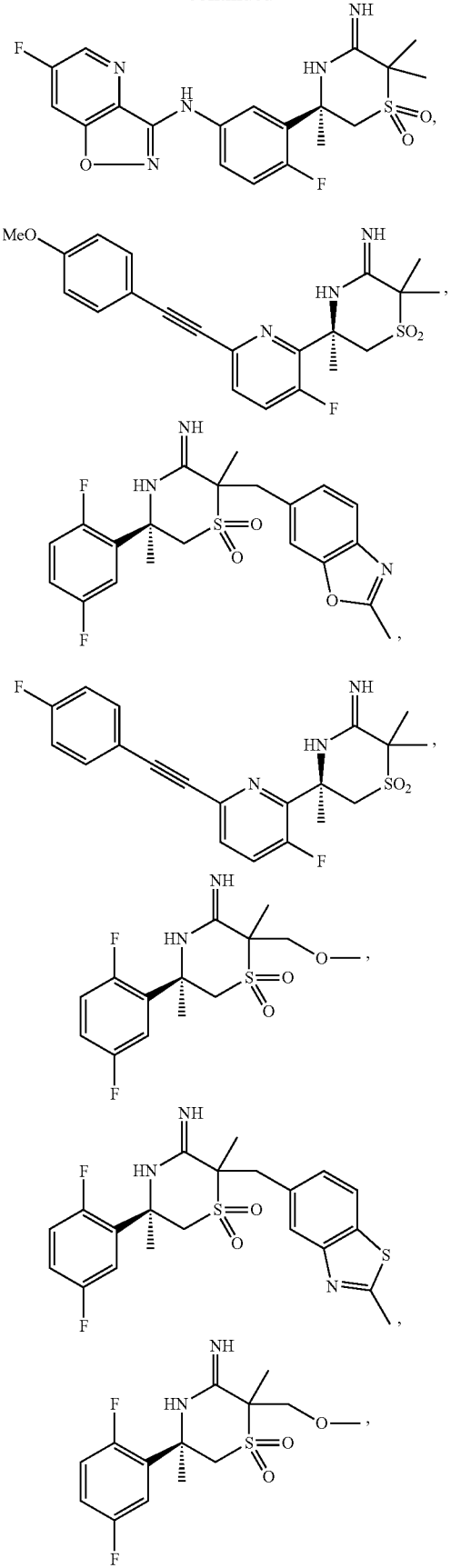

341
-continued
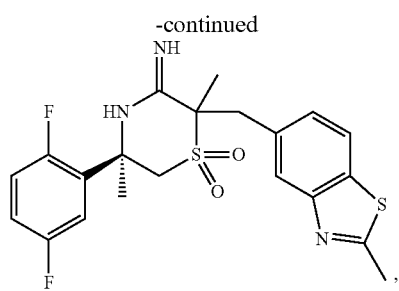
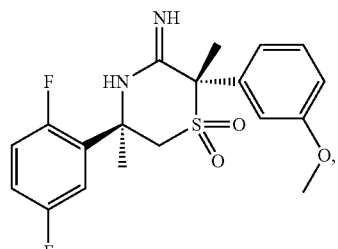
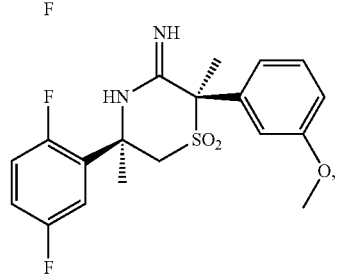
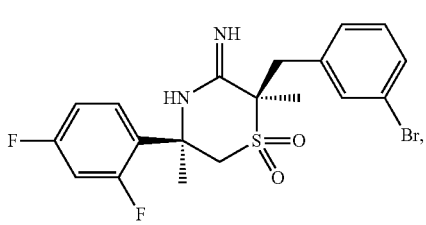
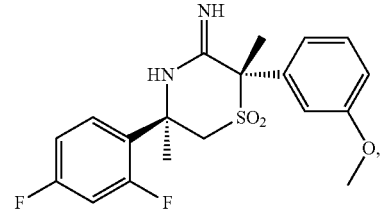
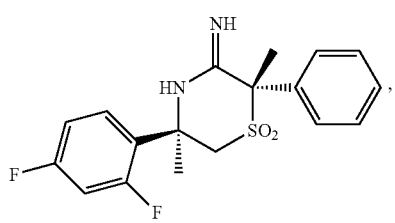
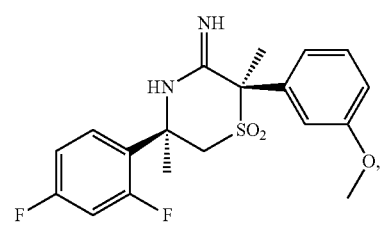
342
-continued
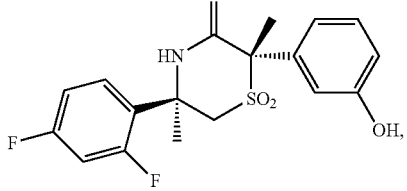
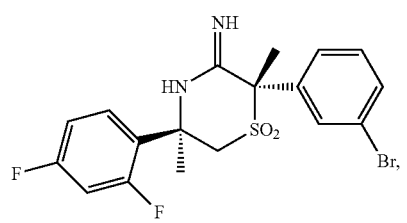
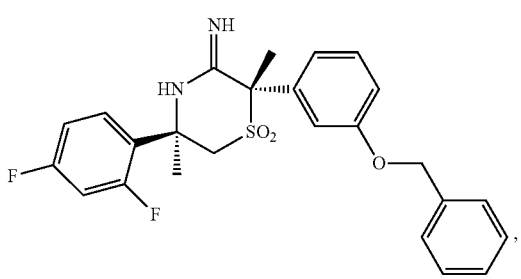
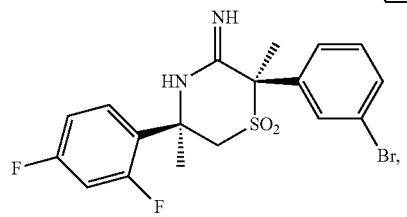
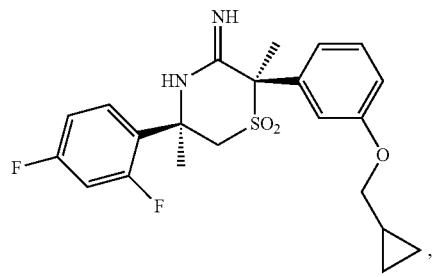
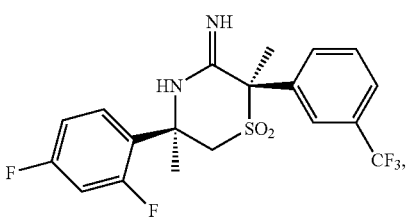
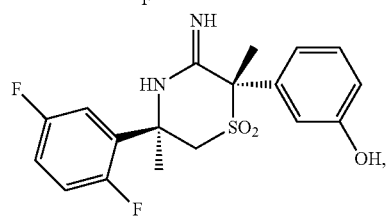

343
-continued
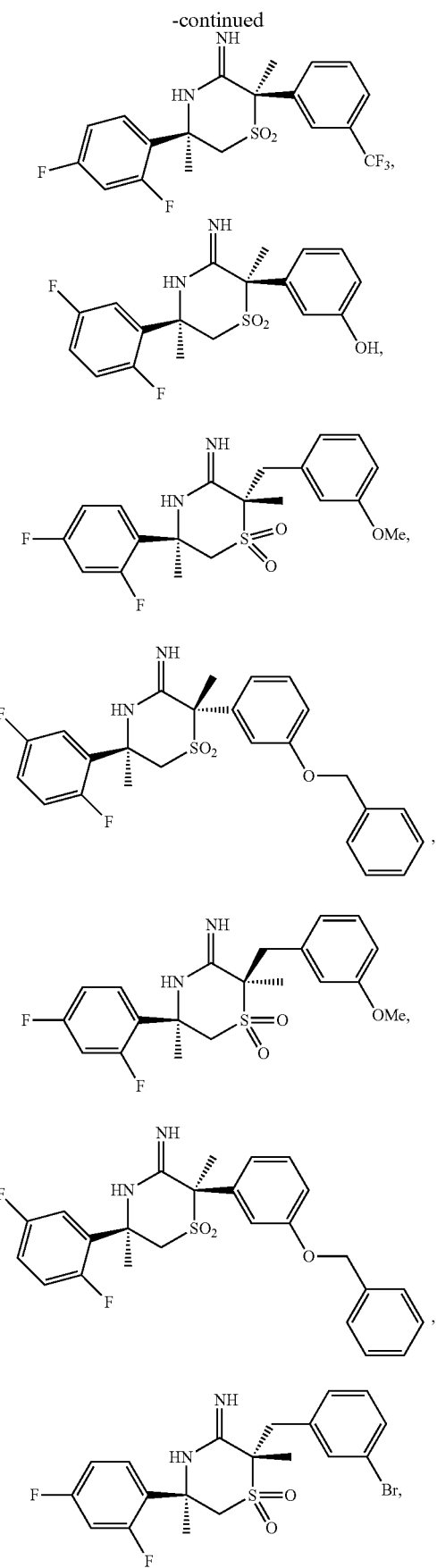
344
-continued
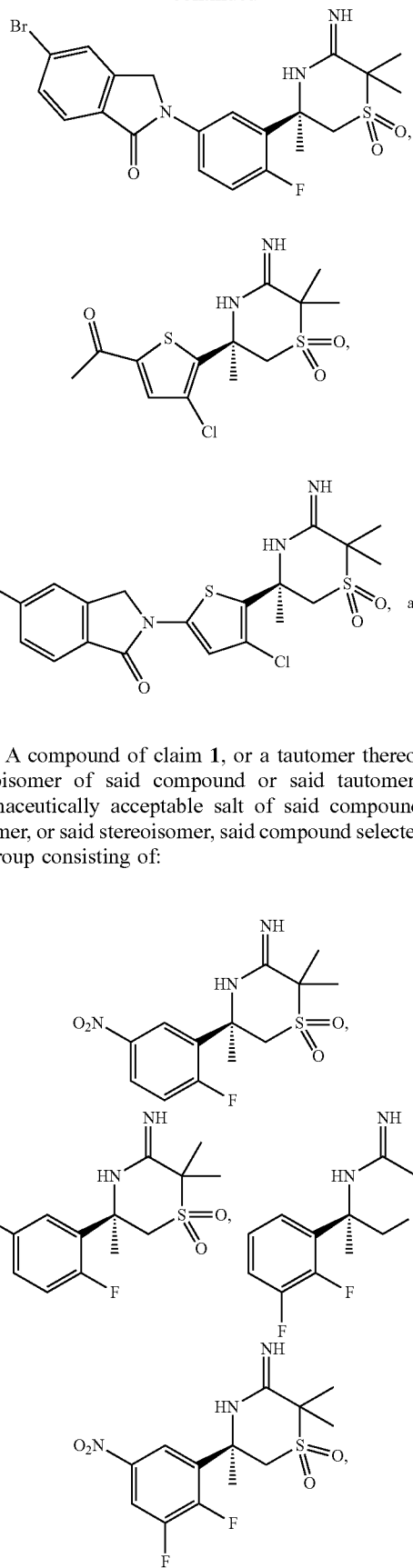
14. A compound of claim 1, or a tautomer thereof, or a stereoisomer of said compound or said tautomer, or a pharmaceutically acceptable salt of said compound, said tautomer, or said stereoisomer, said compound selected from the group consisting of:

345
-continued
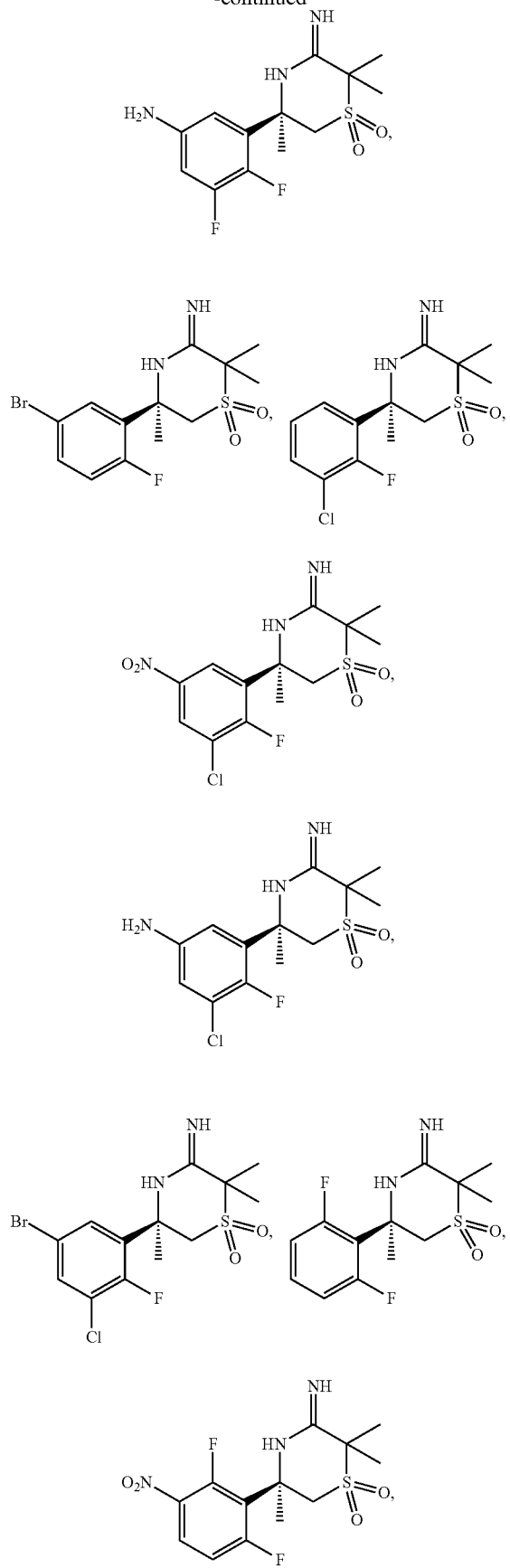
346
-continued
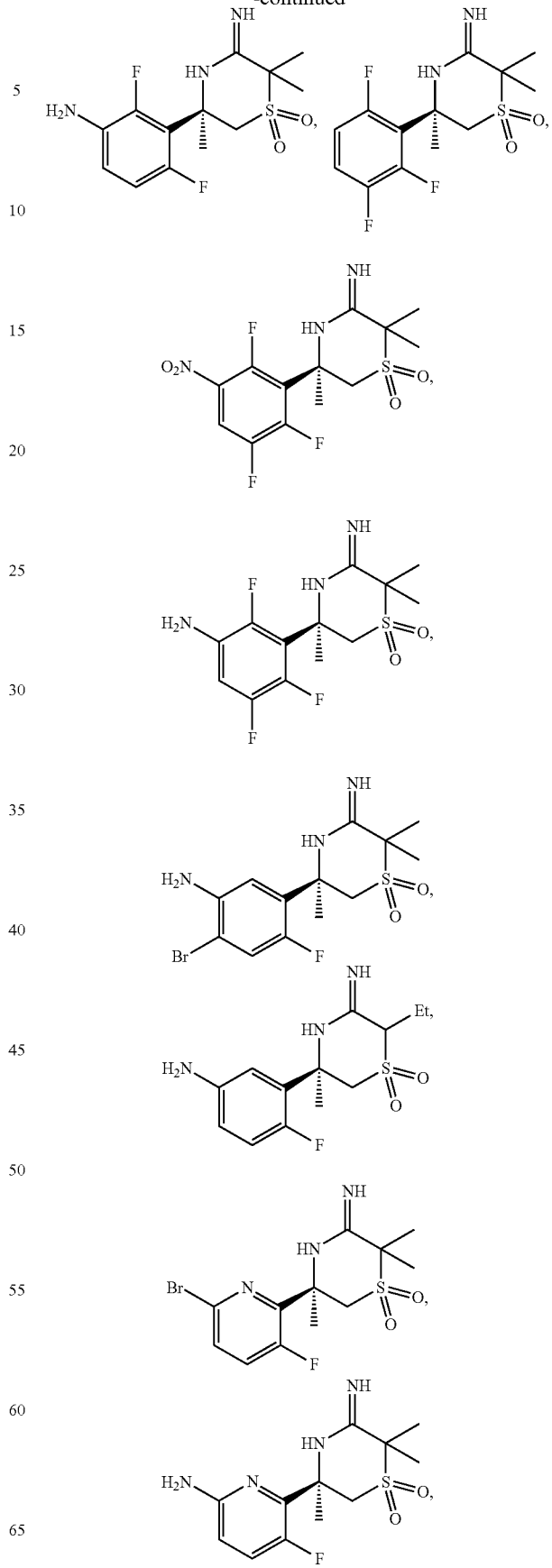

347
-continued
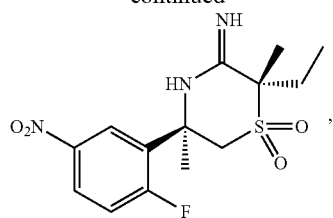,
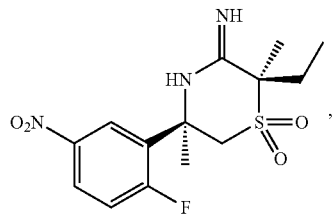,
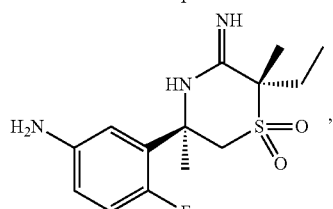,
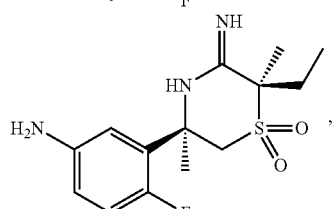,
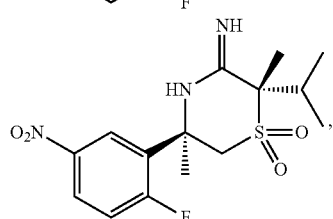,
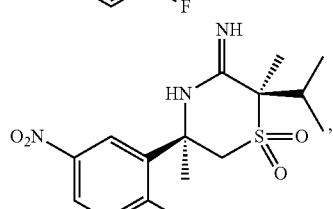,
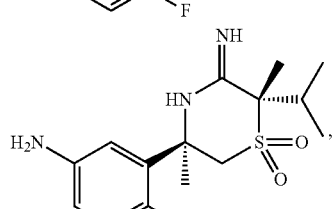,
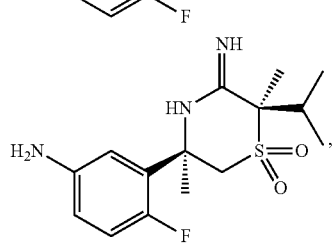,
348
-continued
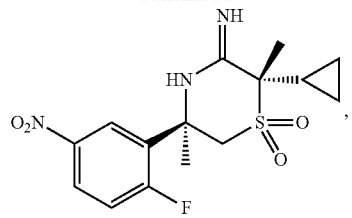,
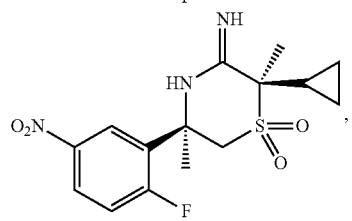,
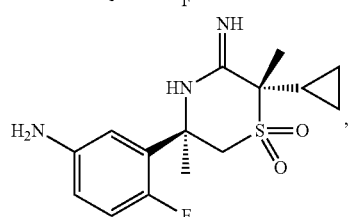,
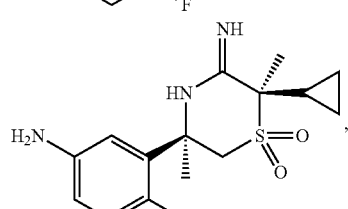,
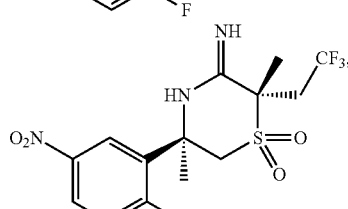,
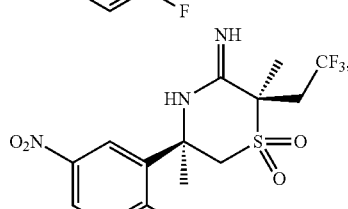,
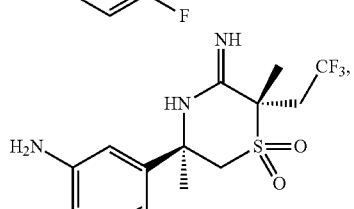,
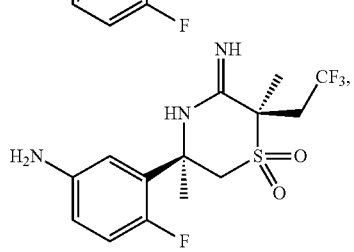,

349
-continued
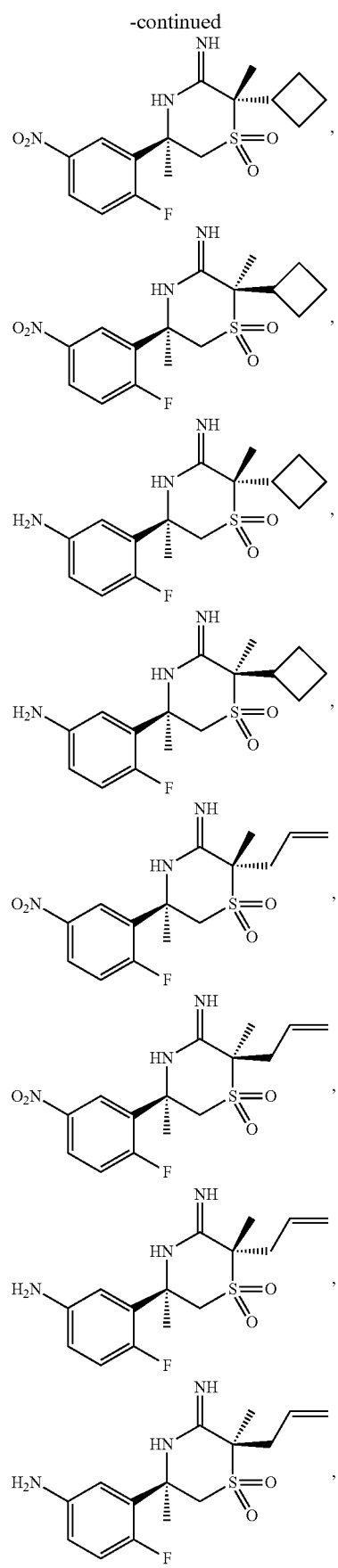
350
-continued
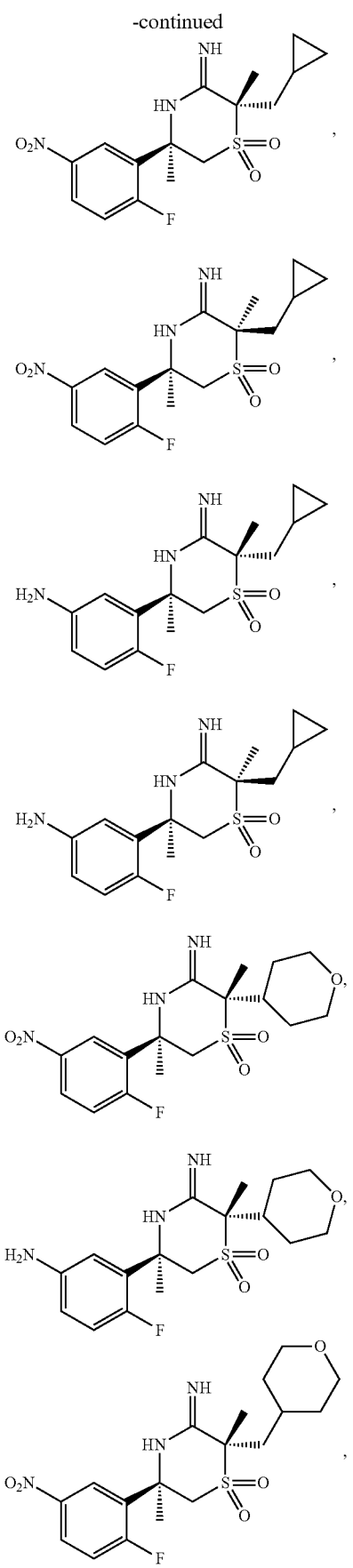

351
-continued
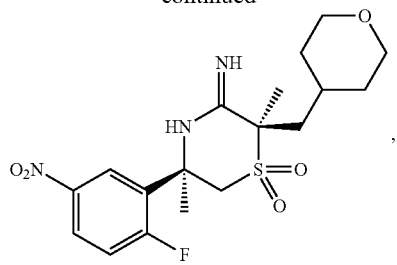,
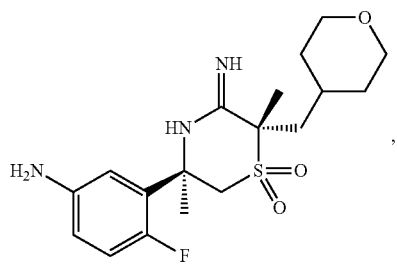,
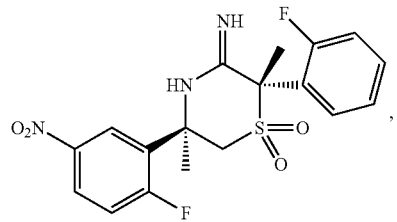,
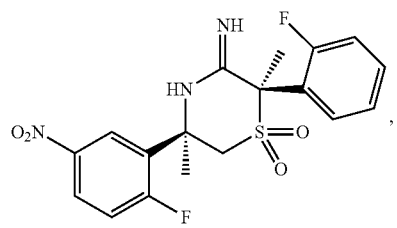,
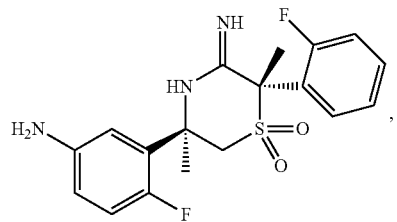,
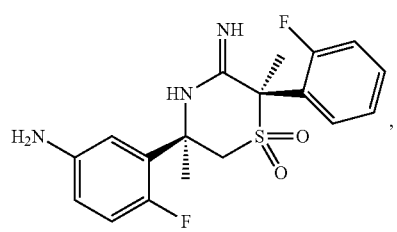,
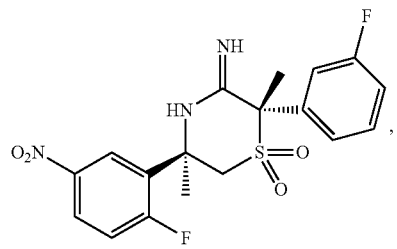,
352
-continued
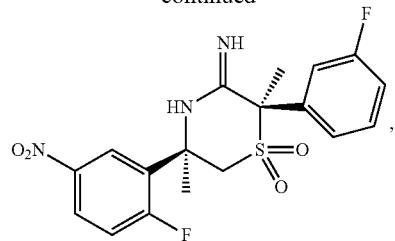,
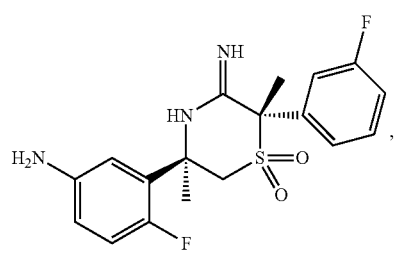,
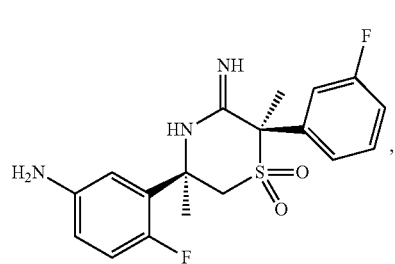,
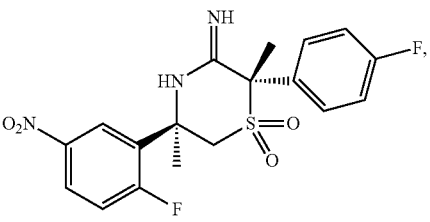,
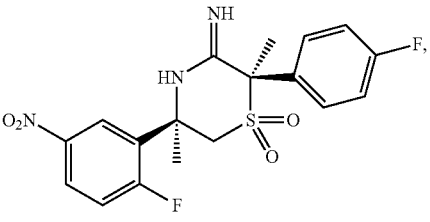,
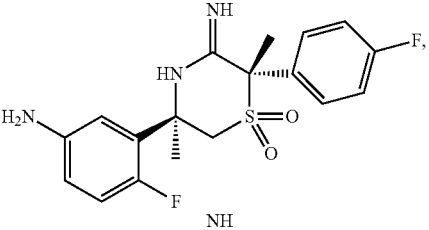,
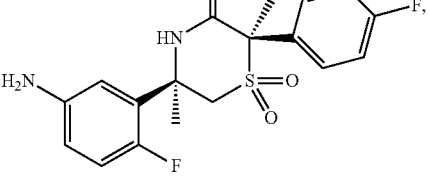, 353
-continued
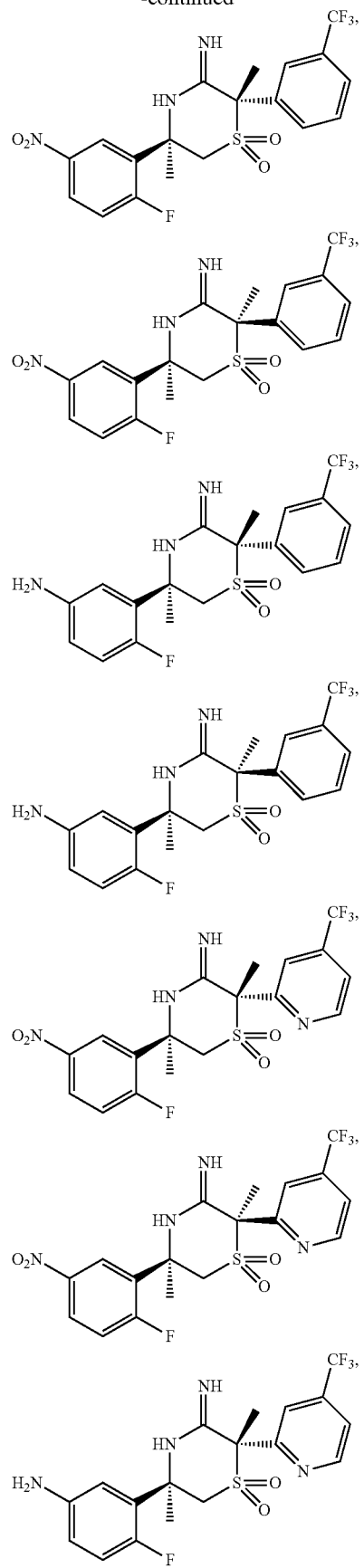
354
-continued
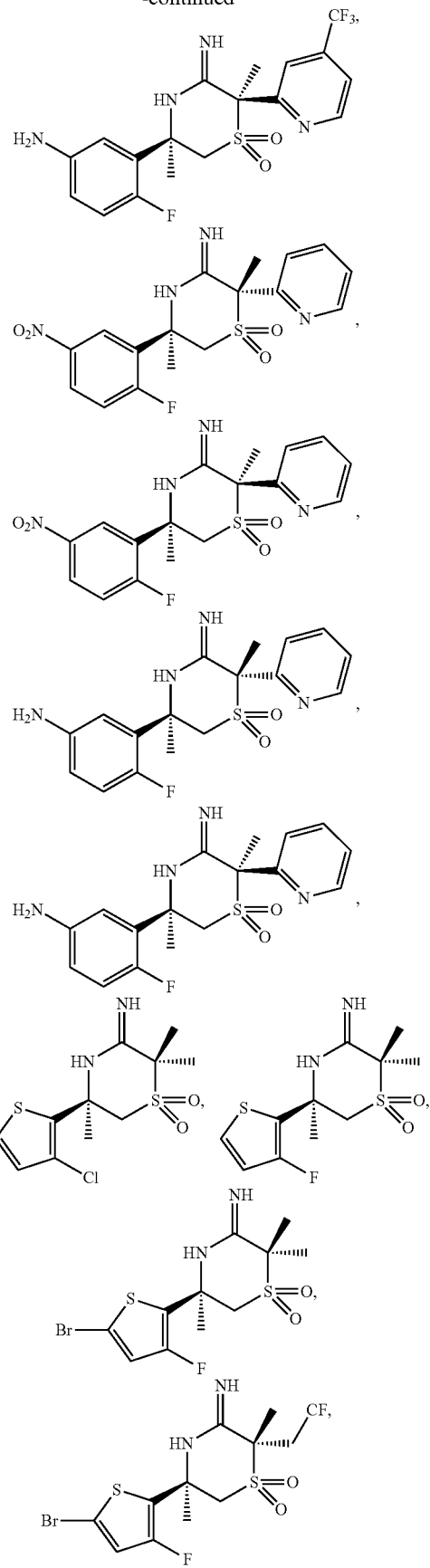

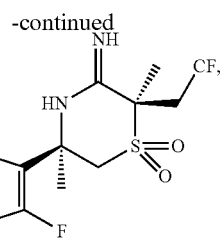
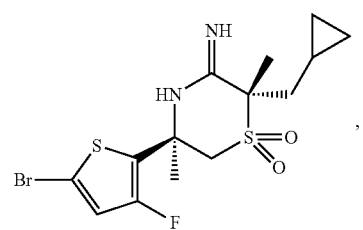
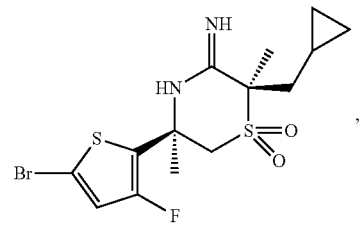
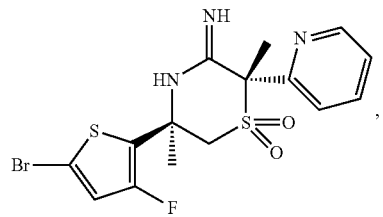
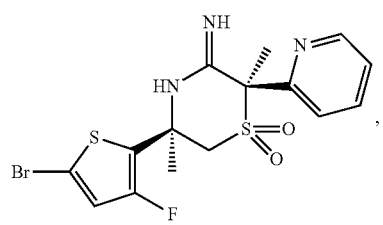
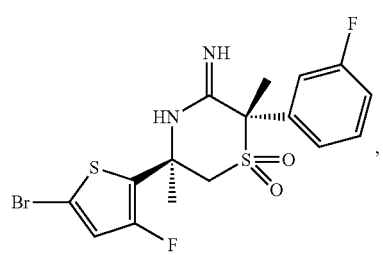
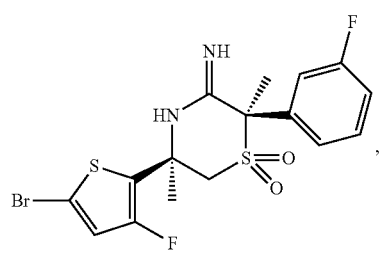
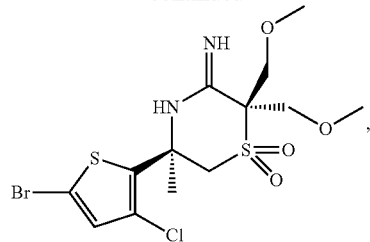
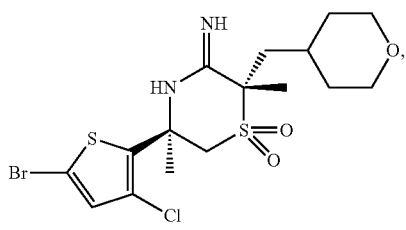
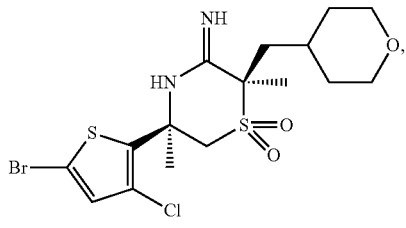
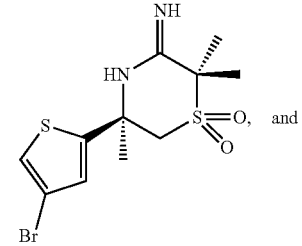
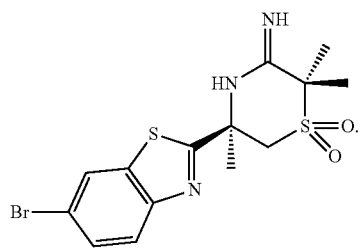
15. A compound of claim 1, or a tautomer thereof, or a stereoisomer of said compound or said tautomer, or a pharmaceutically acceptable salt of said compound, said tautomer, or said stereoisomer, said compound selected from the group consisting of:
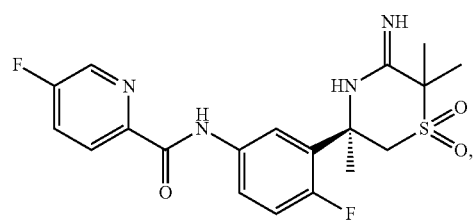

357
-continued
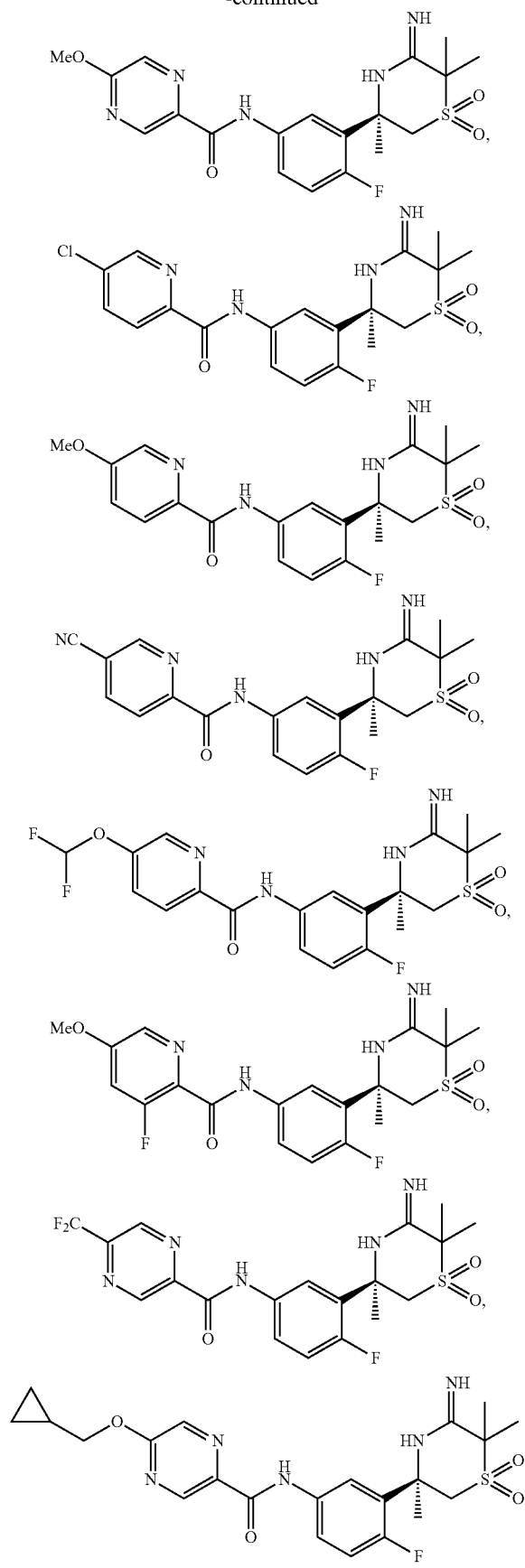
358
-continued
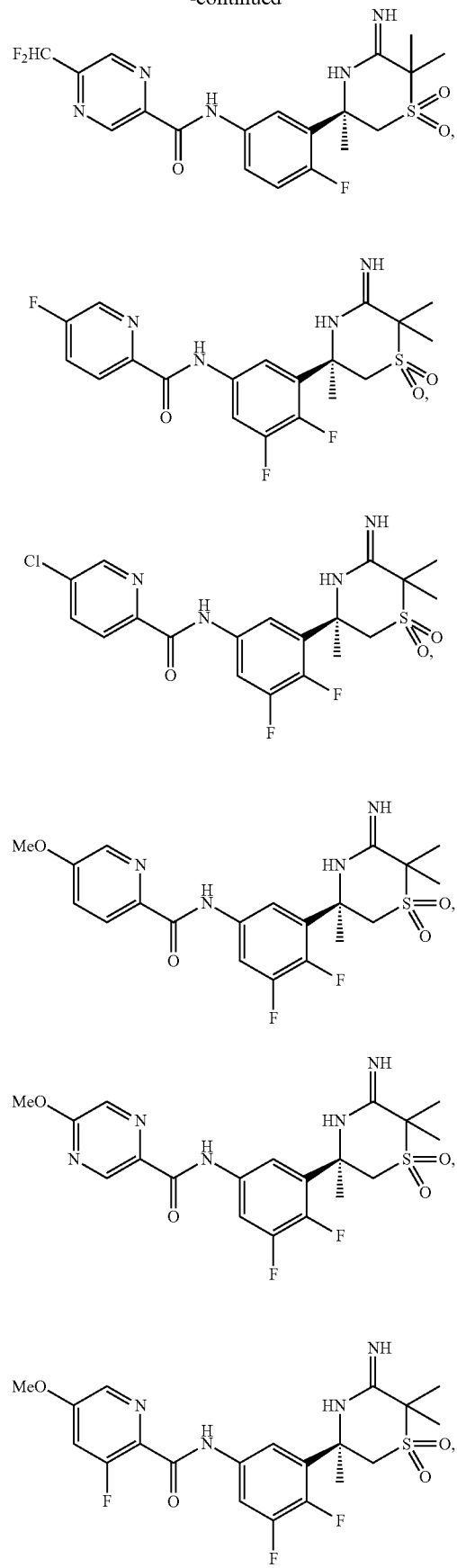

359
-continued
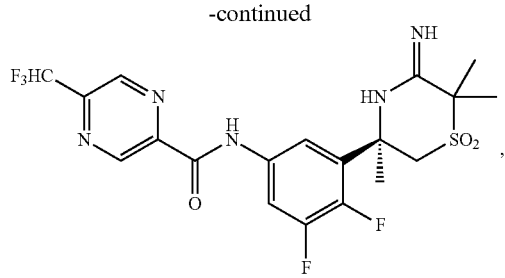
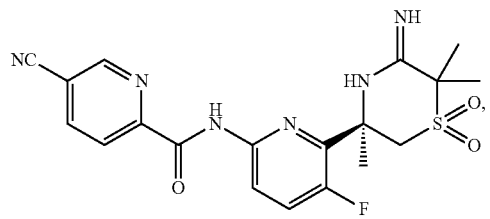
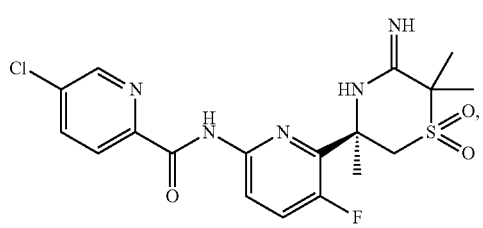
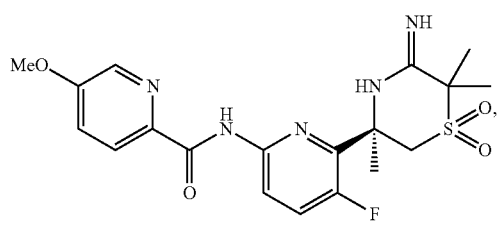
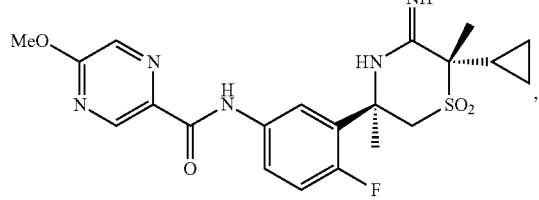
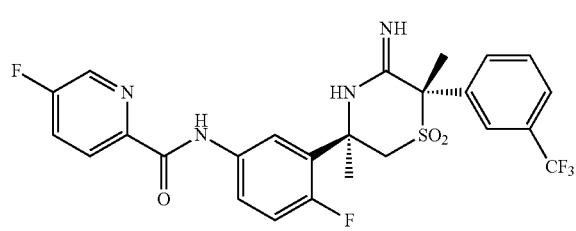
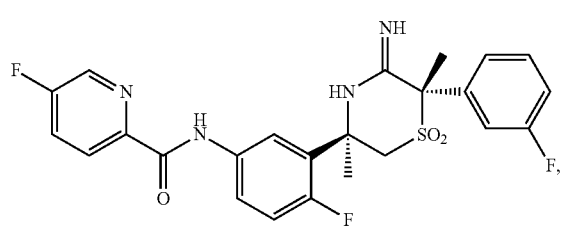
360
-continued
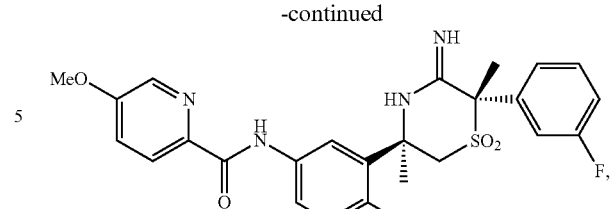
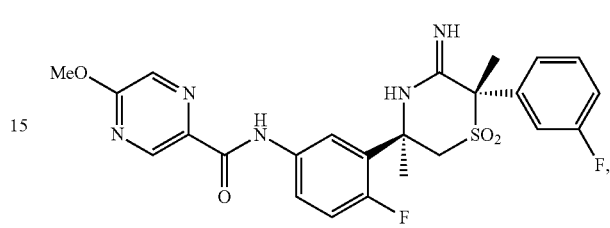
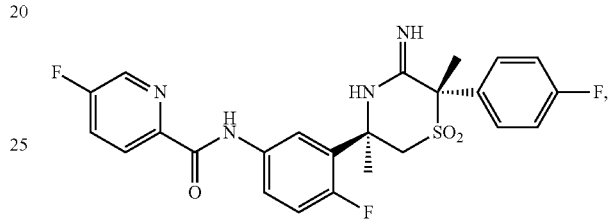
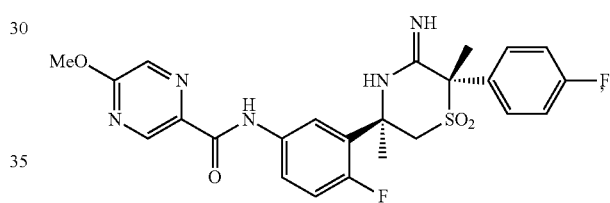
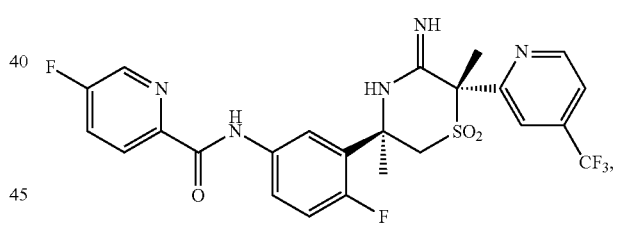
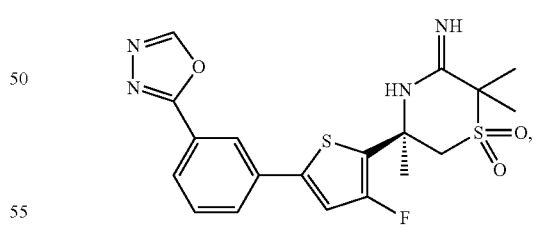
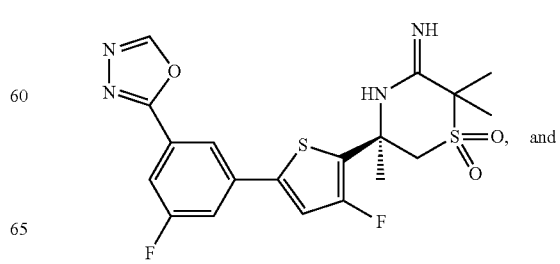

-continued

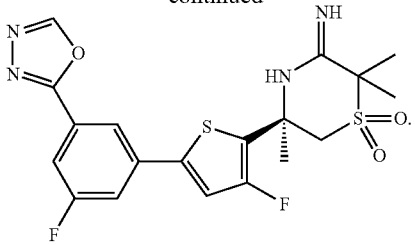

16. A pharmaceutical composition comprising at least one compound of claim 1, or a tautomer thereof, or a stereoisomer of said compound or said tautomer, or a pharmaceutically acceptable salt thereof, and a pharmaceutically acceptable carrier or diluent.

17. A pharmaceutical composition of claim 16, wherein said at least one additional therapeutic agent is at least one agent selected from:
$m_1$ agonists; $m_2$ antagonists; cholinesterase inhibitors; galantamine; rivastigimine; N-methyl-D-aspartate receptor antagonists; combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies; vitamin E; nicotinic acetylcholine receptor agonists; CB1 receptor inverse agonists; CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors; Tau aggregation inhibitors; RAGE inhibitors; anti-Abeta vaccine; APP ligands; agents that upregulate insulin, cholesterol lowering agents; cholesterol absorption inhibitors; combinations of HMG-CoA reductase inhibitors and cholesterol absorption inhibitors; fibrates; combinations of fibrates and cholesterol lowering agents and/or cholesterol absorption inhibitors; nicotinic receptor agonists; niacin; combinations of niacin and cholesterol absorption inhibitors and/or cholesterol lowering agents; LXR agonists; LRP mimics; H3 receptor antagonists; histone deacetylase inhibitors; hsp90 inhibitors; 5-HT4 agonists; 5-HT6 receptor antagonists; mGluR1 receptor modulators or antagonists;
mGluR5 receptor modulators or antagonists; mGluR2/3 antagonists; Prostaglandin EP2 receptor antagonists; PAI-1 inhibitors; agents that can induce Abeta efflux; Metal-protein attenuating compound; GPR3 modulators; and antihistamines.

18. A compound according to claim 7, or a tautomer thereof, or a stereoisomer of said compound or said tautomer, or a pharmaceutically acceptable salt of said compound, said tautomer, or said stereoisomer, wherein:
each $R^2$ (when present) is independently selected from the group consisting of fluorine, chlorine, bromine, —CN, —OMe, methyl, ethyl, cyclopropyl, —$CF_3$, —$CHF_2$, —$OCF_3$, and —$OCHF_2$.

* * * * *